US008431117B2

(12) United States Patent
Terman

(10) Patent No.: US 8,431,117 B2
(45) Date of Patent: Apr. 30, 2013

(54) SICKLED ERYTHROCYTES WITH ANTI-TUMOR AGENTS INDUCE TUMOR VASO-OCCLUSION AND TUMORICIDAL EFFECTS

(76) Inventor: David S Terman, Pebble Beach, CA (US)

( * ) Notice: Subject to any disclaimer, the term of this patent is extended or adjusted under 35 U.S.C. 154(b) by 0 days.

(21) Appl. No.: 13/367,797

(22) Filed: Feb. 7, 2012

(65) Prior Publication Data

US 2012/0195869 A1   Aug. 2, 2012

Related U.S. Application Data

(60) Continuation-in-part of application No. 12/586,532, filed on Sep. 22, 2009, now abandoned, which is a continuation-in-part of application No. 12/276,941, filed on Nov. 24, 2008, which is a continuation-in-part of application No. 12/145,949, filed on Jun. 25, 2008, now Pat. No. 7,803,637, which is a division of application No. 10/937,758, filed on Sep. 8, 2004, now abandoned, which is a continuation of application No. 09/650,884, filed on Aug. 30, 2000, now abandoned.

(60) Provisional application No. 60/151,470, filed on Aug. 30, 1999, provisional application No. 61/215,906, filed on May 11, 2009, provisional application No. 61/211,227, filed on Mar. 28, 2009, provisional application No. 61/206,338, filed on Jan. 28, 2009, provisional application No. 61/192,949, filed on Sep. 22, 2008, provisional application No. 61/205,776, filed on Jan. 22, 2009.

(51) Int. Cl.
 *A01N 63/00* (2006.01)
(52) U.S. Cl.
 USPC ... 424/93.1; 424/93.21; 424/93.7; 424/93.73; 435/363; 435/366; 435/372
(58) Field of Classification Search ............... 424/93.1, 424/93.21, 93.7, 93.73; 435/363, 366, 372
 See application file for complete search history.

(56) References Cited

PUBLICATIONS

Khelifi et al. (Exp. Biol. Med. (Maywood). May 2003; 228 (5): 48105).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Fabry et al. (Proc. Natl. Acad. Sci. USA. May 1986; 86 (10): 3808-12).*
Slavin et al. (Br. J. Surg. Sep. 1992; 79 (9): 918-21).*
Updike et al. (Science. Aug. 20, 1976; 193 (4254): 681-3).*
Zola et al. (Ann. Ist Super Sanita. 1991; 27 (1): 97-103).*
Brown et al. (Magn. Reson. Med. Dec. 2003; 50 (6): 1209-14).*
Lutty et al. (Curr. Eye Res. Sep. 2002; 25 (3): 163-71).*
Goldberg et al. (Med. Hypotheses. Apr. 2010; 74 (4): 629-30).*
Doi et al. (Br. J. Cancer. Aug. 1999; 80 (12):1945-54).*
Huang et al. (Science. Jan. 24, 1997; 275 (5299): 547-50).*
Pulaski, BA, Terman DS, Khan S, Muller E, Ostrand-Rosenberg S Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model Cancer Research 60:2710-2715 (2000).
Stevenson DK, Wong RJ Metalloporphyrins in the management of neonatal hyperbilirubinemia Seminars in Fetal & Neonatal Medicine 15 164-168 (2010).
Vreman HJ, Ekstrand, BC, Stevenson DK Selection of Metalloporphyrin Heme Oxygenase Innibitors Based on Potency and Photoreactivity Pediatric Research 44: 195-199 (1993).
Vreman HJ, Wong RJ, Stevenson DK Alternative Metalloporphyrins for the Treatment of Neonatal Jaundice Journal of Perinatology 21:S108-S113 (2001).
Kerbel R, Human Tumor Xenografts as Predictive Preclinical Models for Anticancer Drug Activity in Humans Cancer Biology & Therapy 2:4:Suppl. 1, S134-S139 (2003).
Rockwell S, Tumor Cell Survival in B.A. Teicher (ed.), Tumor Models in Cancer Research, Cancer Drug Discovery Springer, Boston USA pp. 611-623 (2011)).
Hirai K, Sasahira T,Ohmori H, Fujii K, Kuniyasu H Inhibition of heme oxygenase-1 by zinc protoporphyrin IX reduces tumor growth of LL/2 lung cancer in C57BL mice. Int. J. Cancer 120: 500-505 (2006).
Tanaka S, Akaike T, Fang J, Beppu T, Ogawa M, Tamura F, Miyamoto Y, Maeda H Antiapoptotic effect of haem oxygenase-1 induced by nitric oxide in experimental solid tumour. Brit J Cancer 88: 902-909 (2003).
Schulz S, Wong RJ, Vreman HJ, Stevenson DK. Metalloporphyrins—an update Frontiers Pharmacology 3: 1-16 (2012).
Drummond GS, Kappas A. Prevention of neonatal hyperbilirubinemia by tin protoporphyrin IX, a potent competitive inhibitor of heme oxidation. Proc.Natl.Acad.Sci. U.S.A. 78: 6466-6470. (1981).

\* cited by examiner

*Primary Examiner* — Stephen Rawlings
(74) *Attorney, Agent, or Firm* — Central Coast Patent Agency

(57) ABSTRACT

The present invention provides erythrocytes or nucleated erythrocyte precursors from animals or patients with at least one S hemoglobin allele which are capable of selectively localizing in tumor vasculature resulting in vaso-occlusion, hemolysis and heme release. A tumoricidal effect is achieved when these cells are administered in before during or after administration of (i) an agent(s) that interferes with degradation of reactive oxygen species, (ii) impairs glucose uptake and/or (iii) chemotherapy. These cells also carry oncolytic viruses, antitumor proteins, multidrug resistant proteins, chemotherapy, monoclonal antibodies, superantigens, superantigen conjugates and fusion proteins, siRNAs, plasmids and non-protein toxins and attenuated tumoricidal bacterial cells specifically into the tumors and induce a tumoricidal effect.

4 Claims, 10 Drawing Sheets

Figure 1:
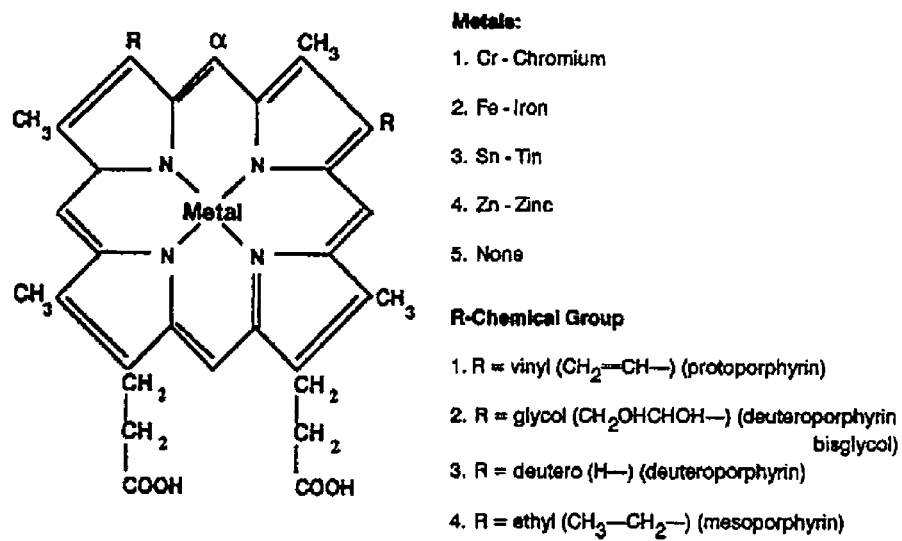

SICKLED ERYTHROCYTES WITH ANTI-TUMOR AGENTS INDUCE TUMOR VASO-OCCLUSION AND TUMORICIDAL EFFECTS

CROSS REFERENCE TO RELATED DOCUMENTS

The present application is a continuation in part of U.S. patent application Ser. Nos. 12/586,532 filed Sep. 22, 2009 (abandoned) which is a continuation in part of U.S. patent application Ser. No. 12/276,941 filed Nov. 24, 2008, which is a CIP of 12/145,949 filed Jun. 25, 2008 which issued as U.S. Pat. No. 7,803,637 on Sep. 28, 2010 which is a divisional of U.S. patent application Ser. No. 10/937,758 filed Sep. 8, 2004 (abandoned) which is a continuation of U.S. patent application Ser. No. 09/650,884 filed Aug. 30, 2000 (abandoned) which is a continuation of U.S. provisional patent application 60/151,470 filed Aug. 30, 1999 (abandoned). All of the above patents and patent applications and their references are incorporated by reference in their entirety.

The present application claims priority to U.S. patent application Ser. No. 12/586,532 filed Sep. 22, 2009 and also claims priority to U.S. provisional application Ser. No. 61/215,906 filed May 11, 2009 (abandoned) and U.S. provisional application Ser. No. 61/211,227 filed Mar. 28, 2009 (abandoned) and U.S. provisional application Ser. No. 61/206,338 filed on Jan. 28, 2009 (abandoned) and U.S. provisional application serial numger 61/205,776 filed Jan. 22, 2009 (abandoned) and U.S. provisional application Ser. No. 61/192,949 filed on Sep. 22, 2008 (abandoned). All of the above patents and patent applications and their references are incorporated by reference in their entirety.

The following applications are related and incorporated by reference: PCT/US07/69869 filed May 29, 2007 (abandoned) and U.S. provisional application Ser. No. 60/809,553 filed on May 30, 2006 (abandoned) and U.S. provisional application Ser. No. 60/819,551 filed on Jul. 8, 2006 (abandoned) and U.S. provisional application Ser. No. 60/842,213 filed on Sep. 5, 2006 (abandoned) and U.S. patent application Ser. No. 10/428,817, filed May 5, 2003 (abandoned) and U.S. provisional application Ser. No. 60/438,686, filed Jan. 9, 2003 (abandoned) and U.S. provisional application Ser. No. 60/415,310, filed on Oct. 1, 2002 (abandoned) and U.S. provisional application Ser. No. 60/406,750, filed on Aug. 29, 2002 (abandoned) and U.S. provisional application Ser. No. 60/415,400, filed on Oct. 2, 2002 (abandoned) and U.S. provisional application Ser. No. 60/406,697, filed on Aug. 28, 2002 (abandoned) and U.S. provisional application Ser. No. 60/389,366, filed on Jun. 15, 2002 (abandoned) and U.S. provisional application Ser. No. 60/378,988, filed on May 8, 2002 (abandoned) and U.S. patent application Ser. No. 09/870,759 filed on May 30, 2001 (abandoned) and U.S. patent application Ser. No. 09/650,884 filed Aug. 30, 2000 (abandoned) and U.S. provisional patent application Ser. No. 60/151,470 filed on Aug. 30, 1999 (abandoned).

FIELD OF THE INVENTION

The invention is in the fields of genetics and medicine and covers compositions and methods for targeted delivery of anti-tumor agents using sickled erythrocytes, their nucleated precursors, and erythroleukemia cells in native state or upregulated for expression of constitutive adhesion molecules and transduced or loaded with hypoxia responsive elements, tumoricidal proteins, toxins, superantigens, hemolysins, oncolytic viruses, chemotherapeutics and anaerobic spores.

DEFINITIONS

Sickle (d) erythrocytes, SS cells, SS erythrocytes, SS RBCs: Any cell containing an S or SS hemoglobin genes and/or capable of expressing sickled hemoglobin. Sickled cells, sickle hemoglobin variants, SS cells with genetic mutations, SS cells with natural or man-made mutations that increase production/expression of photoreactive porphyrins, SS cells with natural or man-made hemoglobin genes or mutations including but not limited to nucleated precursors and progenitors of each expressing receptors/physical properties capable of binding to tumor cells and/or tumor neovasculature. Also included in this definition are man-made cells into which S or SS hemoglobin genes or mutants or intact or SS homologue proteins have been introduced.

SS cell nucleated precursors: Any nucleated cell containing a natural sickled hemoglobin gene. Also included in this definition are man-made nucleated precursor cells to which an S or SS hemoglobin gene or protein has been added or which has been transfected with S or SS hemoglobin genes.

Sickle hemoglobin variants: Erythrocyte or nucleated erythrocyte precursor/progenitor expressing hemizygous sickle S and A hemoglobin, sickle hemoglobin-C disease, sickle beta plus thalassemia, sickle hemoglobin-D disease, sickle hemoglobin-E disease, homozygous C or C—thalassemia, hemoglobin-C beta plus thalassemia, homozygous E or E—thalassemia; any erythrocyte from patients with any form of sickle hemoglobinopathy; any erythrocyte, with or without sickle hemoglobin, their precursors and progenitors expressing receptors capable of binding to tumor cells and/or tumor neovasculature.

Erythroleukemia cells: Mature erythroleukemia cells, their precursors and progenitors expressing receptors capable of binding to tumor cells and/or neovasculature.

BACKGROUND

Resistance of tumors to chemotherapy and radiotherapy may be attributed in part to the unique ultrastructure of the tumor neovasculature and physiological microenvironment of tumor cells. Tumor neovasculature is a disordered network of blood vessels containing multiple anastomotic branches and shunts, resulting in spatial and temporal heterogeneity in blood perfusion. This causes portions of the tumor to show hypoxic oscillations or become frankly hypoxic with $pO_2$ levels ranging from 1-10%. Hypoxia contributes to treatment resistance in a multi-factorial manner. For example, reduction in proliferation and increases in drug resistance pathways, such as glutathione synthetase, occur. In the case of radiation therapy, the presence of molecular oxygen is necessary for the most effective forms of DNA damage. Irregularities in vascular transport also result in inefficient drug delivery. In such a milieu, the effectiveness of chemo- and radiotherapy are unpredictable and ineffective. In the presence of low vascular $pO_2$ typical of tumor microvasculature, erythrocytes become slightly crenated and less deformable, leading to rouxleux formation and increased flow resistance. Erythrocytes from patients with sickle cell anemia undergo more substantial changes under low $pO_2$ conditions. SS hemoglobin desaturates in a time-dependent manner leading to polymerization of deoxy-HbS($\alpha_2\beta^s_2$) tetramers and formation of rigid spicules that attach to the cytoskeleton. A population of nondeformable sickled erythrocytes (SRBCs) emerges that tends to attach to and occlude microvessels. Moreover, activated SS RBCs display multiple adhesion receptors such as BCAM/Lu, ICAM-4 and α4β1, which adhere abnormally to cognate endothelial ligands laminin-α5, αvβ, and VCAM-1, respectively, and are thought to play a major role in SS cell-mediated vaso-occlusive events. Several of these cognate endothelial ligands such as laminin-β5, αvβ3, and VCAM-1 are up-regulated on sickle cell vasculature by oxygenation/reperfusion. Notably, they are also broadly expressed and upregulated on tumor neovessels as a consequence of angiogenesis and tumor hypoxia. Thus, SS cells possess properties that are well suited for adherence to, entrapment in and occlusion of tumor neovessels. Furthermore, SS RBCs involved in vaso-occlusive events produce superoxide/peroxide-driven hydroxyl radicals leading to membrane peroxidation and hemolysis. Hemoglobin released from hemolyzed SS cells is rapidly oxidized from ferro- to ferri-hemoglobin (methemoglobin) generating highly lipophilic heme-nitrosyl complexes that readily intercalate into cell membranes. Intracellular heme and its oxidative product free iron are highly toxic to cells especially in the presence of heme oxygenase inhibitors. Heme catalyzes the oxidation of membrane lipids and DNA and activates caspases and cathepsins leading to perturbations of cytoskeleton and apoptosis (40, 41).

Heme oxygenase (HO-1), a 32-kD microsomal membrane enzyme, is overexpressed in many tumor cells. It is activated by heme, HIF-1 (hypoxia inducible factor-1) and other stress-associated proteins (42-44). It protects cells from oxidative stress by detoxifying ferric ion and cleaving β-type heme molecules to form equimolar quantities of antioxidant bilirubin and antiapoptotic carbon monoxide. HO-1 is upregulated in transgenic sickle mice by hemin and its inhibition by tin protoporphyrin exacerbates vascular stasis and vaso-occlusion (45). Pharmacological inhibition of HO-1 in vivo also enhances the prooxidant and proapoptotic consequences of heme product exposure (46-48). We infused rhodamine-labeled SS RBCs and normal RBCs into mice bearing skin-fold window chambers containing 4T1 mammary carcinomas. At this time a robust neovasculature was observed. We monitored SS RBC behavior via intravital microscopy. After demonstrating occlusion of tumor neovessels, we examined the ability of SS cells to induce a tumoricidal response against an established carcinoma in the presence of a heme oxygenase inhibitor. We surmised that in the absence of the cytoprotective effect of heme oxygenase, constitutive heme and related oxidative products released from SS cells in occluded tumor microvessels would be free to induce a significant anti-tumor response. Attempts to target tumors with liposomes and nanoparticles have yet to surmount the problems of disintegration in the bloodstream, uptake by macrophages and Kupffer cells in liver and spleen and inablilty to pass through the endothelial cell barrier. Pegylated liposomes show reduced uptake by macrophages and a prolonged half-life but still have not exhibited sufficient localization to tumor tissues. Stealth liposomes in which a targeting molecule is attached to a pegylated residue have shown localization to tumors in vivo but to date, no significant therapeutic effects. Once localized to the target cells, liposomes must then traverse the cell membrane. Fusigenic molecules to promote fusion with the cell membrane, penetratin and TAT-mediated translocation, receptor mediated endocytosis have been employed to address this problem but to date have produced no convincing anti-tumor effects (Lasic DD Applications of Liposomes in *Handbook of Biological Physics*, vol. 1, edited by R Lipowsky & E Sackmann, Elsevier Science, p. 491-519 (1995))

The instant inventors also recognized that unlike monoclonal antibodies, these very same SS erythrocytes, their nucleated precursors, sickle hemoglobin variants, erythroleukemia cells are carriers of potent tumoricidal agents into tumors. The inventors contemplate that hemoglobin in nucleated SS precursor erythroblasts is equally effective at polymerizing under hypoxemic conditions while nucleation endows them with the ability to be transduced by oncolytic viruses and to carry these viruses specfically into tumor tissue. Indeed, by placing these viruses under control of a hypoxia responsive transcriptional control element (HRE), they are activated selectively in the hypoxemic tumor vasculature rather than normoxemic tissues (Table 1). The oxygen tension of tumors (as opposed to normal tissues) is in a range appropriate for activation of the HRE especially in concatenated and polymerized form. The nucleated sickle erythroblasts and activated erythroleukemia cells of the present invention are a major improvement over monoclonal antibody, liposome and nanoparticle technology since: (i) they exhibit a higher degree of tumor localization, (ii) they penetrate the tumor vasculature more effectively and obstruct or occlude tumor microvessels, (iii) they can be transduced with tumor specific oncolytic viruses such as the self-replicating, RNA alphaviruses and adenoviruses or vectors comprising tumor specific tumoricidal transgenes. Tumor specific oncolytic-oncotropic viruses proliferate in and lyse the SS or erythroleukemia cells and then proceed to infect and kill tumor cells specifically via a bystander effect. Because of the bystander effect and the specificity of oncolytic viruses for tumor cells only a few tumor cells need be infected by the virus in order to initiate a generalized tumoricidal response. (iv) by placing the tumor specific oncolytic viruses under control of concatenated hypoxia-responsive elements, the activation of the tumor specific oncolytic viruses occurs selectively in the hypoxemic microenvironment of the tumor.

The present invention provides a remedy for specificity and efficacy. It uses a natural cell, the erythrocyte of sickle cell anemia, its nucleated precursors and sickle hemoglobin variants, erythroleukemia cells which the inventors have observed to have a proclivity to deposit selectively in the tortuous neovasculature of tumors. Indeed, sickled cells show exquisite specificity for tumor microvasculature. In the hypoxemic environment of tumors, SS hemoglobin polymerizes resulting in an increase in membrane rigidity, upregulation of adherence molecules. In this state the SS cells are insufficiently flexible to navigate the channels of the tortuous tumor vasculature.

The SS and erythroleukemia cells of the claimed invention differ from other therapies in the field in that they are natural products ideally suited as carriers of tumoricidal agents specifically into tumor cells. They are abundantly available from the large pool of SS patients worldwide and do not require culture conditions for long term maintenance. The native SS erythroblasts and erythroleukemia cells target microvasculature of virtually all tumors without relying on the presence of antibodies or specific signaling molecules. They do not induce the immunosuppression of chemotherapy or the acute toxicity of various toxins. With conventional ABO blood typing SS erythrocytes and erythroleukemia cells can be used as safely in humans as a blood transfusion requiring only one tenth the volume of a conventional unit of blood. Moreover, SS cells do not induce major histoincompatibily-related reactions associated with the use of allogeneic leukocytes. Nor do SS erythroid progenitor cells since they exhibit minimal expression of MHC I and II molecules compared to mature leukocytes and platelets.

LEGENDS TO FIGURES

FIG. 1. Basic porphyrin IX structure with central metal and two ring substitution sites (R).

Figure 2A:
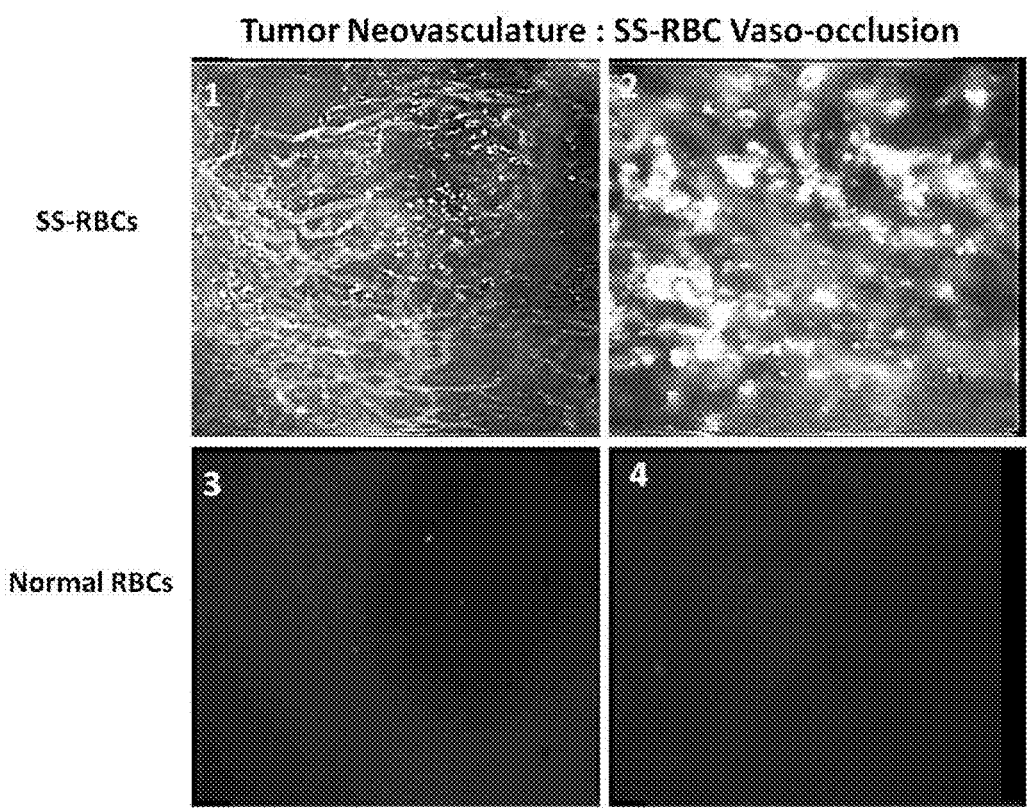

FIG. 2a. SS RBC but not normal RBC adhesion and accumulation in tumor neovasculature Intravital microscopy of 4T1 tumor neovasculature 30 minutes after injection of two mice with SS RBCs (panels 1 and 2) or normal RBCs (panels 3 and 4) is shown. Diffuse vaso-occlusion is evident in mice injected with SS cells but not normal RBCs. Magnification 10× in 1&3, 20× in 2&4.

Figure 2B:
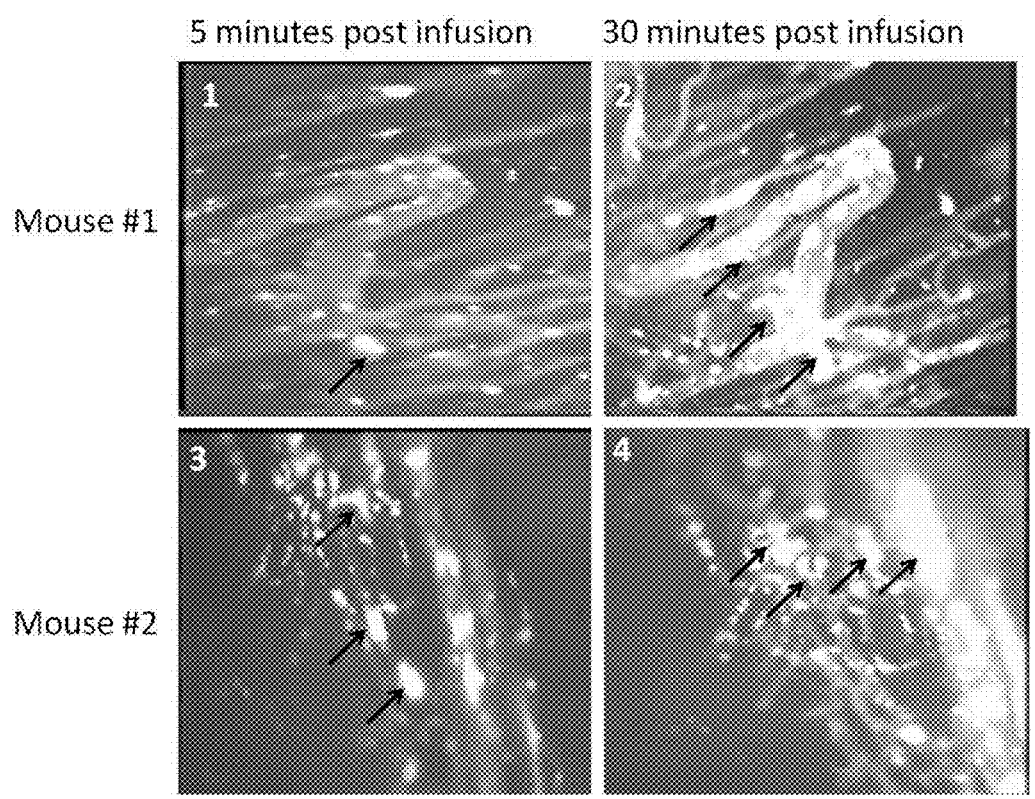

FIG. 2b. SS RBC but not normal RBC adhesion and accumulation in tumor neovasculature are time-dependent. Intravital microscopy images of 4T1 tumor in mouse #1 (panels 1 and 2) and mouse #2 (panels 3 and 4) infused with SS RBCs obtained from 2 different SCD patients visualized 5 (panels 1 and 3) and 30 (panels 2 and 4) minutes post RBC infusion. Blood flow dynamics were observed in tumor neovasculature using a 20× objective. SS RBCs progressively occluded tumor vessels as indicated by arrows.

Figure 2C:
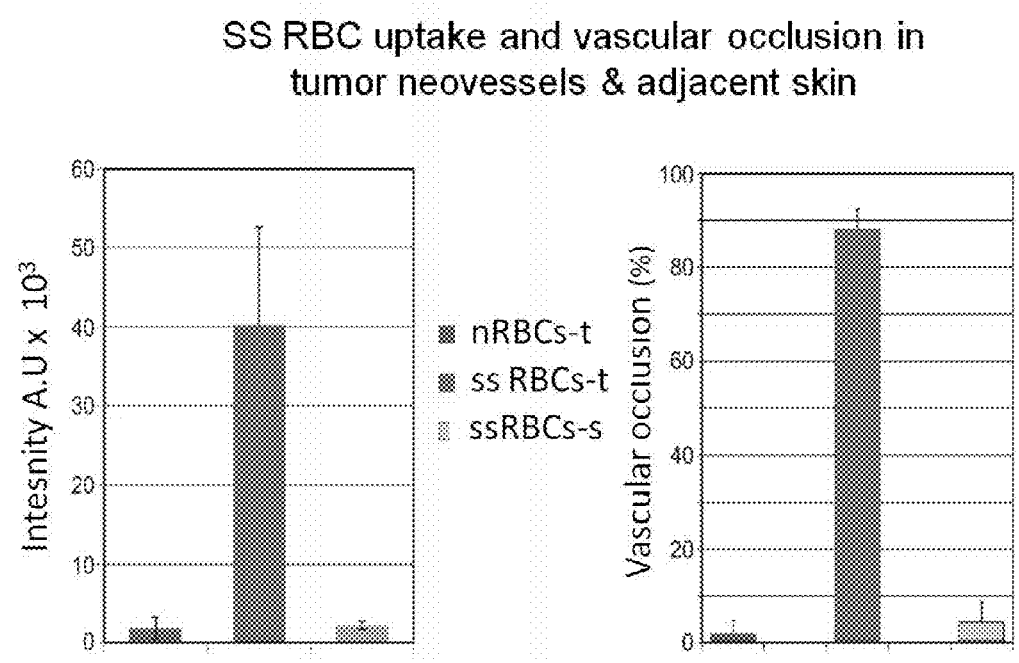

FIG. 2c. Morphometric analysis of SS and normal RBC uptake in tumor neovessels and adjacent normal subcutaneous blood vessels 30 minutes after infusion of either SS RBCs (n=5) or normal RBCs (n=5) using two measurements, fluorescence intensity and percentage of occluded vessels, of video photographs at 20× magnification. SS RBCs showed significantly greater mean fluorescence uptake in tumor neovessels (panel 1) and mean percentage of occluded tumor vessels (panel 2) compared to either adjacent normal cutaneous vessels or normal RBCS in tumor neovessels (p=0.00001 for SS cells in tumor vessels versus respective controls in both panels 1 and 2). Panel 3 shows DiI-fluorescence intensity (DiI-FI) measurement in tumor parenchyma 30 minutes post RBC infusion. DiI-FI measured in tumors of animals (n=6) infused with SS RBCs was significantly greater than DiI-FI in tumors of animals (n=3) infused with normal RBCs (p=0.00001), indicating greater presence of SS RBC than normal RBC in tumor tissue.

Figure 2D:
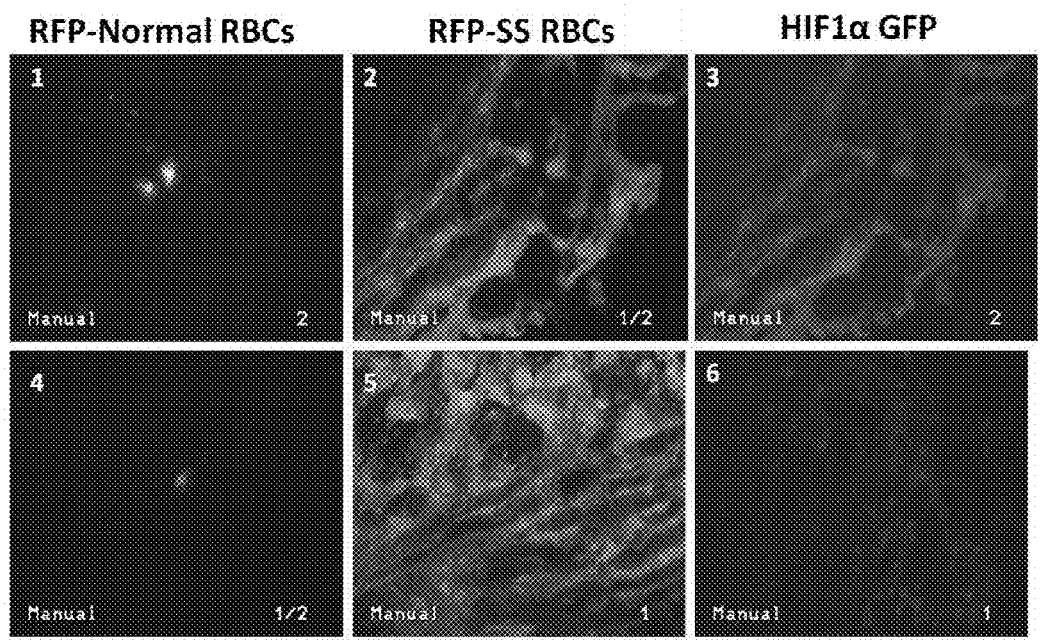

FIG. 2d. DiI-labeled RBCs uptake into tumors 30 minutes post RBC infusion. Micrographs of sections of 4T1 tumors implanted into window chambers of animals infused with SS RBCs (n=2, panels 2 and 5) and animals infused with normal RBCs (n=2, panels 1 and 4), visualized using a 20× magnification. Micrographs indicate that SS RBCs deposited to a degree higher than normal RBC deposition. SS RBC uptake was observed in hypoxic regions of tumors as indicated by HIF1α GFP (green fluorescent protein) expression (panels 3 and 6).

Figure 2E:
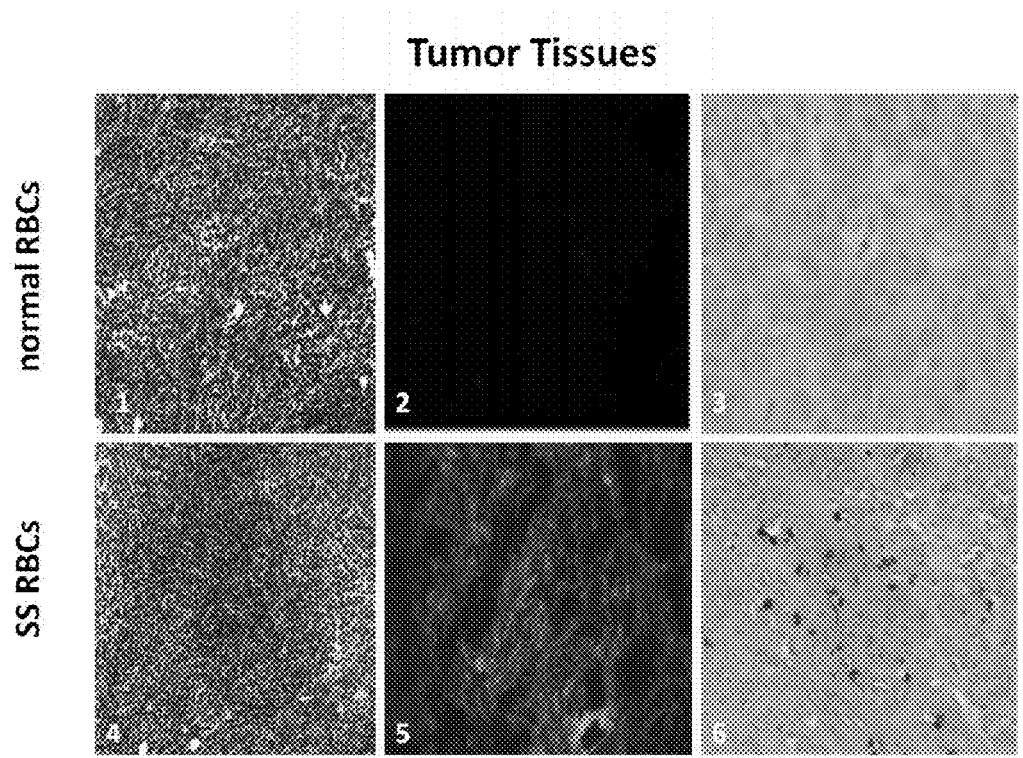

FIG. 2e. H&E and RFP fluorescence in tumor sections 24 hours after normal RBC or SS RBC infusion. H&E tumor sections r from SS RBC— treated mice (panels 5,6) show focal areas of cytoplasmic eosinophilia and engorged blood vessels consistent with focal ischemia not present in tumors treated with normal RBCs (panels 1 and 2). (Magnification 5× in panels 1 and 5 and 20× in panels 2 and 6). RFP-RBC uptake of normal RBCs (panel 3) and SS RBCs (panel 7) in tumors 24 hours after infusion shows the presence of SS-RBCs but not normal RBCs in tumor tissue.(Magnification 10×). Prussian blue staining of tumor sections 20 days after starting treatment with SSx3+ZnPP+Dox (panel 8) or untreated controls (panel 4) shows hemosiderin deposits in the SS-treated tumor (panel 8) but not in the untreated control tumors (panel 4). (Prussian blue, magnification 40×). Color transformation of Prussian Blue to brown is due to reduction of free ferric to ferrous ion in the tumor by the hypoxia marker drug, Pimonidazole, which was administered 4 hours before tumor excision (94).

Figure 2F:
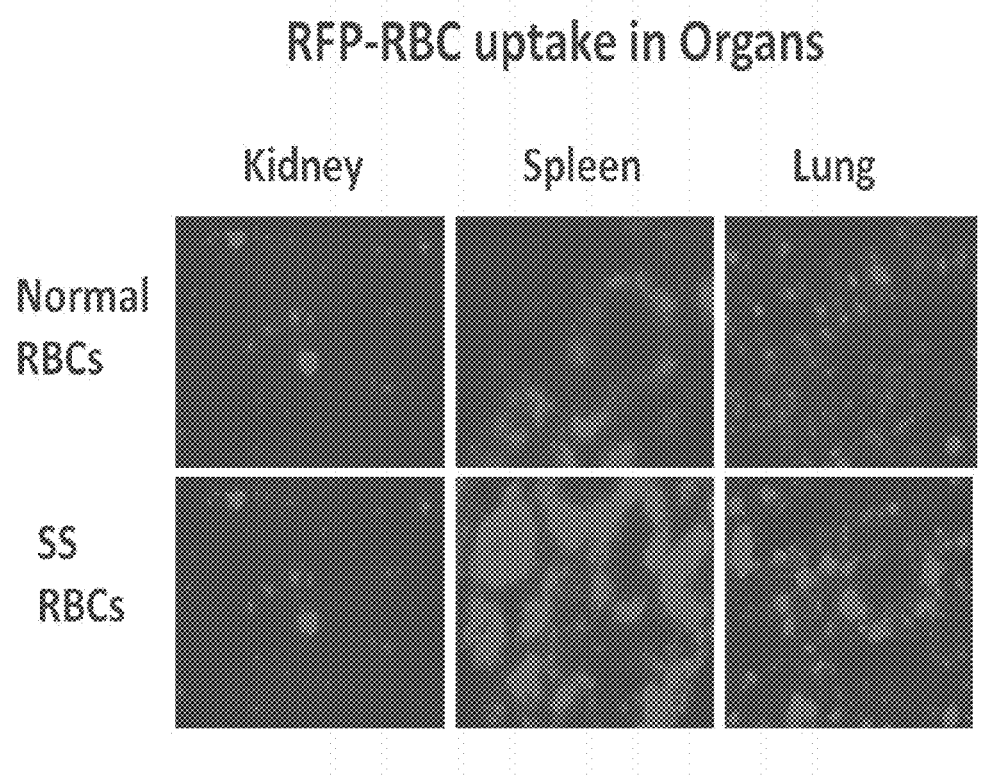

FIG. 2f. Evaluation of DiI-SS RBC uptake in organs 24 hours after SS or normal RBC infusion. Tissue sections of spleen, kidney and lung were examined for RBC uptake using a 10× objective. SS RBCs were trapped in the spleen to a degree higher than normal RBCs. Similar trapping of SS and normal RBCs was also detected in the lungs and to a lesser degree in kidneys.

Figure 3:
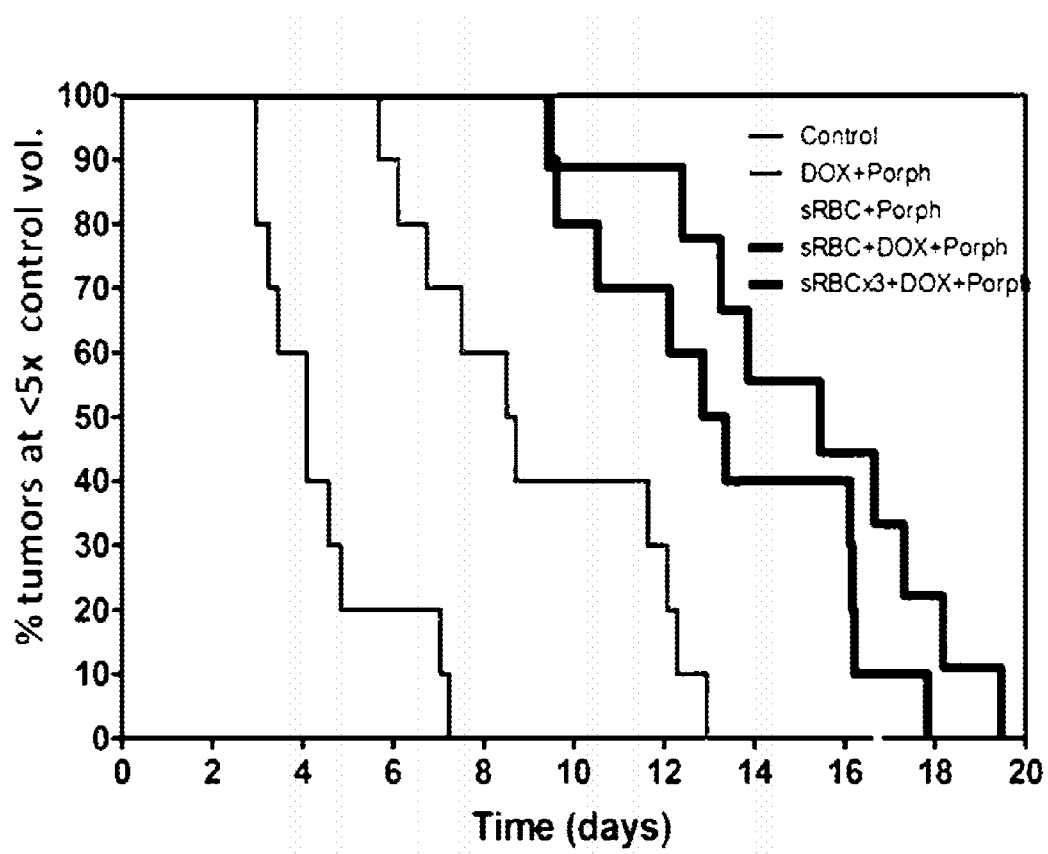

FIG. 3. SS RBCs combined with a heme oxygenase inhibitor induced a tumoricidal effect in mice with established 4T1 carcinoma. Panel shows the fraction of mice with tumors>5× pretreatment volumes over time. All three groups treated with SS RBCS combined with ZnPP given before SS cell infusion showed significant growth delay compared to untreated controls and the ZnPP+Dox group. The SS RBCs×3+Zn-PP+Dox group induced the most significant tumor growth delay compared to untreated controls and the SS RBCs+Zn-PP-treated group.

Figure 4:
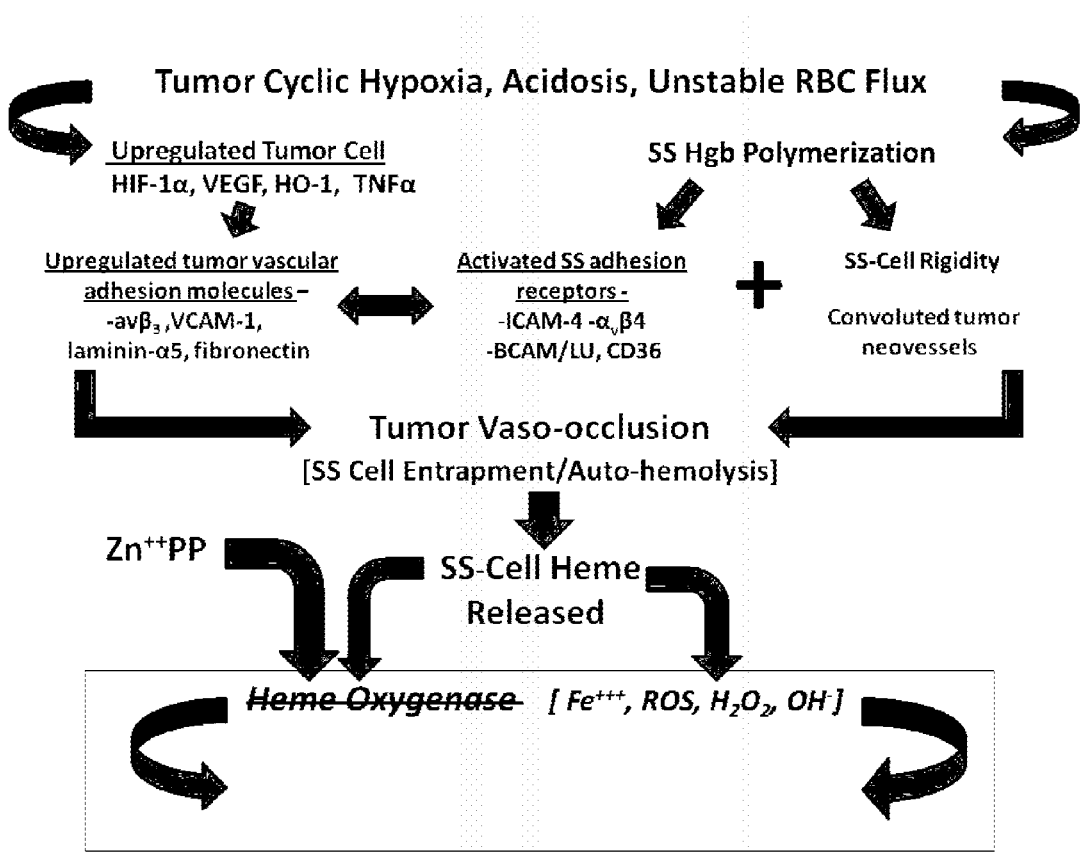

FIG. 4: Schematic depiction of theoretical pathophysiology of tumor killing induced by SS cells and HO-1 inhibitor (ZnPP). The hypoxic and acidic tumor milieu activates HIF1α, which in turn stimulates VEGF, HO-1 and TNFα. TNFα upregulates expression of several adhesion molecules on tumor endothelium including the major adhesion ligands for SS adhesion receptors. In the hypoxemic, acidemic and convoluted tumor microcirculation SS hemoglobin desaturates and polymerizes and SS cells assume a sickled morphology. SS cells also become rigid. SS cells adherence to tumor vascular walls leads to vaso-occlusion. Hemolysis ensues releasing SS hemoglobin which is rapidly converted to methemoglobin and cleaved to liberate heme. Hydrophobic and lipophilic heme and/or heme-nitrosyl complexes intercalate adjacent endothelial and tumor cell membranes where they catalytically oxidize cell lipids, proteins and DNA causing apoptosis. Intracellular heme also activates heme oxygenase (HO-1) which normally cleaves heme to cytoprotective bilirubin reductase and carbon monoxide. In the presence of ZnPP, a competitive inhibitor of HO-1, intracellular heme is free to exert its potent oxidative function via ROS, $H_2O_2$ and $OH^-$ resulting in tumor cell death.

Figure 5:
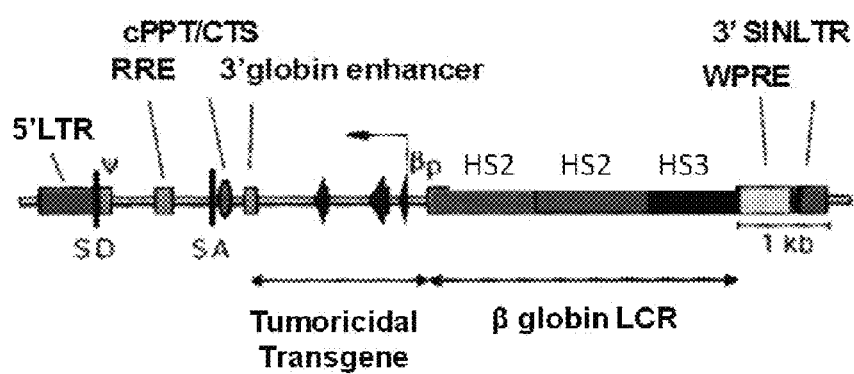

FIG. 5. Insertion of a potent tumoricidal transgene into a lentiviral vector. Genes are illustrated by filled boxes and are represented according to scale. The lentiviral/tumoricidal transgene expression construct is shown. HS2 (1203 bp), HS3 (1213 bp), and HS4 (954 bp) sequences, the 3' globin enhancer, the 266-βp -globin promoter (p) and the β-globin gene whose coding region is replaced by the tumoricidal transgene. The HIV-1 LTR is shown with a 3' SIN deletion; indicates packaging signal; SD and SA, splice donor and acceptor sites, respectively; RRE, Rev-responsive element; cPPT/CTS, central polypurine tract or DNA flap/central termination sequence; and WPRE, woodchuck hepatitis virus post-transcriptional regulatory element.

SUMMARY OF THE INVENTION

The present invention contemplates that SS cells, SS progenitors and erythroleukemia cells deposit in tumor vasculature and undergo hemolysis releasing hemoglobin and heme. The latter is toxic to adjacent tumor endothelium and tumor cells. This is enhanced by heme oxygenase inhibitors. Claimed methodology contemplates the use of SS cells, SS progenitors and erythroleukemia cells 1 inducing a tumoricidal effect in the presence of heme oxygenase inhibition. Other pharmacologic agents that block the breakdown and removal of tumor cell reactive oxygen species are also useful. Chemotherapy and radiation are also more effective when administered in close proximity to SS cells and heme oxygenase inhibitors. SS cell infusion also enhances the effectiveness of agents that inhibit tumor cell glucose uptake. Hence, additional glucose uptake The present invention also provides erythrocytes with SS hemoglobin, their nucleated precursors, sickle hemoglobin variants, erythroleukemia cells for targeted delivery of tumoricidal agents specifically to the microvasculature of the tumors. Selective generation of tumoricidal agents is promoted by transduction of SS nucleated erythrocyte precursors with the hypoxia responsive promoters or other inducible promoters. These transcriptional regulatory elements in the sickled erythrocytes are activated either by endogenous local conditions (e.g., hypoxia) or by the administration of exogenous agents capable of inducing a specific promoter or enhancer. The promoters are operatively linked to nucleic acids encoding oncolytic viruses, toxins and toxin-antibody fusion proteins, superantigens, superantigen conjugates and fusion proteins, siRNAs, multidrug resistant proteins, or other tumoricidal proteins. Likewise mature sickle cells, sickle cell vesicles and ghosts are loaded with chemotherapy, and anaerobic bacterial spores that are released from the these cells once they have deposited and aggregated in the tumor microvasculature. The present invention contemplates that any oncolytic virus is useful (replication competent and incompetent) optionally containing a transgene encoding any tumoricidal protein, toxin or toxin-antibody fusion protein operatively linked to the HRE or any other inducible promoter in a sickle cell, its nucleated precursors nucleated precursors, sickle hemoglobin variants, erythroleukemia cells. These same SS erythrocytes, their nucleated precursors, sickle hemoglobin variants, erythroleukemia cells may also be transduced with more than one viral constructs containing an oncolytic virus and toxin-antibody fusion gene under control of multiple inducible promoters.

The present invention provides erythrocytes with SS hemoglobin, their nucleated precursors, sickle hemoglobin variants, erythroleukemia cells for targeted delivery of tumoricidal agents specifically to the microvasculature of the tumors. Selective generation of tumoricidal agents is effected by transduction of SS nucleated erythrocyte precursors with the a lentiviral or other vector in which the β-globin coding region is replaced by a transgene encoding a tumoricidal molecule such as Staphylococcal enterotoxin coding regions, SEB and SEC amino acid sequences 130-160, Panton Valentine leucocidins or shiga toxin or shiga toxin B chain. Less toxic homologues of these molecules that retain wild type function and structural similarity to the wild type molecules (z value>13 in FASTA) are also useful. Indeed, any other tumoricidal transgene functional in this or other vectors is useful. The tumoricidal transgenes are under transcriptional control of the locus control region containing erythroid specific DNAase hypersensitivity regions, the β-globin promoter/enhancer found in the second intron of the β-globin gene as well as part of the third exon of β-globin and the enhancer located 3' to the human β-globin gene, a poly A sequence and a β-globin Nco sequence. Optionally hypoxia responsive enhancer/promoters or other inducible promoters are also introduced into the vector. These transduced SS progenitor cells differentiate into mature SS erythrocytes that synthesize and secrete these tumoricidal molecules. The transduced SS progenitor cells containing multidrug resistant transporters are further loaded with chemotherapy and actively efflux chemotherapeutic agents. After systemic injection, these cell populations localize in tumor vasculature where they adhere to endothelium, induce vaso-occlusion, secrete and efflux their tumoricidal molecules resulting in tumor cell cytolysis.

DESCRIPTION OF THE PREFERRED EMBODIMENTS

Sickled Erythrocytes and Nucleated Erythroid Precursors for Targeted Delivery of Tumoricidal Agents Carcinomas are significantly hypoxemic relative to normal tissues (see Table 1). Under these conditions of deoxygenation, SS hemoglobin in erythrocytes from patients with sickle cell anemia, sickle cell trait and other SS variants polymerizes leading to a sickled morphology. The cells become rigid and are unable to navigate the tortuous and angular microcirculation of the tumor. Due to expression of integrin complex $\alpha_4\beta_1$, CD36, BCAM-1/Lu, ICAM-4, SS erythrocytes adhere to the tumor microvascular ligands VCAM-1, platelet thrombospondin, and laminin and βvβ33 integrin respectively. ICAM-4 (LW, CD242) is selectively expressed on sickle but not on normal erythrocytes while BCAM-1/Lu is overexpressed and far more reactive with laminin in sickle cells than in normal red blood cells.

In sickle red blood cells, adhesion to laminin, thrombospondin, fibronectin, and αvβ3 integrin in the vasculature dramatically impacts vaso-occlusion events. The least dense sickle erythrocytes are especially involved in hypoxia-sensitive adherence while secondary trapping of SS4 (dense cells) occurs in post capillary venules. In this way the SS red cells aggregate and obstruct tumor microvessels. Laminin-α5 is present in endothelial basement membranes subadjacent to the endothelial cells of the vascular wall and is one of the predominant components of the subendothelial matrix in the tumor microvasculature. Laminin and fibronectin are exposed to circulating erythrocytes because the tumor neovasculature contains stretches of vascular matrix, tumor cell canaliculi and sparse endothelium. Lutheran (Lu) blood group and basal cell adhesion molecule (BCAM) antigens on SS RBCs bind laminin selectively with high affinity under conditions of high shear stress. They exist as two glycoprotein (gp) isoforms Lu and Lu(v13) of 85 and 78 kd respectively and both belong to the IgG superfamily containing identical extracellular domains and differing only by the size of their cytoplasmic tail (Gauthier E, et al., *J Biol. Chem.* 280:30055-62 (2005)). Sickle red cells bind significant amounts of soluble laminin, whereas normal red cells do not.

BCAM/Lu is the major laminin-binding protein of sickle red cells. Indeed, SS red cells have an average of 67% more BCAM/Lu than normal red cells, and low density red cells from sickle cell disease patients express 40-55% more BCAM/Lu than high density SS red cells (Zen Q et al., *J. Biol. Chem.* 274: 728-34 (1999); Udani et al., *J. Clin Invest.* 101: 2550-2558 (1998)). Notably, SS erythrocyte adherence to laminin has recently been documented to be more marked than SS erythrocyte adherence to thrombospondin (Hillary C A et al., *Blood* 87: 4879-4886 (1996)).

In addition, adhesion of sickle cells but not normal erythrocytes to tumor endothelium via laminin α5 and Δvβ3 receptors is enhanced by epinephrine acting through the β2-adrenergic receptor, cAMP and protein kinase-dependent signaling pathway. Indeed, exposure to epinephrine for only 1 minute significantly increases sickle erythrocyte adhesion to both primary and immortalized ECs. Thus adrenergic hormones such as epinephrine upregulate BCAM-1/Lu and ICAM-4 expression on sickle erythrocytes and their binding to laminin and αvβ3 receptors respectively improving their ability to localize in the αvβ3- and laminin-rich tumor microvasculature (Hines P C et al., *Blood.* 101:3281-7(2003); Zennadi R et al., *Blood* 104:3774-81 (2004)).

Because of its marked tortuosity and hypoxemia relative to normal tissues, the neovasculature of carcinomas is especially well suited for selective deposition and aggregation of SS erythrocytes. Under hypoxic conditions, inflammatory cytokines such as TNFα, various interleukins and lipid-mediated agonists (prostacyclins) commonly produced by patients with carcinoma also increase the adhesive and hemostatic properties of tumor neovasculature and promote the adherence of SS cells (Table 1). Indeed, the oscillating oxygen tensions noted in the tumor microvasculature (Lanzen et al., *Cancer Res.*, 66: 2219-23 (2006)) predisposes to a hypoxia-reperfusion form of endothelial injury producing increased adherence of SS erythrocytes to the tumor microvasculature.

TABLE 1

Oxygenation of tumors and normal tissues

| Tumor type | Median $PO_2$ (pt. no.) | Median normal $PO_2$ (pt. no.) |
|---|---|---|
| Glioblastoma | 4.9 (10) | Nd |
|  | 5.6 (14) | Nd |
| Head and Neck Carcinoma | 12.0 (30) | 40 (14) |
|  | 14.7 (23) | 43.8 (30) |
|  | 14.6 (66) | 51.2 (65) |
| Lung Cancer | 7.5 (17) | 38.5 (17) |
| Breast Cancer | 10.0 (15) | Nd |
| Pancreatic Cancer | 2.7 (7) | 51.6 (7) |
| Cervical Cancer | 5.0 (8) | 51.0 (8) |
|  | 5.0 (74) | Nd |
|  | 3.0 (86) | Nd |
| Prostate Cancer | 2.4 (59) | 30.0 (59) |
| Soft Tissue Sarcoma | 6.4 (34) | Nd |
|  | 18.0 (22) |  |

Erythrocytes from Subjects with Sickle Cell Trait and Sickle Cell Variants

For SS erythrocytes, sickling begins at $PO_2$ 40-50 mmHg and is greatest when $PO_2$<20. This occurs in organs with sluggish circulation, high oxygen extraction, localized hypoxia and low pH such as the renal medulla and spleen and bone marrow. The likelihood of erythrocyte sickling by hemoglobin SS variants is related to amount of Hgb S present, e.g., Hgb S: 70-98%. Hgb SA: 10-40%, Hgb SC: 50-60%.

Sickle trait (SA hemoglobin) affects approximately 8% of the black population in the United States or approximately 2.7 million individuals. The incidence is higher in tropical Africa and approaches 40% in some regions. Patients with sickle trait are heterozygous for the sickle cell hemoglobin gene, and less than 50% of the hemoglobin in each cell is hemoglobin-S. Polymerization of deoxy-hemoglobin in erythrocytes from patients with SA hemoglobin can occur under certain conditions and transform silent sickle cell trait into a syndrome resembling sickle cell disease with vaso-occlusion. In particular, sustained exercise and high altitude conditions cause tissue hypoxia, acidosis, dehydration, hyperosmolality, hypothermia can causing splenic infarction, exertional heat illness (exertional rhabdomyolysis, heat stroke, or renal failure) or idiopathic sudden death. Because of their proclivity to sickle and aggregate in hypoxic tissues, erythrocytes with SA hemoglobin are useful in the present invention, Milosevic et al., *Gynecologic Oncology* 83, 428-431 (2001)) showed that erythrocytes from patients with sickle trait may sickle in the microvasculature of solid tumors and contribute to reduced blood flow and the development of hypoxia. Hypoxia is a strong independent prognostic factor in patients with cervix cancer. While this reference did not disclose the use of erythrocytes from patients with sickle cell trait for therapy of cancer, the skilled scientist would recognize that such cells can collect and aggregate under the hypoxic conditions within tumors in a fashion similar to homozygous SS sickle cell anemia. Similarly, under hypoxic conditions hemoglobins in erythrocytes from patients with other SS variants such hemoglobin SC, hemoglobin Antilles are known to polymerize leading to sickling and aggregation.

Thus this population of cells is also considered to be useful therapeutically and may be safe for transfusion since they do not sickle only under hypoxic conditions such as those encountered in tumors and not under normal physiologic conditions.

Erythrocytes with SC hemoglobin

The coinheritance of HbS and HbSC results in a clinically significant sickling disorder similar to that of sickle cell disease (HgbSS). HbSC disease is usually considered less severe than Hb SS disease however, some individuals manifest a condition equal in severity. Hb SC disease exhibits combined symptomatology of both Hb S and Hb C diseases independently.

Like SS disease, SC erythrocytes sickle under hypoxic conditions causing vaso-occlusion in ischemic tissues resulting in stroke, acute chest syndrome (chest pain, fever, dyspnea, and hypoxia), joint necrosis (especially head of femur and humerus), pain crises, acute and chronic organ dysfunction/failure, retinal hemorrhages, and increased risk of infection. Because SC erythrocytes sickle under ischemic conditions, they too are excellent candidates for use in the instant invention.

Erythrocytes with Hemoglobin S Antilles

Hemoglobin S Antilles show two mutations in hemoglobin S gene. The expected mutation of glutamic acid to valine at position β-6 similar to hemoglobin S is accompanied by a second substitution at position β-23 of valine to isoleucine. Since the mutation at β-23 produced no chance in the charge of the hemoglobin, it separated identically to hemoglobin S by standard techniques. Hemoglobin S Antilles is much less soluble than hemoglobin S. The consequence is that people heterozygous for hemoglobin A and hemoglobin S Antilles have symptoms and complications similar to those of patients with homozygous sickle cell disease. Because Hgb S Antilles erythrocytes sickle under hypoxic conditions, these cells are also excellent candidates for use in the present invention.

Nucleated Sickle Cells Transfected with Tumoricidal Agents

Nucleated erythroid precursors or progenitors from patients with sickle cell anemia are the useful in the claimed subject matter. Because they are endowed with nuclei, they are readily transduced with the therapeutic oncolytic viruses and nucleic acids encoding toxins, toxin-tumor specific antibodies, -diabodies, -nanobodies and other therapeutic molecules. The hemoglobin of these cells polymerizes and they undergo characteristic morphological deformation in the form of fine, fragile, elongated spicules consisting of highly organized and tightly aligned hemoglobin fibers in the protruded regions.

The nucleated erythroblasts have a larger volume than mature red cells and more dilute hemoglobin which is confined mostly to the cytoplasm. Under partial or complete deoxygenation they behave much like mature SS red cells, i.e., their sickle hemoglobin polymerizes, they deposit and aggregate in the tumor microcirculation.

Nucleated erythroid precursors/progenitors can be readily obtained in abundance from peripheral blood erythrocytes (Fibach E et al., *Exp Hematology* 26:319-319 (1998); Fibach E et al., *Blood* 73: 100-103 (1989); Panzenbock B et al., *Blood* 1998 92:3658-3668; Arcasoy M O & Jiang X *Brit. J. Haematol.* 130:121-129 (2005)). Peripheral blood (10-20 mL) is drawn from patients with sickle cell anemia. Mononuclear cells isolated by centrifugation on a gradient of Ficoll-Hypaque are cultured according to a two phase liquid culture procedure. In phase 1, the cells are cultured for 7 days in α-minimal essential medium supplemented with 10% fetal calf serum (both from Gifco, Grand Island N.Y.), cyclosporin A (1 μg/mL) (Sandoz, Basel, Switzerland) and 10% conditioned medium collected from bladder carcinoma 5637 cultures. In phase 2, the nonadherent cells are recultured in α-medium supplemented with 30% fetal calf serum, 1% deionized bovine serum albumin, $1\times10^5$M 2-mercaptoethanol, 1.5 mM glutamine, $1\times10^{-6}$M dexamethasone, and 1 U/mL human recombinant erythropoietin (Ortho Pharmaceutical Co., Raritan N.J.). Cultures are incubated at 37° C. in an atmosphere of 5% $CO_2$, with extra humidity. Cell morphology is assessed microscopically on cytocentrifuge-prepared slides (Shandon, Cheshire, UK) stained with alkaline benzidine and Giemsa. Nucleated erythroid precursors/progenitors are obtained from bone marrow or erythroid cells or stem cells. They are also obtained from established erythroid and stem cell lines. The desired nucleated progenitor cells are generally CD34+. All of these cells are identified, isolated and enriched using methods well established in the art.

Cell banks are prepared consisting of ABO and Rh typed, nucleated sickle precursor cells, transfected with the appropriate tumoricidal agents under control of the HRE. Cell banks can also include mature SS, SA and other sickle variants cells incorporating anaerobic bacterial spores, Listeria, S. aureus or tumoricidal drugs for use in patients with solid tumors. Thus it is feasible to use nucleated erythroid precursor cells for transfection of HRE and nucleotides encoding tumoricidal agents.

SS Cells, Nucleated SS Erythroblasts and Erythroleukemia Cells Transduced by Nucleic Acids Encoding Oncolytic Viruses, Tumoricidal Toxins, Toxin-Antibody Proteins, Superantigens, Superantigen Conjugates and Fusion Proteins, Cytokines Optionally Under Control of the Hypoxia Responsive Element (HRE)

The present invention contemplates the transduction of the SS cells, SS erythroblasts and erythroleukemia cells by oncolytic viruses, plasmids encoding oncolytic viruses, tumoricidal toxins, toxin-antibody proteins, therapeutic antibodies or antibody fragments and cytokines all optionally under the control of the hypoxia responsive element (HRE). The HRE has been reported in the 5' or 3' flanking regions of hypoxia responsive molecules VEGF and EPO and phosphoglycerate kinase promoter and several other genes and is indispensable for their hypoxia-induced transcriptional activation. The core consensus sequence is (A/G) CGT (G/C)C (Forsythe, J A et al., Mol. Cell. Biol. 16:4604-4613 (1996); Levy, A P, J. Biol. Chem. 270, 13333-13340 (1995); Gupta, M et al., Blood 96, 491-497 (2000)).

HIF-1, a key transcription factor that binds to HRE, regulates the expression of various hypoxia-responsive molecules such as EPO. HIF-1 is composed of a 120-kDa $O_2$-regulated β subunit and a 91-to 94-kDa constitutively expressed α subunit. HIF-1 activity depends mainly on the intracellular level of HIF-1α protein, which is regulated in inverse relation to the oxygen concentration by an oxygen-dependent enzyme, prolylhydroxylase 2 (PHD2). Under hypoxic conditions, the α subunit is stabilized because of the lack of proline hydroxylation and accumulates. Stabilized HIF-1α translocates into the nucleus and forms an HIF-1 complex with the almost ubiquitously expressed HIF-1β. The HIF-1 complex binds to hypoxia response elements (HREs) found in enhancers or promoters of hypoxia-inducible genes.

In the present invention, the HRE is used preferably in concatenated form of up to 15 or more repeats (Prentice H et al., Cardiovasc Res. 35:567-74 (1997)). It is activated at tissue oxygen partial pressures of 1% and with more recent improvements in concatenation to 2-2.5%. The latter $pO_2$ is well within the range of most carcinomas. The HRE can be used with various promoters (complete or minimal) of which the CMV appears to be the most potent under hypoxic conditions. The present invention contemplates that the HRE as a key promoter in the virus or vector used to transduce SS erythrocytes. The inventor contemplates that preferably the HRE is incorporated into SS erythroblasts ex vivo before administration of the erythrocytes to the patient. After the latter cells are administered to a living body with tumor or suspected tumor (microscopic metastases) they localize in tumor microvasculature. Under hypoxemic conditions of the tumor microenvironment, nucleic acids encoding oncolytic viruses and/or tumoricidal transgenes are activated.

The present invention contemplates sickled erythroid precursors optionally containing the HRE found for example in the EPO and VEGF genes to control the transcription of various tumor selective viruses and tumoricidal agents. When this sickled erythrocyte is trapped in hypoxemic tumor microvasculature, the HRE optionally activates the synthesis of the tumoricidal viruses and proteins producing a targeted tumor killing response. The present invention contemplates any inducible promoter operatively linked to nucleic acids encoding any tumoricidal transgenes or constitutive genes including but not limited to tumoricidal viruses, toxins, toxin-tumor specific antibody fusions, cytokines including but not limited to TNFα and IFNγ, lytic agents including but not limited to perforins, granzyme, hemolysins, holotoxins, autolytic toxins and key constitutive enzymes as useful and functional. Inducible promoters and transcriptional control elements useful in the present invention include but are not limited to estrogen and steroid responsive promoters, tetR gene, radiation inducible promoters such as EGR-1, thyroglobulin promoter, albumin promoter, heat responsive promoters, heavy metal responsive promoters, tissue-restricted transcriptional control elements include the $α_1$-antitrypsin and albumin promoters (hepatocyte-selective), tyrosine hydrolase promoter (melanocytes), villin promoter (intestinal epithelium), glial fibrillary acidic protein promoter (astrocytes), myelin basic protein (glial cells), and the immunoglobulin gene enhancer (B lymphocytes), tumor-selective promoter elements include α-fetoprotein (hepatoma), DF3/MUC1 (breast and other carcinomas), thyroglobulin (thyroid carcinoma), prostate-specific antigen (prostate carcinoma), and carcinoembryonic antigen (breast, lung, and colorectal carcinomas), DF3/MUC1 promoter, Myc/Max family. The erythroid precursor can accept, encode and deliver plasmids of any kind including those expressing tumoricidal viruses and manmade virus constructs with tumoricidal activity The present invention contemplates adeno- or self-replicating RNA viral vectors incorporated into SS erythrocytes, their nucleated precursors, sickle hemoglobin variants, erythroleukemia cells and activated by their HREs under hypoxic conditions of the tumor microvasculature leading to hemolysis and shedding of the HRE-containing adeno- or Sindbis virus. By placing the viral gene essential for transcription optionally under the hypoxia responsive promoter element (HRE), viral proliferation is activated under conditions of severe hypoxia present in most tumors and carcinomas in particular. Notably, the HRE also confers these viruses with a natural tropism for tumor cells exhibiting high levels of HIF-1. The ability of this promoter to preferentially direct transcription in hypoxic cells can be assessed by producing a plasmid that contains the promoter operatively linked to several well known fluorescent coding sequences. The HRP-fluorescent marker construct is used to establish stable sublines from tumor cell lines: Cells grown in normoxic conditions do not express the marker whereas cells from stably transduced sublines exposed to hypoxic conditions (with oxygen tension at 0.5 to 1.5%) showed excellent expression of the marker.

Conditional replication competence using the HRE constructs results in selective vector replication in sickle cells localized in the hypoxic tumor microcirculation. An oncolytic virus (preferably tumor selective/specific) linked to the HRE proliferates and hemolyzes the erythrocyte. The virus with an HRE-viral construct has an affinity for tumor cells with high levels of HIF-1. Other excellent viral constructs such as d11530 and Sindbis viruses by themselves have an affinity for tumor cells deficient in p53 and laminin receptors respectively and are preferably linked to an HRE enhancer. Virus is shed from the burst erythrocyte to infect tumor cells with high levels of HIF-1 (and/or P53 deficiency or laminin receptors). High replication of the vector is achieved in the tumor cells while replication in surrounding non-neoplastic cells is minimal.

For genes that are upregulated in response to hypoxia, wherein the precise sequence that confers hypoxia inducibility is unknown, the responsive sequence can be identified by methods known to the average artisan. Within a candidate promoter region, the presence of regulatory proteins bound to a nucleic acid sequence is detected with variety of methods well known to those skilled in the art (Ausubel et al, ed. Short Protocols in Molecular Biology. New York: Green Publishing Associates and John Wiley & Sons. P.26-33 (1992)). Briefly, in vivo footprinting assays demonstrate protection of DNA sequences from chemical and enzymatic modification within living or permeabilized cells Likewise, in vitro footprinting assays show protection of DNA sequences from chemical or enzymatic modification using protein extracts. Nitrocellulose filter-binding assays and gel electrophoresis mobility shift assays (EMSAs) track the presence of radiolabeled regulatory DNA elements based on provision of candidate transcription factors. Computer analysis programs, for example TFSEARCH version 1.3 (Yutaka Akiyama: "TFSEARCH: Searching Transcription Factor Binding Sites") can also be used to locate consensus sequences of known transcriptional regulatory elements within a genomic region. A hypoxia inducible promoter is concatamerized, polymerized or combined with additional elements to amplify transcriptional activity and mRNA translation in response to hypoxia. The hypoxia inducible promoter comprises 5-10 tandem copies of the HRE from the human VEGF or EPO gene linked to the CMV minimal promoter or many other promoters well known in the art.

A hypoxia inducible promoter of the presently claimed subject matter is responsive to non-hypoxic stimuli that can be used in combined therapy. For example, the mortalin promoter is induced by low doses of ionizing radiation (Sadekova S et al., Int J Radiat Biol. 72:653-60 (1997)), the hsp27 promoter is activated by 17beta-estradiol and estrogen receptor agonists (Porter J et al., J Mol Endocrinol. 26:31-42 (2001)), the HLA-G promoter is induced by arsenite, and hsp promoters can be activated by photodynamic therapy (Luna M C et al., Cancer Res. 60:1637-44 (2000)). Thus, a hypoxia inducible promoter can comprise additional inducible features or additional DNA elements. Virus administration can be provided before, during, or after radiotherapy; before, during, or after chemotherapy; and/or before, during, or after photodynamic therapy. Moreover, a hypoxia inducible promoter can be derived from any biological source such as the human VEGF or EPO promoter that can direct efficient hypoxia inducible expression as in bovine pulmonary artery endothelial (BPAE) cells (Liu Y et al., Circ Res. 77:638-43 (1995)).

Viral Vectors with Fusogenic Membrane Glycoprotein Expression

A major limitation of tumor-targeted replication competent virus is their relatively poor efficiency in spreading throughout the tumor mass, thereby requiring repeated viral injections administered at multiple sites and over several days. The present invention contemplates oncotropic/oncolytic vectors expressing fusogenic membrane glycoprotein transfected into SS cells, SS progenitors and erythroleukemia cells. Fusogenic proteins are typically derived from enveloped viruses such as HIV1, measles virus (MV-F, MV-H), gibbon ape leukemia virus (GALV), vesicular stomatitis virus G (VSV-G) that use them to fuse membranes, penetrate cells and cause massive syncytium formation and cell death. HIV1, measles virus (MV-F, MV-H) fusion proteins have been inserted in the adenovirus genome. Fusogenic recombinant adlvector obtained spreads more efficiently through tumor xenografts and is superior to the cytotoxicity caused by wild type adenovirus alone or transfection of tumor cells with HSV-tk or cytosine deaminase suicide genes killing at least 1 log more virus.

To create a fusogenic recombinant adenovirus bicistronic expression cassette from measles virus glycoproteins F and H is used to replace the E1 gene region within the plasmid pAdEasyl which contains the other essential regions of the adenovirus genome. The E1 gene deletion is critical since FMG fusion in wild type adenovirus is reduced significantly. To drive the expression of the F and H, either the major immediate cytomegalovirus early promoter (CMVpromoter) or the adenovirus major late promoter (MLP) is used. The mRNA consists of the coding region for H followed by the encephalomyocarditis virus internal ribosomal entry site (IRES) and the F coding region. Transfection of the E1 deficient-MFG virus into SS cells, SS progenitors or erythroleukemia cells not only enhances selective virus localization in vivo to tumor sites but also confers protection of the virus from neutralizing antibodies in the systemic circulation. Erythroleukemia cells of any kind or their progenitors such as human K562 or murine MEL cells stably transfected with nucleic acids encoding the BCAM/Lu gene are the preferred carriers. The histone deacetylase inhibitor FR901228 enhances adenovirus infection of erythroleukemic cells and is useful in the claimed invention as described by Kitazone M et al., *Blood* 99: 2248-2251 (2002).

Tumoricidal Transgenes

In order to more efficiently kill a tumor cell that is infected with an adenovirus vector a transgene is provided. A transgene comprises a therapeutic gene, including, but not limited to a tumor suppressor gene, an apoptosis-inducing gene, an anti-angiogenic gene, a suicide prodrug, converting enzyme gene, a bacterial toxin gene, an antisense gene, a tumor suppressor gene, an immunostimulatory gene, or combinations thereof. A "transgene" A transgene includes a gene that is partly or entirely heterologous (i.e., foreign) to the organism from which the cell was derived, or can be a nucleotide sequence identical or homologous to a gene already contained within the cell.

Transgenes may also be delivered by replication-competent vectors which may be noncytopathic. Transgenes comprise nucleic acids encoding a polypeptide having a therapeutic biological activity. Exemplary therapeutic polypeptides include but are not limited to TNF$\alpha$, IFN$\gamma$, and immunostimulatory molecules, various cell toxins such as superantigens alone or fused or conjugated to a tumor targeting agent, tumor suppressor gene products/antigens, suicide gene products, and anti-angiogenic factors and antibodies, or prodrug-activating enzymes that release well-defined cytotoxins on reduction in hypoxic cells such as nitrobenzyl phosphoramidate mustards, nitroheterocyclic methylquaternary salts, cobalt(III) complexes and indoloquinones (see Mackensen et al., *Cytokine Growth Factor Rev.* 8:119-28 (1997); Walther et al., *Mol. Biotechnol.* 13:21-8 (1999); Kirk et al., *Human Gene Ther.* 11:797-806 (2000)) and references cited therein. In addition the transgene can express a ligand such as hergulin which binds overexpressed human epidermal growth factor receptor (HER). The RNA alphaviruses exemplified by the Sindbis virus which selectively targets overexpressed laminin receptors on tumor cells may be incorporated into sickled erythrocytes or erythroblasts optionally under control of the HRE or promoters. Upon lysis of the sickled erythrocyte by the virus, free virus is shed into the tumor microenvironment where it can selectively target surrounding tumor cells. A suicide gene encoding a protein that causes cell death directly, for example by inducing apoptosis, is referred to as an "apoptosis-inducing gene" and includes but is not limited to TNFα (Idriss et al., *Microsc Res Tech.* 50:184-95 (2000)), TRAIL (Srivastava *Neoplasia* 3:535-46 (2001)), Bax, and Bcl-2 (Shen et al., *Adv Cancer Res.* 82:55-84 (2001)).

Other genes that encode proteins that kill cells directly include bacterial toxin genes, which are normally found in the genome of certain bacteria and encode polypeptides (i.e. bacterial toxins) that are toxic to eukaryotic cells. Bacterial toxins include but are not limited to diphtheria toxin, pseudomonas exotoxin A and superantigens (Frankel et al., *Curr Opin Investig Drugs* 2:1294-301 (2001)). A list of superantigens useful in this construct is given in the instant application with a preference for the staphylococcal enterotoxins of the enterotoxin gene complex (egc).

Additional suicide genes encode a polypeptide that converts a prodrug to a toxic compound. Such suicide prodrug converting enzymes include, but are not limited to the HSV-tk polypeptide, which converts ganciclovir to a toxic nucleotide analog (Freeman et. al., *Semin Oncol.* 23:31-45 (1996); cytosine deaminase, which converts the non-toxic nucleotide analog 5-fluorocytosine into a toxic analog, 5-fluorouracil (Yazawa et al. *World J Surg* 26:783-9 (2002); and cytochrome p450, which converts certain aliphatic amine N-oxides into toxic metabolites (Patterson L H *Curr Pharm Des.* 8:1335-47 (2002).

Additionally, a suicide gene can encode a polypeptide that interferes with a signal transduction cascade involved with cellular survival or proliferation. Such cascades include, but are not limited to, the cascades mediated by the Flt1 and Flt1; receptor tyrosine kinases (reviewed in Klohs et al., *Curr Opin Oncol.* 9:562-8 (1997)). Polypeptides that can interfere with Flt1 and/or Flk1 signal transduction include, but are not limited to, a soluble Flt1 receptor (s-Flt1; Shibuya M *Int J Biochem Cell Biol.* 33:409-20 (2001) and an extracellular domain of the Flk-1 receptor (ex-Flk1; Lin P et al., *Cell Growth Differ.* 9:49-58 (1998)).

When entering the hypoxic tumor microcirculation, the sickled erythrocyte adheres to the tumor vasculature and the HRE is activated inducing the formation of nucleotides encoding the hemolysins which hemolyze the erythrocyte releasing oncolytic virus into the tumor site. Sickle cell deposition in tumor vessels leads to reduced SS cell velocity, upregulation of endothelial VCAM-1, TNFα, and p-selectin, trapping of additional sickled cells and micro-occlusion of the tumor microvasculature.

For proteins such as *Pseudomonas* exotoxin A and superantigens, 4-9 copies of the EPO HRE consensus sequence (SEQ ID NO:1) (CCGGGTAGCTGGCGTACGTGCTG-CAG) are optionally inserted into the pβgal-promoter plasmid between SmaI and HindIII sites (CLONTECH) upstream of the simian virus 40 (SV40) or CMV promoter. The expression cassette (nine copies of optional EPO HRE, SV40 minimal promoter, LacZ gene, and SV40 polyadenylation signal) is cloned into an AAV vector between two inverted terminal repeats to generate the AAVH9LacZ vector as shown.

AAVH9 *Pseudomonas* Exotoxin A or AAVH9 SEG is generated by replacing LacZ gene in AAVH9LacZ with *Pseudomonas* exotoxin A or Staphylococcal enterotoxin G respectively.

The HRE is optionally fused to various nucleic acids encoding tumoricidal proteins including but not limited to superantigens (preferably staphylococcal enterotoxins G, I, M, N, O), superantigen antibody conjugates, pseudomonas exotoxins (exotoxin A being the best characterized), verotoxins and/or subunits, diptheria toxin, pertussis toxin, complement membrane attack complex, perforins, holins, *S. aureus* autolysins, granzymes, tumor specific antibodies, chemokines, cytokines and chemoattractants.

Likewise a hemolysin such as *S. aureus* alpha toxin, *Listeria* or *E. Coli* hemolysin are fused to the HRE to facilitate the internal lysis of the SS erythroid precursors under hypoxic conditions.

Truncated and mutant forms of bacterial toxins such as superantigens and superantigen antibody conjugates are useful in this invention are shown in FIG. 3 of Kreitman R J & Pastan I *Adv Drug Deliv Rev* 31: 53-88 (1998) as described below. Amino acid 607 of PE and the remaining carboxyl terminal amino acids 608-613 are depicted. *Pseudomonas* exotoxin (PE) contains domains Ia (amino acids 1-252), I (amino acids 253-364), Ib (amino acids 365-399) and III (amino acids 400-613) are shown below. In PE4E, basic amino acids at positions 57, 246, 247 and 249 of PE are replaced by glutamate residues. In PE40, domain Ia has been removed from PE. In PE38, amino acids 365-380 have been removed from domain Ib of PE40. In PE38 KDEL, the carboxyl terminal amino acids REDLK of PE38 have been replaced with KDEL. PE35 contains methionine followed by amino acids 281-364 and 381-613 of PE, and the only cysteine residue in PE35 is shown at position 287. Diphtheria toxin (DT) contains a methionine preceding amino acids 1-5 (GADDV). DT contains an A chain (amino acids 1-193) and a B chain (amino acids 194-535). In DAB486, amino acids 486-535 of DT are removed, and in DT388 or DAB3g, amino acids 389-535 of DT are removed. All of these forms are useful in the claimed invention.

Any tumor specific antibody, fv, Fab fragment either single or double chain or tumor targeting ligand e.g., EGF, chemokine receptor ligand specific for any and all human tumors listed herein is useful in the present invention. The mesothelin tumor specific monoclonal antibody which has been fused to PE40 and shown broad anti-tumor activity is particularly preferred. Likewise, any other tumoricidal molecules or molecules that promote tumor killing, e.g., Panton-Valentine leukocidin (PVL) including but not limited to ricin, diphtheria toxin, pertussis toxin either alone or coupled to a tumor specific targeting structure is useful in this invention. A targeting device and tumor toxin are conjugated as fusion proteins or biochemically cross linked using well established technology.

A typical pharmaceutical toxin composition for intravenous administration includes about 0.1-10 mg per patient per day. Dosages from 0.1 up to about 100 mg per patient per day may be used particularly if the agent is administered to a secluded site and into the circulatory or lymph system such as into a body cavity or into a lumen of an organ. This amount of toxin can be readily generated in approximately 10-100 cc of sickled erythrocytes once activated under hypoxemic conditions. Actual methods for preparing administrable compositions will be known or apparent to those skilled in the art are siRNA RNA interference (RNAi) is a highly conserved gene silencing mechanism that uses double-stranded RNA (dsRNA) as a signal to trigger the degradation of homologous mRNA. The mediators of sequence-specific mRNA degradation are 21- to 23-nt small interfering RNAs (siRNAs) generated by ribonuclease III cleavage from longer dsRNAs. A short (usually 21-nt) double-strand of RNA (dsRNA) with 2-nt 3' overhangs either end. Twenty-one-nucleotide siRNA duplexes trigger specific gene silencing in mammalian somatic cells without activation of the nonspecific interferon response. Transfection of an exogenous siRNA is enhanced by introduction of a loop between the two strands, thus producing a single transcript, which can be processed into a functional siRNA. Such transcription cassettes typically use an RNA polymerase III promoter (e.g. U6 or H1), which usually direct the transcription of small nuclear RNAs (snR-NAs) (U6 is involved in gene splicing; H1 is the RNase component of human RNase P). The resulting siRNA transcript is then processed by Dicer. In one embodiment of the present invention, SS cells or SS erythroblasts are transduced in vitro with vectors encoding siRNAs directed to RNA species that induce or contribute to tumoricidal activity. The therapy is applicable to carcinomas, sarcomas, gliomas, melanomas and lymphomas/leukemias. The spectrum of vectors that have been used effectively as vehicles for siRNAs transfection in experimental tumor models to date is given in Table 2. The present invention contemplates as useful any of these vectors containing an FMG optionally under control of the HRE or other suitable promoter. Typically, the SS cells and sickled erythroblasts are transfected in vitro with the siRNA using siRNA expression vectors or PCR products. Synthetic siRNAs chemically synthesized or in vitro transcribed siRNAs can be transfected into cells or injected into mice. A self-replicating cytopathic alphavirus vector is preferred such as the SINrep5 which expresses Sinbis virus structural proteins that recognize laminin receptors on tumor cells. The siRNA of choice is integrated into the cloning region of these viruses or cotransfected with them.

When administered parenterally, to tumor bearing hosts, the transfected SS cells or SS erythroblasts are capable of lysing the erythroblast and shedding the vector containing the siRNA to infect surrounding tumor cell selectively. Alternatively, the FMG containing vectors can fuse with and transfer siRNA to the target tumor or endothelial cells.

Alphaviruses with self replicating replicons containing an FMG such as the Sindbis and SFV that can lyse the SS erythroblast carrier or fuse with and infect adjacent tumor cells are preferred but other tumor specific viruses shown in Tables 1A and 1B such as d11150 and those avid for HIF in tumor cells are also useful. Optionally, the VP22 or other peptides that promote cell to cell transfer are cointegrated into the alphavirus (pRep5) vector together with the siRNA. DNA fragments encoding VP22 are isolated by digesting pcDNA3-VP22, respectively, with XbaI and PmeI restriction enzymes. These isolated DNA fragments are further cloned into the corresponding XbaI and PmeI sites of the SINrep5 vector to generate SINrep5-siRNA-VP22 constructs.

An adenovirus is one of the most well-known viral vectors for gene delivery. Intratumoral injection of an adenovirus encoding the hypoxia-inducible factor-1 (HIF-1)-targeted siRNA had a significant effect on tumor growth when combined with ionizing radiation (Zhang et al., *Cancer Res.* 64:8139-42 (2004)). The very same construct optionally containing the FMG is used to infect SS cells, SS erythroblasts or erythroleukemia cells that are lysed by the virus leading to viral shedding into surrounding tumor tissue. Other viruses are useful including but not limited to the alphaviruses and any other virus that can maintain viability in and the ability to transfect tumor cells from within the carrier SS cells. The virus selectively infects hypoxic tumor cells expressing HIF-1 and induces apoptosis via siRNA targeting of HIF-1.

Oncotropic/oncolytic viruses similarly transfected with a siRNA targeting a gene overexpressed in tumor cells can lyse the tumor cell via siRNA inactivation of a key genetic function or by endogenous self-replication. Excellent candidate siRNAs for transfection into carrier SS cells include those which inhibit antioxidant pathways in tumor cells including but not limited to siHIF-1$\alpha$ and $\beta$ (Example 2), siHO-1 and Glut-1 (Example 2) (representative of the Glut glucose transporter family) targeting hypoxia inducible transcription factor-1, heme oxygenase and Glut-1 respectively in tumor cells and tumor endothelial cells. One or more siRNA with different specificities may be used in the same carrier SS cell or erythroleukemia cells. Alternatively, one or more clones of siRNA transfected SS cells or erythroleukemia cells may be administered simultaneously in a single infusion or each may be administered sequentially in multiple infusions. Cycles of infusion may be repeated every 3-12 days for up to 6 months.

Candidate target genes for RNAi-mediated knockdown are selected from several key oncogenes, antiapoptotic genes such as heme oxygenase or tumor promoting genes, including growth and angiogenic factors or their receptors. As a matter of course cancer-specific genes selectively overexpressed, mutated or translocated are chosen. Initial in vitro studies have demonstrated effective silencing of a wide variety of mutated oncogenes such as K-Ras, mutated p53, Her2/neu and bcr-abl. SiRNA software is available for design of effective siRNA sequences (Takeshita F., *Cancer Sci* 97: 689-696 (2006)).

TABLE 2

Delivery of small interfering RNA (siRNA) in cancer models

| Carriers | Routes | Type of cancer (cell line) | Implanted site (target organ) | Target gene |
|---|---|---|---|---|
| Naked siRNA | i.p., i.v., s.c., i.t. | Fibrosarcoma (JT8) | s.c. | VEGF |
| Naked siRNA + gemcitabine | i.v. | Pancreatic adenocarcinoma (PANC1, | Orthotopic pancreas | FAK |
| Naked siRNA | i.v. | Pancreatic adenocarcinoma (BxPC3) | s.c., Orthotopic pancreas | CEACAM |
| Naked siRNA | i.v. | Pancreatic adenocarcinoma (PANC1, MIAPaCa2, BxPC3, | s.c., Orthotopic pancreas, liver metastasis | EphA2 |

TABLE 2-continued

Delivery of small interfering RNA (siRNA) in cancer models

| Carriers | Routes | Type of cancer (cell line) | Implanted site (target organ) | Target gene |
|---|---|---|---|---|
| Naked siRNA + gemcitabine | i.v. | Pancreatic adenocarcinoma (PANC1, MIAPaCa2, BxPC3, | s.c., Liver metastasis | RRM2 |
| Naked siRNA | i.v. | Breast cancer (MDA-MB-231) | Lung metastasis | CXCR4 |
| Liposome | i.p. | Colon cancer (HTC116) | s.c., i.p. | β-Cateni |
| Liposome | i.v. | Liver metastatic spleen cancer (A549) | Liver | bcl-2 |
| Liposome | i.t. | Bladder cancer (UM-UC-3-LUC) | Bladder | PLK-1 |
| Liposome | i.t. | Pancreatic carcinoma (Capan-1) | s.c. | Somatostati |
| CCLA (NeoPhectin-AT) | i.v. | Prostate cancer (PC-3) | s.c. | Raf-1 |
| CCLA | i.v. | Breast cancer (MDA-MB-231) | s.c. | c-raf |
| shRNA plasmid + immunoliposome | i.v. | Glioma (U87) | Brain | EGFR |
| PEI | i.p. | Ovarian carcinoma cells (SKOV-3) | s.c. | HER-2 |
| shRNA plasmid + PEI | i.t. | Ewing's sarcoma (TC71) | s.c. | VEGF |
| Adenovirus vector | i.t. | Cervical adenocarcinoma, colon cancer (HeLa, HTC116) | s.c. | HIF-1α |
| Adenovirus vector | i.t. | Lung cancer (ACC-LC-172) | s.c. | Skp-2 |
| shRNA plasmid | i.t. | Glioblastoma (SNB19) | Brain | MMP-9+ |
| shRNA plasmid | i.t. | Glioma (SNB19) | Brain | Cathepsin |
| shRNA plasmid + ATA | i.v. | Cervical adenocarcinoma, lung cancer (HeLa S3, A549) | s.c. | PLK1 |
| PEI-PEG-RGD | i.v. | Neuroblastoma (N2A) | s.c. | VEGF-R2 |
| CDP-AD-PEG-transferrin | i.v. | Ewing's sarcoma (TC71) | Multiple organ metastasis | EWS-FLI1 |
| HVJ envelope vector + cisplatin | i.t. | Cervical adenocarcinoma (HeLa) | Intradermally | Rad51 |
| ErbB2-protamine fusion protein | i.t., i.v. | Melanoma (B16) | s.c. | c-myc MDM2 VEGF |
| Atelocollagen | i.t. | Prostate cancer (PC-3) | s.c. | VEGF |
| Atelocollagen | i.t. | Germ-cell tumor (NEC8) | Testis | FGF-4 |
| Atelocollagen | i.v. | Prostate cancer (PC-3M-Luc) | Bone metastasis | EZH2, p110α |

AD-PEG, adamantane-PEG5000; ATA, aurintricarboxylic acid, nuclease inhibitor; CCLA, cationic cardiolipin analog-based liposome; CDP, cyclodextrin-containing polycations; i.p., intraperitoneal; i.t., intratumoral; i.v., intravenous; PEG, polyethylene glycol; PEI, polyethylenimine; RGD, Arg-Gly-Asp; s.c., subcutaneous The preparation of siRNA duplexes specific for and capable of inactivating the target genes given in Table 2 are described in Example 2.

SS Erythrocytes, SS Erythroblasts and Erythroleukemia Cells Transduced with Multi-Drug Resistant Genes The multi-drug resistance gene, MDR1 encodes an ATP-dependent plasma membrane efflux pump, P-glycoprotein (P-gp). These transporters and several others including the ABG transporters are present in SS hematopoietic progenitors and erythroleukemia cells. In contrast to the products of other drug resistance genes, the P-gp extrudes a broad range of hydrophobic drugs from cells, including vinca alkaloids, anthracyclines, epipodophyllotoxins, colchicine, actinomycin D and taxotere. Transfer and expression of human MDR1 in marrow cells has been used to protect hematopoietic cells against myelotoxic drugs. Transgenic mice expressing the human MDR1 gene and normal mice transplanted with marrow from MDR1 expressing transgenic mice did not develop leukopenia after treatment with cytotoxic drugs presumably due to chemo protection of transduced cells by MDR1 gene expression. MDR1 has been combined with other drug resistance genes to broaden the spectrum of drugs for combinatorial chemo protection of transduced human stem cells. Mutants of P-gp have been used to tailor drug resistance profiles and are useful in this invention. For instance, the wild-type version of human MDR1 (containing Gly at position 185) confers preferential resistance against vinblastine while the mutant with Val at position185 confers resistance to colchicine.

In the claimed invention, nucleic acids encoding the MDR1 optionally placed under the transcriptional control of the HRE enhancer are transfected ex vivo into sickle erythroblasts, hematopoietic stem cells or nucleated erythroleukemia cells stably transfected with BCAM/Lu or other molecule(s) which bind to tumor neovasculature. These cells are then co-cultured with tumor cytotoxic drugs preferably in prodrug form. Loading of the cells with drug is accomplished by osmotic diffusion or electroporation and other methods well established in the art. These cells are then infused into the tumor bearing host. The transduced erythroblasts or erythroleukemia cells deposit in the hypoxemic tumor microvasculature wherein the MDR1 gene is activated leading to efflux of the resident cytotoxic drug or prodrug into surrounding tumor tissue. The cytotoxic drug kills tumor cells directly. The invention is not confined to the MDR gene. ABG group of transporters and any other drug transporters in SS hematopoietic precursors are relevant and useful in this invention for the transport of tumoricidal drugs and toxins.

The expression of drug metabolizing cytochrome P450s (CYPs) notably 1A, 1B, 2C, 3A, 2D subfamily members has been identified in a wide range of human cancers. Individual tumor types have distinct P450 profiles as studied by detection of P450 activity, identification of immunoreactive CYP protein and detection of CYP mRNA. Selected P450s, especially CYP1B1, are overexpressed in tumours including cancers of the lung, breast, liver, gastrointestinal tract, prostate, bladder. Several prodrug anti-tumour agents have been identified as P450 substrates. Those in clinical use include prodrug alkylating agents cyclophosphamide, ifosphamide, dacarbazine, procarbazine, Tegafur, a prodrug fluoropyrimidine, methoxymorphylinodoxorubicin, a metabolically activated anthracycline, as well as flutamide and tamoxifen, two non-steroidal hormone receptor antagonists that are significantly more active following CYP-hydroxylation. New agents selectively dependent on tumor CYP activation include 2-(4-aminophenyl) benzothiazoles exclusively in CYP1A1 inducible tumors. Some CYPs operate most effectively under hypoxemic conditions. Indeed, bioreductive prodrugs such as the indolequinone AQ4N (a CYP3A substrate) and MUP 98176 are activated to cytotoxic metabolites specifically in hypoxic tumor regions after bioreduction.

In the present invention, drug resistant SS hematopoietic stem cells are produced by sustained exposure to prodrugs ex vivo. These cells are then administered to tumor bearing hosts and localize in the tumor vasculature where the bioreductive prodrug is transported out of the cell and taken up by surrounding tumor cells. Tumor cells overexpress oxyreductase systems cytochrome P450 enzymes and/or its congeners, oxidize prodrugs to their reduced and active state resulting in oncolysis. Several of these active metabolites are significantly more cytotoxic under hypoxemic conditions within tumor cells. For example, an SS cell progenitor or erythroleukemia cell stably transfected with an adhesion receptor such as BCAM/Lu whose cognate ligand laminin-$\alpha$5 is expressed on tumor neovasculature is rendered drug resistant by exposure to chemotherapy for period known to induce resistance to a particular drug. At the end of this time frame, the drug-resistant cells are known to expel drug at a rate 4-10 fold faster than control non-drug resistant cells. Specifically, the K562 erythroleukemic cell line stably transfected with BCAM/Lu or other molecule(s) that bind to tumor neovasculature is rendered drug resistant after continuous exposure to small doses of Adriamycin for 120 hours after which Adriamycin is completely expelled from the cell over a period of 30 minutes (Yanovich et al., Cancer Res. 44, 4499-4505 (1989)). In the present invention, erythroleukemia cells or hematopoietic precursors stably transfected with BCAM/Lu or SS progenitor cells are exposed to various forms of chemotherapy and the optimal time course for development of drug resistance and release following discontinuation of drug is determined. After induction of drug resistance, these cells ($10^8$-$10^{12}$) are infused into tumor-bearing hosts where they deposit and release their drug directly into the tumor mileau. All forms of chemotherapy for which drug transport systems exist the erythroleukemia or SS progenitor population are eligible for this treatment including but not limited to the MDR and ABG transporters. Drug resistant erythroleukemia cells or erythroblasts are preferred drug carriers because the chemotherapeutic that is expelled from the cell does minimal damage to the cell itself.

Optionally, ex vivo exposure of both drug resistant and non-drug resistant cells (incubated with a tumoricidal drug for 8-120 hours) to light radiation (200-900 nM) that induces a hemolysis t½ of 20-60 minutes is useful to ensure release of the drug from the carrier SS cells, SS progenitors or erythroleukemia cells once they have deposited in the tumor vasculature. In this way chemotherapy can be specifically targeted to and concentrated in the tumor.

Likewise, nucleic acids encoding monoclonal antibodies specific for epitopes expressed on tumor cells, tumor parenchyma or tumor vasculature can be transfected into the SS progenitor or erythroleukemia cells using recombinant vectors well established in the art. An example of one such monoclonal antibody is Avastin specific for VEGF receptors on tumor endothelium. SS cells or erythroleukemia cells localized in the tumor vasculature release the VEGF-specific monoclonal antibodies into the tumor mileau. The tumor neovasculature is within easy reach of the recombinant antibodies and expresses epitopes expressed on tumor endothelium and endothelial matrix such as VEGF and laminin-$\alpha$5. In this way, anti-angiogenic therapy such anti-VEGF is concentrated at the site of its cognate ligand in the tumor neovasculature, produces an increase in the therapeutic index of the drug and reduction in its systemic side effects.

The compositions of the claimed invention are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas.

The compositions are also be useful for the prevention of metastases from the tumors described above either when used alone or in combination with radiotherapeutic, photodynamic, and/or chemotherapeutic treatments conventionally administered to patients for treating disorders, including angiogenic disorders. Treatment of a tumor with surgery, photodynamic therapy, radiation and/or chemotherapy is followed by administration of the compositions to extend the dormancy of micrometastases and to stabilize and inhibit the growth of any residual primary tumor or metastases. The compositions can be administered before, during, or after radiotherapy; before, during, or after chemotherapy; and/or before, during, or after photodynamic therapy.

The present invention contemplates that erythrocytes or erythroblasts from patients with any form of sickle hemoglobinopathy are useful. These include erythrocytes or erythroblasts from hemizygous sickle S and A hemoglobin, sickle hemoglobin-C disease, sickle beta plus thalassemia, sickle hemoglobin-D disease, sickle hemoglobin-E disease, homozygous C or C-thalassemia, hemoglobin-C beta plus thalassemia, homozygous E or E-thalassemia. Indeed, any erythrocyte or erythroblasts with or without sickle hemoglobin expressing receptors capable of binding to tumor neovasculature are useful in the inventions described herein. Particularly useful are those cells which express hemoglobin S in combination with other types of hemoglobin. Both mature and nucleated forms of these cells are useful. In addition, the present invention contemplates that normal or leukemic erythrocytes or their nucleated progenitors transduced with hemoglobin genes from patients with hemoglobinopathies to produce a cell that behaves substantially like an SS or SA erythrocyte or erythrocyte precursor is useful. The present invention also contemplates that normal or sickle erythrocytes or sickle variants, e.g., HbSC cells, and nucleated progenitors which are upregulated by hormones, cytokines, biologically active agents, drugs, chemical or physical treatments to express adhesive properties or to enhance expression of adhesive properties are also useful in this invention.

SS Erythrocytes or Nucleated Progenitors Plus Heme Oxygenase Inhibitors, Chemotherapy and Radiation SS RBCs exhibit an enhanced rate of auto-oxidation and greater superoxide/peroxide-driven hydroxyl radical generation compared to normal erythrocytes. The accumulation of membrane oxidant damage contributes to the accelerated membrane senescence of these cells. In the presence of both superoxide and peroxide, hydroxyl radical generation, membrane peroxidation is greatly facilitated by membrane-bound heme and hemichrome.

SS erythrocytes also naturally show an enhanced rate of hemolysis especially under conditions of vaso-occlusion. Indeed, SS cell stasis and vaso-occlusion in the tumor microcirculation promotes SS cell lysis with resultant release of heme from heme proteins. Extracellular hemoglobin is easily oxidized from ferro- to ferri-hemoglobin (methemoglobin), which readily releases its heme moieties. Nitric oxide produced by heme induction of nitric oxide synthase also generates ferrihemoglobin. Following SS cell hemolysis, the tumor endothelium is exposed to high levels of heme (20 mM in sickled erythrocytes) and ROS catalyzed by plasma hemoglobin, heme, and free iron. Ferrihemoglobin in the presence of activated PMN-derived oxidants greatly amplifies oxidant-mediated endothelial injury.

The endothelial cell toxicity of free heme derives from the ease with which this highly hydrophobic compound enters and crosses cell membranes whereupon it greatly enhances endothelial susceptibility to oxidant-mediated cytotoxicity during brief exposure. Normally heme is neutralized by serum haptoglobin, hemopexin, albumin, CD163 the hemoglobin scavenger protein, and endothelium-derived nitrous oxide. However these systems are overwhelmed as highly lipophilic heme escapes from met-hemoglobin (met-Hb) to form heme-nitrosyl complexes that are rapidly intercalated into the membranes of cells. Normal cellular levels of free heme of approximately 100 nM or less are exceeded resulting in oxidative injury to endothelial cells.

Once within the cell, heme induces oxidative damage directly or via iron released from oxidative degradation of heme and heme oxygenase-catalyzed heme cleavage. In plasma and intracellular membranes, heme iron initially lodges within the hydrophobic intersticies of the phospholipid bilayer and acts as an active catalyst of oxidation of cell membrane lipid, protein denaturation and perturbations of the integrity of the attached cytoskeleton. Heme also impairs the activity of cytosolic enzymes, including glucose-6-phosphate dehydrogenase and glutathione reductase and activates cell-damaging enzymes such as caspases and cathepsins. Heme oxidatively denatures DNA in vitro. Mitochondria, exposed to heme in pathophysiologically relevant amounts, exhibit a prompt increase in respiration followed by a decline and then a complete cessation in oxygen consumption. Such susceptibility to heme reflects the facile permeation of the lipid-rich, mitochondrial membranes by heme. The relatively small amounts of peroxides normally generated in the course of mitochondrial respiration exacerbate the pro-oxidant effects of heme on these organelles. In this regard, increased yet nontoxic amounts of heme and hydrogen peroxide, when present concomitantly, are remarkably cytolytic. Peroxides degrade heme and promote the release of iron which induces mitochondrial and cellular release of cytochrome c.

Heme also enhances endothelial cell adhesion molecule expression, increasing SS cell and PMN adhesion. Heme iron-induced oxidative stress in endothelial cells activates redox-sensitive transcription factors such as NF-κB and activator protein-1. These transcription factors in turn induce the expression of E-selectin, VCAM-1, and ICAM-1 and the recruitment of adherent leukocytes in venules. Heme uptake by endothelial cells therefore exacerbates damage by activated polymorphonuclear leukocytes (PMNs) cells that tend to marginate along endothelial surfaces in the presence of inflammatory mediators.

The vasculature defends itself against reactive heme released during hemolysis by inducing cytoprotective genes, heme oxygenase (HO-1), activation of interleukin-10 (IL-10), biliverdin reductase, and P21. These systems possess catalytic antioxidant, anti-inflammatory, and antiproliferative properties. Heme oxygenase (HO) a 32-kDa inducible heat shock protein is the rate-limiting enzyme of heme catabolism and is upregulated in sickle cell disease in response to the hemolysis and increased heme burden. HO-1 catalyses the breakdown of heme into equimolar amounts of carbon monoxide, iron and biliverdin. Biliverdin is converted to bilirubin by cytosolic biliverdin reductase, and free iron is sequestered into ferritin. Three isoforms transcribed from separate genes have been characterized. HO-1 is highly expressed in liver and spleen, whereas the constitutive HO-2 is expressed mainly in brain and testis. HO-3 is a recently identified isoform whose mRNA has been detected in many organs including spleen, liver, thymus, prostate, heart, kidney, brain and testis. However, the physiological function of HO-3 remains unclear. HO-1 is inducible by a variety of agents in addition to its substrate heme. Other conditions and agents including ultraviolet irradiation, hyperthermia, inflammatory cytokines and heavy metals, oxidants, hypoxia, endotoxin, reactive oxygen species (ROS), reactive nitrogen species, hydrogen peroxide ($H_2O_2$) and nitric oxide (NO) potently stimulate HO-1 expression. These and other stimuli share in common the ability to generate cellular oxidative stress.

Heme oxygenase (HO-1) is activated by heme degradation particularly iron liberated from its porphyrin ring and protects endothelial cells and tumor cells from a wide variety of apoptotic stimuli. Induction of HO-1 and is critical to the survival and function of the vascular endothelium. Indeed, HO-1 is a quintessential stress-induced protein with anti-inflammatory functions. HO-1 protects cells from toxic stimuli by multiple mechanisms: a) decreasing the prooxidant levels (heme); b) increasing antioxidant levels (bilirubin); c) producing the antiapoptotic molecules CO; d) inducing ferritin, which removes and detoxifies free ferric ion. HO-1 induction activates apoferritin that has a capacity to bind 4,500 iron molecules and store nonreactive $Fe^3$ via its heavy chain ferroxidase activity. Induction of HO-1 has been shown to protect tissues and cells against ischemia/reperfusion injury, oxidative stress, inflammation, transplant rejection, apoptosis, and cell proliferation. HO-1 upregulation also ameliorates inflammation, in part, through its ability to inhibit endothelial cell adhesion molecule expression and leukocyte adhesion. In experimental models, pharmacologic inhibition of HO-1 has been shown to exacerbate renal ischemia-perfusion injury, sickle cell tubulointerstitial nephritis, heme-induced renal inflammation and cisplatinum nephrotoxicity.

HO-1 has a role in controlling growth and cell proliferation in a cell-specific manner. Increased expression of HO-1 has been observed in prostate tumors, brain tumors, oral squamous cell carcinomas, pancreatic and renal cell carcinomas and HO-1 has been demonstrated in colon cancer, hepatoma, renal cell carcinoma, prostate tumors, and lymphosarcomas. Increased levels of HO-1 correlate with activation of molecules involved in cellular transformation such as p53 and estrogen receptors. In contrast, in human tongue cancer, low HO-1 expression has been associated with an increased risk of developing lymph node metastasis. In addition, HO-1 induction protected the AH136B hepatoma model in rats against hypoxic stress and nitric oxide-mediated cytotoxicity. HO-1 induction by cadmium or hemin also resulted in resistance to apoptosis induced by tumor necrosis factor-α (TNFα) and cycloheximide in gastric cancer cells and thyroid carcinoma or tyrosine kinase inhibition in chronic myelogenous leukemia cells.

Furthermore, HO-1 is a major regulator of vascular endothelial growth factor (VEGF) secretion, and angiogenesis. In various tumors including human gliomas and melanomas and murine pancreatic carcinoma HO-1 has been shown to promote angiogenesis and accelerate growth. Indeed, HO-1 is upregulated by several key molecules active in tumor angiogenesis such as interleukins 1 and 6 (IL-1 and IL-6), tumor necrosis factor (TNF), transforming growth factor β, prolactin, 15-deoxy-A12,14-prostaglandin I, and atrial natriuretic peptide. These finding show therefore that HO-1 causes not only stimulation of tumor growth and but also tumor angiogenesis and that HO-1 inhibition promotes tumor apoptosis.

Pharmacological inhibition of tumoral HO activity with ZnPP or its pegylated derivative (PEG-ZnPP) significantly reduced growth of SW480 colon carcinoma and sarcoma S-180 tumors in vivo. HO-1 inhibition by pegylated Zn protoporphyrin enhanced the cytotoxicity of hydroperoxides and anticancer drugs in these tumors. These same HO-1 inhibitors also increase the expression of adhesion molecules on tumor endothelium.

Metalloporphyrin Heme Oxygenase Inhibitors

Porphyrins consist of a ring of four pyrrole nuclei linked each to the next at the positions (i.e., those adjacent to the nitrogen atoms) through a methine group (—CH=). The structure is aromatic and tautomeric, two hydrogen atoms being associated with any two of its four nitrogen atoms. Many of the di- and trivalent metal ions are chelated by porphyrin through these four central nitrogen atoms. The porphyrin family includes any member of synthetic or naturally occurring derivatives or analogues of the porphyrins as defined in the previous three sentences.

Metalloporphyrins (MPs) are structural analogs of heme with a metal cation associated with the porphyrin ring taking the place of the iron and with different ring substituents. The metal is bound equally to all four nitrogen atoms of the pyrrole rings (FIG. 1). Natural and synthetic porphyrins and metalloporphyrins are effective in vitro and in vivo as competitive inhibitors of heme oxygenase.

Natural and synthetic derivatives of heme (iron protoporphyrin) or porphyrins (Ps) have been found to inhibit competitively in vitro and in vivo heme oxygenase activity. The identified effective porphyrin and MP heme oxygenase inhibitors include but are not limited to zinc (Zn2+), tin (Sn4+), chromium (Cr2+), manganese (Mn2+) porphyrins along with their ring modifications to yield deutero—(DP), proto—(PP), meso—(MP), and bisglycol (BG) derivatives (FIG. 1). Natural and synthetic derivatives of heme (iron protoporphyrin) or porphyrins (Ps) have been found to inhibit competitively in vitro and in vivo heme oxygenase activity.

| Partial List of Porphyrin Types Based on Ring Substituent and Chelated Metal | | | | |
|---|---|---|---|---|
| Metal | Deutero-porphyrin (R = —H) | Meso-porphryin (R = —CH,CH$_3$) | Proto-porphyrin (R = —CH=CH$_2$) | Bis Glycol Porphryin (R = —CHOH—CH$_2$OH) |
| Metal-Free | MfDP | MfMP | MfPP | MfBG |
| Iron (Fe$^{2+}$) | FeDP | FeMP | FePP (Heme) | FeBG |
| Zinc(Zn$^{2+}$) | ZnDP | ZnMP | ZDPP | ZnBG |
| Tin (Sn$^{4+}$) | SnDP | SnMP | SnPP | SnBG |
| Chromium (Cr$^{3+}$) | CrDP | CrMP | CrPP | CrBG |
| Manganese (Mn$^{2+}$) | MnDP | MnMP | MrtPP | MnBG |
| Copper (Co$^{2+}$) | CuDP | CuMP | CuPP | CuBG |
| Nickel (Ni$^{2+}$) | NiDP | NiMP | NiPP | NiBG |
| Magnesium (Mg$^{2+}$) | MgDP | MgMP | MgPP | MgBG |

Heme oxygenase inhibition in vivo is evidenced by suppression of plasma bilirubin, total body CO excretion and biliary heme excretion. For inclusion in the group of the instant invention, a candidate molecule must demonstrate both structural and functional properties. Structurally, the candidate molecule such as functional derivatives must possess the fundamental porphyrin pyrrole structure as described above with a metal ion metal bound equally to all four nitrogen atoms of the pyrrole rings. Functional derivatives include but are not limited to pyrrole ring modifications such as deutero—(DP), proto—(PP), meso—(MP), and bisglycol (BG) derivatives or any other derivative of the fundamental pyrrole ring provided such derivative retains the fundamental porphyrin structure as described above. Functionally, a candidate agent must be an effective inhibitor of heme oxygenase in vitro in the heme oxygenase inhibition assays described below with a concentration of released CO of <0.1 or a CO level significantly different (based on statistical analysis given below) than the I50 CO of the negative control (no porphyrin or NADH added) determined by interpolation. It is desirable but not absolutely required that the candidate Ps show minimal to negligible photosensitizing activity in the assay described below. Examples of these properties are shown below.

| Clinically Relevant Properties of Porphyrin and Metalloporphyrins Heme Oxygenase Inhibitors | | | | | |
|---|---|---|---|---|---|
| Property | SnMP | CrMP | ZnBG | ZnPP | ZnMP |
| Naturally Occurring | No | No | No | Yes | NO |
| Biocompatible Metal | | | Yes | Yes | Yes |
| Statistically significant HO inhibition* | Yes | Yes | Yes | Yes | Yes |
| Photoreactive | Yes | No | Yes | No | Yes |
| Optimal Duration of Action | Yes | Yes | Yes | Yes | UK |
| Degraded by HO | No | No | No | No | No |
| Minimal Toxicity in vivo | UK | UK | UK | Yes | UK |

*Measurement of heme oxygenase activity and statistical significance

*Measurement of Heme Oxygenase Activity and Statistical Significance

The ability of each Mp to inhibit tissue HO activity is determined by measuring the decrease of CO produced from the breakdown of heme. In a typical assay, brain, liver, and spleen tissue preparations (20 µL each, representing a mean of 9.1, 23.8, and 11.6 mg protein/mL, respectively) with 20 µL 4.5 mM NADPH, 20 µL 150 µM methemalbumin, and 2.5 µL 600 µM (25 µM) metalloporphyrin. Twenty ml of tissue supernatant, representing 4 mg (for brain) or 2 mg (for spleen) fresh weight of tissue, is mixed in 2-ml amber glass vials containing 20 µL of 150 µM methemalbumin and 20 ml of 4.5 mM nicotinamide adenine dinucleotide phosphate, 2.5 µL 600 µM (25 µM) metalloporphyrin and incubated for 15 min at 37° C. for 5 min. For the blank reaction vials, the nicotinamide adenine dinucleotide phosphate is replaced by an equal volume of buffer. The vials are then purged with CO-free air and the incubation is continued. After 15.0 min post purging, the reactions are terminated by the addition of 2 ml 60% (w/v) sulfosalicylic acid. To determine the concentration needed to inhibit HO activity by 50% (I50) for each Mp and varying concentrations of each inhibitor are added to additional total reaction vials in minute ($\geqq 1.0$ ml) volumes. Results are standardized to total protein. HO activity is expressed as nmol $CO \cdot mg^{-1} protein \cdot h^{-1}$. Control reactions contained no metalloporphyrin. Statistically significant inhibition compared with control ($p<0.05$, $n=3$) (Vreman H J et al., *Can J Physiol Pharmacol* 74: 278-285 (1996); Wong et al., *Journal of Perinatology* 31, S35-S41(2011)). These references are incorporated in entirety by reference with their references.

CO Determination

CO generated into the vial headspace during each reaction is quantitated by gas chromatography with a Reduction Gas Analyzer (Peak Laboratories, LLC, Mountain View, Calif., USA). The headspace gas is passed with CO-free carrier air (~55 ml min$^{-1}$) through a stainless steel column (68×0.53 cm i.d.) packed with 13× molecular sieve (Alltech Associates, Deerfield, Ill., USA) and operated at 140° C. Analyzer response to CO, which has a retention time of ~30s, is recorded with an integrating recorder (CR-3A, Shimadzu Scientific Instruments, Columbia, Md., USA) by measuring peak area. The gas chromatography is standardized daily with 0-250 ml volumes of 10.8 µl of CO l$^{-1}$ air (482 nmol CO l$^{-1}$) (Vreman H J et al., supra (1996); Wong et al., supra (2011)).

Photoreactivity Assay

Metalloporphyrins have been shown to oxidize organic molecules such as lipids, proteins, and nucleic acids to as yet unidentified products in the presence of light. NADH is particularly sensitive to photooxidation. Therefore to determine the photoreactivity, 60 µL of 5 mM of NADH was reacted with 25 µM metalloporphyrin in the presence of cool white light (30 W/m$^2$). The rate of CO generated (nmol CO/15 min) is used as an index of the photoreactive potential of a compound (Vreman H J et al., supra (1996); Wong J et al., supra (2011)).

Calculations

HO activity is defined as the difference in CO production in the total reaction vial (in the presence of nicotinamide adenine dinucleotide phosphate) minus that of the blank reaction vial. HO activity is expressed as mean±s.d. pmol of CO produced per hour per mg fresh weight. Inhibition is defined as the suppression of HO activity due to the presence of Mp or Mf porphyrin.

Percentage of HO activity is defined as the amount of CO formed at each porphyrin concentration divided by the amount of CO formed by the control vial that is, with no porphyrin added, times 100.

$$\% \text{ HO Activity} = \frac{\text{CO produced at each } (\mu M)}{\text{CO produced by control}} \times 100$$

The concentration of each porphyrin needed to inhibit CO production by 50% (the I50 value) is determined by interpolation (Vreman et al., supra (1996); Wong et al., supra (2011)).

Statistical Analysis

All data are presented as means±SD. A one-way, factorial analysis of variance is performed on the data to test significance (Statview, v. 4.02). Significance is defined as $p<0.05$ (Vreman H J et al., supra (1996); Wong et al., supra (2011)).

Most metalloporphyrin heme oxygenase inhibitors function by competitive inhibition of heme. ZnPP a naturally occurring Mp is a prototypical metalloporphyrin heme oxygenase inhibitor. Because it is naturally occurring in humans, constitutive mechanisms are in place for the injected drug to perform its function and to be disposed of safely. ZnPP shares numerous chemical properties with other MPs such as its solubility and stability in strongly alkaline aqueous solution. MPs are also very soluble in basic organic solvents such as pyridine and ethanolamine as well as in some surfactants. ZnPP shows moderate heme oxygenase inhibitory potency (I50 for spleen and brain: 7.4 and 5.3 µM, respectively) and is not degraded by heme oxygenase. It is not a significant photosensitizer and is minimally toxic in vivo. It was used in the instant application (Example 3) to inhibit heme oxygenase in vivo and shown to synergize with sickle cell infusions in producing an anti-tumor effect without toxicity in the hosts.

ZnBG is a synthetic derivative of ZnPP of very high potency (I50 spleen and brain: 0.3 and 0.07 µM, respectively), uses a biocompatible metal but is a photosensitizer like SnMP and SnPP. It is not degraded by HO. Because of its great potency, appropriate dosages in vivo enable its heme oxygenase inhibition and minimize photoreactivity to insignificance.

CrMP is a synthetic Mp of high potency (I50 spleen and brain: 0.08 and 0.02 µM, respectively is photochemically inactive is not degraded by HO. This compound could be administered in a low dose that only affects HO-1.

SnMP is a synthetic Mp of high potency (I50 spleen and brain: 0.08 and 0.02 µM, respectively) but possesses photoreactive properties like SnPP and ZnBG. It has been shown to be effective in suppressing plasma bilirubin levels in vivo. It is not degraded by HO and is the only compound currently approved as an investigational drug.

Additional Mps also demonstrate efficacy. Of the other Mps, MfBG, SnBG, and SnDP SnPP, SnMP, ZnMP, MnPP, MnMP, CrPP, CrMP, NiPP, and MgPP are significant photosensitizers while MnBG, CrBG, ZnPP, CrDP and ZnDP are non-photoreactive. Because of their low photoreactivity and relative HO inhibitory potency the Zn, Mn and Cr analogs appear to be excellent clinical candidates.

Metalloporphyrins ZnPP, CrPP, CrMP and CrBG are available in pure form from Porphyrin Products (Logan, Utah). Metalloporphyrin stock solutions of 5.0 mM are prepared by dissolving 16.0 grams of ZnPP, 16.2 mg CrPP, 16.2 mg CrMP, or 17.0 mg CrBG in 0.25 ml of 10% (v:v) ethanolamine. The solutions are prepared in distilled water and titrated to pH 8.0 with 1 N HCl. The final volume is 5 ml. Solutions are prepared fresh daily, stored in the dark, and used within 2 hr of preparation time.

Principles of synthesis of porphyrins, metalloporphyrins, porphyrin derivatives and pegylated porphyrins with actual or potential heme oxygenase activity are provided in Example 8. In some cases, complexation of the fundamental porphyrin structure with metals, vinyl groups (protoporphyrins), glycol (deutero bisglycol porphyrins), deutero (deuteroporphyrins), ethyl groups(mesoporphyrins), pegylation, can confer more effective HO inhibition and/or tumor localizing properties while minimizing phototoxicity. Some of these agents are useful in the instant invention if the satisfy the dual structural and functional criteria given above for a porphyrin heme oxygenase inhibitor. The following references incorporated in entirely by reference with their references specifically disclose chemical synthesis of these porphyrin derivatives and metal complexes such that they may be produced by one skilled in the art without undue experimentation: Shanmugathasan S et al., *Tetrahedron* 56 (2000) 1025-1046; Dolphin, D., Ed *The Porphyrins*; Academic Press: New York, 1978; Vols. 1-6; Sahoo S K et al., *Bioconjugate Chem.* 13, 1031-1038 (2002); Hu B et al., Synthesis of Metallo-Deuteroporphyrin Derivatives and the Study of Their Biomimetic Catalytic Properties, in On Biomimetics, Pramatarova L D., Ed., Tech Publishing, Aug. 2011, pages 163-194; Vreman H J et al., *Can. J. Physiol. Pharmacol.* 74: 278-285 (1996); Kappas A et al., *J Clin Invest* 77: 335-339 (1986); Vreman H J *Ped Res* 33:195-200 (1993); Chemick R J et al., *Hepatology* 10: 365-369 (1989)).

siRNAs

In the present invention, HO-1 expression is specifically suppressed by introduction of 21-nucleotide duplex small interfering RNA (siRNA), which targets nucleotides 612 to 630 of the HO-1 mRNA coding sequence. The sequences of the ribonucleotides used were (SEQ ID NO:2) 5'-rGACUGCGUUCCUGCUCAACdTdT-3' and (SEQ ID NO:3) 5'-rGUUGAGCAGGAACGCAGUCdTdT-3' (Ambion, Inc., Austin, Tex.). The tumor cells are plated on 6-well plates (Nunc, Roskilde, Denmark) in density of 100,000 cells per well and preincubated overnight, after which 2 µg per well of siRNA is introduced into the cells using LipofectAMINE 2000 (Invitrogen, Carlsbad, Calif.) according to the manufacturer's directions. The Silencer Negative Control siRNA 1 (Ambion, Austin, Tex.) is used as a negative control and is introduced into the cells using the same protocol (Berberat P O et al., *Clin Cancer Res* 11: 3790-3798 (2005)). The siRNA treated tumor cells are then implanted in the host. Alternatively, the siRNA is electroporated into mature SS cells, SS erythrocyte ghosts, SS progenitors (collectively SS carrier cells) or erythroleukemia carrier cells. The siRNA is also integrated into a viral vector or phage containing a fusogenic membrane glycoprotein (FMG) as described in the instant specification and these constructs are electroporated into the same SS carrier cells. The SS carrier cells containing the siRNA are administered parenterally to mice with established tumors in tumor models described in the instant specification. The cells deposit in tumor vasculature wherein the FMG in the siRNA constructs promotes fusion and entry of the siRNA into surrounding tumor cells and tumor endothelial cells. A particularly attractive carrier for siRNA is a non-cytopathic Sindbis virus in which the siRNA is integrated into the structural genome of the virus and fuses with the non-structural genome containing the replicase function. The siRNA may also be placed in the non-structural genome while the FMG is incorporated into the structural genome (Frolov et al., *Proc Natl Acad Sci* 93: 11371-11377 (1996); Zhang et al *J Gene Med* 6: 1082-1091 (2004); Agapov E V et al., *Proc Natl Acad Sci* 95: 12989-12994 (1998); Schlesinger S *Exp Opin Biol Ther* 12: 177-191 (2001). siRNAs used in viral constructs and vectors are not only directed to heme oxygenase. The present invention envisions other siRNAs delivered as viral vectors or constructs incorporated within SS cells, SS progenitors or erythroleukemia cells and directed to HIF-1α and β genes, the Glut family of glucose transporters and key enzymes in the glycolytic pathway of tumor cells such as hexokinase. Other alphaviruses such as Semliki forest virus, Venezuelan equine virus and RNA viruses including but not limited to vesicular stomatitis virus are preferred but any virus that proliferates in SS RBCs such as Friend and Raucher virus is acceptable in this invention.

Phage phi29 that forms dimeric hexamers and is capable of controllable self-assembly into poly-mers used to construct polyvalent nanoparticles expressing siRNA and other species recognizing tumor specific receptors/ligands/antigens as described by Guo P et al., Molecular Microbiology 64: 886-903 (2007)) which is incorporated by reference including references cited therein is also useful as are any other phages that are capable of expressing siRNAs and transferring them from SS RBCs to tumor cells.

The siRNA may be carried to the tumor cell by SS erythrocytes, SS RBC ghosts, SS progenitors or erythroleukemia cells as described in the instant specification.

Several major chemotherapeutic therapeutic agents including but not limited to doxorubicin and camptothecin cause oxidative apoptosis in target cells by generating $H_2O_2$ HO-1 protects cells from oxidative apoptosis while PEG-ZnPP increases the cytotoxic action of chemotherapy by increasing oxidative stress and ROS formation in these cells. In addition to doxorubicin and camptothecin, radiotherapy and other anticancer agents are expected to act in this fashion including but not limited to vinblastine, inostamycin, mitomycin C, etoposide, neo-carzinostatin, 2-methoxyestradiol, N-(4-hydroxyphenyl)retinamide and pegylated xanthine oxidase. Various other anticancer agents activate caspase-3-like proteases that subsequently stimulate $H_2O_2$-generating enzymes such as NADPH oxidase. The present invention contemplates a heretofore unforeseen synergism between SS erythrocytes (or their nucleated progenitors and erythroleukemia cells), pharmacologic inhibitors of heme oxygenase and chemotherapy or radiation in producing an anti-tumor effect against primary and metastatic tumors. In the course of sickle cell vaso-occlusion in the tumor, heme and oxidized heme is released in close proximity to the tumor endothelium and tumor cells. Heme is taken up by these cells and induces oxidative stress resulting in the generation of ROS ultimately leading to tumor and endothelial apoptosis.

The present invention recognizes that the toxic effects of heme and its oxidative metabolites on tumor cells and tumor endothelium are counteracted by heme oxygenase and p21 present in each of these cells. Thus, the inventor contemplates that the addition of heme oxygenase and/or p21 inhibitors abrogate the anti-apoptotic effects of heme oxygenase and promote heme-induced apoptosis. The present invention envisions a synergistic anti-tumor effect when siRNAs and pharmacologic inhibitors of heme oxygenase are administered following infusion of SS cells. Agents used to induce heme oxygenase inhibition include but are not limited to zinc and tin protoporphyrins and deutroporphyrins. These HO-1 inhibitors are administered parenterally in doses of 5-50 µg/ml for 1-12 days before and 1-14 days after the delivery of SS cells to the tumor bearing host. Pharmacologic inhibition of p21 and AKT given simultaneously with HO-1 inactivation is also useful in promoting endothelial cell apoptosis after SS cell infusion. Inhibitors of agents known to scavenge free radicals such as superoxide dismutase that converts superoxide $O_2^-$ radicals to $H_2O_2$ as well as catalase and glutathione peroxidase that inactivate $H_2O_2$ are also useful in this invention.

Pharmacologic inhibitors of heme oxidase not only enhance the antitumor effects of SS cell infusion but also the tumoricidal effect of oxidant-dependent chemotherapeutic agents. Indeed, heme oxygenase inhibition serves the dual function of abrogating the catabolisim of toxic heme in tumor endothelial cells and tumor cells induced by SS cell infusion and enhancing the antitumor effects of chemotherapeutic agents. The present invention also contemplates that the antitumor effects of sickle cell infusion and heme oxygenase blockade are amplified further by the use of chemotherapeutic agents and radiation. Chemotherapeutic agents of all kinds are useful in this invention but those dependent on activating oxidative systems in tumor cells are preferred. They are administered before, together with or after the administration of SS cells and heme oxygenase inhibitors although the preferred timing is immediately after SS cell infusion and the completion of the heme oxygenase inhibition treatment. The murine models of established tumors for these studies are given in the section herein on tumor models and include but are not limited to carcinomas, sarcomas, leukemias/lymphomas, brain tumors and neuroblastomas. Chemotherapeutic, anti-angiogenic and anti-growth factor receptor agents useful in this invention are given in the section under chemotherapy. These include but are not limited to cisplatinum, doxorubicin, gemcitabine, vincristine, cyclophosphamide, avastin and traztuzimab. These agents are administered parenterally in conventional doses or doses reduced by up to 70% due to their synergistic interaction with SS cell infusion and heme oxygenase inhibitors. The SS cell infusions, heme oxygenase inhibitors and chemotherapy are administered in the course of 1-10 cycles commencing every 14 to 60 days. The present invention also contemplates the use of radiation therapy to tumors that are treated with SS cell infusion, heme oxygenase inhibition and chemotherapy. Radiation is given with SS infusion alone, SS infusion plus HO-1 inhibitors or SS infusion, HO-1 inhibitors and chemotherapy. The type and dose of radiation in this invention are given herein. In general, a conventional radiation dose is employed but in view of the tumor cell injury induced the other two therapies, a synergy with radiation exists enabling the reduction of radiation dose up to 70%.

SS Erythrocytes or Nucleated Progenitors Plus Inhibitors of GLUT/SLC2A Family of Glucose/Polyol Transport Facilitators The facultative glucose transporter/solute carrier GLUT/SLC2A family comprises at least fourteen highly homologous, integral membrane transport proteins that catalyze the entry of monosaccharide sugars such as glucose into mammalian cells. These proteins display 12 membrane spanning helices and several conserved sequence motifs. The GLUT/SLC2A proteins are expressed in a tissue- and cell-specific manner and exhibit distinct kinetic and regulatory properties. The full definitions and unique functional characteristics for each of the GLUT protein isoforms is outlined in Table 1 of Airley R E et al., *Chemotherapy* 53: 233-256 (2007) which is herein incorporated by reference in entirety including the references cited therein. GLUT/SLC2A family members have sequence similarities that are divided into three subclasses. Class I contains the originally identified, well-characterized glucose transporters GLUT1-4 which are distinguishable by their tissue distribution, kinetic properties, and regulation by hormones, especially insulin. GLUT1 is found in very low levels in most tissues, but is especially abundant in erythrocytes, and blood-tissue endothelial and epithelial borders, such as the blood-brain barrier, retina, and placenta. GLUT2 is a low affinity, high $K_m$ isoform expressed in the liver, gut and pancreatic islets. GLUT3 is primarily expressed in brain where it is localized exclusively to neurons but other sites of expression include placenta, sperm, and human platelets. GLUT4 is an 'insulin-responsive' isoform expressed in skeletal muscle, heart, white and brown adipose tissue, tissues which respond to insulin or contraction by acutely increasing their rates of glucose uptake. Class II consists of the fructose transporter GLUT5 and three related GLUT7, GLUT9 and GLUT11. Class III GLUT/SLC2A members show a lack of a glycosylation site in the extracellular loop 1, and by the presence of such a site in loop 9.

Overexpression of GLUT1 in Tumors

Glucose transporters are overexpressed in a wide variety of tumor types and have an application as markers of malignancy. GLUT 1 transcription or protein expression is upregulated for virtually all cell lines tested. 43% of breast cancer tissues express the insulin-responsive GLUT1 isoform while human MCF-7 and MDA-468 breast cancer cell lines transport fructose and glucose via the fructose transporter GLUT5 and glucose transporter GLUT12 respectively. GLUT1 is expressed in non-small cell lung cancer, colorectal, head and neck cancers, esophageal carcinomas, bladder, gallbladder, gastric, cervical, thyroid, pancreas, endometrial carcinomas, gliomas, neuroblastoma and rhabdomyosarcoma.

Control Of Glucose Transporters in Malignancy

The expression and functionality of glucose transporters in tumors is regulated by oncogenes in response to tumor hypoxia and inhibition of oxidative phosphorylation. Activation of the c-myc, ras, src and bcr-abl tyrosine kinases oncogenes in tumor cells by hypoxia leads to the transcription of glucose transporter GLUT1 expression via upregulation of HIF-1/carbohydrate response element (ChoRE) and its glycolytic enzymes. HIF-1 binding leads directly to activation of GLUT1. HIF-1 induces GLUT1 overexpression in cancer cells via stabilization and subsequent dimerization of the HIF-Iα subunit with the HIF-Iβ subunit leading to complex formation with the hypoxia response element (HRE) an enhancer sequence found in the promoter regions of GLUT1, GLUT3, and the glycolytic enzymes.

The stimulation of GLUT1-mediated glucose transport by hypoxia occurs in three stages. Initially, acute hypoxia stimulates the activation or 'unmasking' of glucose transporters preexisting on the plasma membrane. In anoxic conditions, and in the presence of metabolic inhibitors, stimulation of glucose transport occurs due to de-suppression of GLUT1. In normoxic conditions, or in the absence of metabolic inhibitors, GLUT1 is a facilitative transporter (i.e. it facilitates the exchange of extracellular for intracellular sugar). Metabolic inhibition converts GLUT1 to a uniport mechanism, ensuring a hypoxia-induced increase of glucose uptake. GLUT1 is an ATP-binding protein and functions as a uniporter. It requires a loss of intracellular ATP that occurs as a result of reduced oxidative phosphorylation. Acute hypoxia induces translocation of both GLUT1 and GLUT3 from intracellular vesicles to the plasma membrane. More chronically hypoxic tumor cells ultimately increases glucose transport via de novo synthesis of GLUT1 (and GLUT3).

The reduction of tissue oxygen levels is accompanied by a 30% elevation of glucose metabolic rate. This metabolic switch to anaerobic glycolysis is regulated by HIF-1 transcription factor and inhibitors of oxidative phosphorylation which activate GLUT1 expression. Indeed, the region lying 5' to the GLUT1 gene codes for the response to both mitochondrial inhibitors such as rotenone as well as the response to hypoxia per se.

The present invention contemplates the use of pharmacologic and genetic inhibitors (siRNA) of glucose transport in tumor endothelial cells and tumor cells in conjunction with SS cell, SS progenitor or erythroleukemia cell infusion. Tumor cell hypoxia and HIF-1α are known to induce expression and activation of the GLUT family of transporters. Under anaerobic conditions of glycolysis, the tumor cell becomes more dependent on glucose as an energy source resulting in upregulation of the glucose transporter proteins. The claimed subject matter covers the inhibition of these key transport proteins with pharmacologic agents as well as siRNA directed to GLUT-1 and/or related family members. Methodology for preparation of the siRNA for Glut-1 is given in Example 6.

Pharmacologic inhibitors of glucose uptake such as phloretin and 2-deoxyglucose which blocks the GLUT family of glucose transporters not only enhance the antitumor effects of SS cell infusion but also the tumoricidal effect of oxidant-dependent chemotherapeutic agents. Indeed, Glut inhibition serves the dual function of promoting intracellular oxidant injury in tumor cells induced by toxic heme following SS cell infusion as well as enhancing the antitumor effects of chemotherapeutic agents. The present invention thus contemplates that the anti-tumor effects of sickle cell infusion together with HIF-1α and heme oxygenase blockade are amplified further by GLUT inhibition. Chemotherapeutic agents of all kinds are useful in this invention but those dependent on activating oxidative stress in tumor cells are preferred. They are administered before, together with or after the administration of SS cells and GLUT inhibitors although the preferred timing is immediately after SS cell infusion and the completion of the GLUT inhibition treatment. The murine models of established tumors for these studies are given in the section on tumor models and include carcinomas, sarcomas and leukemias/lymphomas. Chemotherapeutic, anti-angiogenic and anti-growth factor receptor agents useful in this invention are given in the section under chemotherapy. These include but are not limited to cisplatinum, doxorubicin, gemcitabine, vincristine, cyclophosphamide, avastin and traztuzimab. These agents are administered parenterally in conventional doses or doses reduced by up to 70% due to their synergistic interaction with SS cell infusion and heme oxygenase inhibitors. The SS cell infusions, GLUT-1 inhibitors and chemotherapy are administered in the course of 1-10 cycles commencing every 14 to 60 days.

The present invention also contemplates the use of radiation therapy to tumors that are treated with SS cell infusions (SS), GLUT inhibition and chemotherapy. Radiation is given with SS alone, SS plus Glut inhibitors and chemotherapy. The type and dose of radiation in this invention are given herein. In general, a conventional radiation dose is employed but in view of the tumor cell injury induced the other two therapies, a synergy with radiation exists enabling the reduction of radiation dose of up to 70% of the normal dose.

SS Erythrocytes Producing Tumoricidal Agents: Vectors Comprising Tumoricidal Transgene(s) Under Control of the β-Globin Promoters/Enhancers, Locus Control Region, DNase Hypersensitivity Sites.

The present invention contemplates SS erythroid progenitors or erythroleukemia cells transfected with a lentiviral vector in which the viral LTR is deleted and the β-globin promoter/enhancer and a tumoricidal transgene are inserted preferably in frame rendering these cells capable of synthesizing a tumoricidal molecule. Erythroid progenitor cells transfected with this vector express the tumoricidal transgene in quantity. By including an erythroid-specific transcriptional signal in the vector along with a tumoricidal transgene, the present invention exploits the genetic programming of the red blood cell which devotes almost its entire synthetic capabilities to the production of hemoglobin. SS progenitors transduced with this vector are also capable of differentiating into mature SS RBCs which continue to synthesize the tumoricidal molecule even after their nuclei have been extruded.

Virtually no other cell in the body is devoted to the synthesis of a single protein product to the extent that erythroid cells are committed to the synthesis of hemoglobin. The developing red blood cell down-regulates the expression of the vast majority of its genes in order to focus its synthetic machinery on the production of hemoglobin; in doing so it loses its nucleus and most other organelles and becomes, essentially, a membrane-bound packet of hemoglobin. The domination of the red cell's synthetic capabilities is effected, to a large extent, by a formidable surge of transcription of globin genes upon commitment to differentiation. By redirecting the red cell transcriptional signals toward inducing expression of a tumoricidal transgene by substituting it for the β-globin coding region, the present invention exploits the genetic programming of erythroid cells and thereby provides an efficient method for producing a tumoricidal transgene in quantity.

In humans, the β-globin gene cluster is located on chromosome 11 and comprises one embryonic (e) two fetal ($^{o}\gamma$ and $^{A}\gamma$) and two adult δ- and β-globin genes, which reside within approximately 50 kb of chromosomal DNA in the order 5'-£-$^{o}\gamma$-$^{A}\gamma$-δ-β-3' (Fritsch et al. 1980, *Cell* 19:959-972). Expression of the human β-like globin genes is confined to only erythroid tissue during defined stages of development. They produce β-globin proteins at very high levels. Full expression of the β-globin gene requires inclusion of the promoter and several enhancer sequences and sequences at the extreme ends of the human β-globin locus including the erythroid-specific DNase I super-hypersensitive sites fused upstream of the human β-globin gene.

Four regulatory elements are required for appropriate expression of the human β-globin gene include: (I) a β-globin specific promoter element; (ii) a putative negative regulatory element, and (iii and iv) two downstream regulatory sequences with enhancer-like activity, one of which is located in the second intron of the β-globin gene and the other located approximately 800 basepairs (bp) downstream of the gene (Behringer et al. 1987. *Proc. Natl. Acad. Sci.* 84:7056-7060 (1986); Hesse et al., *Proc. Natl. Acad. Sci.* U.S.A. 83:4312-4316 (1986) (iv) sites that are super-hypersensitive to DNase I digestion 6-22 kilobases (kb) upstream of the 8-globin gene and 19 kb downstream of the β-globin gene (Tuan et al. *Proc. Natl. Acad. Sci.* 82:6384-6388 (1985); Forrester et al. *Proc. Natl. Acad. Sci.* 83:1359-1363 (1986)) (v) major DNase I hypersensitive sites, HS I, HS II, and HS IV situated upstream of the β-globin gene define locus activation regions dramatically enhance β-like globin gene expression specifically in erythroid cells.

The preferred vector of the present invention is of lentiviral origin modified as follows. The β-globin promoter/enhancer (2.3-kb) along with a tumoricidal transgene of choice are subcloned into the pWPT-GFP vector replacing the EF1a promoter and green fluorescent protein (GFP). This self-inactivating (SIN) vector contains a deletion in the U3 region of the 3' long terminal repeat (LTR) from nucleotide 418 to nucleotide 18 that inhibits all transcription from the LTR. The vector also contains a tumoricidal transgene which replaces the coding region of the β-globin gene. It also comprises the β-globin promoter (266 bp), the PstI 3' globin enhancer (260 bp), and a 375-bp RsaI fragment deletion of IVS2. The lentiviral-globin LTR contains in addition to the 3' globin enhancer, the β-globin promoter and the β^AS3 globin gene, a 3' SIN deletion, a ψ packaging signal, splice donor and acceptor sites, RRE indicating Rev-responsive element, cPPT/CTS indicating central polypurine tract or DNA flap/central termination sequence and WPRE specifying woodchuck hepatitis virus post-transcriptional regulatory element. DNase 1 hypersensitive sited (HS) fragments 5' HS4, 3, and 2 are amplified by polymerase chain reaction (PCR) from a 22-kb fragment of the LCR. Nucleotide coordinates from GenBank accession no. U01317 are: HS4 592-1545, HS3 3939-5151, and HS2 8013-9215. The entire HS4 3.2 β-globin gene construct is verified by sequencing. The full length lentiviral vector containing a tumoricidal transgene vector is modified from Levasseur T et al., *Blood* 102: 4312-4319 (2003) in the present invention by substituting the tumoricidal transgene for the β^AS3-globin gene resulting in production of a tumoricidal transgene.

In a particularly preferred embodiment a modified lentiviral vector is employed as described in Levasseur T et al., supra (2003). A tumoricidal transgene is substituted for the coding region of the β-globin gene in this vector under control of the β-globin promoter/enhancer that will drive expression of tumoricidal transgenes. Any tumoricidal transgene can be inserted at this site with the expectation of robust expression. The portion of the β-globin locus which includes the enhancer found in the second intron of the β-globin gene as well as part of the third exon of β-globin and the enhancer located 3' to the human β-globin gene, poly A sequence and a β-globin Nco sequence are retained for coding stabilization. Also retained in the vector are the locus control region (LCR) and DNAase hypersensitivity regions.

The staphylococcal enterotoxin (SEB) is attractive candidate for insertion into the β-globin coding region. The coding region of SEB is described in Jones C J et al., *J Bacteriol* 166: 16629-33 (1986); Ranelli D M et al., *Proc. Natl. Acad. Sci.* 82: 5850-5854 (1985). The whole plasmid described in Ranelli et al., supra 1985 contains a 6-kb HindIII fragment from that includes the SEB gene cloned into the HindIII site of pUC19. The cloned fragment is described in Ranelli et al supra 1985 pages 5850-5854 (attached). The pSK401 plasmid is similar to that described in Ranelli et al., supra 1985 except that the vector is high copy pUC19 in place of pBR322. The sequence of the SEB gene and surrounding region is described in Jones and Khan supra, pages 29-33 paper (attached). The ATG codon of SEB precursor is at position 244 of the sequence and the mature SEB coding sequence starts at position 325.

```
SEB Gene Ranelli DM et al., Proc. Natl. Acad. Sci. U.S.A. 82,
5850-5854 (1985) (SEQ ID NO: 4)
   1  GAACTAGGTA GAAAAATAAT TATGAGAAAA CACTATGTTG TTAAAGATGT
  51  TTTCGTATAT AAGTTTAGGT GATGTATAGT TACTTAATTT TAAAAGCATA
 101  ACTTAATTAA TATAAATAAC ATGAGATTAT TAAATATAAT TAAGTTTCTT
 151  TTAATGTTTT TTTAATTGAA TATTTAAGAT TATAACATAT ATTTAAAGTG
 201  TATCTAGATA CTTTTTGGGA ATGTTGGATA AAGGAGATAA AAAATGTATA
 251  AGAGATTATT TATTTCACAT GTAATTTTGA TATTCGCACT GATATTAGTT
 301  ATTTCTACAC CCAACGTTTT AGCAGAGAGT CAACCAGATC CTAAACCAGA
 351  TGAGTTGCAC AAATCGAGTA AATTCACTGG TTTGATGGAA AATATGAAAG
 401  TTTTGTATGA TGATAATCAT GTATCAGCAA TAAACGTTAA ATCTATAGAT
 451  CAATTTCTAT ACTTTGACTT AATATATTCT ATTAAGGACA CTAAGTTAGG
 501  GAATTATGAT AATGTTCGAG TCGAATTTAA AAACAAAGAT TTAGCTGATA
 551  AATACAAAGA TAAATACGTA GATGTGTTTG GAGCTAATTA TTATTATCAA
 601  TGTTATTTTT CTAAAAAAAC GAATGATATT AATTCGCATC AAACTGACAA
 651  ACGAAAAACT TGTATGTATG GTGGTGTAAC TGAGCATAAT GGAAACCAAT
 701  TAGATAAATA TAGAAGTATT ACTGTTCGGG TATTTGAAGA TGGTAAAAAT
 751  TTATTATCTT TTGACGTACA AACTAATAAG AAAAAGGTGA CTGCTCAAGA
 801  ATTAGATTAC CTAACTCGTC ACTATTTGGT GAAAAATAAA AAACTCTATG
 851  AATTTAACAA CTCGCCTTAT GAAACGGGAT ATATTAAATT TATAGAAAAT
 901  GAGAATAGCT TTTGGTATGA CATGATGCCT GCACCAGGAG ATAAATTTGA
 951  CCAATCTAAA TATTTAATGA TGTACAATGA CAATAAAATG GTTGATTCTA
1001  AAGATGTGAA GATTGAAGTT TATCTTACGA CAAAGAAAAA GTGAAATTAT
1051  ATTTTAGAAA AGTAAATATG AAGAGTTAGT AATTAAGGCA GGCACTTATA
1101  GAGTACCTGC CTTTTCTAAT ATTATTTAGT TATAGTTATT TTTGTTATAT
1151  CTCTCTGATT TAGCATTAAC CCCTTGTTGC CATTATAGTT TTCACCAACT
```

-continued

```
1201  TTAGCTGAAA TTGGGGGATC ATTTTTATCT TTACTATGGA TAGTTACTGT
1251  GTCGCCGTTT TTAACGATTT GTTTCTCTTT TAATTTGTCA GTTAATTTTT
1301  TCCATGCATC ATTTGCGTCA AACCTATTTC CATTTGGATT TATTCTTGAC
1351  AAATCAATTC TTTTAACACT ATCGGTATTA ATCGGCTTGT TATTAAAATT
1401  ACTAAGTTCA TCTAAATCAG CTGTACCCGT AATACTACTT TCGCCACCAT
1451  TATTTAAATT GTACGTAACA CCAACTGTCT CATTTGCTGT TTTATCGATA
1501  ATATTTGCTT CTTTCAAAGC ATCTCTTACA TTTTTCCATA AGTCTCTATC
1551  TGTTATTTCA GAAGCCTTTG CAACGTTATT AATACCATTA TAATTTGAAG
1601  AAGAATGAAA ACCTGAACCT ACTGTTGTTA AAACTAAAGC ACTTGCTATC
1651  AATGTTCTTG TTAATAGTTT TTTATTCATT TTATTTTCTC CTATAACTTA
1701  TTTGCAATCG AT
```

The above described sequence contains a 27 amino acid signal sequence near the amino-terminal, a stop codon, an NcoI linker and BamH linker inserted into the β-globin NcoI site. The insertion site consists of an NcoI ATG. Alternatively a BamH modified site is prepared downstream (FIG. 4). Additional vectors comprising nucleic acids encoding superantigen homologue-antibody conjugates as described by Forsberg et al U.S. Pat. No. 7,125,554 B2 incorporated in entirety by reference are also useful for integration into the lentiviral vector as described above.

The cloned enterotoxins B (entB) gene is subcloned into several known vectors such as the pC194 and pE194 as vector plasmids. It has also been subcloned in to the pHβ-actin-neo vector and transfected successfully into 4T1 carcinoma cells. These mammalian tumor cells expressed and secreted SEB and induced a tumoricidal response in vivo (Terman PCT/US 1999/008399; Pulaski et al., *Cancer Res.* 60-2710-15 (2000)). Recombinant plasmids containing the entB gene in both orientations direct the synthesis of SEB, suggesting that the gene is being transcribed from its own promoter. The complete nucleotide sequence of the entB gene, including the 5' and 3' flanking regions is shown in FIG. 2 of Jones et al., supra 1986. Starting from an ATG codon at nucleotide 244, there an open reading frame (ORF) of 798 nucleotides terminates in a TGA stop codon at nucleotide 1042. This corresponds to the SEB precursor which consisted of 266 amino acids, with a calculated molecular weight of 31,400. The SEB precursor contains a putative signal sequence of 27 amino acid residues. The calculated molecular weight of the 239-amino acid mature SEB is 28,366. ATG codon at nucleotide 244 is the translational start site and is the first ATG in the first initiating codon upstream of the GAG codon (glutamic acid) at nucleotide 325 that encodes the NH2-terminal residue of SEB. The ATG codon is preceded by a strong Shine-Dalgarno sequence, AAAGGAG and a strong ribosome-binding sequence. The ATG codon at nucleotide 244 is signal peptide of 27 amino acids. The 5' flanking region of the entB gene contains a possible—10 TATAT sequence which is an acceptable fit to the canonical TATAAT sequence. Forty nucleotides downstream from the TGA stop codon of the entB gene is a palindromic sequence that is a transcription terminator.

Other native SEs, SE homologues and fragments with tumoricidal activity are also useful for insertion into the lentiviral vector in this invention. To qualify as an SE homologue or fragment of a wild type SE the molecule must demonstrate T cell mitogenicity in a conventional T cell proliferation assay and show a z>13 in FASTA when compared to the wild type SEs. Details of this methodology are given herein in the section on protein homologues.

Additional SE fragments and structural homologues are useful in this invention that have a z value>13 in FASTA and demonstrate direct tumor cell cytotoxicity versus carcinoma cell lines in vitro with or without the aid of MHCII antigen presenting cells. These fragments do not demonstrate T cell mitogenicity in a conventional T cell mitogenicity assay. In contrast to the wild type enterotoxins they are non-toxic in vivo. The present invention contemplates that the active site on SEC is homologous to the 130-160 amino acid fragments of wild type SEB. Any other molecule that is cytotoxic for tumor cells in an MHCII-independent manner and shows a z>13 in FASTA compared to the wild type SEB 130-160 fragment is also useful in this invention.

```
SEB 130-160 fragment Papageorgiou, A.C. et al.
J. Mol. Biol. 277:61-79 (1998)
  130  rsitvrvfedgknllsfdvqtnkkkvtaqel SEC 157-187 (Bohach, G.A. et al., Mol. Gen. Genet.
209:15-20 (1987))
  156  nvlirvyenkrntisfevqtdkksvtaqel
```

In an example of MHCII independent tumor cell killing, SEC shows dose dependent cytotoxicity against $MHCII_{neg}$ CRL5800 lung carcinoma cell lines in an MTT assay. Incubation of various quantities of SEC with CRL5800 cells in the absence of MHCII antigen presenting molecules resulted in a dose dependent tumor killing as shown below.

Direct cytolysis of CRL5800 cells by SEC

| SEC dose (μg/ml) | Cells alive (%) |
|---|---|
| 0 | 100 |
| 1 | 80 |
| 2 | 75 |
| 5 | 50 |
| 10 | 52 |

Staphylococcal Enterotoxins and Culture Conditions:

SEC was obtained from Toxin Technology, USA. T84 human colon carcinoma cells were purchased from the American type culture collection. The T84 colon carcinoma and CRL5800 NCI H23 (CRL5800) human non-small cell lung adenocarcinoma was purchased from Cellulotheque, France. CRL5800 cells were grown in 1:1 Ham's F12 Medium: Dulbecco's modified Eagle's medium (DMEM/F-12, Gibco) supplemented with 5% fetal bovine serum, 2% NaHCO$_3$, 200 mM L-glutamine, 1% penicillin-streptomycin, and 1.5 mM HEPES. Cultures were maintained as monolayers in a humidified 5% CO$_2$ mixture with ambient air at 37° C. SEC, in doses of 0.01-100 µg/ml were added to the tumor cells monolayers and incubated for 48-144 hours at 37° C. after which the tumor cells were tested in the MTT assay.

MTT Assay:

Cell viability and proliferation was quantified by measuring the reduction of yellow 3-(4, 5-dimethylthiazolyl-2)-2,5-diphenyltetrazolium bromide (MTT, Calbiochem) to the blue, water-insoluble formazan. For cytotoxicity studies, cells were seeded in 96-well plates and treated with various concentrations of cisplatin and SEC and grown for a designated number of days to 100% confluence at 37° C., 5% CO$_2$. MTT was added to each well at a final concentration of 0.5 mg/mL. After 4 hours of incubation, 100 µl Cell Lysis Buffer (10% SDS, 0.04N HCl) was added to each well and allowed to sit overnight at 37° C. MTT reduction was quantified by measuring absorbance at 570 nm against a 650 nm reference using the microplate reader. All MTT assays were done in triplicate for each experiment. Results were recorded as the average of three determinations and fraction of the untreated control values.

In contrast, supernatants from PBMCs incubated with SEC in doses up 100 ng/ml or 96 hours induced no cytolysis of T84 cells. Cisplatin in various doses co-cultured with CRL5800 cells for 72 hours induced a dose related tumor cell death as shown below.

| Cisplatin-induced cytolysis of T84 cells | |
|---|---|
| Cisplatin dose (µM) | Cells alive (%) |
| 0 | 100 |
| 1 | 95 |
| 10 | 45 |
| 20 | 40 |
| 50 | 38 |
| 100 | 5 |

However, when subcytolytic doses of SEC plus a non-cytolytic dose of supernatant from PBMCs incubated with SEC were incubated with tumor cells in the presence of a non-cytolytic dose of cisplatin, significant tumor cell killing was observed. Table below shows that subcytotoxic SEC (1 µg/ml) and non-cytolyic supernatant from SEC-primed PBMCs sensitized tumor cells to killing by subcytotoxic doses of cisplatin (1 µM) (see area shaded in blue). The cytotoxic moiety in the SE molecule is expressed on SEB 130-160 which recognizes a receptor for superantigen on tumor cells. Contact of the superantigen with tumor cell induces via the superantigen receptor induces transcytosis that ultimately primes the cell for diffusion of water soluble chemotherapy leading to cell death.

| Subcytolytic doses of SEC & supernatant from SEC-primed T cells sensitize tumor cells to lysis by sublethal doses Cisplatin | | | |
|---|---|---|---|
| SEC dose (µg) | Supernatant* | Cisplatin Dose (µM) | Cells alive (%) |
| 0 | − | 0 | 100 |
| 0 | + | 0 | 90 |
| 0 | + | 1 | 79 |
| 0 | + | 10 | 55 |
| 0.01 | − | 0 | 82 |
| 0.01 | + | 0 | 82 |
| 0.01 | + | 1 | 60 |
| 0.01 | + | 10 | 40 |
| 0.1 | − | 0 | 85 |
| 0.1 | + | 0 | 64 |
| 0.1 | + | 1 | 50 |
| 0.1 | + | 10 | 28 |
| 1.0 | − | 0 | 90 |
| 1.0 | + | 0 | 48 |
| 1.0 | + | 1 | 20 |
| 1.0 | + | 10 | 20 |
| 10 | − | 0 | 40 |
| 10 | + | 0 | 22 |
| 10 | + | 1 | 20 |
| 10 | + | 10 | 20 |

*Supernatant from PBMCs (20% of starting volume) incubated with SEC 1 ug for 72 hours at 37° C.

Isolation of PBMCs:

PBMCs were isolated from the buffy coat interface after ficoll density centrifugation of blood from healthy volunteers. Cells were resuspended in culture medium at 10$^6$/ml and used within 30 min of isolation. At least 3 donors were used for tests involving PBMCs.

In Vitro Studies:

PBMCs (10$^6$ cells) were incubated with various SEC (1-10 ng/ml) or a mixture of egc SEs for 96 hours at 37° C. Supernatants were collected after removal of the cells by centrifugation at 1000 rpm for 30 min. The supernatants in 1 ml aliquots were added to CRL500 cells and incubated for 96 hours after which the cells were collected by centrifugation at 1000 rpm for 30 min and tested in the MTT. In some experiments, SEC (0.01-10 µg/ml) was added to the tumor cells at the same time as the supernatants.

Statistical Methods

ED$_{50}$ and standard errors were calculated with the Sigma-Plot 10 program using a four parameter logistic function. Statistical comparison of ED$_{50}$s and standard errors was carried out in the SigmaPlot 3.5 program using a 1 way ANOVA and Bonferroni adjustment.

The present invention envisions the incorporation of nucleic acids encoding Panton Valentine leukocidin (PVL) into the lentiviral vector under control of SS β-globin enhancer as described above. PVL induces cytolysis of polymorphonuclear leukocytes a key cell population in promoting endothelial and tumor cell death in the course of SS cell-induced tumor vaso-occlusion. Shortly after SS vaso-occlusion, PMNs are activated, recruited to and infiltrate sites of SS cell adherence to tumor endothelium resulting in endothelial cell injury and tumor cell death. The tumor endothelium not only promotes the recruitment of inflammatory leukocytes to sites of SS adherence but also sends additional activating signals that are crucial for vascular injury. Endothelial E-selectin-mediated signals are transduced via ESL-1 (E-selectin ligand) and locally activate the integrin α$_M$β$_2$ at the leading edge of crawling neutrophils. Activated α$_M$β$_2$ clusters mediate heterotypic interactions with circulating RBCs and platelets, which promote vascular occlusion and damage. The release of PVL via the β-globin gene in SS cells entrapped in tumor vasculature leads to up-regulation in PMNs of CD11b/CD18 glycoprotein, activation of phospholipase A2, release of oxygen metabolites, IL-18 and leukotriene B4 resulting in DNA fragmentation, cell lysis with release of proteases, oxidants and phospholipase. These agents induce necrosis of the proximate tumor endothelium and adjacent tumor cells PVL has high cytolytic specificity for human polymorphonuclear cells and macrophages. PVL, leukocidins and staphylococcal γ-hemolysins are bicomponent toxins of *Staphylococcus aureus*. PVL and γ-hemolysin are composed of five separate and complete proteins termed "F" and "S". Class S and F proteins are secreted separately as lytically inactive components but act synergistically on the target cell membrane to form membrane pores. The assembly of the both components on the surface of the PMN is required for it cytolytic activity.

Pore formation of the staphylococcal leukocidal toxins is associated with the assembly of a heptameric β barrel structure from the monomer pairs of S and F proteins, (e.g., LukS-PV/LukF-PV, HlgA/HlgB, HlgC/HlgB) which is the active pore-forming configuration of the toxin. The GM1 receptor on target PMNs and monocytes is recognized by soluble class S molecules (e.g., LukS) binds with high affinity. Binding of S components to cell membranes is requisite before binding of F components can take place. S components consist of LukS-PV, HlgA (32 kDa), HlgC (32 kDa) with 63 to 75% identity, and class F components include LukF-PV, HlgB (34 kDa) with 70% identity. The PVL class F component (LukF-PV) are shared in common with γ-hemolysin. The target cell specificities of both bi-component toxins are mainly determined by the class S(Hlg2 for γ-hemolysin and LukS-PV for PVL) proteins. There are seven possible functional combinations of S and F components. All seven are leukocytolytic, however, the couples HlgC/LukF-PV and LukS-PV/HlgB show only leukotoxic properties. Two of the couples, LukS-PV/LukF-PV and HlgA-LukF-PV, also display dermonecrotic activity on rabbit skin. The two γ-hemolysin combinations, HlgA/HlgC and HlgA/HlgB, and the hybrid couple, HlgA+LukF-PV, induce both leukocytolysis and hemolysis.

The preferred sequence couples for use in humans are HlgC/LukF-PV LukS-PV/HlgB as shown below.

```
HlgC Cooney, J et al., J. Gen. Microbiol. 134 (Pt 8), 2179-2188 (1988) (SEQ ID NO: 7)
protein genpept    12719453    1000000    74268
     1    mlknkilttt lsvsllapla npllenakaa ndtedigkgs dieiikrted ktsnkwgvtq 61    niqfdfvkdk kynkdalilk mqgfissrtt yynykktnhv kamrwpfqyn iglktndkyv 121    slinylpknk iestnvsqtl gyniggnfqs apslggngsf nysksisytq qnyvseveqq 181    nsksvlwgvk ansfatesgq ksafdsdlfv gykphskdpr dyfvpdselp plvqsgfnps 241    fiatvshekg ssdtsefeit ygrnmdvtha ikrsthygns yldghrvhna fvnrnytvky 301    evnwktheik vkgqn LukF-PV Narita, S et al., Gene 268, 195-206 (2001) (SEQ ID NO: 8)
     1    mkkivkssvv tsiallllsn tvdaaqhitp vsekkvddki tlykttatsd sdklkisqil 61    tfnfikdksy dkdtlilkaa gniysgytkp npkdtissqf ywgskynisi nsdsndsvnv 121    vdyapknqne efqvqqtvgy syggdinisn glsgggngsk sfsetinykq esyrtsldkr 181    tnfkkigwdv eahkimnngw gpygrdsyhs tygnemflgs rqsnlnagqn fleyhkmpvl 241    srgnfnpefi gvlsrkqnaa kkskitvtyq remdrytnfw nqlhwignny kdenrathts 301    iyevdwenht vklidtqske knpms LukS-PV Takano,T et al., Antimicrob. Agents Chemother. 52, 837-845 (2008) (SEQ ID NO: 9)
     1    mvkkrllaat lslgiitpia tsfheskadn nienigdgae vvkrtedtss dkwgvtqniq 61    fdfvkdkkyn kdalilkmqg finskttyyn ykntdhikam rwpfqynigl ktndpnvdli 121    nylpknkids vnvsqtlgyn iggnfnsgps tggngsfnys ktisynqqny isevehqnsk 181    svqwgikans fitslgkmsg hdpnlfvgyk pysqnprdyf vpdnelpplv hsgfnpsfia 241    tvshekgsgd tsefeitygr nmdvthatrr tthygnsyle gsrihnafvn rnytvkyevn 301    wktheikvkg hn HlgB Cooney, J et al., J. Gen. Microbiol. 134, 2179-2188 (1988) (SEQ ID NO: 10)
     1    mkmnklvkss vatsmalllll sgtanaegki tpvsvkkvdd kvtlykttat adsdkfkisq 61    iltfnfikdk sydkdtlvlk atgninsgfv kpnpndydfs klywgakynv sissgsndsv 121    nvvdyapknq neefqvqntl gytfggdisi snglsgglng ntafsetiny kqesyrttls 181    rntnyknvgw gveahkimnn gwgpygrdsf hptygnelfl agrqssayag qnfiaqhqmp 241    llsrsnfnpe flsvlshrqd gakkskitvt ygremdlyqi rwngfywaga nyknfktrtf 301    kstyeidwen hkvklldtke tennk
```

In the rabbit VX 2 carcinoma model, VX2 fragments are implanted in the lateral thigh female rabbits 3-4 kg in body weight are used and as described in U.S. Pat. No. 6,340,461 which is herein incorporated in entirely by reference. Human mature SS erythrocytes or SS progenitors (2-10 ml) synthesizing the PVL gene via the lenteviral vector described above are injected intravenously three times weekly for two weeks. The treatment is started when the tumors have grown to at least 1 cm$^3$. Control tumor bearing rabbits are treated with SS cells that do not contain the PVL gene. Tumor measurements in treated and control rabbits are evaluated statistically by methods well established in the art. Median survival of treated and control groups is also determined at an arbitrary time points such as 30, 60, 90 and 120 days after starting treatment and the groups compared statistically by established methodology as described in U.S. Pat. No. 6,340,461 incorporated in entirety by reference. The present invention contemplates that wild type shiga toxins, Shiga toxin mutants (two of which are shown below) and chain B are useful for integration in the above lentiviral vectors and transfection into SS progenitor cells. The mature SS cell containing the shiga toxin genes deposits in tumor vasculature wherein it produces the toxin locally. These agents recognize globotriaosylceramide (Gb3) binding sites expressed on breast, ovarian and colon carcinoma and are capable of inducing tumor cell apoptosis. The B subunit is responsible for the binding of the holotoxin to GB3 on the target human tumor cells. After binding to the Gb-3 receptors, STxB enters cells through clathrin-independent or -dependent endocytosis and uses retrograde transport to deliver the A subunit to the cytosol. The A subunit causes endohydrolysis of the N-glycosidic bond at one specific adenosine on the 28S rRNA resulting in tumor cell apoptosis.

Shiga-like toxin contains a single subunit A and five copies of subunit B. There are three Gb3-binding sites in each subunit B monomer, allowing for a tighter binding to the target cell. Sites 1 and 2 have higher binding affinities than site 3. The A subunit is responsible for inhibiting protein synthesis through the catalytic inactivation of 60S ribosomal subunits. After endocytosis, the A subunit is cleaved by furin in two fragments, A1 and A2: A1 is the catalytically active fragment, and A2 is essential for holotoxin assembly with the B subunits. Mutant forms of the wild type toxin and the B chain alone are less toxic than the wild type Shiga toxin and are also useful in the present invention. Biologically active mutants or variants the wild type Shiga toxin qualify as authentic shiga toxin homologues if they demonstrate binding to the Gb3 ligand using well established assays in the art and show a z>13 in FASTA versus the wild type shiga toxin.

```
Wild type shiga toxin A chain Calderwood, S.B., et al., Proc. Natl. Acad.
Sci. U.S.A. 84 (13), 4364-4368 (1987); De Grandis, S., J. Bacteriol. 169,
4313-4319 (1987) (SEQ ID NO: 11)
   1 mkiiifrvlt fffvifsvnv vakeftldfs taktyvdsln virsaigtpl qtissggtsl 61 lmidsgsgdn lfavdvrgid peegrfnnlr livernnlyv tgfvnrtnnv fyrfadfshv 121 tfpgttavtl sgdssyttlq rvagisrtgm qinrhsltts yldlmshsgt sltqsvaram 181 lrfvtvtaea lrfrqiqrgf rttlddlsgr syvmtaedvd ltlnwgrlss vlpdyhgqds 241 vrvgrisfgs inailgsval ilnchhhasr varmasdefp smcpadgrvr githnkilwd 301 sstlgailmr rtiss
```

Shiga toxin A chain mutant Stx1$^{W203F}$ Cao et al., Int. J. Gynecol. Cancer 18, 667-691 (2008) (SEQ ID NO: 12)
```
   1 mkiiifrvlt fffvifsvnv vakeftldfs taktyvdsln virsaigtpl qtissggtsl 61 lmidsgsgdn lfavdvrgid peegrfnnlr livernnlyv tgfvnrtnnv fyrfadfshv 121 tfpgttavtl sgdssyttlq rvagisrtgm qinrhsltts yldlmshsgt sltqsvaram 181 lrfvtvtaea lrfrqiqrgf rttlddlsgr syvmtaedvd ltlnfgrlss vlpdyhgqds 241 vrvgrisfgs inailgsval ilnchhhasr varmasdefp smcpadgrvr githnkilwd 301 sstlgailmr rtiss
```

Shiga toxin A chain mutant Stx1R$^{170H}$ Cao et al., Int. J. Gynecol. Cancer 18, 667-691 (2008) (SEQ ID NO:3)
```
   1 mkiiifrvlt fffvifsvnv vakeftldfs taktyvdsln virsaigtpl qtissggtsl 61 lmidsgsgdn lfavdvrgid peegrfnnlr livernnlyv tgfvnrtnnv fyrfadfshv 121 tfpgttavtl sgdssyttlq rvagisrtgm qinrhsltts yldlmshsgt sltqsvaram 181 lrfvtvtaea lhfrqiqrgf rttlddlsgr syvmtaedvd ltlnwgrlss vlpdyhgqds 241 vrvgrisfgs inailgsval ilnchhhasr varmasdefp smcpadgrvr githnkilwd 301 sstlgailmr rtiss
```

Wild type shiga toxin B chain Calderwood, S.B., et al., Proc. Natl. Acad. Sci. U.S.A. 84 (13), 4364-4368 (1987); De Grandis, S., J. Bacteriol. 169, 4313-4319 (1987) (SEQ ID NO: 13)
```
   1 mkktlliaas lsffsasala tpdcvtgkve ytkynddtf tvkvgdkelf tnrwnlqsll 61 lsaqitgmtv tiktnachng ggfsevifr
```

The present invention contemplates that additional tumoricidal transgenes are inserted into β-globin coding region of the lentiviral vector including but not limited to IFN-β, TNFα, IL-12 or the FAS death domain RIP and any biocompatible tumor killing molecule, tumor specific or tumor vascular endothelium (anti-VEGF), specific monoclonal antibody, superantigen, superantigen homologue, superantigen-tumor associated antibody, antibody fragment or receptor conjugates (Forsberg et al U.S. Pat. No. 7,125,554 B2; Shaw et al., Br J Cancer 96: 567-574 (2007); Antonsson P et al Semin Immunopathol 17:397-410 (1996)), anti-angiogenesis agents, therapeutic or tumor specific monoclonal antibodies and immunotoxins, anti-tumor growth factor inhibitors, suicide agents such as thymidine kinase, cytosine deaminase, drug or prodrug or any biocompatible small peptide, protein, protein or peptide homologue or conjugate that is directly or indirectly involved in therapeutic tumor killing.

One skilled in the art recognizes that many other vectors are capable of introducing a tumoricidal transgene or siRNAs into SS progenitor cells, erythroblasts or erythroleukemia cells under the β-globin promoter/enhancer and are useful in this invention. These include baculoviruses (Granqiero L et al., J Immunol Meth 25: 131-139 (1997)) and adenoviruses (Je T C Proc Natl Acad Sci 95:12509-12514 (1998)) and Sindbis virus (Koller D et al., gNat Med 19: 851-855 (2001; Boorsma Metal., Nat Biotech 18:429-432 (2000)). Several additional vector systems with tropism for erthyroid stem cells, progenitor cells or erythroblasts or erythroleukemia cells are useful given in Verhoeyen et al., J Gene Med 6:S83-S94 (2004) are also useful with the β-globin promoter/enhancer. DNA reaction products may be cloned using any method known in the art. A large number of vector-host systems known in the art may be used. Possible additional vectors include, but are not limited to cosmids plasmids or modified viruses, but the vector system must be compatible with the host cell used. Such vectors include, but are not limited to, bacteriophages such as lambda derivatives, or plasmids such as pBR322, pUC, or Bluescript (Stratagene) plasmid derivatives. Recombinant molecules can be introduced into host cells via transformation, transfection, infection, electroporation, etc. Additional lentiviral vectors in the art that accommodate both the β-globin promoter/enhancer and a tumoricidal transgene are given in Tiscornia G et al., Nature Protocols 1: 241-244 (2006); Pellinen R et al., Int J Oncol 25:753-62 (2004); Loimas S Gene Ther Mol Biol 5: 147-155 (2000) and siRNAs (Robinson D A Nat Genet. 33: 401-486 (2003); Schomber T et al., Blood 103: 4511-4513 (2004)) and are useful in the present invention.

The above lentiviral vectors are produced by transient transfection into 293T cells. A DNA cocktail containing 5 μg envelope-coding plasmid pMD.G, 15 μg of the packaging plasmid pCM-VDR8.91 (which expresses Gag, Pol, Tat, and Rev) and 20 μg SIN transfer vector plasmid. A total of $2.5 \times 10^6$ 293T cells are seeded in 10-cm—diameter dishes containing Dulbecco modified Eagle medium (DMEM) with 10% fetal bovine serum (FBS) 24 hours prior to transfection of 293 cells. Forty micrograms of plasmid DNA are used for transfection of one 10-cm dish. Transfection medium is removed after 14 to 16 hours and replaced with DMEM/F12 without phenol red (Invitrogen, Carlsbad, Calif.) containing 2% FBS. Viral containing supernatant is collected after an additional 24 hours, cleared by low-speed centrifugation, and filtered through a 0.22-μm polyethersulfone filter (Millipore, Beford, Mass.). The virus is concentrated 1000-fold by one round of centrifugation at 26,000 rpm for 90 minutes at 8° C., resuspended into serum-free stem cell growth medium (SCGM) (Cellgenix, Freiburg, Germany) and allowed to incubate on ice for 2 hours before storage at −80° C. Virus titer is determined by infecting murine erythroleukemia (MEL) cells, plating individual cells into wells of a 96 well plate and assaying DNA from the cultures by PCR for the human globin gene.

The constructs are removed from vector sequences by digestion with the appropriate enzymes and isolated in low-gelling temperature agarose (FMC) gels. Gel slices are melted, extracted twice with buffered phenol, once with phenol/chloroform, and once with chloroform and precipitated with ethanol. After suspension in TE (10 mM Tris-HCl (pH 8.0), 1.0 mM EDTA), the fragments are again extracted with phenol, phenol/chloroform, and chloroform and precipitated with ethanol. The purified fragments are washed with 70% ethanol resuspended in sterile TE, and transfected into erythroid cells.

SS human (CD34+) or murine (TER119$^+$ and CD71$^+$ or SCA$^+$, cKit$^+$ and Lin$^-$) erythroblasts/progenitors are used preferentially for transduction by the lentiviral vector containing the tumoricidal transgene described above although erythroid precursors at any stage of development or differentiation and erythroleukemia cells are useful in this invention. Transduction with this vector is carried out by suspending the SS erythroblasts/progenitors in IMDM medium containing 10 μg/mL dextran sulfate and 1% FBS. One thousand cells are infected at a MOI of 30 in a total volume of 100 μL at 37° C. in 5% $CO_2$ for 4 hours. These cells are induced to differentiate into large scale numbers of mature SS RBCs by established methods in the art (Lu et al., Blood published online Aug. 19, 2008; doi:10.1182/2008-05-157198). Cells are initially suspended in Stemline II medium, mixed with blast-colony growth media (BGM)($5 \times 10^5$ cells/ml), plated in 100 mm ultra low dishes (10 ml/dish) and expanded for 9-10 days in BGM. The addition of 20 ng/ml of βFGF and 2 ug/ml of the recombinant tPTD-HoxB4 fusion protein to BGM significantly enhances hematopoietic cell proliferation. HoxB4 protein promotes hematopoietic development in both mouse and human ESC differentiation systems. The grape-like blast colonies are usually visible by microscopy after 4-6 days, and expanded rapidly outward. In step 2, additional BGM is added to keep the density of blast cells at $1-2 \times 10^6$ cells/ml. Erythroid cell differentiation and expansion is carried out from day 11-20. At the end of step 2, the cell density is often very high ($\geq 2 \times 10^6$/ml). Equal volumes of BGM, containing 3 units/ml of erythropoietin (EPO) (total EPO is 6 units/ml) without HoxB4, are added to supplement the existing BGM. The blast cells are further expanded and differentiated into erythroid cells for an additional 5 days. For further expansion, the erythroid cells are transferred into 150 mm Petri dishes and Stemline II-based medium containing SCF (100 ng/ml), Epo (3 units/ml) and 0.5% methylcellulose added every 2-3 days. When the cells reach confluence, the cells are split at a ratio of 1:3 to allow maximum expansion for an additional 7 days (cell density $2-4 \times 10^6$/ml). Enrichment of SS erythroid cells is carried out on day 21. SS erythroid cells are diluted in 5 volumes of IMDM plus 0.5% BSA medium and collected by centrifugation at 1000 rpm for 5 minutes. The cell pellets are washed twice with IMDM medium containing 0.5% BSA, and plated in tissue culture flasks overnight to allow non-erythroid cells (usually the larger cells) to attach. The non-adherent cells are then collected by brief centrifugation.

The present invention contemplates that siRNAs or microRNAs are also incorporated into the lentivirus vector or other functional vectors by methods known in the art (Schomer et al., Blood 103:4511-4513 (2004)); Rubinson et al., Nat Gen 33: 401-406 (2003)). These siRNAs and microRNAs silence nucleic acids regulating enucleation, apoptosis, angiogenesis, metastases and those promoting synthesis of antiviral proteins such as IRF-3, NFκB, cJUN/ATF-2.

In another embodiment of the invention, two or more species of such recombinant tumoricidal DNA molecules or an siRNA or microRNA comprising different tumoricidal or tumoristatic genes may be co-introduced into cells in culture in order to produce a protein comprising multiple, distinct subunit proteins, each of which corresponds to one of the species of recombinant DNA molecules introduced. In particular, according to the invention, a protein of interest having more than one species of subunit may be produced in erythroid cells by a method comprising (i) introducing into SS erythroid cells as DNA transfected into an erythroid cell line more than one recombinant nucleic acid construct, each of which comprises a gene encoding a subunit of the tumoricidal molecule and at least one SS erythroid-specific DNase I hypersensitive site; (ii) growing the cells under conditions in which erythroid-specific gene expression occurs (in cell lines this may involve induction of differentiation). In a specific embodiment of the invention, recombinant DNA constructs comprising tumoricidal molecules together with at least one DNase I HS site are co-introduced into an erythroid cell in order to produce the tumoricidal molecule in quantity in the erythroid cells. It is preferable, in the case of multidomain molecules, to coinject both constructs into the same erythroid cell.

Specific signal sequences on the therapeutic transgenes that target intracellular polypeptides into the secretory pathway and facilitates exodus from the cell are useful in the present invention. Signal peptides have a common structure: a short, positively charged aminoterminal region (n-region); a central hydrophobic region (h-region); and a more polar carboxy-terminal region (c-region) containing the site that is cleaved by the signal peptidase. A secretory peptide is selected from those given in the Signal Peptide Database http://proline.bic.nus.edu.sg/spdb, a repository of experimentally determined and computationally predicted signal peptides (Choo K H et al., *BMC Bioinformatics*, 6:249-257 (2005)). In the lentiviral expression vector, nucleic acids encoding the selected secretory signal polypeptide are positioned 3' or 5' preferably in frame to the β-globin promoter/enhancer and tumoricidal transgene. Nucleic acids encoding the secreted polypeptide may also be operatively-linked to one or more transcriptional regulatory elements. The host cells transformed or transfected with the lentiviral expression vector is therefore able to express and secrete the polypeptide tumoricidal molecules into the external environment. The same secretory signals are useful in the self-replicating vectors synthesizing tumoricidal transgenes, the oncolytic viral constructs and in vectors containing the SS β-globin promoter/enhancer used to transduce tumor cells and T cell described below.

To confer additional level of specificity to the β-globin promoter/tumoricidal transgene construct, the present invention contemplates that the hypoxia responsive enhancer (HRE) is positioned in frame with the β-globin promoter/enhancer and optionally concatenated as described above. This ensures that transcriptional activation of the β-globin promoter and its downstream transgene occurs selectively in the hypoxic environs of the tumor vasculature. Methodology for introducing the HRE to the lentiviral or other vectors is given above in the instant specification. The HRE is also useful in the self-replicating vectors synthesizing tumoricidal transgenes, the oncolytic viral constructs and the vectors comprising the β-globin promoter/enhancer used to transduce tumor cells and T cell described below.

Viral vector-mediated transduction of defined factors has been used to generate induced pluripotent stem (iPS) cells from embryonic or adult somatic cells in both mouse and human. iPS cells have been shown to be are equivalent to embryonic stem (ES) cells maintaining a full capacity for differentiation with the ability to form teratomas, generate chimeras, and contribute to the germline. This technology can be readily applied to many cell types in addition to fibroblasts as numerous cell types have been shown to be amenable to direct reprogramming including pancreatic beta cells, neural precursors, and terminally differentiated B cells. iPS cell technology has emerged as the most promising method for cell-based therapies of regenerative medicine.

In the present invention, a humanized knock-in mouse model of sickle cell anemia in which the mouse α-globin genes were replaced with human α-globin genes, and the mouse b-globin genes were replaced with human Ag and bS (sickle) globin genes is used. Homozygous mice for the human bS allele remain viable for up to 18 months but develop typical disease symptoms such as severe anemia due to erythrocyte sickling, splenic infarcts, urine concentration defects, and overall poor health.

Reprogramming of Tail Tip Fibroblasts from SS Mice to Embryonic Stem Cells with Lentiviral Vectors Encoding Transcription Factors This representative method is from Chang C W et al., *Stem Cells* 27:1042-1049 (2009). Adult skin fibroblasts from a humanized mouse model of sickle cell disease are reprogrammed reliably by lentivirus to iPS cells by transduction with a polycistronic lentiviral vector encoding mouse cDNAs for Oct4, Sox2, Klf4, and c-Myc. and the reprogramming sequences can be efficiently deleted from the iPS cell genome.

Production of OSK Polycistronic Lentiviral Vector

Briefly, human Oct4 cDNA (Clone 40125986; Open Biosystems, Huntsville, Ala.) is PCR amplified and modified with primers OCT4-F and OCT4-R to contain Not I and Swa I restriction sites at the 5' end and a Kozak consensus sequence. At the 3' end, the Oct4 stop codon was eliminated and replaced with nucleotides (nt) from PTV1 2A that will form a 22-nt overlap with the 5' end of the Sox2 amplicon. Human Sox2 cDNA (Clone 2823424; Open Biosystems) is PCR amplified and modified with primers SOX2-F and SOX2-R to overlap with the 3' end of the Oct4 amplicon and to append 2A nt sequences upstream of the Sox2 ATG. At the 30 end, the Sox2 stop codon is eliminated and replaced with nt from PTV1 2A that will form a 22-nt overlap with the 5' end of the Klf4 amplicon. human Klf4 cDNA (Clone 51111134; Open Biosystems) is PCR amplified and modified with primers KLF4-F and KLF4-R to overlap with the 3' end of the Sox2amplicon and to append 2A nt sequences upstream of the Klf4 ATG. At the 30 end, the Klf4 stop codon is retained and Swa I and Sal I restriction sites were added. After PCR the individual amplicons are gel purified and used in a three-element fusion PCR at a 1:100:1 (Oct4/Sox2/Klf4) molar ratio along with primers OCT4-F and KLF4-R to produce a 3,623-bp amplicon containing the polycistron. The polycistron is gel purified and cloned into the general cloning vector pKP114 using the NotI and SalI restriction sites (enzymes from Roche Diagnostics, Basel, Switzerland) to produce pKP330 and sequenced for authenticity, Subsequently, the polycistron was removed from pKP330 as a SwaI (Roche Diagnostics) fragment and subcloned into a SwaI site downstream of the elongation factor 1 alpha (EF-1α) promoter in the lentiviral vector pDL171 to produce the OSK polycistronic lentiviral vector pKP332, which is also sequenced for authenticity. By the same strategy a second polycistronic lentival vector, pKP333, is produced that substitutes the PTV1 2A peptide between Sox2 and Klf4 with the Thosea asigna virus 18 amino acid 2A-like sequence: (SEQ ID N:15) GSG (linker) EGRGSLLTCGDVEENPGP.

Cell Culture and Viral Infections

Embryonic stem (ES) cells and iPS cells were cultured on irradiated MEFs in ES cell media consisting of Dulbecco's modified Eagle's medium supplemented with 1× nonessential amino acids, 1× penicillin-streptomycin, 1×L-glutamine (all from Mediatech, Manassas, Va.), 1× nucleosides (Chemicon, Temecula, Calif.), 15% fetal bovine serum (FBS; HyClone, Logan, Utah), 2-mercaptoethanol (Sigma-Aldrich, St. Louis, Mo.), and leukemia inhibitory factor (laboratory preparation). For preparation of lentivirus, 140 µg of the polycistronic vector (pKP332), 70 µg of the envelope plasmid (pMDG), and 105 µg of the packaging plasmid (pCMB-VdR8.9.1) were cotransfected into $1.7 \times 10^7$ 293T cells by the $CaCl_2$ method as previously described, Virus-containing supernatant was collected 2 days after transfection, passed through a 0.45-µm filter, and concentrated by centrifugation at 26,000 rpm for 90 minutes at 8° C. in an SW-28 rotor using a Beckman XL-100 ultracentrifuge.

For iPS cell induction, $3 \times 10^1$ adult 12-week-old hbS/hbS male mouse tail-tip fibroblasts (TTFs) are seeded onto one well of a six-well plate. The next day, 2.5 µl of the concentrated virus is mixed with 2 ml of ES cell medium containing 8 µg/ml polybrene and added to the TTFs. Fortyeight hours later, the TTFs are trypsinized and transferred to a 100-mm dish without MEFs and continuously cultured on the same dish for 3 weeks with daily media changes. Potential iPS cell colonies started to appear after 2-3 weeks. These colonies are individually picked and expanded on MEFs for analysis. To remove the integrated lentiviral and polycistronic sequences, iPS cells are either electroporated with a Cre-expressing plasmid (pCAGGS-Cre) or infected with a Cre-expressing adenovirus (rAd-Cre-IE). Individual colonies are picked and Cre-mediated removal of floxed sequences is verified by PCR and Southern blot analysis.

For the construction of rAd-Cre-IE (rAd-Cre-IRES-EGFP), Cre cDNA is PCR amplified from pCAGGS-Cre and inserted between the NheI and EcoRI sites of the expression vector pECIE, which contains an IRES-EGFP downstream of the MCS. The Cre-IE expression cassette is flanked by attL1 and attL2 sites, thus allowing transfer of the Cre-IE sequence from pEC-IE to pAd/pl-DEST (Invitrogen, Carlsbad, Calif.) by the LR reaction. The recombinant adenovirus is packaged in 293A cells according to the manufacturer's instructions. With the exception of the pKP332 construction, all of the PCRs performed in this study used ExTaq polymerase (Takara).

The reprogrammed embryonic stem cells are transfected with the lentiviral vector encoding the SS hemoglobin gene with the coding region of SEB gene substituted for the beta globin coding region by methods described above.

In Vitro Differentiation of the Embryonic, SEB Transfected, SS Hematopoietic Cells Into Mature SS Erythrocytes Producing SEB This representative method is from Shen J. Qu CK. In Vitro Hematopoietic Differentiation of Murine Embryonic Stem Cells in *Methods in Molecular Biology, vol.* 430: pp. 103-118 *Hematopoietic Stem Cell Protocols* Edited by: K. D. Bunting© Humana Press, Totowa, N.J.

In Vitro Differentiation of ES Cells

1. Differentiation medium (the methylcellulose differentiation media contains the same reagents as liquid differentiation media, except that methylcellulose is added to 1% of the final volume):

a. Iscove's Modified Dulbecco's Medium (IMDM) (Invitrogen, Cat. No. 12440-053).
b. 15% FBS (Hyclone, regular FBS).
c. $4.5\times10^{-4}$ M α-Monothioglycerol (MTG, Sigma, Cat. No. M-6145).
d. 2 mM 1-Glutamine (see above).
e. 50 μg/ml Ascorbic acid. Dissolve ascorbic acid at 5 mg/ml in $H_2O$ and filter through 0.22 μm sterilization filter.
f. 200 μg/ml Human transferrin (Sigma, Cat. No. T8158).
g. 1% Methylcellulose (2× stock, Fluka, Cat. No. 64630).

2. ES-IMDM: 15% FBS (ES cell serum, see above), 1000 U/ml LIF, and $1.5\times10^{-4}$ M of MTG in IMDM.

3. Gelatin: Prepare a 0.1% solution of gelatin in H2O, dissolve, and sterilize by autoclaving.

4. Methylcellulose-based feed medium:
a) 1/2 (v/v) primary differentiation medium (from above or freshly prepared).
b) 15% regular FBS.
c) $1.5\times10^{-4}$M of MTG
d) 150 ng/ml murine Kit Ligand/Stem Cell Factor (mSCF) (R&D systems, Minneapolis, Minn., USA, Cat. No. 455-MC)
e) 30 ng/ml murine Interleukin-3 (mIL-3) (R&D systems, Cat. No. 403-ML).
f) 20 ng/ml mouse Interleukin-6 (hIL-6) (R&D systems, Cat. No. 406-ML).
g) 3 U/ml human Erythropoietin (EPO)(R&D systems, Cat. No. 287-TC-500).
h) IMDM to the final volume.

5. 2× cellulose. Dissolve cellulose (Sigma, Cat. No. C-1794) in PBS at 2 U/ml. Filter sterilize through 0.45-1 μm filter.

6. Collagenase. Dissolve 1g of collagenase (Sigma, Cat. No. C0310) in 320 ml PBS. After filter sterilization, add 80 ml of FBS. Aliquot and keep at −20° C.

7. Hemangioblast colony methylcellulose mixture:
a) 1% methylcellulose.
b) 10% FBS.
c) SCF (100 ng/ml recombinant mSCF or 1% conditioned medium that was derived from medium conditioned by CHO cells transfected with mouse SCF expression vectors).
d) 25% D4T endothelial cell-conditioned medium (D4T endothelial cells are cultured in IMDM with 10% FBS. Remove media and change to 4% FBS in IMDM when it becomes 80% confluent. Culture additional 72 h and collect the supernatant. Spin down for 5 min at 228g, Beckman GS-6, GH-3.8 rotor to remove the cell debris and filter sterilize the supernatants by 0.45-1 μm filter. Make 5- to 10-ml aliquots and keep at −80° C. Once thawed, it is kept at 4° C. for about 1 week).
e) 5 ng/ml mouse VEGF (R&D systems, Cat. No. 494-VE).
f) 10 ng/ml human IL-6.
g) IMDM to a final volume.

8. Hemangioblast expansion Medium:
a) 10% FBS.
b) 10% horse serum (Invitrogen, Cat. No. 26050-088).
c) 5 ng/ml mouse VEGF.
d) 10 ng/ml mouse insulin-like growth factor-1 (IGF-1) (R&D systems, Cat. No. 791-MG).
e) 2 U/ml human EPO.
f) 10 ng/ml mouse basic fibroblast growth factor (bFGF) (R&D systems, Cat. No. 3139-FB).
g) 50 ng/ml mouse IL-11 (R&D systems, Cat. No. 418-ML).
h) 100 ng/ml SCF.
i) IL-3 [30 ng/ml recombinant murine IL-3 or 1% conditioned medium obtained from medium conditioned by X63 AG8-653 myeloma cells transfected with a vector expressing IL-3 (20)].
j) 1% 1-Glutamine.

k) 4.5×10-4 M of MTG.
l) IMDM to a final volume.
9. Matrigel-coated wells (the stock bottle of Matrigel should be thawed slowly once, diluted 1:1 populations is carried out in microtiter wells pretreated with a thin layer of Matrigel. The wells are coated by first spreading 5-1 of diluted Matrigel over the surface with an Eppendorf pipette tip. The plate should be kept on ice during this procedure. When the required number of wells has been coated, incubate the plate on ice for 10-15 min. Following this incubation, remove excess Matrigel from each well and then incubate at 37° C. for an additional 15 min before use.
11. Hematopoietic differentiation medium:
a) 1% methylcellulose.
b) 10% plasma-derived serum (Antech, Inc., Colorado, USA, Tyler, Tex., USA).
c) 5% protein-free hybridoma medium (PFHM-II; Invitrogen, Cat. No. 12040-077).
d) SCF (100 ng/ml mSCF or 1% conditioned medium).
e) 5 ng/ml mouse thrombopoietin (R&D System, Cat. No. 488-TO).
f) 2 U/ml human EPO.
g) 25 ng/ml mouse IL-11.
h) IL-3 (30 ng/ml recombinant mIL-3 or 1% conditioned medium).
i) 30 ng/ml mouse granulocyte-macrophage colony-stimulating factor (GMCSF) (R&D systems, Cat. No. 415-ML).
j) 30 ng/ml mouse G-CSF (R&D systems, Cat. No. 414-CS).
k) 5 ng/ml mouse M-CSF (R&D systems, Cat. No. 416-ML).
l) 5 ng/ml mouse IL-6.
m) IMDM to the final volume.

In Vitro Hematopoietic Differentiation of Murine ES Cells:
Primary Differentiation Step, Formation of EBs Two different culture methods usually have been used to promote hematopoietic differentiation: 1) Methylcellulose-based semisolid media, a highly viscous media that does not encourage cellular migration or aggregation once seeded; 2) Liquid suspension culture, where cells are free to aggregate and move within the culture media.

Methylcellulose-Based Semisolid Culture
1. Two days before setting up differentiation, split ES cells ($4 \times 10^5$ ES cells per 60-mm dish) into ES-IMDM medium without feeder cells in the dishes. All plates should be gelatinized.
2. Change the medium the next day.
3. Aspirate the medium from the dishes.
4. Add 1 ml of trypsin-EDTA, swirl, and remove quickly.
5. Add 1 ml trypsin and wait until cells start to come off. It usually takes about 1-2 min.
6. Stop the reaction by adding 1 ml FBS and 4 ml IMDM and pipette up and down to make single cell suspension.
7. Centrifuge for 5-10 min at 228 g.
8. Wash the cell pellet in 10 ml IMDM (without FBS).
9. Resuspend the cell pellet in 5 ml IMDM (with 10% FBS), count viable ES cells.
10. For differentiation as follows: add 6,000-10,000 ES cells per milliliter of methylcellulose differentiation media to obtain day 2.75-3 EBs. Add 4,000-5,000 cells per milliliter to obtain day 4-5 EBs. Add 500-2,000 cells per milliliter to obtain day 6-10 EBs.
11. Place dishes into a larger covered Petri dish along with an open 35-mm Petri dish containing 3 ml of sterile water and incubate at 37° C. in a 5% $CO_2$ and moisture-saturated incubator until further analysis is performed.

Suspension Culture
1. Follow steps 1-10 as described for Methylcellulose-based semisolid culture.
2. Plate into low-adherence Petri dishes at $4 \times 10^5$ cells per dish. Small aggregates (simple EBs) will be visible in 24 h. These simple EBs can be transferred into methylcellulose between 24 and 48 h.
3. If continuing in the liquid culture system, the media must be changed every 3-4 days. The EBs will tend to aggregate into clumps with regions of necrosis. To avoid this, break clumps apart by using a large mouth pipet (25 ml) such that you do not disrupt the EBs themselves. Transfer the EBs to a tube and allow them to sink to the bottom. Carefully aspirate off the old media, replace with fresh medium, and replate into the Petri dish.

Harvest of ES Cell-Derived Embryoid Bodies (EBs)
1. For EBs in liquid: transfer media containing EBs into 50-ml tubes. Wash the plate with IMDM and incubate at room temperature for 10-20 min. EBs settle to the bottom of the tube. For EBs in methylcellulose: add equal volume of cellulose (2 U/ml, final 1 U/ml) and incubate 20 min at 37° C. Collect EBs in 50-ml tubes. Wash the plate with IMDM and add to the tube to ensure all EBs are collected. Incubate at room temperature for about 10-20 min and EBs will settle down to the bottom of the tube.
2. Aspirate off media, add Trypsin-EDTA, or collagenase.
a) For EBs up to 8 days old, add 2-3 ml Trypsin—EDTA and incubate for 2-3 min at 37° C. Add IMDM containing 5% FBS to neutralize trypsin. Disrupt EBs by passing through a 20-G needle on a 3-cc syringe three times.
b) For EBs 9 or more days old, add 2-3 ml of collagenase and incubate at 37° C. for 1 h, swirling gently following 30 min of incubation. Ensure the EBs remain in solution and are not on walls of tubes. Add IMDM containing 5% FBS to neutralize collagenase. Disrupt EBs by passing through a 20-G needle on a 3-cc syringe three times as above.
3. Transfer to a 14-ml tube and pellet cells by centrifugation at 350 g for 5-8 min.
4. Remove supernatant and resuspend the cells in a minimum volume of IMDM with 2% FBS.
5. Count the viable cells.

Second Differentiation Step, Clonal Assays of EBs
In the presence of vascular endothelial growth factor (VEGF) in methylcellulose cultures, these EB-derived precursors generate blast cell colonies that display hematopoietic and endothelial potential. These progenitors or BL-CFC are present transiently within the EBs for approximately 36 h, between day 2.5 and 4 of differentiation, preceding the onset of primitive erythropoiesis. The BL-CFC represents the in vitro equivalent of the hemangioblast and the earliest stage of hematopoietic. Beyond day 4 of differentiation, the number of BL-CFC declines with the commitment to the hematopoietic program with the appearance of significant numbers of primitive erythroid progenitors. Hematopoietic progenitors present within EBs are successfully analyzed by flow cytometry and by direct replating EB cells into methylcellulose cultures to measure the frequency of hematopoietic progenitors. Additionally, EB cells are sorted for early hematopoietic markers to further analyze their hematopoietic cell potential.

Hemangioblast Stage
Most BL-CFC express Flk1, and a subpopulation of Flk1+ cells also expresses the transcription factor Sc1. The lack of significant Flk1 expression indicates that the population has not yet progressed to the hemangioblast stage of development. Thus BL-CFC can be initially screened by levels of expression of the receptor Flk1 or other marker gene colonies. Blast colonies develop within 3-4 days of culture and are recognized as clusters of cells readily distinguished from secondary EBs developing from residual undifferentiated ES cells. Blast colonies and secondary EBs are the predominant type of colonies present in these cultures.

1. Add 3–6×10⁴ EB cells per milliliter of hemangioblast colony methylcellulose mixture. Add 1 ml of the mixture into each of 35-mm Petri dishes.
2. Gently swirl the dishes to disperse the mixture evenly.
3. Place dishes into a larger covered Petri dish along with an open 35-mm Petri dish containing 3 ml of sterile water and incubate at 37° C. in a humidified 5% $CO_2$ incubator for 3-4 days.
4. For FACS analysis, antibody staining is carried out as follows: Cells are collected and resuspended in 100 µl of PBS containing 10% FBS and 0.02% sodium azide. An appropriate amount of antibody is added, and the cells are incubated on ice for 20 min. Following the staining step, the cells are washed two times with the same media and then resuspended in
300 µl of staining buffer, then transferred to a 5-ml polypropylene tube for analysis.
5. To analyze the hematopoietic of the blast colonies, individual colonies are picked from the methylcellulose and cultured further in hemangioblast expansion medium on matrigel-coated microtiter wells. After 4 days of growth, the non-adherent cells of each well are harvested and assayed for hematopoietic progenitor potential in 1 ml hematopoietic differentiation medium used for the growth of hematopoietic precursors.

Hematopoietic Stage

Shortly after the peak of the hemangioblast stage of development, committed hematopoietic progenitors are detected within the EBs by morphology or cytological staining. When EB cells are directly replated, day 5-6 EBs are typically used for a primitive erythroid colony, and day 7-10 EBs for definitive erythroid progenitor analysis. The following is the protocol for direct EB replating.

1. Prepare methylcellulose-based hematopoietic differentiation medium.
2. Add 0.3 ml of cells at 1–5×10⁵ per milliliter to each tube containing the 3-ml hematopoietic differentiation medium and vortex thoroughly and allow to stand 3-5 min.
3. Plate 1.1 ml of the cell suspension per 35-mm low-adherence Petri dish.
4. Place dishes into a larger covered Petri dish along with an open 35-mm Petri dish containing 3 ml of sterile water and incubate at 37° C. in a humidified 5% $CO_2$ incubator.
5. Primitive erythroid colonies are scored at day 5-6 of culture, whereas definitive erythroid, macrophage, and multilineage colonies are counted after 7-10 days of culture.

Globin genes are isolated from any of the number of clones containing portions of the β-globin locus of humans are widely available in the art. Globin genes from patients suffering from hemoglobinopathies may be cloned by preparing a genomic library from DNA harvested from the patient (for example, from leukocytes) using methods known in the art and then using globin gene probes derived from cloned genes of the normal globin locus (which are widely available) to identify, by hybridization, genomic clones containing globin gene sequences (Benton and Davis *Science* 196:180 (1977); Grunstein and Hogness, *Proc. Natl. Acad. Sci.* 72:3961-3965 (1975)). Genomic clones identified in this manner may then be analyzed by restriction mapping and sequencing techniques to potentially identify genes bearing mutations.

DNase I hypersensitivity sites associated with the β-globin gene locus may be used according to the invention to direct the expression of any gene of interest in erythroid cells. DNase I HS sites derived from human β-globin genes may be used, as may any DNase I HS site from any erythroid specific gene whatsoever, provided that the DNase I HS site in question results in substantial transcription of the gene in question in erythroid cells. According to the invention, β-globin DNase I HS sites HIS, HS II, HS III, HSIV, HSV or HSVI. Any combination thereof, or any duplication thereof, may be used according to the invention; it appears however, that a single copy of HS I may not be sufficient to effectively boost transcription.

Globin DNase I HS sites may be isolated from any of the cloned regions of the globin clusters widely available to those in the art, or alternatively, from the following recombinant DNA molecules described herein including, HS I-V-β and HSI-V which have been deposited with the American Type Culture Collection (ATCC) and assigned the accession numbers 40666 and 40664 respectively. In addition, DNase I HS sites that have been mapped may be obtained using any clone of the globin locus and then using the standard technique of chromosome walking to reach a previously identified DNase I HS site. In addition, new erythroid-specific DNase I hypersensitivity sites may be identified by sensitivity to DNase I digestion and utilized according to the invention.

The extent of expression of the tumoricidal molecule can be controlled by altering the number of DNase I HS sites in the recombinant constructs of the invention. In general, the greater the number of HS sites included, the higher the level of expression of the gene of interest that will result.

The tumoricidal transgene and at least one β-globin HS site may be inserted into a cloning vector which can be used to transfect and transform appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endo-nuclease cleavage sites into the oligonucleotide primers used in polymerase chain reaction to facilitate insertion into vectors. Any site desired may be produced by ligating nucleotide sequences (linkers) onto the DNA termini; these ligated linkers may comprise specific chemically synthesized oligonucleotides encoding restriction endonuclease
recognition sequences. In an alternative method, the cleaved vector and gene of interest may be modified by homopolymeric tailing. In addition, in particular embodiments of the invention the recombinant nucleic acid molecule of the invention may be inserted into any viral vector capable of infecting erythroid cells, including but not limited to lentiviral vectors, retroviruses and Friend Virus A provided that the dominant element controlling transcription of the gene of interest is the erythroid-specific HS site and the β-globin promoter/enhancer.

Provided an erythroid-specific DNase I HS site is included, the recombinant nucleic acid vectors of the invention may include any transcriptional promoter known in the art, including but not limited to the SV40 early promoter region (Bernoist and Chambon *Nature* 290:304-310 (1981), the promoter contained in the 3' long terminal repeat of Rous sarcoma virus (Yamamoto. et al., *Cell* 22:787-797 (1980), the herpes virus thymidine kinase promoter (Wagner et al., *Proc. Natl. Acad Sci* 78:144-1445 (1981)). The regulatory sequences of the metallothionine gene (Brinster et al., *Nature* 296:39-42 (1982) and the following animal transcriptional control regions, which exhibit tissue specificity and have been utilized in transgenic animals: elastase I gene control region which is active in pancreatic acinar cells (Swift et al., *Cell* 38:639-646 (1984); Ornitz et al., *Cold Spring Harbor Symp.*

Quant. Biol. 50:399-409 (1986); MacDonald *Hepatology* 7:425-515 (1987); insulin gene control region which is active in pancreatic beta cells (Hanahan *Nature* 315:115-122 (1985). Immunoglobulin gene control region which is active in lymphoid cells (Grosschedl et al., *Cell* 38:647-658 (1984); Adames et al., *Nature* 318:533-538 (1985); Alexander et al., *Mol Cell Biol*. 7:1436-1444 (1987), mouse mammary tumor virus control region which is active in testicular, breast, lymphoid and mast cells (Leder et al., *Cell* 45:485-95 (1986), albumin gene control region which is active in liver (Pinkert et al., *Genes Dev* 1:268-276 (1987), alpha-fetoprotein gene control region which is active in liver (Krumlauf et al., *Mol Cell Biol* 5:1639-1648 (1985); Hammer et al., *Science* 235: 53-58 (1987), alpha 1-antitrypsin gene control region which is active in the liver (Kelsey et al., *Gene Dev* 1:161-171 (1987), beta-globin gene control region which is active in myeloid cells (Mogram et al., *Nature* 315:338-340 (1985); Kollias et al., *Cell* 46:89-94 (1986), myelin basic protein gene control region which is active in oligodendrocyte cells in the brain (Readhead et al., *Cell* 48:703-712 (1987), myosin light chain-2 gene control region which is active in skeletal muscle (Sani et al., *Nature* 314:283-286 (1985) and gonadotropic releasing hormone gene control region which is active in the hypothalamus (Mason et al., *Science* 234:1372-1378 (1986)).

Transfection of cell lines may be performed by the DEA dextran method (McCutchen & Pagano *J Natl Cancer Inst* 41:351-357 (1968)), the calcium phosphate procedure (Graham et al., *J Virol* 33:739-748 (1973)) or by any other method known in the art including but not limited to microinjection, lipofection and electroporation.

The recombinant molecules of the invention may be used to induce expression of the tumoricidal transgene in erythroid cells due to the presence of the erythroid-specific DNase I HS sites. In a preferred embodiment of the invention, the recombinant molecules of the invention may be used to produce a tumoricidal transgene product in the erythroid cells of a human or non-human animal. According to the present invention, erythroid cells may be harvested and the tumoricidal protein product may be harvested and identified by lysing the cells and purifying the protein product using methods known in the art including but not limited to chromatography (e.g. ion exchange affinity, and sizing column chromatography, centrifugation differential solubility, electrophoresis, or any other standard technique for the purification of proteins). It may be necessary to transform the cells, using any method known in the art while the cells are in a relatively undifferentiated state, and then to induce the cells to differentiate and subsequently produce the tumoricidal protein. For example, and not by way of limitation, the recombinant molecules of the invention may be transfected into erythroid cells which may then be induced to differentiate (e.g. using dimethylsulfoxide).

Use of constitutive multi-drug resistant genes in SS erythroid precursors for conjoint delivery of chemotherapy and toxins to tumors The instant invention envisions chemotherapeutically resistant SS progenitor cells as useful in the present invention. Naïve SS progenitor cells contain the multi-drug resistance gene, MDR1 encoding an ATP-dependent plasma membrane efflux pump, P-glycoprotein (P-gp) and ABG transporters. The P-gp extrudes a broad range of hydrophobic drugs from cells, including vinca alkaloids, anthracyclines, epipodophyllotoxins, colchicine, actinomycin D and taxotere. These SS progenitor cells are used as a cell line in the naïve state or transduced with tumoricidal molecules such as superantigens or superantigen homologues and superantigen (or superantigen homologue)-tumor specific antibody conjugates, superantigen fragments, toxins such as pseudomonas exotoxin, diphtheria, ricin, shiga toxins, Panton Valentine leucocidins as described above. Exposure to cytolytic chemotherapeutic agents during the loading and extrusion process does not injure the SS progenitor cells and in particular spares their genetic and secretory apparatus.

Chemotherapeutic resistance in SS progenitor cells occurs by uninterrupted or periodic exposure to the chemotherapeutic for periods ranging from 1 hour to 2 weeks. Once the chemotherapeutic is removed from the media the drug is actively expelled from the SS progenitor cell 4 to 10 times faster than a cell which is not drug resistant. Thus shortly after removal of the chemotherapeutic agent from the media the cells are collected and administered to the patient. Within minutes after injection SS progenitor cells become entrapped in the tumor endothelium and actively extrude as much as 50% of their intracellular chemotherapeutic content into the tumor parenchyma.

Chemotherapeutic resistance is also be induced in naïve SS progenitor cells or SS progenitors that have been transduced previously as described above with the vectors encoding tumoricidal molecules such as superantigens and homologues, staphylococcal enterotoxin fragments, superantigen and superantigen homologue-tumor specific antibody conjugates, pseudomonas exotoxins, diphtheria, ricin etc. Thus when the SS progenitor cell adheres to the tumor endothelium it actively extrudes a chemotherapeutic and secretes a tumoricidal toxin. In addition, as the SS progenitor cell undergoes oxidant-induced lysis it releases constitutive heme. All three tumoricidal molecules work synergistically to kill the tumor.

Constitutive MDR1 can be combined with other drug resistance genes transduced into the SS progenitor cells in order to broaden the spectrum of drugs that are extruded from the cell. For instance, the wild-type version of human MDR1 (containing Gly at position 185) confers preferential resistance against vinblastine while the mutant with Val at position 185 confers resistance to colchicine).

SS progenitor cells can also be loaded with cytotoxic drugs in prodrug form. Loading of the cells with chemotherapeutic drugs or prodrugs is accomplished by osmotic diffusion or electroporation and other methods well established in the art. The drug metabolizing cytochrome P450s (CYPs) notably 1A, IB, 2C, 3A, 2D subfamily members have been identified in a wide range of human cancers. Individual tumor types have distinct P450 profiles as studied by detection of P450 activity, identification of immunoreactive CYP protein and detection of CYP mRNA. Selected P450s, especially CYP1B1, are overexpressed in tumours including cancers of the lung, breast, liver, gastrointestinal tract, prostate, bladder. Several prodrug anti-tumour agents have been identified as P450 substrates. Those in clinical use include prodrug alkylating agents cyclophosphamide, ifosphamide, dacarbazine, procarbazine, Tegafur, a prodrug fluoropyrimidine, methoxymorphylinodoxorubicin, a metabolically activated anthracycline, as well as flutamide and tamoxifen, two non-steroidal hormone receptor antagonists that are significantly more active following CYP-hydroxylation. New agents selectively dependent on tumor CYP activation include 2-(4-aminophenyl)benzothiazoles exclusively in CYP1A1 inducible tumors. Some CYPs operate most effectively under hypoxemic conditions. Indeed, bioreductive prodrugs such as the indolequinone AQ4N (a CYP3A substrate) and MUP 98176 are activated to cytotoxic metabolites specifically in hypoxic tumor regions after bioreduction.

In vivo, bioreductive prodrugs are transported out of the SS progenitor cells and taken up by surrounding tumor cells. Tumor cells overexpress oxyreductase systems cytochrome P450 enzymes and/or its congeners, oxidize prodrugs to their reduced and active state resulting in oncolysis. Several of these active metabolites are significantly more cytotoxic under hypoxemic conditions within tumor cells. As an example, SS erythroid precursors are rendered drug resistant after continuous exposure to small doses of Adriamycin for 120 hours after which Adriamycin is completely effluxed from the cell over a period of 30 minutes (Yanovich et al., Cancer Res. 44: 4499-4505 (1989)). In the present invention SS hematopoietic precursors or SS progenitor cells are exposed to various forms of chemotherapy and the optimal time course for development of drug resistance and release following discontinuation of drug is determined. After induction of drug resistance, these cells ($10^8$-$10^{13}$) are infused into tumor-bearing hosts where they deposit in tumors and actively expel their drug directly into the tumor parenchyma. Optionally, ex vivo exposure of both drug resistant and non-drug resistant cells (incubated with a tumoricidal drug for 8-120 hours) to light radiation (200-900 nM) that induces a hemolysis t½ of 20-60 minutes is useful to ensure release of the drug from the carrier SS cells, SS progenitors or erythroleukemia cells once they have deposited in the tumor vasculature. In this way chemotherapy can be specifically targeted to and concentrated in the tumor.

Likewise, nucleic acids encoding monoclonal antibodies specific for epitopes expressed on tumor cells, tumor parenchyma or tumor vasculature can be transfected into the SS progenitor or erythroleukemia cells using described above. An example of one such monoclonal antibody is Avastin specific for VEGF receptors on tumor endothelium. SS cells or erythroleukemia cells localized in the tumor vasculature release the VEGF-specific monoclonal antibodies into the tumor mileau. The tumor neovasculature is within easy reach of the recombinant antibodies and expresses epitopes expressed on tumor endothelium and endothelial matrix such as VEGF and laminin-α5. In this way, anti-angiogenic therapy such anti-VEGF is concentrated at the site of its cognate ligand in the tumor neovasculature, produces an increase in the therapeutic index of the drug and reduction in its systemic side effects. The compositions of the claimed invention are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas.

The compositions are also be useful for the prevention of metastases from the tumors described above either when used alone or in combination with radiotherapeutic, photodynamic, and/or chemotherapeutic treatments conventionally administered to patients for treating disorders, including angiogenic disorders. Treatment of a tumor with surgery, photodynamic therapy, radiation and/or chemotherapy is followed by administration of the compositions to extend the dormancy of micrometastases and to stabilize and inhibit the growth of any residual primary tumor or metastases. The compositions can be administered before, during, or after radiotherapy; before, during, or after chemotherapy; and/or before, during, or after photodynamic therapy.

The present invention contemplates that erythrocytes or erythroblasts from patients with any form of sickle hemoglobinopathy are useful. These include erythrocytes or erythroblasts from hemizygous sickle S and A hemoglobin, sickle hemoglobin-C disease, sickle beta plus thalassemia, sickle hemoglobin-D disease, sickle hemoglobin-E disease, homozygous C or C-thalassemia, hemoglobin-C beta plus thalassemia, homozygous E or E-thalassemia. Indeed, any erythrocyte or erythroblasts with or without sickle hemoglobin expressing receptors capable of binding to tumor neovasculature are useful in the inventions described herein. Particularly useful are those cells which express hemoglobin S in combination with other types of hemoglobin. Both mature and nucleated forms of these cells are useful. In addition, the present invention contemplates that normal or leukemic erythrocytes or their nucleated progenitors transduced with hemoglobin genes from patients with hemoglobinopathies to produce a cell that behaves substantially like an SS or SA erythrocyte or erythrocyte precursor is useful. The present invention also contemplates that normal or sickle erythrocytes or sickle variants, e.g., HbSC cells, and nucleated progenitors which are upregulated by hormones, cytokines, biologically active agents, drugs, chemical or physical treatments to express adhesive properties or to enhance expression of adhesive properties are also useful in this invention.

SS erythroid progenitor cells, mature SS cells or erythroleukemia cells ($10^5$-$10^{11}$) synthesizing a tumoricidal transgene preferably a superantigen or superantigen-tumor specific monoclonal antibody conjugate or siRNAs are administered parenterally every other day for up to 6 days preferably intravenously to tumor bearing mice in protocols described in detail in the section on tumor models and outcomes. These cells localize in tumor sites where they occlude tumor neovessels, and secrete their tumoricidal protein into the tumor parenchyma. The tumor killing effect is augmented by prior or concomitant treatment with a heme oxygenase inhibitor and chemotherapy as described in the section on heme oxygenase inhibitors and chemotherapy and Example 2.

SS cells, erythroid progenitors/erythroblasts transduced by genomic oncolytic viral DNA comprising SS β-globin promoter/enhancer and LCR The present invention contemplates infecting SS cells, erythroid progenitors/erythroblasts and erythroleukemia cells with the lentiviral vector described above containing genomic DNA of an oncolytic virus under control of the β-globin promoter/enhancer. The genomic viral DNA vector may retain its promoter or its promoter may be removed before subcloning into the lentiviral vector. The transduced erythroid cells containing the lentiviral vector synthesize the oncolytic virus are capable of differentiating into mature RBCs. Despite enucleation the latter cells are capable of sustaining oncolytic viral synthesis. Because these cells do not produce interferon, interferon-dependent oncolytic viruses replicate freely in the mature SS RBC.

In an example of this method, plasmid pVSV-XN2 (Lawson N D et al., Proc Natl Acad Sci 92:4477-4481 (1995)) is used which contains the entire vesicular stomatitis virus (VSV) genome and gives rise to infectious VSV. It has unique XhoI site flanked by T7 bacteriophage promoter and the VSV N nucleic acids. It displays genes encoding the five proteins N, P, M, G, and L and the pBSSK+ vector sequence as well as regions generated by PCR. Transcription from the T7 promoter generates the complete positive-strand VSV RNA. Plasmid pVSV-XN2 with its T7 reverse transcriptase promoter of pVSV-XN2 is subcloned into the lentiviral vector substituting for the β-globin coding region. This may be enhanced by digestion of pVSV-XN2 with XhoI. Transcription of infectious oncolytic/oncotropic recombinant (rVSV) is thus under control of the β-globin promoter/enhancer as described above. SS erythroblasts/progenitors or erythroleukemia cells are infected with this vector and differentiate in vitro into mature SS cells containing the VSV virus using methods described in the preceding section.

The mature SS cells, SS progenitors, erythroblasts or erythroleukemia cells ($10^5$-$10^{h1}$) producing the oncolytic virus are administered parenterally (preferably by injection or infusion intravenously or intraarterially) to tumor bearing hosts as described herein in the "Tumor Models" section and deposit in the tumor neovasculature where they undergoes hemolysis releasing oncolytic virus particles and/or tumoricidal molecules into the tumor parenchyma. DNA encoding any oncolytic virus or oncolytic viral fragment or viral homologue optionally containing a tumoricidal transgene is useful in this invention. Oncolytic viral genomes that are useful in the above method include but are not limited to measles virus (Schneider et al., *J Virol* 74:9928-36 (2000)); reovirus (Roner et al., *Proc Natl Acad Sci* 98: 8036-8041 (2001)); Sindbis virus (Strauss et al., *J Virol* 133:92-110 (1984)); Semliki forest virus (Kaariainen et al., *J. Cell Sci Suppl*. 7: 231-250 (1987)); Venezuelan equine encephalitis virus, (Kinney et al., *Virology* 191:569-580 (1992)); Newcastle disease virus (NCBI GenBank AF309418); poliovirus; (Racaniello et al., *Proc. Natl. Acad. Sci*. 78: 4887-4891 (1981)); herpes simplex virus (NCBI GenBank Z86099). Viral vectors for this purpose may be genomic viral DNA or RNA or a fragment of a homologue of viral DNA or RNA.

The above viral genome also incorporates nucleic acids encoding tumoricidal molecules and siRNAs. Tumoricidal transgenes including but not limited to IL-4, IFN-β, and TNFα are useful. siRNAs are also useful in silencing tumor cell oncogenes, or nucleic acids encoding cyclins, VEGF, hypoxia inducible elements, heme oxygenase, catalase, superoxide dismutase or IFN-β initiator genes, any anti-apoptotic, pro-angiogenesis, pro-proliferative or pro-metastatic molecule. Tumoricidal molecules and siRNAs are inserted between the G and L nucleic acids of the pVSV-XN2 vector (Obuchi M et al., *J Virol* 77: 8843-56 (2003); Fernandez M et al., *J Virol* 76:895-904 (2002)). Tumoricidal transgenes are amplified from pLEGFP-C1 (Clontech Laboratories, Palo Alto, Calif.) plasmids, by PCR. For IL-4 and IFN-β, the primers (SEQ ID NO:16) 5'GGCACTCGAGATGGGTCT-CAACCCCCAGCTAGTTG and (SEQ ID NO:17) 5'GCCGTCTAGACTACGAGTAATCCATTTG-CATGATGC are used (foreign gene is in bold). Substitution mutations in the M molecule of the VSV have been shown to inactivate the interferon activator in tumor cells. This construct is also useful in the present invention under control of the SS β-globin promoter/enhancer (Stojdl D F et al., *Nat. Med*. 6: 821-825 (2000); Lichty B D et al., *Hum Gene Ther* 15: 821-831 (2004)). Indeed SS β-globin promoter/enhancer promoter is useful with any alteration of the VSV viral genome that improves viral oncotropic and/or oncolytic activity.

Pseudotyping Viruses with Erythrocyte Binding Ligands and Adaptor Molecules to Facilitate Infection of Mature SS Erythrocytes The present invention contemplates SS erythroid progenitor/erythroblasts, erythroleukemia cells or mature SS cells infected with oncotropic/oncolytic viruses pseudotyped for binding to SS erythrocyte receptors. Erythrocyte binding ligands are incorporated genetically into these oncotropic/oncolytic viral DNA. Erythrocyte binding ligands useful for this purpose include the erythrocyte binding antigen 175 (EBA-175) from *P. falciparum* that binds glycophorin A and the Duffy blood group binding ligand from *Plasmodium vivax* and *Plasmodium knowlesi* merozoites that binds the Duffy blood group expressed on SS erythrocytes during invasion. Nucleic acids encoding the erythrocyte binding ligand 175 (EBA-175) and the Duffy binding ligand are provided in Tolia et al., *Cell* 122:183-193 (2005) and NCBI XM_001351282.1 (XP_001351318.1) respectively. DNA encoding these ligands is integrated into genomic DNA of any oncolytic virus, viral fragment or viral-tumoricidal transgene conjugates endowing the virus with pseudotropism for the mature SS RBCs. Methods for incorporation of the new viral pseudotype into genomic DNA of an oncolytic virus are given below.

Alternatively, oncolytic viruses such as adenovirus are fitted with an adaptor molecule that binds to an erythrocyte membrane receptor, e.g., Duffy receptor, glycophorin A and a viral epitope. Methods for synthesis of adapter molecules using receptor ligand complexes, chemical conjugation, avidin-biotin, monoclonal antibodies are given in Waehler et al., *Nat Rev Gen* 8: 573-587 (2007) incorporated by reference and its references. Viruses possessing erythrocyte binding ligands via genomic integration or adaptor molecules are used to infect mature SS erythrocytes or erythroblasts by incubation ex vivo at 1-300 MOIs. The viral-infected mature SS cells are harvested and $10^5$-$10^{11}$ cells and injected intravenously into tumor bearing mice as described in section on "Tumor models."

SS cells are also loaded with viruses via electroporation or with the aid of fusion molecules (e.g., GP64 or GP64-6HIS) that facilitate the entry of virus into cells. These include but are not limited to Gp64, a homotrimeric membrane glycoprotein, which is polarly present on the rod-shaped virion of Baculovirus. It consists of 512 amino acids with four glycosylation sites at asparagine residues and has N-terminal signal sequence (20 aa), oligomerization and fusion domains and a hydrophobic transmembrane domain near the C-terminus (7 aa). Gp64 causes pH-mediated envelope as do Ld130 and G-protein of vesicular stomatitis virus. Other viral fusion proteins useful in this invention, i.e., capable of infecting mature SS cells, SS progenitor or erythroblasts and erythroleukemia cells are disclosed in Verhoeyen et al., *J Gene Med* 6: S83-S94 (2004)). These molecules can be incorporated directly into the oncolytic viral genome as described above. Additional methods for using these agents to promote fusion of viruses with RBCs are well established in the prior art at a MOI of 1 or greater. Any oncolytic virus can be introduced into mature SS erythrocytes, SS erythroblasts, progenitors or erythroleukemia cells by genetic integration of erythrocyte ligands and/or fusion molecules with or without conventional electroporation. These include but are not limited to vesicular stomatitis virus, measles virus, reovirus, herpes simplex virus, Sindbis virus, Semliki forest virus, Venezuelan equine encephalitis virus, Newcastle disease virus, parvovirus and poliovirus.

Mature SS cells, SS erythroid progenitor cells or erythroleukemia cells ($10^5$-$10^{11}$), synthesizing an oncotropic/oncolytic virus optionally incorporating nucleic acids encoding a tumoricidal molecule and/or siRNAs are administered parenterally every other day for up to 6 days preferably intravenously to tumor bearing mice as described in the section on "Tumor models" and localize in tumor sites where they occlude tumor neovessels. These cells ultimately lyse and induce tumor killing via release of constitutive heme, oncolytic virus and associated tumoricidal molecules into the tumor parenchyma. Vaso-occlusion and hemolysis of the SS erythrocytes ensues and oncolytic virus is shed from the hemolyzed SS cells to infect and lyse adjacent tumor cells. The tumor killing effect is augmented by prior or concomitant treatment with a heme oxygenase inhibitor and chemotherapy as described in the section on chemotherapy and Example 2.

Tumor Cells and T Cells Transduced with the SS Hemoglobin Genes

The present invention contemplates transduction of T cells, tumor cells with metastatic phenotype and erythroleukemia cells with the lentiviral vector comprising the 2.3-kb recombinant human $\beta^S$ coding region substituted for the $\beta$-globin coding region as described in the preceding section and FIG. 4. The vector also contains the $\beta$-globin promoter/enhancer, locus control region (LCR) and at least one DNase hypersensitivity site. SS hemoglobin transduction confers rigidity to these tumor cells and T cells under deoxygenating conditions. Thus, like SS RBCs they are readily entrapped in the tortuous tumor neovasculature. Following transduction, tumor cells are optionally incubated with IFN-$\gamma$ that upregulates surface adhesion molecules and promotes adherence to the tumor vasculature.

Tumor cells and T cells are transduced with the lentiviral vector containing the $\beta^S$-globin coding region using electroporation, $Ca_2PO_4$, lipofectamine or other methods established in the art. The vectors comprise at least one of the major DNase I hypersensitivity sites associated with the $\beta^S$-globin locus. T cells or tumor cells are transfected with human $\beta^S$-globin genes under the transcriptional control of two $\beta$-globin locus DNase I hypersensitivity sites. The transfected T cells and/or tumor cells synthesize human SS hemoglobin.

An additional method for SS hemoglobin transfection of tumor cells and T cells utilizes the pcDNA3.1 directional Expression Kit (Invitrogen, Carlsbad, Calif., USA) expressing $\beta^S$- globin chain or a tumoricidal transgene described above. To generate a full length coding sequence of SS-beta chain, PCR is performed using cDNA that is reverse transcribed from a placental RNA obtained from a patient with homozygous sickle cell anemia. This reaction generates a 443 bp PCR product that contained CACC sequence in front of the ATG start codon and deletes TAG stop codon from the original SS beta globin sequence. The PCR product is electrophoresed with 2.0% NuSieve GTG agarose (Cambrex Bio Science Rockland Inc., Rockland, Me., USA) and stained with ethidium bromide. The proper size of the PCR product is excised and nucleic acid extracted with QIAquick Gel Extraction kit (QIAGEN, Tokyo, Japan). In all, 4 µl of gel-extracted PCR product is ligated into pcDNA3.1 expression vector with 30 min incubation at room temperature. The ligated plasmid is mixed with 100 µl of one-shot chemically competent *Escherichia coli* (Invitrogen), incubated on ice for 30 min, heat shocked at 42° C. for 30 seconds and placed on ice immediately. Transformed *E. coli* are incubated in 300 µl of SOC medium (Invitrogen) at 37° C. and then 100 µl of cultured SOC medium is plated on the LB plate containing 100/µg ml$^{-1}$ ampicillin and incubated at 37° C. overnight. Several colonies are selected and sequences confirmed. Proper clone is incubated in LB medium at 37° C. overnight and plasmid DNA is extracted using QIAfilter Plasmid Midi Kit (QIAGEN).

Expression vector pcDNA comprising the $\beta^S$-globin coding region is transfected into murine or human T cells or carcinoma cells. Human non-small cell lung adenocarcinoma cells (A539) and (H441) and murine mammary carcinoma 4T1 cells are used for transfection of the $B^S$-globin vectors. A539 and H441 cells express human alpha and beta globin chains and produce hemoglobin mRNA and hemoglobin protein. These carcinoma cells are used as a model of carcinoma cells generally. However, any other carcinoma cell line including but not limited to breast, lung, gastrointestinal, colorectal, kidney, bladder, brain, head and neck, neuroblastoma is useful in this invention. The AT539 and H441 cells are maintained in media as given in Table 2 of Brower et al. *Cancer Res* 46: 798-806 (1986) incorporated by reference in entirety. In short, carcinoma cells are maintained as a monolayer culture in plastic tissue culture flasks in Dulbecco's modification of Eagle's minimum essential medium with 10% heat inactivated (56° C., 30 min) fetal calf serum containing 200 IU/ml penicillin G and 200 µg/ml streptomycin. Cultures are incubated at 37° C. The cell line is transferred by treatment with 0.1% trypsin in PBS with a 1:10 split every 10 to 14 days. A549 cells have been viably frozen in 7.5% DMSO at multiple passage levels over the past three years, and the frozen cells are maintained in liquid nitrogen (Lieber et al., *Int. J. Cancer:* 17, 62-70 (1976)).

4T1 mammary carcinoma cells are also used. They are cultured in a 24-well plate the cells reach 60-70% confluence within 24 hours. In all, 200 ng of pcDNA SS-Hgb is mixed in 50 µl of Opti-MEM I medium (Invitrogen) and siPORT XP-1 (Ambion, Austin, Tex., USA) in accord with XP1 to yield pcDNA ssHgb/XP-1 complex. The complex is transfected into arranged 4T1 cells and cultured up to 7 days. On days 0, 3, 5 and 7 cells are collected and RNA extracted with TRIzol (InVitrogen, Carsbad, Calif.). The exogenous expression of the SS-Hgb is confirmed with both SQ-PCR and Q-PCR.

Tumor cells such as non-small cell carcinomas and testicular tumors which constitutively express alpha globin (Newton et al., *J Biol Chem* 281: 5668-5676 (2006)) are particularly useful in this invention. In the case of tumor cells and T cells that do not express alpha-globin, it is necessary to transduce these cells with both SS $\beta$-globin and normal $\alpha$-globin genes in order to effect the expression of SS hemoglobin in the target cells. These two different transgenes can be expressed by two separate vectors using self-inactivating insulated lentiviral or other vectors carrying two internal independent promoters (Semple-Rowland S et al., *Molecular Vision* 13:200'-11 (2007); Klump H et al. *Gene Ther* 8: 811-817 (2001); Emerman & Temin *Mol Cell Biol.* 6: 792-800 (1986)). The most common approach to multiple gene transfer relies on using internal ribosome entry sites (IRESs)(Martinez-S alas E *Curr Open Biotech* 10: 458-464 (1999)). Coordinate transgenesis may also be employed using the coding regions for alpha and SS beta globin incorporated in lentiviral vectors carrying synthetic bidirectional promoters as described by (Amendola Metal., *Nature Biotechnol* 23:108-116 (2005)). The SS beta globin coding region and the normal alpha coding region are also cloned into lentiviral or other vectors containing dual promoter as described in Semple-Rowland S et al., supra (2007). Both molecules are expressed in the target cells leading to the appearance of functional SS hemoglobin. Sufficient guidance is provided in the references provided in this paragraph which are incorporated by reference and their references in entirety for the skilled scientist to actuate the invention.

The present invention contemplates replacement of the $\beta$-globin coding region by a tumoricidal transgene encoding a superantigen, superantigen-antibody conjugate or any tumoricidal molecule. This transgene in the lentiviral vector shown in FIG. 4 remains under the transcriptional control of the β-globin promoter/enhancer, LCR, and DNase I hypersensitivity sites as described above for β$^S$-globin. Methodology for construction of the lentiviral vector is described above. Tumoricidal transgenes useful in this vector include but are not limited to superantigens, superantigen mutants, superantigen conjugates and fusion proteins as described in Erlandsson E et al., *J Mol Biol* 333, 893-905 (2003) and Forsberg et al., U.S. Pat. No. 7,444,332, TNFα, IFN-α,β or γ, IL-12, pseudomonas exotoxins, diphtheria toxins, ricin toxin, non-enterotoxin staphylococcal toxins and Panton-Valentine exotoxin, streptococcal superantigens, pyrogenic exotoxins. Integration of these transgenes into the lentiviral or other vectors are carried out by methods well established in the art.

Tumor cells of all kinds are transfected including carcinomas, sarcomas, lymphoma and leukemia cells. Naïve T cell are useful but non-specific cytotoxic T cells or cytotoxic T cells with specificity for tumor associated epitopes or receptors are particularly preferred. Cytotoxic T cells specific for the human β-globin are particularly useful. They are primed by repeated exposure to the human β-globin and are specific for β-globin expressed in tumor neovascular pericytes by methods previously described (Komita et al., *Cancer Res* 68:8076-8084 (2008). These T cells are prepared and isolated by methods described in the art (Wonderlich et al., Induction and measurement of cytotoxic T lymphocyte activity *Curr Protocol Immunol Chapter* 3, Unit 3.11; 2006). Following transduction, tumor cells and T cells proliferate in tissue culture, the latter with the aid of IL-2. The cells are harvested and administered by well established methods for adoptive T cell transfer.

These tumor cells or T cells ($10^5$-$10^{11}$) transduced with nucleic acids encoding β$^2$-globin or tumoricidal transgene under the control of the β-globin regulatory regions in a lentiviral or other suitable vector are administered to tumor bearing mice parenterally preferably intravenously every other day for up to 6 days as described herein in the section on tumor models. Nude or SCID mice are used for implantation of the untransfected 4T1 and human carcinoma cell lines as detailed in Example 2. Tumors are allowed to grow to 0.5 cm in diameter which is usually achieved between days 4 and 6 after tumor implantation. The transfected cells are then injected and localize in tumor sites where they occlude tumor neovessels, ultimately lyse and induce tumor killing via release of constitutive heme, oncolytic virus and associated tumoricidal molecules into the tumor parenchyma. The tumor killing effect of the infused T cells or tumor cells is augmented by prior or concomitant treatment with a heme oxygenase inhibitor and chemotherapy using methodology described above and in Example 2.

Use of Sickle Erythroblasts, Erythrocytes, Erythroleukemia Cells In Vivo

Subjects

The subjects treated are preferably human subjects and any mammalian species in which treatment or prevention of cancer is desirable, particularly agricultural and domestic mammalian species.

Administration

Suitable methodology for administration of sickle erythrocytes, erythroblasts, sickle variants and erthroleukemia cells transduced with the various plasmids, vectors, oncolytic viruses, tumoricidal transgenes, proteins, antibodies, enzymes of the claimed invention is parenteral infusion or injection in a manner similar to a conventional blood transfusion with delivery between 5-1000 ml of cells/hr via a secure intravenous catheter.

Dose

An effective dose of sickle erythrocytes is administered to a subject in need thereof. A "therapeutically effective amount" is an amount of the therapeutic composition sufficient to produce a measurable response (e.g., a cytolytic response in a subject being treated). Actual dosage levels of active ingredients in the pharmaceutical compositions of the claimed compositions are varied so as to administer an amount that is effective to achieve the desired therapeutic response for a particular subject. The potency of a therapeutic composition can vary, and therefore a "therapeutically effective" amount can vary. However, using the assay methods described herein below, one skilled in the art can readily assess the potency and efficacy of a candidate modulator of this presently claimed subject matter and adjust the therapeutic regimen accordingly.

One of ordinary skill in the art can tailor the dosages to an individual patient, taking into account the particular formulation, method of administration to be used with the composition, and tumor size considering patient height and weight, severity and stage of symptoms, and the presence of additional deleterious physical conditions. Such adjustments or variations as well as evaluation of when and how to make such adjustments or variations are well known to those of ordinary skill.

Toxicity is assessed using criteria set forth by the National Cancer Institute and is reasonably defined as any grade 4 toxicity or any grade 3 toxicity persisting more than 1 week. Dose is also modified to maximize anti-tumor or anti-angiogenic activity.

Chemotherapeutic and Other Agents

Chemotherapeutic agents can be used before, together with or after parenteral/systemic-administration of sickle erythrocytes, their nucleated precursers, sickle hemoglobin variants, erythroleukemia cells to enhance the tumor-killing effect. The sickle erythrocytes are defined in Definitions on page 1 as mature sickled cells, their nucleated precursors, sickle hemoglobin variants and erythroleukemia cells. These cells in native form or transduced with viral vectors/transgenes or upregulated with adrenergic agents are delivered by injection, instillation or infusion by any route including intravenously, intramuscularly, intradermally, intravesicularly, intrathecally, intrapleurally, intrapericardially, subcutaneously, intraperitoneally, and any other parenteral route. Chemotherapy is administered by infusion, instillation or injection by any parenteral route such as intrathecally, intratumorally, intravenously, intratumorally, intramuscularly, intradermally, intravesicularly, intrathecally, intrapleurally, intrapericardially, subcutaneously, intraperitoneally concomitantly with sickle erythrocyte. Preferably chemotherapy is given together with, before or 1-12 days after sickled erythrocytes, including native transgenes and their homologues, fragments, fusion proteins or mixtures thereof alone. Anti-cancer chemotherapeutic drugs useful in this invention include but are not limited to antimetabolites, anthracycline, vinca alkaloid, anti-tubulin drugs, antibiotics and alkylating agents. Representative specific drugs that can be used alone or in combination include cisplatinum (CDDP), adriamycin, dactinomycin, mitomycin, caminomycin, daunomycin, doxorubicin, tamoxifen, paclitaxel, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, aminopterin, combretastatin(s) and derivatives and prodrugs thereof.

A variety of chemotherapeutic and pharmacological agents may be given separately. Those of ordinary skill in the art will know how to select appropriate agents and doses, although, as disclosed, the doses of chemotherapeutic drugs are preferably reduced when used in combination with sickle erythrocyte in the present invention.

Another newer class of drugs that are also termed "chemotherapeutic agents" comprises agents that induce apoptosis. Any one or more of such drugs, including genes, vectors, antisense constructs, siRNA constructs, and ribozymes, as appropriate, may be used in conjunction with sickle erythrocytes. Other agents useful herein are anti-angiogenic agents, such as Avastin, angiostatin, endostatin, vasculostatin, canstatin and maspin. Avastin or Bevacizumab is a recombinant humanized monoclonal antibody directed against vascular endothelial growth factor (VEGF). Human VEGF mediates neoangiogenesis in normal and malignant vasculature. It is overexpressed in most malignancies, and high levels have correlated with a greater risk of metastasis. Avastin or bevacizumab binds VEGF and prevents its interaction with receptors (Flt-1 and KDR) on the surface of endothelial cells. Avastin 5 mg/kg intravenously is given every 14 days until disease progression is detected. The initial dose of Avastin is delivered over 90 minutes as an IV infusion. sickle erythrocyte, preferably sickle erythrocyte, are administered before, during or after avastin and ususally given once or twice weekly for up to 10 weeks.

Chemotherapeutic agents are administered as single agents or multidrug combinations, in full or reduced dosage per treatment cycle. They can be administered before, during or after intrathecal or intratumoral, intravesicular and parenteral sickle erythrocyte composition. In a preferred schedule, the chemotherapeutic agent is administered within 36 hours of the last of two to four treatments of sickle erythrocyte compositions administered intrathecally (intrapleurally) or intratumorally or intravenously. The combined use of the preferred sickle erythrocyte compositions with low dose, single agent chemotherapeutic drugs is particularly preferred. Indeed, this synergy of sickle erythrocyte with chemotherapy allows the use of the more toxic superantigens in lower and subtoxic doses as a means of priming a tumor for killing by chemotherapy. The choice of chemotherapeutic drug in such combinations is determined by the nature of the underlying malignancy. For lung tumors, cisplatinum is preferred. For breast cancer, a microtubule inhibitor such as taxotere is the preferred. For malignant ascites due to gastrointestinal tumors, 5-FU is preferred. "Low dose" as used with a chemotherapeutic drug refers to the dose of single agents that is 10-95% below that of the approved dosage for that agent (by the U.S. Food and Drug Administration, FDA). If the regimen consists of combination chemotherapy, then each drug dose is reduced by the same percentage. A reduction of >50% of the FDA approved dosage is preferred although therapeutic effects are seen with dosages above or below this level, with minimal side effects.

Tumors that are treated with sickle erythrocytes and chemotherapy are preferably at least 6 cm$^3$ and visible by x-ray, CT, ultrasound, bronchoscopy, laparoscopy, culdoscopy. Localization of the agent delivered is facilitated with fluoroscopic, CT or ultrasound guidance. Representative tumors that are treatable with this approach include but are not limited to hepatocellular carcinoma, lung tumors, brain tumors, head and neck tumors and unresectable breast tumors. Multiple tumors at different sites may be treated by intrathecal or intratumoral chemotherapy and parenterally administered sickle erythrocytes. The chemotherapeutic agent(s) selected for therapy of a particular tumor preferably is one with the highest response rates against that type of tumor. For example, for non-small cell lung cancer (NSCLC), cisplatinum-based drugs have been proven effective. Cisplatinum may be given parenterally or intratumorally. When given intratumorally, cisplatinum is preferentially in small volume around 1-4 ml although larger volumes can also work. The smaller volume is designed to increase the viscosity of the cisplatinum containing solution in order to minimize or delay the clearance of the drug from the tumor site. Other agents useful in NSCLC include the taxanes (paclitaxel and docetaxel), vinca alkaloids (vinorelbine), antimetabolites (gemcitabine), and camptothecin (irinotecan) both as single agents and in combination with a platinum agent.

The optimal chemotherapeutic agents and combined regimens for all the major human tumors are set forth in *Bethesda Handbook of Clinical Oncology*, Abraham J et al., Lippincott William & Wilkins, Philadelphia, Pa. (2001); *Manual of Clinical Oncology*, Fourth Edition, Casciato, D A et al., Lippincott William & Wilkins, Philadelphia, Pa. (2000) both of which are herein incorporated in entirety by reference.

In one embodiment, these recommended chemotherapeutic agents are used alone or combined with other chemotherapeutics in subtherapeutic or full doses. Alternatively, they may be administered parenterally by infusion, instillation or injection in doses 10-95% below the FDA recommended therapeutic dose. For intratumoral administration, the dose of a chemotherapeutic drug or biologic agent is preferably reduced 10- to 50-fold below the FDA-recommended dose for parenteral administration. Chemotherapy in full or reduced dose can be administered parenterally by injection, instillation or infusion parenterally by any route such as intrathecally, intratumorally intravenously, intramuscularly, intradermally, intravesicularly, intrathecally, intrapleurally, intrapericardially, subcutaneously, intraperitoneally concomitant with, before or after the SAg.

Cisplatinum has been widely used to treat cancer, with effective parenteral doses of 20 mg/m$^2$ for 5 days every three weeks for a total of three courses. Preferred dose per treatment for cisplatinum given intratumorally is 5-10 mg whereas for intrathecal use 20-80 mg may be administered. Intratumoral cisplatinum may be given every 7-14 days for 10-20 treatments whereas intrathecal cisplatinum may be given every 2-6 weeks for 10-20 treatments. Cisplatinum delivered in small volumes, e.g., 5-10 mg/1-3 ml saline is extremely viscous and may be retained in the tumor for a sustained period acting much like a controlled release drug from an inert surface. This is indeed one preferred mode of administration of cisplatinum when administered intratumorally with or without the superantigen.

When used before, together with or after sickle erythrocyte administration, doses of chemotherapy are used preferably in full doses but may be reduced 10-95% below the FDA recommended therapeutic dose. For intratumoral administration, the dose of a chemotherapeutic drug or biologic agent may be reduced 10- to 50-fold below the FDA-recommended dose for parenteral administration. Cisplatinum is preferably given systemically with effective doses of 20 mg/m$^2$ for 5 days every three weeks for a total of three courses. For intratumoral use a cisplatinum dose of is 5-50 mg/lesion is given whereas for intrathecal use 20-80 mg may be administered. Intratumoral cisplatinum may be given every 7-14 days for 10-20 treatments whereas intrathecal cisplatinum may be given every 2-6 weeks for 10-20 treatments. Cisplatinum delivered in small volumes, e.g., 5-10 mg/1-3 ml saline is extremely viscous and may be retained in the tumor for a sustained period acting much like a controlled release drug from an inert surface. However the cisplatinum or chemotherapy is also effective when given in non-viscous form before, together with or after egc SAg therapy.

Other agents and therapies that are useful together with or after parenteral (e.g., intratumoral, intrapleural, intraperitoneal, intravesicular, intravenous) sickle erythrocytes include, radiotherapeutic agents, antitumor antibodies with attached anti-tumor drugs such as plant-, fungus-, or bacteria-derived toxin or coagulant, ricin A chain, deglycosylated ricin A chain, ribosome inactivating proteins, sarcins, gelonin, aspergillin, restricticin, a ribonuclease, a epipodophyllotoxin, diphtheria toxin, or *Pseudomonas* exotoxin. Additional cytotoxic, cytostatic or anti-cellular agents capable of killing or suppressing the growth or division of tumor cells include anti-angiogenic agents, interferons alpha and gamma, apoptosis-inducing agents, coagulants, prodrugs or tumor targeted forms, tyrosine kinase inhibitors (Siemeister et al., *Cancer Metastasis Rev.* 17:241-8 (1998), antisense strategies, RNA aptamers, siRNA and ribozymes against VEGF or VEGF receptors (Saleh M et al., *Cancer Res.* 56:393-401 (1996); Cheng et al., *Proc Natl Acad Sci* 93:8502-7 (1996); Ke et al., *Int J. Oncol.* 12:1391-6 (1998); Parry et al., *Antisense Nucleic Acid Drug Dev.* 9:271-7 (1999)); each incorporated herein by reference. Any of a number of tyrosine kinase inhibitors is useful when administered before, together with, or after, intratumoral sickle erythrocytes. These include, for example, the 4-aminopyrrolo[2,3-d]pyrimidines (U.S. Pat. No. 5,639, 757). Further examples of small organic molecules capable of modulating tyrosine kinase signal transduction via the VEGF-R2 receptor are the quinazoline compounds and compositions (U.S. Pat. No. 5,792,771). Tarceva or Erlotinib attaches to EGF receptors and thereby blocks the EGF-mediated activation of tyrosine kinase. Tarceva 150 mg daily is administered before during or after parenteral (intrathecal, intrapleural and/or intravenous) sickle erythrocyte treatment and continued until disease progression or unacceptable toxicity occurs.

Other agents which may be employed in combination with sickle erythrocytes are steroids such as the angiostatic 4,9 (11)-steroids and C21-oxygenated steroids (U.S. Pat. No. 5,972,922). Thalidomide and related compounds, precursors, analogs, metabolites and hydrolysis products (U.S. Pat. Nos. 5,712,291 and 5,593,990) may also be used in combination with SAgs and other chemotherapeutic drugs agents to inhibit angiogenesis. These thalidomide and related compounds can be administered orally. Certain anti-angiogenic agents that cause tumor regression may be administered before, together with, or after, intrathecal, intrapleural, intratumoral, intravenous or parenteral sickle erythrocytes. These include the bacterial polysaccharide CM101 (currently in clinical trials as an anti-cancer drug) and the antibody LM609. CM101 has been well characterized for its ability to induce neovascular inflammation in tumors. CM101 binds to and cross-links receptors expressed on dedifferentiated endothelium that stimulate the activation of the complement system. It also initiates a cytokine-driven inflammatory response that selectively targets the tumor. CM101 is a uniquely antiangiogenic agent that downregulates the expression VEGF and its receptors. Thrombospondin (TSP-1) and platelet factor 4 (PF4) may also be used together with or after intratumoral SAg. These are both angiogenesis inhibitors that associate with heparin and are found in platelet α granules.

Interferons and metalloproteinase inhibitors are two other classes of naturally occurring angiogenic inhibitors that can be used before, together with or after intratumoral SAg. Vascular tumors in particular are sensitive to interferon; for example, proliferating hemangiomas are successfully treated with IFNα. Tissue inhibitors of metalloproteinases (TIMPs), a family of naturally occurring inhibitors of matrix metalloproteases (MMPs), can also inhibit angiogenesis and can be used in combination (before, during or after) the SAgs.

Radiation Therapy

Local radiation to any tumor sites or the mediastinum using the traditional standard dose of 60-65 gy is given concomitant with parenteral (e.g., intrathecal, intravenous, intravesicular, intrapleural, intralymphatic or intratumoral) administration of sickled erythrocytes. The radiotherapy is also be given before, during or after the sickled erythrocyte therapy but in either case there is a hiatus of no more than 30 days between the start of sickled erythrocyte therapy and the start or conclusion of radiotherapy. The median survival of patients given this type of radiotherapy alone is 5% at one year whereas the combined modality improves the median survival to more than two years.

In general, local radiation therapy alone has minimal efficacy in contributing to long-term disease control in advanced carcinomas. While radiation is an effective palliative measure to relieve symptoms, only a very small minority of patients achieve long-term survival when treated with radiation alone. However, radiation synergizes with sickle erythrocyte therapy in shrinking tumors and prolonging survival. Radiation is given to bulky or symptomatic lung lesions before, during or after sickle erythrocyte therapy. Preferably it is started 1-2 weeks before sickle erythrocyte treatment and continued simultaneously with sickle erythrocyte for 1-4 weeks until the full courses of sickle erythrocyte and radiation are completed. It may also be started after sickle erythrocyte treatment preferably within 24 hours of the last sickle erythrocyte treatment. Radiation may also be given to a malignant lesion or a tumorous body cavity before, together with or after the site has been injected with sickle erythrocyte intratumorally or intrathecally and/or systemic/parenteral chemotherapy. It may also be administered to a malignant lesion or site not injected specifically with sickle erythrocytes. In this case the sickle erythrocyte may be given systemically or intrathecally but not directly to the radiated tumor mass or site. Regimens for the use of intratumoral sickle erythrocytes and intratumoral and/or systemic use of chemotherapy are described in previous sections on chemotherapy. Radiation may also be used with chemotherapy in these settings together with systemic and/or intratumoral sickle erythrocyte treatment and intratumoral or systemic chemotherapy.

Radiation techniques are preferably continuous rather than split. Hyper-fractionated radiation, employing multiple daily fractions of radiation is preferred to conventionally fractionated radiation. Radiation doses vary from 40-70 gy although a dose between 60 and 70 gy dose is preferred. It is contemplated that radiation doses considered being subtherapeutic and up to 70% below the conventional doses are also useful when used before, during or after a course of sickle erythrocyte therapy.

Production and Isolation of Superantigens

The superantigens disclosed herein are prepared by either biochemical isolation, or, preferably by recombinant methods. The following SAgs, including their sequences and biological activities have been known for a number of years. Studies of these SAgs are found throughout the biomedical literature. For, biochemical and recombinant preparation of these SAgs see the following references: Borst D W et al., *Infect. Immun.* 61: 5421-5425 (1993); Couch J L et al., *J. Bacteriol.* 170: 2954-2960 (1988); Jones C L et al., *J. Bacteriol.* 166: 29-33 (1986); Bayles K W et al., *J. Bacteriol.* 171: 4799-4806 (1989); Blomster-Hautamaa, D A et al., *J. Biol. Chem.* 261:15783-15786 (1986); Johnson, L P et al., *Mol. Gen. Genet.* 203, 354-356 (1986); Bohach G A et al., *Infect. Immun.* 55: 428-433 (1987); Iandolo J J et al., *Meth. Enzymol*

165:43-52 (1988); Spero L et al., *Meth. Enzymol* 78(Pt A):331-6 (1981); Blomster-Hautamaa D A, *Meth. Enzymol* 165: 37-43 (1988); Iandolo J J *Ann. Rev. Microbiol.* 43: 375-402 (1989); U.S. Pat. No. 6,126,945 and U.S. provisional patent application 60/389,366 filed Jun. 15, 2002. These references and the references cited therein are hereby incorporated by reference in their entirety.

These SAgs are Staphylococcal enterotoxin A (SEA), Staphylococcal enterotoxin B (SEB), Staphylococcal enterotoxin C (SEC—actually three different proteins, SEC1, SEC2 and SEC3)), Staphylococcal enterotoxin D (SED), Staphylococcal enterotoxin E (SEE) and toxic shock syndrome toxin-1 (TSST-1) (U.S. Pat. No. 6,126,945 and U.S. provisional patent application 60/389,366 filed Jun. 15, 2002, and the references cited therein). The amino acids sequences of the above group of native (wild-type) SAgs are given in the following: SEA (Huang I Y et al., *J. Biol. Chem.* 262:7006-7013 (1987)); SEB (Papageorgiou A C et al. *J. Mol. Biol.* 277:61-79 (1998)); SEC1(Bohach G A et al., *Mol. Gen. Genet.* 209:15-20 (1987)); SEC2 (Papageorgiou A C et al., *Structure* 3:769-779 (1995)); SEC3 (Hovde C J et al., *Mol. Gen. Genet.* 220:329-333 (1990)); SED (Bayles K W et al., *J. Bacteriol.* 171:4799-4806 (1989)); SEE (Couch J L et al., *J. Bacteriol.* 170:2954-2960 (1988)); TSST-1 (Prasad G S et al., *Protein Sci.* 6:1220-1227 (1997))

The sections which follow discuss SAgs which have been discovered and characterized more recently.

Staphylococcal Enterotoxins SEG, SEH, SEI, SEJ, SEK, SEL, SEM, SEN, SEQ, SEP, SEQ, SER, SEU New Staphylococcal enterotoxins G, H, I, J, K, L and M (SEG, SEH, SEI, SEJ, SEK, SEL, SEM, SEN, SEQ, SEP, SEQ, SER, SEU; abbreviated below as "SEG-SEU") were described in Jarraud, S. et al., *J. Immunol.* 166: 669-677 (2001); Jarraud S et al., *J. Clin. Microbiol.* 37: 2446-2449 (1999) and Munson, S H et al., *Infect. Immun.* 66:3337-3345 (1998). SEG-SEU show superantigenic activity and are capable of inducing tumoricidal effects. The homology of these SE's to the better known SE's in the family ranges from 27-64%. Each induces selective expansion of TCR Vβ subsets. Thus, these SEs retain the characteristics of T cell activation and Vβ usage common to all the other SE's. RT-PCR was used to show that SEH stimulates human T cells via the Vα domain of TCR, in particular Vα (TRAV27), while no TCR VP-specific expansion was seen. This is in sharp contrast to all other studied bacterial superantigens, which are highly specific for TCR Vβ. Vβ binding superantigens form one group, whereas SEH has different properties that fit well with Vα reactivity. It is suggested that SEH directly interacts with the TCR Vα domain (Petersson K et al., *J Immunol.* 170:4148-54 (2003)). SEG and SEH of this group and other enterotoxins including SPEA, SPEC, SPEG, SPEH, SME-Z, SME-Z2, (see below) utilize zinc as part of high affinity MHC class II receptor. Amino acid substitution(s) at the high-affinity, zinc-dependent class II binding site are created to reduce their affinity for MHC class II molecules.

Jarraud S et al., 2001, supra, discloses methods used to identify and characterize egc SEs SEG-SEM, and for cloning and recombinant expression of these proteins. The egc comprises SEG, SEI, SEM, SEN, SEQ and pseudogene products designated ψent 1 and ψent 2. Purified recombinant SEN, SEM, SEI, SEQ, and SEGL29P (a mutant of SEN) were expressed in *E. coli*. Recombinant SEG, SEN, SEM, SEI, and SEQ consistently induced selective expansion of distinct subpopulations of T cells expressing particular Vβ genes.

Jarraud S et al., 2001, supra, indicates that the seven genes and pseudogenes composing the egc (enterotoxin gene cluster) operon are co-transcribed. The association of related co-transcribed genes suggested that the resulting peptides might have complementary effects on the host's immune response. One hypothesis is that gene recombination created new SE variants differing by their superantigen activity profiles. By contrast, SEGL29P failed to trigger expansion of any of 23 Vβ subsets, and the L29P mutation accounted for the complete loss of superantigen activity (although this mutation did not induce a major conformational change). It is believed that this substitution mutation located at a position crucial for proper superantigen/MHC II interaction.

Overall, TCR repertoire analysis confirms the superantigenic nature of SEG, SEI, SEM, SEN, SEQ. These investigators used a number of TCR-specific mAbs (Vβ specificity indicated in brackets) for flow cytometric analysis: E2.2E7.2 (Vβ2), LE89 (Vβ3), IMMU157 (Vβ5.1), 3D11 (Vβ5.3), CRI304.3 (Vβ6.2), 3G5D15 (Vβ7), 56C5.2 (Vβ8.1/8.2), FIN9 (Vβ9), C21 (Vβ11), S511 (Vβ12), INIMU1222 (Vβ13.1), JIJ74 (Vβ13.6), CAS1.1.13 (Vβ14), Tamayal.2 (Vβ16), E17.5F3 (Vβ17), βA62.6 (Vβ18), ELL1.4 (Vβ20), IG125 (Vβ21.3), IMMU546 (Vβ22), and HUT78.1 (Vβ23). Flow cytometry also revealed preferential expansion of CD4+ T cells in SEI and SEM cultures. By contrast, the CD4/CD8 ratios in SEQ-, SEN-, and SEG-stimulated T cell lines were close to those in fresh PBL.

Recombinant and biochemical preparation of the egc SEs is given in U.S. 60/799,514, PCTUS05/022638, US60/583,692, US60/665,654, US60/626,159 which incorporated by reference and their references in their entirety.

The amino acid sequences of SEG-SEU are as follows: SEG (Baba, T. et al., Lancet 359, 1819-1827 (2002)); SEG (Jarraud, S et al., *J. Immunol.* 166: 669-677 (2001)); SEH (Omoe, K. et al., *J. Clin. Microbiol.* 40: 857-862 (2002)); SEI (Kuroda, M. et al., *Lancet* 357 (9264), 1225-1240 (2001)); SEJ (Zhang S. et al., *FEMS Microbiol. Lett.* 168:227-233 (1998)); SEK (Baba T., et al., *Lancet* 359: 1819-1827 (2002)); SEL (Kuroda M. et al., *Lancet* 357: 1225-1240 (2001)); SEM (Kuroda M. et al., *Lancet* 357: 1225-1240 (2001)); SEN (Jarraud S et al., *J. Immunol.* 166: 669-677 (2001)); SEO (Jarraud S et al., *J. Immunol.* 166: 669-677 (2001)); vent/(Jarraud S et al., *J. Immunol.* 166: 669-677 (2001)); ψent 2 (Jarraud S et al., *J. Immunol.* 166: 669-677 (2001)); SEP (Kuroda M. et al., Lancet 357, 1225-1240 (2001); SEQ (Lindsay, J A et al., *Mol. Microbiol.* 29, 527-543 (1998)); SER Omoe K et al., ACCESSION BAC97795; SEU (Letertre C et al., *J. Appl. Microbiol.* 95, 38-43 (2003))

Streptococcal Pyrogenic Exotoxins (SpEs)

The SpE's SPEA, SPEB, SPEC, SPEG, SPEH, SME-Z, SME-Z2 and SSA are superantigens induce tumoricidal effects. SPEA, SPEB, SPEC have been known for some time and their structures and biological activities described in numerous publications.

SPEG, SPEH, and SPEJ genes were identified from the *Streptococcus pyogenes* Ml genomic database and described in detail in Proft, T et al., *J. Exp. Med.* 189: 89-101 (1999) which also describes SMEZ, SMEZ-2. This document also describes the cloning and expression of the genes encoding these proteins.

The smez-2 gene was isolated from the *S. pyogenes* strain 2035, based on sequence homology to the streptococcal mitogenic exotoxin z (smez) gene. SMEZ-2, SPE-G, and SPE-J are most closely related to SMEZ and SPEC, whereas SPEH is most similar to the SEs than to any other streptococcal toxin. As described by Proft, T et al supra, rSMEZ, rSMEZ-2, rSPE-G, and rSPE-H were mitogenic for human peripheral blood T lymphocytes. SMEZ-2 appears to be the most potent SAg discovered thus far. All these toxins, except rSPE-G, were active on murine T cells, but with reduced potency.

Binding to a human B-lymphoblastoid line was shown to be zinc dependent with high binding affinity of 15-65 nM. Analysis of competition for binding between toxins of this group revealed overlapping but discrete binding to subsets of class II molecules in the hierarchical order (SMEZ, SPE-C) >SMEZ-2>SPE-H>SPE-G. The most common targets for these SAgs were human Vβ2.1- and Vβ4-expressing T cells.

Streptococcus Pyrogenic Exotoxin A (SPEA)

SPEA can be purified from cultures of *S. pyogenes* as described by Kline et al., *Infect. Immun.* 64:861-869 (1996). Plasmids that include the spea1 gene which encode SPEA, and the expression and purification of recombinant SPEA ("rSPEA") are described by Kline et al., supra. The native SPEA sequence is given in Papageorgiou, A. C. et al., *EMBO J.* 18:9-21 (1999).

Streptococcus Pyrogenic Exotoxin B (SPEB)

Purification of native SPEB is described by Gubba, S. et al., *Infect. Immun.* 66: 765-770 (1998). Expression and purification of recombinant SPEB are also described in this reference. The native SPEB sequence is given in Kapur, V. et al., *Microb. Pathog.* 15:327-346 (1993).

Streptococcus Pyrogenic Exotoxin C(SPEC)

Methods of isolation and characterization of SPEC is carried out by the methods of Li, P L et al., *J. Exp. Med.* 186: 375-383 (1997). These references also describe T cell proliferation stimulated by this SAg and the analysis of its selectivity for TCR Vβ regions. The native sequence of SPEC is given in Kapur, V. et al., *Infect. Immun.* 60: 3513-3517 (1992).

Streptococcal Superantigen (SSA)

SSA is a ~28-kDa superantigen protein isolated from culture supernatants as described by Mollick J et al., *J. Clin. Invest.* 92: 710-719 (1993) and Reda K et al., *Infect. Immun.* 62: 1867-1874 (1994). SSA stimulates proliferation of human T cells bearing Vβ1, Vβ3, Vβ5.2, and Vβ15 in an MHC class II-dependent manner. The first 24 amino acid residues of SSA are 62.5% identical to SEB, SEC1, and SEC3. Purification and cloning of SSA is described in Reda K et al., *Infect. Immun.* 62: 1867-1874 (1994). The native sequence of SSA is given in Reda, K B. et al., *Infect. Immun.* 64: 1161-1165 (1996).

Streptococcal Pyrogenic Exotoxins G and H and SMEZ

The sequences of the more recently discovered Streptococcal exotoxin SAgs are provided below:

*Yersinia pseudotuberculosis* Mitogen (Superantigen) (YPM) Cloning, expression and purification of YPM is described by Miyoshi-Akiyama, T. et al., *J. Immunol.* 154: 5228-5234 (1995). The above reference described assays of YPM using lymphoid cells and murine L cells transfected with human HLA genes, including T cell proliferation and cytokine (IL2) secretion.

Staphylococcal Exotoxin Like Proteins (SET)

The identification characterization of the SETs (SET-1 and SET-2) and the cloning and purification of SET-1 is described in Williams, R. J. et al., *Infect. Immun.* 68: 4407-4414 (2000). This reference discloses the distribution of the set1 gene among Staphylococcal species and strains. The set1 nucleotide sequences are deposited in the GenBank database under accession numbers AF094826 (set gene cluster fragment), AF188835 (NCTC 6571 setl gene), AF188836 (FR1326 set1 gene), and AF188837 (NCTC 8325-4 set1 gene). Recombinant SET-1 protein stimulates production of the proinflammatory cytokines IL-1β, IL-6, and TNFα

Functional Homologues and Derivatives of Tumoricidal Proteins, Superantigens or Peptides The present invention contemplates, in addition to native proteins incorporated in the sickle cells, the use of homologues of native proteins that have the requisite biological activity to be useful in accordance with the invention.

Thus, in addition to native proteins and nucleic acid compositions described herein, the present invention encompasses functional derivatives, among which homologues are preferred. By "functional derivative" is meant a "fragment," "variant," "mutant," "homologue," "analogue," or "chemical derivative. Homologues include fusion proteins, chimeric proteins and conjugates that include a SAg portion fused to or conjugated to a fusion partner polypeptide or peptide. A functional derivative retains at least a portion of the biological activity of the native protein which permits its utility in accordance with the present invention. For superantigens, such biological activity includes stimulation of T cell proliferation and/or cytokine secretion, stimulation of T cell-mediated cytotoxic activity, as a result of interactions of the SAg composition with T cells preferably via the TCR Vβ or Vα region. For pseudomonas exotoxin A, a homologue must retain tumor cell cytolytic activity.

A "fragment" refers to any shorter peptide. A "variant" refers to a molecule substantially similar to either the entire protein or a peptide fragment thereof. Variant peptides may be conveniently prepared by direct chemical synthesis of the variant peptide, using methods well-known in the art.

A homologue refers to a natural protein, encoded by a DNA molecule from the same or a different species. Homologues, as used herein, typically share at least about 50% sequence similarity at the DNA level or at least about 18% sequence similarity at the amino acid level, with a native protein.

An "analogue" refers to a non-natural molecule substantially similar to either the entire molecule or a fragment thereof.

A "chemical derivative" contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

A fusion protein comprises a native protein, a fragment or a homologue fused by recombinant means to another polypeptide fusion partner, optionally including a spacer between the two sequences. Preferred fusion partners are antibodies, Fab fragments, single chain Fv fragments. Other fusion partners are any peptidic receptor, ligand, cytokine, domain ("ECD") of a molecule and the like.

The recognition that the biologically active regions of the proteins, for example, are substantially homologous, i.e., that the sequences are substantially similar, enables prediction of the sequences of synthetic peptides which will exhibit similar biological effects in accordance with this invention.

The following terms are used in the disclosure of sequences and sequence relationships between two or more nucleic acids or polypeptides: (a) "reference sequence", (b) "comparison window", (c) "sequence identity", (d) "percentage of sequence identity", and (e) "substantial identity"

As used herein, "reference sequence" is a defined sequence used as a basis for sequence comparison. A reference sequence may be a subset or the entirety of a specified sequence; for example, as a segment of a full-length cDNA or other polynucleotide sequence, or the complete cDNA or polynucleotide sequence. The same is the case for polypeptides and their amino acid sequences.

As used herein, "comparison window" includes reference to a contiguous and specified segment of a polynucleotide or amino acid sequence, wherein the sequence may be compared to a reference sequence and wherein the portion of the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of nucleotide and amino acid sequences for comparison are well-known in the art.

For comparison, optimal alignment of sequences may be done using any suitable algorithm, of which the following are examples:
(a) the local homology algorithm ("Best Fit") of Smith and Waterman, *Adv. Appl. Math.* 2: 482 (1981);
(b) the homology alignment algorithm (GAP) of Needleman and Wunsch, *J. Mol. Biol.* 48: 443 (1970); or
(c) a search for similarity method (FASTA and TFASTA) of Pearson and Lipman, *Proc. Natl. Acad. Sci.* 85 2444 (1988);

In a preferred method of alignment, Cys residues are aligned. Computerized implementations of these algorithms, include, but are not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG) (Madison, Wis.). The CLUSTAL program is described by Higgins et al., *Gene* 73:237-244 (1988); Higgins et al., *CABIOS* 5:151-153 (1989); Corpet et al., *Nuc Acids Res* 16:881-90 (1988); Huang et al., *CABIOS* 8:155-65 (1992), and Pearson et al., *Methods in Molecular Biology* 24:307-331 (1994).

A preferred program for optimal global alignment of multiple sequences is PileUp (Feng and Doolittle, *J Mol Evol* 25:351-360 (1987) which is similar to the method described by Higgins et al., 1989, supra). The BLAST family of programs which can be used for database similarity searches includes: NBLAST for nucleotide query sequences against database nucleotide sequences; XBLAST for nucleotide query sequences against database protein sequences; BLASTP for protein query sequences against database protein sequences; TBLASTN for protein query sequences against database nucleotide sequences; and TBLASTX for nucleotide query sequences against database nucleotide sequences. See, for example, Ausubel et al., eds., *Current Protocols in Molecular Biology*, Chapter 19, Greene Publishing and Wiley-Interscience, New York (1995) or most recent edition. Unless otherwise stated, stated sequence identity/similarity values provided herein, typically in percentages, are derived using the BLAST 2.0 suite of programs (or updates thereof) using default parameters. Altschul et al., *Nuc Acids Res.* 25:3389-3402 (1997).

As is known in the art, BLAST searches assume that proteins can be modeled as random sequences. However, many real proteins comprise regions of nonrandom sequence which may include homopolymeric tracts, short-period repeats, or regions rich in particular amino acids. Alignment of such regions of "low-complexity" regions between unrelated proteins may be performed even though other regions are entirely dissimilar. A number of low-complexity filter programs are known that reduce such low-complexity alignments. For example, the SEG (Wooten et al., *Comput. Chem.* 17:149-163 (1993) and XNU (Clayerie et al., *Comput. Chem.*, 17:191-201 (1993) low-complexity filters can be employed alone or in combination.

As used herein, "sequence identity" or "identity" in the context of two nucleic acid or amino acid sequences refers to the residues in the two sequences which are the same when aligned for maximum correspondence over a specified comparison window. It is recognized that when using percentages of sequence identity for proteins, a residue position which is not identical often differs by a conservative amino acid substitution, where a substituting residue has similar chemical properties (e.g., charge, hydrophobicity, etc.) and therefore does not change the functional properties of the polypeptide. Where sequences differ in conservative substitutions, the % sequence identity may be adjusted upwards to correct for the conservative nature of the substitution, and be expressed as "sequence similarity" or "similarity" (combination of identity and differences that are conservative substitutions). Means for making this adjustment are well-known in the art. Typically this involves scoring a conservative substitution as a partial rather than as a full mismatch, thereby increasing the percentage sequence identity. Thus, for example, where an identical amino acid is given a score of "1" and a non-conservative substitution is given a score of "0"zero, a conservative substitution is given a score between 0 and 1. The scoring of conservative substitutions is calculated, e.g., according to the algorithm of Meyers et al., *CABIOS* 4:11-17 (1988) as implemented in the program PC/GENE (Intelligenetics, Mountain View, Calif., USA).

As used herein, "percentage of sequence identity" refers to a value determined by comparing two optimally aligned sequences over a comparison window, wherein the portion of the nucleotide or amino acid sequence in the comparison window may comprise additions or deletions (i.e., gaps) as compared to the reference sequence (which lacks such additions or deletions) for optimal alignment, such as by the GAP algorithm (supra). The percentage is calculated by determining the number of positions at which the identical nucleotide or amino acid residue occurs in both sequences to yield the number of matched positions, dividing that number by the total number of positions in the window of comparison and multiplying the result by 100, thereby calculating the percentage of sequence identity.

The term "substantial identity" of two sequences means that a polynucleotide or polypeptide comprises a sequence that has at least 60%, preferably at least 70%, more preferably at least 80%, even more preferably at least 90%, and most preferably at least 95% sequence identity to a reference sequence using one of the alignment programs described herein using standard parameters. Values can be appropriately adjusted to determine corresponding identity of the proteins encoded by two nucleotide sequences by taking into account codon degeneracy, amino acid similarity, reading frame positioning, etc.

One indication that two nucleotide sequences are substantially identical is if they hybridize to one other under stringent conditions. Because of the degeneracy of the genetic code, a number of different nucleotide codons may encode the same amino acid. Hence, two given DNA sequences could encode the same polypeptide but not hybridize under stringent conditions. Another indication that two nucleic acid sequences are substantially identical is that the polypeptide encoded by the first nucleic acid is immunologically cross reactive with the polypeptide encoded by the second nucleic acid. Clearly, then, two peptide or polypeptide sequences are substantially identical if one is immunologically reactive with antibodies raised against the other. A first peptide is substantially identical to a second peptide, if they differ only by a conservative substitution. Peptides which are "substantially similar" share sequences as noted above except that nonidentical residue positions may differ by conservative substitutions. Thus, in one embodiment of the present invention, the Lipman-Pearson FASTA or FASTP program packages (Pearson, W. R. et. al., 1988, supra; Lipman, D. J. et al, *Science* 227:1435-1441 (1985)) in any of its older or newer iterations may be used to determine sequence identity or homology of a given protein, preferably using the BLOSUM 50 or PAM 250 scoring matrix, gap penalties of −12 and −2 and the PIR or SwissPROT databases for comparison and analysis purposes. The results are expressed as z values or E( ) values. To achieve a more "updated" z value cutoff for statistical significance, preferably corresponding to a z value>10 based on the increase in database size over that of 1988, in a FASTA analysis using the equivalent 2001 database, a significant z value would exceed 13.

A more widely used and preferred methodology determines the percent identity of two amino acid sequences or of two nucleic acid sequences after optimal alignment as discussed above, e.g., using BLAST. In a preferred embodiment of this approach, a polypeptide being analyzed for its homology with native protein is at least 20%, preferably at least 40%, more preferably at least 50%, even more preferably at least 60%, and even more preferably at least 70%, 80%, or 90% as long as the reference sequence. The amino acid residues (or nucleotides) at corresponding positions are then compared. Amino acid or nucleic acid "identity" is equivalent to amino acid or nucleic acid "homology".

In a preferred comparison of a putative polypeptide or peptide homologue polypeptide and a native protein, the percent identity between two amino acid sequences is determined using the Needleman and Wunsch alignment algorithm (incorporated into the GAP program in the GCG software package using either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between the encoding nucleotide sequences is determined using the GAP program in the GCG software package (also available at above URL), using a NWSgapdna.CMP matrix and a gap weight of 40, 50, 60, 70, or 80 and a length weight of 1, 2, 3, 4, 5, or 6. In another embodiment, the algorithm of Meyers et al., supra (incorporated into the ALIGN program, version 2.0), is implemented using a PAM120 weight residue table, a gap length penalty of 12 and a gap penalty of 4.

The wild-type (or native) SAg-encoding nucleic acid sequence or the SAg protein sequence can further be used as a "query sequence" to search against a public database, for example, to identify other family members or related sequences. Such searches can be performed using the NBLAST and XBLAST programs, supra (see Altschul et al. (1990) *J. Mol. Biol.* 215:403-10). BLAST nucleotide searches can be performed with the NBLAST program, score=100, wordlength=12 to identify nucleotide sequences homologous to native SAgs. BLAST protein searches can be performed with the XBLAST program, score=50, wordlength=3 to identify amino acid sequences homologous to identify polypeptide molecules homologous to a native SAg. To obtain gapped alignments for comparison purposes, Gapped BLAST can be utilized as described in Altschul et al. (1997, supra). Default parameters of XBLAST and NBLAST are well established in the art.

Using the FASTA programs and method of Pearson and Lipman, a preferred SAg homologue is one that has a z value>10. Expressed in terms of sequence identity or similarity, a preferred SAg homologue for use according the present invention has at least about 20% identity or 25% similarity to native SAg. Preferred identity or similarity is higher. More preferably, the amino acid sequence of a homologue is substantially identical or substantially similar to a native protein molecule as those terms are defined above.

One group of substitution variants (also homologues) are those in which at least one amino acid residue in the peptide molecule, and preferably, only one, has been removed and a different residue inserted in its place. Deletion and addition variants are also homologues if they satisfy the structural and functional criteria set forth herein with respect to their parent or native molecules. For a detailed description of protein chemistry and structure, see Schulz, G. E. *Principles of Protein Structure* Springer-Verlag, New York, 1978, and Creighton, T. E., *Proteins: Structure and Molecular Properties*, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1-2 of Schulz et al. (supra) and FIGS. 3-9 of Creighton (supra). Based on such an analysis, conservative substitutions are defined herein as exchanges within one of the following five groups:
1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, kg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Tyr, because of its hydrogen bonding potential, has some kinship with Ser, Thr, etc.

More substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of Gly or Pro; (b) substitution of a hydrophilic residue, e.g., Ser or Thr, for (or by) a hydrophobic residue, e.g., Leu, Ile, Phe, Val or Ala; (c) substitution of a Cys residue for (or by) any other residue; (d) substitution of a residue having an electropositive side chain, e.g., Lys, Arg or His, for (or by) a residue having an electronegative charge, e.g., Glu or Asp; or (e) substitution of a residue having a bulky side chain, e.g., Phe, for (or by) a residue not having such a side chain, e.g., Gly.

The deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays, for example direct or competitive immunoassay of cytotoxicity or biological assay of T cell function as described herein. For non-superantigen homologues, the screening test(s) selected to assay function reflect the intrinsic functional activity of the native protein particularly its tumoricidal activity in the context of the inventions described herein. Modifications of such proteins or peptide properties as redox or thermal stability, hydrophobicity, susceptibility to proteolytic degradation or the tendency to aggregate with carriers or into multimers are assessed by methods well known to the ordinarily skilled artisan.

Chemical Derivatives

Covalent modifications of the SAg proteins or peptide fragments thereof, preferably of SEs or peptide fragments thereof, are included herein. Such modifications may be introduced into the molecule by reacting targeted amino acid residues of the protein or peptide with an organic derivatizing agent that is capable of reacting with selected side chains or terminal residues. This may be accomplished before or after polymerization.

Cysteinyl residues most commonly are reacted with a-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, α-bromo-(5-imidozoyl) propionic acid, chloroacetyl phosphate, N-alkylmaleimides, 3-nitro-2-pyridyldisulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; 0-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides as noted above. Aspartyl and glutamyl residues are converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecule Properties*, W. H. Freeman & Co., San Francisco, pp. 79-86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980).

Superantigen Homologues

The variants or homologues of native SAg proteins or peptides including mutants (substitution, deletion and addition types), fusion proteins (or conjugates) with other polypeptides, are characterized by substantial sequence homology to (a) the long-known SE's—SEA, SEB, SEC1-3, SED, SEE and TSST-1;

(b) long-known SpE's;

(c) more recently discovered SE's (SEG, SEH, SEI, SEJ, SEK, SEL, SEM, SEN, SEQ, SEP, SER, SEU, SETs 1-5); or (d) non-enterotoxin superantigens (YPM, *M. arthritides* superantigen).

Preferred homologues were disclosed above.

Table 1 in PCT US05/022638 filed Jun. 27, 2005 incorporated in its entirety by reference lists a number of native SEs and exemplary homologues (amino acid substitution, deletion and addition variants (mutants) and fragments) with z values>10 (range: z=16 to z=136) using the Lipman-Pearson algorithm and FASTA. These homologues also induce significant T lymphocyte mitogenic responses that are generally comparable to native SE's.

In addition, as shown in Table 2 of PCT US05/022638 filed Jun. 27, 2005 incorporated in its entirety by reference, several of these homologues also promote antigen-nonspecific T lymphocyte killing in vitro by a mechanism termed "superantigen-dependent cellular cytotoxicity" (SDCC) or, in the case of SAg-mAb fusion proteins, "superantigen/antibody dependent cellular cytotoxicity (SADCC)."

According to the present invention, other SE homologues (e.g., z>10 or, in another embodiment, having at least about 20% sequence identity or at least about 25% sequence similarity when compared to native SEs), exhibiting T lymphocyte mitogenicity, SDCC or SADCC, are useful anti-tumor agents when administered to a tumor bearing host.

Pharmaceutical Compositions and Administration

The sickled erythrocytes may be administered parenterally preferably intravenously by infusion or injection but also may be implanted or injected intratumorally, intrapleurally, intrathecally, intrapericardially, intravesicularly, subcutaneously, intralymphatically, intraarticularly, intradermally, intracranially, intraarticularly or intramuscularly. They may be administered in a controlled release formulation.

The pharmaceutical compositions of the present invention will generally comprise an effective amount of sickled erythrocytes dissolved or dispersed in a pharmaceutically acceptable carrier or aqueous medium. One or more administrations may be employed, depending upon the lifetime of the drug at the tumor site and the response of the tumor to the drug. Administration may be by syringe, catheter or other convenient means allowing for introduction of a flowable composition. Administration may be every three days, weekly, or less frequent, such as biweekly or at monthly intervals.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by U.S. Food and Drug Administration.

Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

Injectable Formulations

The sickle cells compositions of the present invention are preferably formulated for parenteral administration, e.g., introduction by injection, infusion. They may also be administered intravenously, intramuscularly, intradermally, intraperitoneally, intrapleurally, intraarticularly. Means for preparing aqueous compositions that contain the SAg compositions are known to those of skill in the art in light of the present disclosure. Typically, such compositions can be prepared as for a typical blood transfusion, either as liquid solutions or suspensions; solid forms suitable for using to prepare solutions or suspensions upon the addition of a liquid prior to injection can also be prepared.

The techniques of preparation are generally well known in the art as exemplified by Remington's Pharmaceutical Sciences, 16th Ed. Mack Publishing Company, 1980, or most recent edition, incorporated herein by reference. Moreover, for human administration, preparations should meet sterility, pyrogenicity, general safety and purity standards as required by the U.S. Food and Drug Administration. Upon formulation, the therapeutic compositions are administered in a manner compatible with the dosage formulation and in such amount as is therapeutically effective.

Pharmaceutical Compositions of Heme Oxygenase Inhibitors and Chemotherapy

The metalloporphyrin heme oxygenase inhibitors and chemotherapeutic anti-cancer agents of the present invention may be employed alone or in conjunction with other compounds, such as carriers or other therapeutic compounds.

Pharmaceutical compositions of the present invention comprise sickle cells combined with an effective amount of one or more metalloporphyrin heme oxygenase inhibitors and one or more anti-cancer agents, for example a chemotherapeutic agent, such as a cytostatic agent, and may also contain additional agents, dissolved or dispersed in a pharmaceutically acceptable carrier.

The phrases "pharmaceutical or pharmacologically acceptable" refer to substances, e.g., compositions, that do not produce an adverse, allergic or other untoward reaction when administered to a mammal, such as, for example, a human. The preparation of a pharmaceutical composition that contains at least one metalloporphyrin heme oxygenase inhibitors and an anti-cancer agent will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes, e.g., solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The metalloporphyrin heme oxygenase inhibitors and anti-cancer agents may comprise different types of carriers depending on how they are to be administered. The metalloporphyrin heme oxygenase inhibitors are possibly administered intravenously, intrapleurually, intraperitoneally, intrathecally, intravesicularly. The chemotherapeutic agents may possibly be administered intravenously, intradermally, transdermally, intrathecally, intraarterially, intraperitoneally, intranasally, intravaginally, intrarectally, topically, intramuscularly, sub-cutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The metalloporphyrin heme oxygenase inhibitors and anti-cancer agent may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the metalloporphyrin heme oxygenase inhibitors and chemotherapeutic agents of the present invention suitable for administration are provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined e.g., a carrier in any convenient and practical manner, e.g., by solution, suspension, emulsifica-tion, admixture, encapsulation, absorption and the like. Such procedures are routine for those skilled in the art. In further embodiments, the present invention may concern the use of a pharmaceutical lipid vehicle compositions that include metalloporphyrin heme oxygenase inhibitors and/or an anti-cancer agent, as well as, one or more lipids, and an aqueous solvent. As used herein, the term "lipid" will be defined to include any of a broad range of substances that are characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (e.g., designed or produced by man). However, a lipid is usually a biological substance. Biological lipids are phospholipids, phosphoglycerides, steroids, terpenes, lyso-lipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

Those of ordinary skill in the art are familiar with the range of techniques that can be employed for dispersing a composition in a lipid vehicle. For example, the metalloporphyrin heme oxygenase inhibitors and/or a anti-cancer agents may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can routinely be determined by one of skill in the art by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject. Such determinations are known and used by those of skill in the art.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. Such determinations are known and used by those of skill in the art.

Regimens for Combined Therapy with Sickle Cells, Heme Oxygenase Inhibtiors and Chemotherapy Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician may often be best suited to make such decisions based on his or her skill in the art and the known efficacy and toxicity (if any) of the therapeutic formulations.

Preferably, patients to be treated will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

To kill tumor cells, inhibit tumor cell growth, inhibit tumor metastasis, decrease tumor or tissue size and otherwise reverse or reduce the malignant phenotype of tumor cells, using the methods and compositions of the present invention, one would generally contact a tumor cell or neoplasm or cancer cell with a combination of sickle cells, a metalloporphyrin heme oxygenase inhibitor at least one anticancer agent, such as a cytostatic agent and/or a radiotherapeutic agent.

The routes of administration of the sickle cells parenteral preferably intravenously. The routes of the metalloporphyrin heme oxygenase inhibitors and chemotherapeutic agents will vary, naturally, with the location and nature of the lesion, and will include, e.g., intradermal, transdermal, parenteral, intravenous, intrapleural, intravesicular, intrapertoneal, intrathecal, intramuscular, intranasal, subcutaneous, percutaneous, intratracheal, intratumoral, perfusion, lavage, direct injection, and oral administration and formulation.

In certain embodiments, the treatment regimen of the present invention may involve contacting the neoplasm or tumor cells with the sickle cells, metalloporphyrin heme oxygenase inhibitor and chemotherapeutic agent at the same time. This may be achieved by contacting the tumor cell with a single composition or pharmacological formulation that includes all three agents, or by contacting the cell with three distinct compositions or formulations, at the same time, wherein one composition includes the sickle cells and the other includes the metalloporphyrin heme oxygenase inhibitor and the chemotherapeutic agent.

Alternatively, the sickle cells of the present invention may precede or follow the metalloporphyrin heme oxygenase inhibitor and anticancer agent by intervals ranging from minutes, days to weeks. In embodiments where the other anticancer agent and the sickle cells are applied separately to the cell, one would generally ensure that a significant period of time did not expire between the time of each delivery, such that the superantigen and anticancer agent would still be able to exert an advantageously combined effect on the cell. In such instances, it is contemplated that one may contact the cell with both modalities within about 12-72 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

The terms "contacted" and "exposed," as used herein means when applied to a cell, are used herein to describe the process by which the sickle cells and a metalloporphyrin heme oxygenase inhibitor and chemotherapeutic agent or a radiotherapeutic agent are delivered to a target cell or are placed in direct juxtaposition with the target cell. To achieve cell killing or stasis, all three agents are delivered to a cell in a combined amount effective to kill the cell or prevent it from dividing. This delivery may be sequentially timed as described herein.

Timing of the metalloporphyrin heme oxygenase inhibitor and chemotherapeutic regimen may be related to the half-live of the anticancer agent, such as a cytostatic agent. Half-life of a cytostatic agent can be determined using the below equation $$\text{Half-Life} = (0.693 \times V_d)/CL$$

CL is defined as the clearance of the agent or drug clearance, which is the volume of plasma cleared of drug per unit time. $V_d$ is defined as the volume of distruibution, which is the amount or concentration of the agent in the plasma or blood to the total amount in the body. The half-life can be used to determine the timing for sequential administration of a metalloporphyrin heme oxygenase inhibitor, chemotherapeutic agent followed by sickle cell therapy. Thus, in practicing the present invention, one skilled in the art would know that sickle cell therapy could be sequentially administered in combination with a metalloporphyrin heme oxygenase inhibitor and chemotherapeutic agent, for example, by first treating with the metalloporphyrin heme oxygenase inhibitor or a chemotherapeutic agent. Once the effective concentrations of these agents have in the patient below a functional inhibitory level based upon the half-life of the agent, the sickle cells can be administered to the patient.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time.

As used in the present invention, a combination treatment regimen consists of administering a superantigen and at least one anticancer agent, for example a cytostatic drug or a radiotherapeutic agent. Yet further, it may be desirable to combine the combination treatment regimen with other agents effective in the treatment of neoplastic diseases or cancers, such as other anticancer agents, such as other include biological agents (biotherapy) and/or hormonal therapy, etc.

Included within the scope of the present invention is the systemic (e.g., via intravenous (iv) administration) of porphyrins and/or anti-cancer agents, for example chemotherapeutic drugs, for example cytostatic drugs. Also included is the local administration (e.g., via direct administration of the agent to the tumor, for example by intrathecal administration) of porphyrins and/or anti-cancer agents, for example chemotherapeutic drugs, for example cytostatic drugs. Also included is the combination of local and systemic administration of porphrins and/or anti-cancer agents, for example chemotherapeutic drugs, for example cytostatic drugs (for example, systemic administration of porphyrins combined with local administration of an anti-cancer agent (e.g., a chemotherapeutic drug) and vice versa).

Combined Therapy

As used herein, the term "sequential dosage" and related terminology refers to the administration of at least one superantigen, with at least one anticancer agent, for example, but not limited to a chemotherapeutic agent, such as but not limited to a chemotherapeutic drug, such as but not limited to cytostatic chemotherapeutic drug. This definition includes staggered doses of these agents and variations in dosage amounts. This includes one agent being administered before, overlapping with (partially or totally), after, or totally separate from another agent. This term generally considers the best administration scheme to achieve a synergistic combination of at least one superantigen and at least one anticancer agent and/or to achieve administration of at least one superantigen while limiting or eliminating the generation of an antibody response to the superantigen. Determining sequential dosage administration plans is within the skill of one in the art, from the background skill and teaching in the art and the teaching of this application. For example, one of skill in the art, e.g., based on known drug half-lifes, is able to determine when an anticancer agent or cytostatic agent is below a functional inhibitory level. A functional inhibitory level of the anticancer agent is determined based upon the agent's half-life. Thus, a skilled artisan would know that in order for the superantigen therapy to be effective it must be administered after the cytostatic agent is below a functional inhibitory level.

Typically, one of skill in the art considers chemotherapy and radiotherapy to have anti-proliferative properties, and therefore would generally be expected to interfere with immune stimulating agents such as tumor vaccines, biological response modifiers and superantigens. The present invention utilizes the combination of these known anti-proliferative therapies in combination with sickle cells and a heme oxygenase inhibitor.

Most chemotherapeutic drugs act during a short period of high drug exposure, and elimination of the drug generally occurs within 24 hours after administration. Typically, serum half-lifes of the commonly used drugs gemcitabine and docetaxel are 42-94 minutes and 11.1 hours respectively. Other half-lifes and half-live determinations are discussed above, which is incorporated herein.

In a general combination therapy schedule sickle cell treatment may be integrated with porphyrin heme oxygenase inhibitor and one or more standard chemotherapy (at well established standard doses) in such a way that sickle cells are given shortly (e.g., within 0-3 days or, e.g., 0-6 days) before or after administration of the porphyrin heme oxygenase inhibitor and chemotherapeutic drug.

Parenteral Compositions and Formulations

In further embodiments, porphyrin heme oxygenase inhibitors and/or an anti-cancer agent (e.g., a chemotherapeutic agent, such as a cytostatic drug) may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, intrapleurally, intrapericaridally, intravesicularly, intratumorally, subcutaneous, or intraperitoneally.

Solutions of the active compounds as free base or pharmacologically acceptable salts may be prepared in water suitably mixed with a surfactant, such as hydroxypropylcel-lulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologies standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other embodiments of the invention, porphyrin heme oxygenase inhibitors and/or an anti-cancer agent (e.g, a chemotherapeutic agent, such as a cytostatic drug) may be formulated for administration via various miscellaneous routes, for example, topical (e.g., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emul-sifiers, gelling agents, and antimicrobial preservatives as necessary to preserve the active ingredient and provide for a homogenous mixture. Transdermal administration of the present invention may also comprise the use of a "patch." For example, the patch may supply one or more active substances at a predetermined rate and in a continuous manner over a fixed period of time.

Animal and Human Testing

The effects of murine sickled erythrocytes are tested murine tumor models as given in the section titled "Tumor Models and Procedures for Evaluating Anti-Tumor Effects Studies" (pp. 72-82 instant specification). The sickled erythrocytes are obtained from mice with models of sickle cell disease as shown in the Table 3 below of mouse models and also include from mice with sickle-thalassemia containing little or no HbA hemoglobin.

TABLE 3

Transgenic Murine models for Sickle Cell disease

| Mouse Model | Mouse $\alpha$ Globin | Mouse $\beta$ Globin | Human $\alpha$ Globin | Human $\beta$ Globin | $\%\beta^s$ |
|---|---|---|---|---|---|
| Normal | Yes | Yes | No | No | 0 |
| New York (NY) | Yes | Deleted | No | $\beta^s$ | 32 |
| Berkeley (B) | Yes | Deleted | No | $\beta^{s\text{-}Antilles}$ | 29 |
| Hybrid(H) [NY_B] | Yes | Deleted | No | $\beta^s$ $\beta^{s\text{-}Antilles}$ | 42.2 35.9 |
| Paszty(P) | Deleted | Deleted | Yes | $\beta^s$ | 39 |

For testing any of the above transgenic mouse models of sickle cell disease or trait in the C57/B1 background are useful. Other murine genetic backgrounds are suitable as well. The tumors are those indigenous to the mouse strain of the donor sickled erythrocytes. In one example, it would be the MCA 205-207 sarcoma which is indigenous to the C57/B1 mouse. Other tumors indigenous to this strain are the B16F10 melanoma, Lewis lung carcinoma, CT-26 colon carcinoma and hepatocellular carcinomas. In a typical experiment, C57B1 mice with established Lewis Lung carcinomas are injected intravenously with 0.1-0.2 ml of nucleated erythrocytes from a homozygous SS mouse. The SS erythrocytes may also be transduced with nucleic acids encoding a superantigen or toxins given above, a hemolysin, oncolytic virus or anaerobic bacterial spore fused to a CMV promoter optionally with an HRE element The injected SS cells aggregate and cluster in the tumor vasculature using real time intravital microscopy. Repeated injections every 2-7 days produce an objective reduction of tumor mass. Human studies are described in Example 1

Tumor Models and Procedures for Evaluating Anti-Tumor Effects Studies

The various sickle cell compositions described herein are tested for therapeutic efficacy in several well established rodent models which are considered to be highly representative of a broad spectrum of human tumors. These approaches are described in detail in Geran, R. I. et al., "Protocols for Screening Chemical Agents and Natural Products against Animal Tumors and Other Biological Systems (Third Edition)", *Canc. Chemother. Reports*, Pt 3, 3:1-112, which is hereby incorporated by reference in its entirety.

In general the SS cells, SA cells, SS variant cells, SS progenitors, erthroleukemia cells, erythroleukemia cells transfected with BCAM/LU, SS porphyric cells, SS ghosts are loaded with tumoricidal virus, protein, drug, toxin, antibody, toxin-antibody conjugate as and optionally pre-treated with light therapy or photosensitizers as described as described herein. The cells are administered to tumor bearing mice by intravenous infusion or injection in doses of 0.05 to 0.20 ml over 30 seconds to 2 minutes. The treatment is repeated every day or every second or third day for up to 10 treatments.

A. Calculation of Mean Survival Time (MST)

MST (days) is calculated according to the formula $\frac{S + AS(A-1) - (B+1)NT}{S(A-1) - NT}$ Day: Day on which deaths are no longer considered due to drug toxicity. For example, with treatment starting on Day 1 for survival systems (such as L1210, P388, B16, 3LL, and W256): Day A=Day 6; Day B=Day beyond which control group survivors are considered "no-takes."
S: If there are "no-takes" in the treated group, S is the sum from Day A through Day B. If there are no "no-takes" in the treated group, S is the sum of daily survivors from Day A onward.
S(A-1): Number of survivors at the end of Day (A-1).
Example: for 3LE21, S(A-1)=number of survivors on Day 5.
NT: Number of "no-takes" according to the criteria given in Protocols 7.300 and 11.103.

B. T/C Computed for all Treated Groups $$T/C = \frac{MST \text{ of treated group}}{MST \text{ of control group}} \times 100$$

Treated group animals surviving beyond Day B are eliminated from calculations (as follows):

| No. of survivors in treated group beyond Day B | Percent of "no-takes" in control group | Conclusion |
|---|---|---|
| 1 | Any percent | "no-take" |
| 2 | <10 | drug inhibition |
|   | ³10 | "no-takes" |
| ³3 | <15 | drug inhibitions |
|   | ³15 | "no-takes" |

Positive control compounds are not considered to have "no-takes" regardless of the number of "no-takes" in the control group. Thus, all survivors on Day B are used in the calculation of T/C for the positive control. Surviving animals are evaluated and recorded on the day of evaluation as "cures" or "no-takes."

Calculation of Median Survival Time (MedST)

MedST is the median day of death for a test or control group. If deaths are arranged in chronological order of occurrence (assigning to survivors, on the final day of observation, a "day of death" equal to that day), the median day of death is a day selected so that one half of the animals died earlier and the other half died later or survived. If the total number of animals is odd, the median day of death is the day that the middle animal in the chronological arrangement died. If the total number of animals is even, the median is the arithmetical mean of the two middle values. Median survival time is computed on the basis of the entire population and there are no deletion of early deaths or survivors, with the following exception:

C. Computation of MedST from Survivors

If the total number of animals including survivors (N) is even, the MedST (days) (X+Y)/2, where X is the earlier day when the number of survivors is N/2, and Y is the earliest day when the number of survivors (N/2)-1. If N is odd, the MedST (days) is X.

D. Computation of MedST From Mortality Distribution

If the total number of animals including survivors (N) is even, the MedST (days) (X+Y)/2, where X is the earliest day when the cumulative number of deaths is N/2, and Y is the earliest day when the cumulative number of deaths is (N/2)+1. If N is odd, the MedST (days) is X. "Cures" and "no-takes" in systems evaluated by MedST are based upon the day of evaluation. On the day of evaluation any survivor not considered a "no-take" is recorded as a "cure." Survivors on day of evaluation are recorded as "cures" or "no-takes," but not eliminated from the calculation.

E. Calculation of Approximate Tumor Weight From Measurement of Tumor Diameters with Vernier Calipers The use of diameter measurements (with Vernier calipers) for estimating treatment effectiveness on local tumor size permits retention of the animals for lifespan observations. When the tumor is implanted sc, tumor weight is estimated from tumor diameter measurements as follows. The resultant local tumor is considered a prolate ellipsoid with one long axis and two short axes. The two short axes are assumed to be equal. The longest diameter (length) and the shortest diameter (width) are measured with Vernier calipers. Assuming specific gravity is approximately 1.0, and Pi is about 3, the mass (in mg) is calculated by multiplying the length of the tumor by the width squared and dividing the product by two. Thus, $$\text{Tumor weight (mg)} = \frac{\text{length (mm)} \times (\text{width [mm]})2}{2}$$

or $$\frac{L \times (W)2}{2}$$

The reporting of tumor weights calculated in this way is acceptable inasmuch as the assumptions result in as much accuracy as the experimental method warrants.

F. Calculation of Tumor Diameters

The effects of a drug on the local tumor diameter may be reported directly as tumor diameters without conversion to tumor weight. To assess tumor inhibition by comparing the tumor diameters of treated animals with the tumor diameters of control animals, the three diameters of a tumor are averaged (the long axis and the two short axes). A tumor diameter T/C of 75% or less indicates activity and a T/C of 75% is approximately equivalent to a tumor weight T/C of 42%.

G. Calculation of Mean Tumor Weight From Individual Excised Tumors

The mean tumor weight is defined as the sum of the weights of individual excised tumors divided by the number of tumors. This calculation is modified according to the rules listed below regarding "no-takes." Small tumors weighing 39 mg or less in control mice or 99 mg or less in control rats, are regarded as "no-takes" and eliminated from the computations. In treated groups, such tumors are defined as "no-takes" or as true drug inhibitions according to the following rules:

| Percent of small tumors in treated group | Percent of "no-takes" in control group | Action |
| --- | --- | --- |
| ≦17 | Any percent | no-take; not used in calculations |
| 18-39 | <10 | drug inhibition; use in calculations |
|  | ≧10 | no-takes; not used in calculations |
| ≧40 | <15 | drug inhibition; use in calculations |
|  | ≧15 | Code all nontoxic tests "33" |

Positive control compounds are not considered to have "no-takes" regardless of the number of "no-takes" in the control group. Thus, the tumor weights of all surviving animals are used in the calculation of T/C for the positive control (T/C defined above) SDs of the mean control tumor weight are computed the factors in a table designed to estimate SD using the estimating factor for SD given the range (difference between highest and lowest observation) (Biometrik Tables for Statisticians Pearson E S & Hartley H G eds. Cambridge Press, vol. 1, table 22, p. 165).

II. Specific tumor models

A. Lymphoid Leukemia L1210

Summary

Ascitic fluid from donor mouse is transferred into recipient BDF1 or CDF1 mice. Treatment begins 24 hours after implant. Results are expressed as a percentage of control survival time. The key parameter is mean survival time. Origin of tumor line: induced in 1948 in spleen and lymph nodes of mice by painting skin with MCA (*J Natl Cancer Inst.* 13:1328 (1953)).

| Animals | One sex used for all test and control animals in one experiment. |
| --- | --- |
| Tumor Transfer | Inject ip, 0.1 ml of diluted ascitic fluid containing $10^5$ cells |
| Propagation | DBA/2 mice (or BDF1 or CDF1 for one generation). |
| Time of Transfer | Day 6 or 7 |
| Testing | BDF1 (C57BL/6 x DBA/2) or CDF1 (BALB/c x DBA/2) |
| Time of Transfer Weight | Day 6 or 7 Within a 3-g range, minimum weight of 18 g for males and 17 g for females. |
| Exp Size (n) | 6/group; No. of control groups varies according to number of test groups. |

Testing Schedule

| DAY | PROCEDURE |
| --- | --- |
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 4 wks of therapy. |
| 5 | Weigh animals and record. |
| 20 | If there are no survivors except those treated with positive control compound, evaluate |
| 30 | Kill all survivors and evaluate experiment. |

Quality Control:

Acceptable control survival time is 8-10 days. Positive control compound is 5-fluorouracil; single dose is 200 mg/kg/injection, intermittent dose is 60 mg/kg/injection, and chronic dose is 20 mg/kg/injection. Ratio of tumor to control (T/C) lower limit for positive control compound is 135%.

Evaluation:

Compute mean animal weight on Days 1 and 5, and at the completion of testing compute T/C for all test groups with >65% survivors on Day 5. A T/C value 85% indicates a toxic test. An initial T/C 125% is considered necessary to demonstrate activity. A reproduced T/C 125% is considered worthy of further study. For confirmed activity a composition should have two multi-dose assays that produce a T/C 125%.

B. Lymphocytic Leukemia P388

Summary:

Ascitic fluid from donor mouse is implanted in recipient BDF1 or CDF1 mice. Treatment begins 24 hours after implant. Results are expressed as a percentage of control survival time. The key parameter is MedST. Origin of tumor line: induced in 1955 in a DBA/2 mouse by painting with MCA (*Scientific Proceedings, Pathologists and Bacteriologists* 33:603 (1957)).

| Animals | One sex used for all test and control animals in one experiment. |
| --- | --- |
| Tumor Transfer | Inject ip, 0.1 ml of diluted ascitic fluid containing $10^6$ cells |
| Propagation | DBA/2 mice (or BDF1 or CDF1 for one generation). |
| Time of Transfer | Day 7 |
| Testing | BDF1 (C57BL/6 x DBA/2) or CDF1 (BALB/c x DBA/2) |
| Time of Transfer Weight | Day 6 or 7 Within a 3-g range, minimum weight of 18 g for males and 17 g for females. |
| Exp Size (n) | 6/group; No. of control groups varies according to number of test groups. |

Testing Schedule

| DAY | PROCEDURE |
| --- | --- |
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 4 wks of therapy. |
| 5 | Weigh animals and record. |
| 20 | If there are no survivors except those treated with positive control compound, evaluate |
| 30 | Kill all survivors and evaluate experiment. |

Acceptable MedST is 9-14 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135% Check control deaths, no takes, etc.

Quality Control:

Acceptable MedST is 9-14 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135%. Check control deaths, no takes, etc.

Evaluation:

Compute mean animal weight on Days 1 and 5, and at the completion of testing compute T/C for all test groups with > 65% survivors on Day 5. A T/C value of 85% indicates a toxic test. An initial T/C of 125% is considered necessary to demonstrate activity. A reproduced T/C 125% is considered worthy of further study. For confirmed activity a composition should have two multi-dose assays that produce a T/C 125%.

C. Melanotic Melanoma B16

Summary:

Tumor homogenate is implanted ip or sc in BDF1 mice. Treatment begins 24 hours after either ip or sc implant or is delayed until an sc tumor of specified size (usually approximately 400 mg) can be palpated. Results expressed as a percentage of control survival time. The key parameter is mean survival time. Origin of tumor line: arose spontaneously in 1954 on the skin at the base of the ear in a C57BL/6 mouse (*Handbook on Genetically Standardized Jax Mice*. Jackson Memorial Laboratory, Bar Harbor, Me., 1962. See also *Ann NY Acad Sci* 100, Parts 1 and 2, (1963)).

| Animals | One sex used for all test and control animals in one experiment. |
|---|---|
| Propagation Strain | C57BL/6 mice |
| Tumor Transfer | Implant fragment sc by trochar or 12-g needle or tumor homogenate* every 10-14 days into axillary region with puncture in inguinal region. |
| Testing Strain | BDF1 (C57BL/6 x DBA/2) |
| Time of Transfer | Excise sc tumor on Day 10-14 from donor mice and implant as above |
| Weight | Within a 3-g range, minimum weight of 18 g for males and 17 g for females. |
| Exp Size (n) | 10/group; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 μg of the test composition in 0.5 ml saline. Controls receive saline alone. Treatment is one dose/week. Any surviving mice are sacrificed after 8 wks of therapy. |
| 5 | Weigh animals and record. |
| 60 | Kill all survivors and evaluate experiment. |

Quality Control:

Acceptable control survival time is 14-22 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135% Check control deaths, no takes, etc.

Evaluation:

Compute mean animal weight on Days 1 and 5, and at the completion of testing compute T/C for all test groups with > 65% survivors on Day 5. A T/C value of 85% indicates a toxic test. An initial T/C of 125% is considered necessary to demonstrate activity. A reproduced T/C 125% is considered worthy of further study. For confirmed activity a composition should have two multi-dose assays that produce a T/C 125%.

Metastasis after IV Injection of Tumor Cells $10^5$ B16 melanoma cells in 0.3 ml saline are injected intravenously in C57BL/6 mice. The mice are treated intravenously with 1 g of the composition being tested in 0.5 ml saline. Controls receive saline alone. Mice sacrificed after 4 weeks of therapy, the lungs are removed and metastases are enumerated.

C. 3LL Lewis Lung Carcinoma

Summary:

Tumor may be implanted sc as a 2-4 mm fragment, or im as a $2 \times 10^6$-cell inoculum. Treatment begins 24 hours after implant or is delayed until a tumor of specified size (usually approximately 400 mg) can be palpated. Origin of tumor line: arose spontaneously in 1951 as carcinoma of the lung in a C57BL/6 mouse *Cancer Res* 15:39, (1955)). See also Malave I et al., *J. Natl. Canc. Inst.* 62:83-88 (1979).

| Animals | One sex used for all test and control animals in one experiment. |
|---|---|
| Propagation Strain | C57BL/6 mice |
| Tumor Transfer | Inject cells im in hind leg or implant fragment sc in axillary region with puncture in inguinal region. Transfer on day 12-14 |
| Testing Strain | BDF1 (C57BL/6 x DBA/2) or C3H mice |
| Time of Transfer | Same as above |
| Weight | Within a 3-g range, minimum weight of 18 g for males and 17 g for females. |
| Exp Size (n) | 6/group for sc implant, or 10/group for im implant.; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 μg of the test composition in 0.5 ml saline. Controls receive saline alone. Treatment is one dose/week. Any surviving mice are sacrificed after 4 wks of therapy. |
| 5 | Weigh animals and record. |
| Final day | Kill all survivors and evaluate experiment. |

Quality Control:

Acceptable im tumor weight on Day 12 is 500-2500 mg. Acceptable im tumor MedST is 18-28 days. Positive control compound is cyclophosphamide: 20 mg/kg/injection, qd, Days 1-11. Check control deaths, no takes, etc.

Evaluation:

Compute mean animal weight when appropriate, and at the completion of testing compute T/C for all test groups. When the parameter is tumor weight, a reproducible T/C of 42% is considered necessary to demonstrate activity. When the parameter is survival time, a reproducible T/C of 125% is considered necessary to demonstrate activity. For confirmed activity a composition must have two multi-dose assays D. 3LL Lewis Lung Carcinoma Metastasis Model This model has been utilized by a number of investigators. See, for example, Gorelik, E. et al., *J. Natl. Canc. Inst.* 65:1257-1264 (1980); Gorelik, E. et al., *Rec. Results Canc. Res.* 75:20-28 (1980); Isakov, N. et al., *Invasion Metas.* 2:12-32 (1982) Talmadge J E et al., *J. Nat'l. Canc. Inst.* 69:975-980 (1982); Hilgard, P. et al., *Br. J. Cancer* 35:78-86 (1977)).

Mice:

male C57BL/6 mice, 2-3 months old. Tumor: The 3LL Lewis Lung Carcinoma was maintained by sc transfers in C57BL/6 mice. Following sc, im or intra-footpad transplantation, this tumor produces metastases, preferentially in the lungs. Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95-99% (by trypan blue dye exclusion). Viable tumor cells ($3\times10^4$-$5\times10^6$) suspended in 0.05 ml PBS are injected into the right hind foot pads of C57BL/6 mice. The day of tumor appearance and the diameters of established tumors are measured by caliper every two days. In experiments involving tumor excision, mice with tumors 8-10 mm in diameter are divided into two groups. In one group, legs with tumors are amputated after ligation above the knee joints. Mice in the second group are left intact as nonamputated tumor-bearing controls. Amputation of a tumor-free leg in a tumor-bearing mouse has no known effect on subsequent metastasis, ruling out possible effects of anesthesia, stress or surgery. Surgery is performed under Nembutal anesthesia (60 mg veterinary Nembutal per kg body weight).

Determination of Metastasis Spread and Growth

Mice are killed 10-14 days after amputation. Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125I}$dUrd into lung cells (Thakur M L et al., *J. Lab. Clin. Med.* 89:217-228 (1977)). Ten days following tumor amputation, 25 mg of $^{125}$IdUrd is inoculated into the peritoneums of tumor-bearing (and, if used, tumor-resected mice. After 30 min, mice are given 1 mCi of $^{125}$IdUrd. One day later, lungs and spleens are removed and weighed, and a degree of $^{125}$IdUrd incorporation is measured using a gamma counter.

Statistics:

Values representing the incidence of metastases and their growth in the lungs of tumor-bearing mice are not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of large doses of 3LL cells ($1$–$5\times10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $10^6$ 3LL cells. Amputation of tumors produced following inoculation of $10^5$ tumor cells dramatically accelerated metastatic growth. These results were in accord with the survival of mice after excision of local tumors. The phenomenon of acceleration of metastatic growth following excision of local tumors had been observed by other investigators. The growth rate and incidence of pulmonary metastasis were highest in mice inoculated with the lowest doses ($3\times10^4$-$10^5$ of tumor cells) and characterized also by the longest latency periods before local tumor appearance. Immunosuppression accelerated metastatic growth, though nonimmunologic mechanisms participate in the control exerted by the local tumor on lung metastasis development. These observations have implications for the prognosis of patients who undergo cancer surgery.

E. Walker Carcinosarcoma 256

Summary:

Tumor may be implanted sc in the axillary region as a 2-6 mm fragment im in the thigh as a 0.2-ml inoculum of tumor homogenate containing $10^6$ viable cells, or ip as a 0.1-ml suspension containing $10^6$ viable cells. Origin of tumor line: arose spontaneously in 1928 in the region of the mammary gland of a pregnant albino rat (*J Natl Cancer Inst* 13:1356, (1953)).

| | |
|---|---|
| Animals | One sex used for all test and control animals in one experiment. |
| Propagation Strain | Random-bred albino Sprague-Dawley rats |
| Tumor Transfer | S.C. fragment implant is by trochar or 12-g needle into axillary region with puncture in inguinal area. I.m. implant is with 0.2 ml of tumor homogenate (containing $10^6$ viable cells) into the thigh. I.p. implant is with 0.1 ml suspension (containing $10^6$ viable cells) Day 7 for im or ip implant; Days 11-13 for sc implant |
| Testing Strain | Fischer 344 rats or random-bred albino rats |
| Time of Transfer | Same as above |
| Weight | 50-70 g (maximum of 10-g weight range within each experiment) |
| Exp Size (n) | 6/roup; No. of control groups varies according to number of test groups. |

| Test system | Prepare drug on day: | Administer drug on days: | Weigh animals on days | Evaluate on days |
|---|---|---|---|---|
| 5WA16 | 2 | 3-6 | 3 and 7 | 7 |
| 5WA12 | 0 | 1-5 | 1 and 5 | 10-14 |
| 5WA31 | 0 | 1-9 | 1 and 5 | 30 |

In addition the following general schedule is followed

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 4 wks of therapy. |
| Final day | Kill all survivors and evaluate experiment. |

Quality Control:

Acceptable i.m. tumor weight or survival time for the above three test systems are: 5WA16: 3-12 g.; 5WA12: 3-12 g.; 5WA31 or 5WA21: 5-9 days.

Evaluation:

Compute mean animal weight when appropriate, and at the completion of testing compute T/C for all test groups. When the parameter is tumor weight, a reproducible T/C 42% is considered necessary to demonstrate activity. When the parameter is survival time, a reproducible T/C 125% is considered necessary to demonstrate activity. For confirmed activity F. A20 lymphoma $10^6$ murine A20 lymphoma cells in 0.3 ml saline are injected subcutaneously in Balb/c mice.

Tumor growth is monitored daily by physical measurement of tumor size and calculation of total tumor volume. After 4 weeks of therapy the mice are sacrificed.

Having now generally described the invention, the same will be more readily understood through reference to the following examples which are provided by way of illustration, and are not intended to be limiting of the present invention, unless specified.

EXAMPLE 1

For human studies, SS erythrocytes or nucleated SS erythrocyte precursors are obtained from patients with homozygous S or sickle thalassemia hemoglobin, hemizygous sickle S and A hemoglobin, sickle hemoglobin-C disease, sickle beta plus thalassemia, sickle hemoglobin-D disease, sickle hemoglobin-E disease, homozygous C or C—thalassemia, hemoglobin-C beta plus thalassemia, homozygous E or E—thalassemia. Nucleated erythroleukemia cells are obtained from patients with erythroleukemia. The erythocytes are ABO- and Rh-matched for compatibility with recipients. Mature or progenitor SS cell transfected with lentiviral or other suitable vector encoding tumoricidal transgenes and/or oncolytic viruses as described herein are used. The cells are optionally incubated with epinephrine $1\times10^{-2}$ μM per $10^8$ cells for 2 minutes at 37° C. SS erythroblasts and erythroleukemia cells stably transfected with nucleic acids encoding BCAM/Lu are transfected with oncolytic viruses as described herein. Additional groups of SS progenitors and nucleated erythroleukemic cells are rendered drug-resistant by ex vivo exposure to cisplatinum or Adriamycin as described herein. Mature SS cells are loaded with antitumor drugs or oncolytic viruses operative in enucleated SS RBCs as described herein. All cells are optionally irradiated with light before administration to induce a photohemolysis t½ h of 10-60 minutes after intravenous administration. The total amount of antitumor drug administered per treatment with the any of these cell types is in a range of 25-100 mg. Tumors of any type are susceptible to therapy with these agents. The cells are administered intravenously or intrarterially in a blood vessel perfusing a specific tumor site or organ, e.g. carotid artery, portal vein, femoral artery etc. over the same amount of time required for the infusion of a conventional blood transfusion. The quantity of cells to be administered in any one treatment ranges from one tenth to one half of a full unit of blood. The treatments are generally given every 2-7 days for a total of 1-12 treatments. However, the treatment schedule is flexible and may be given for a longer of shorter duration depending upon the patients' response. All treated patients have histologically confirmed malignant disease including carcinomas, sarcomas, melanomas, lymphomas and leukemias and have failed conventional therapy. Patients may be diagnosed as having any stage of metastatic disease involving any organ system. Staging describes both tumor and host, including organ of origin of the tumor, histologic type and histologic grade, extent of tumor size, site of metastases and functional status of the patient. A general classification includes the known ranges of Stage I (localized disease) to Stage 4 (widespread metastases). Patient history is obtained and physical examination performed along with conventional tests of cardiovascular and pulmonary function and appropriate radiologic procedures. Histopathology is obtained to verify malignant disease.

Results:

A total of 1011 patients are patients treated, 339 with mature SS cells, 338 with SS progenitor cells and 339 with erythroleukemia cells stably tranfected with BCAM/Lu. All cells are stably transfected with or have encapsulated oncolytic virus as described herein and irradiated with light before intravenous administration. The overall number of patients for each tumor type and the results of treatment are summarized in Table 4. Positive tumor responses are observed in as high as 85-95% of the patients with breast, gastrointestinal, lung, prostate, renal and bladder tumors as well as melanoma and neuroblastoma as follows.

Eight hundred and ninety one of 1011 entered with all tumors exhibit objective clinical responses for an overall response rate of 89%. Tumors generally start to diminish and objective remissions are evident after four weeks of therapy. Responses endure for a mean of 36 months.

TABLE 4

SS cells, SS progenitor cells and erythroleukemia cells loaded with oncogenic virus

| Patients/Tumors | No. | Response | % of Patients Responding |
|---|---|---|---|
| All Patients | 891 | CR + PR | 88 |
| Tumor Type | | | |
| Breast adenocarcinoma | 165 | CR + PR | 90% |
| Gastrointestinal carcinoma | 156 | CR + PR | 90% |
| Lung Carcinoma | 200 | CR + PR | 95% |
| Brain glioma/astrocytoma | 60 | CR + PR | 85% |
| Prostate Carcinoma | 130 | CR + PR | 85% |
| Lymphoma/Leukemia | 61 | CR + PR | 80% |
| Head and Neck Cancer | 82 | CR + PR | 80% |
| Renal and Bladder Cancer | 53 | CR + PR | 95% |
| Melanoma | 67 | CR + PR | 85% |
| Neuroblastoma | 37 | CR + PR | 85% |

Toxicity consists of mild short-lived fever, fatigue and anorexia not requiring treatment. The incidence of side effects (as % of total treatments) are as follows: chills—12; fever—15; pain—6; nausea—3; respiratory—2; headache—2; tachycardia—4; vomiting—4; hypertension—1; hypotension—2; joint pain—3; rash—1; flushing—4; diarrhea—2; itching/hives—1; bloody nose—1; dizziness—<1; cramps—< 1; fatigue—<1; feeling faint—<1; twitching—< 1; blurred vision—<1; gastritis<1; redness on hand—<1. Fever and chills are the most common side effects observed.

In an additional study, 986 patients are treated, 328 with SS progenitor cells 329 with erythroleukemia cells and 327 with mature SS cells. SS progenitor cells and erythroleukemia cells are rendered resistant to anti-tumor drugs in vitro as described herein and mature SS cells have encapsulated antitumor drugs as described herein. The chemotherapeutic agent selected for loaded into cells the one to which the tumor is known to be most sensitive as described herein. All cells are irradiated with light before intravenous administration as described herein. The overall number of patients for each tumor type and the results of treatment are summarized in Table 5. Positive tumor responses are observed in as high as 85-95% of the patients with breast, gastrointestinal, lung, prostate, renal and bladder tumors as well as melanoma and neuroblastoma.

Eight hundred and seventy of 986 patients entered with all tumors exhibit objective clinical responses for an overall response rate of 89%. Tumors generally start to diminish and objective remissions are evident after three to four weeks of therapy. Responses endure for a mean of 36 months.

TABLE 5

SS cells, SS progenitor cells, erythroleukemia cells loaded with anti-tumor drugs

| Patients/Tumors | No. | Response | % of Patients Responding |
|---|---|---|---|
| All Patients | 870 | CR + PR | 89 |
| Tumor Type | | | |
| Breast adenocarcinoma | 162 | CR + PR | 90% |
| Gastrointestinal carcinoma | 153 | CR + PR | 90% |
| Lung Carcinoma | 195 | CR + PR | 95% |
| Brain glioma/astrocytoma | 57 | CR + PR | 85% |
| Prostate Carcinoma | 127 | CR + PR | 85% |
| Lymphoma/Leukemia | 61 | CR + PR | 80% |
| Head and Neck Cancer | 80 | CR + PR | 80% |
| Renal and Bladder Cancer | 51 | CR + PR | 95% |
| Melanoma | 63 | CR + PR | 85% |
| Neuroblastoma | 37 | CR + PR | 85% |

Toxicity consists of mild fatigue, anorexia and nausea not requiring treatment. The incidence of side effects (as % of total treatments) are as follows: fatigue—15; nausea—12; anorexia—10; chills—3; fever—1; pain—2;; respiratory—2; headache—2; tachycardia—4; vomiting—4; hypertension—2; hypotension—1; joint pain—2; rash—1; flushing—1; diarrhea—4; itching/hives—1; bloody nose—1; dizziness—<1; cramps—<1; feeling faint—<1; twitching—<1; blurred vision—<1; gastritis<1; redness on hand—<1.

EXAMPLE 2

Preparation of siRNA duplexes

21-Nucleotide RNAs complementary to target genes as listed in Table 2 are preferably chemically synthesized using appropriately protected ribonucleoside phosphoramidites and a conventional DNA/RNA synthesizer. Suppliers of RNA synthesis reagents are Proligo (Hamburg, Germany), Dhannacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). A typical 0.2 μmol-scale RNA synthesis provides about 1 milligram of RNA, which is sufficient for 1000 transfection experiments using a 24-well tissue culture plate format.

Transfection of siRNA Duplexes

A single transfection of siRNA duplex is carried out using OLIGOFECTAMINE Reagent (Invitrogen) with assay for silencing 2 days after transfection. Transfection efficiencies are typically around 90-95%. No silencing is observed in the absence of transfection reagent. Oligofectamine has the advantage of being non-toxic to cells and the medium does not to be changed after transfection. siRNA transfection is also possible by using TransIT-TKO: small interfering RNA (siRNA) Transfection Reagent, which is provided by Mirus. Transit-TKO reagent is more difficult to handle than OLIGO-FECTAMINE, because concentrations required for effective transfection also cause cytotoxic effects. Typical side effects of Transit-TKO siRNA transfection are morphologic changes such as formation of extended lamellipodia as well as oval-shaped nuclei, and which appear about 2 days after transfection. These effects are observed using between 4.0 and 4.5 μL of Transit-TKO reagent. Two other siRNA transfection reagent were recently introduced by Polyplus-transfection SAS, termed jetSI, and by Upstate, termed siIMPORTER.

For one well of a 24-well plate 0.84 μg siRNA duplex (60 pmole in 3 μl annealing buffer) is used. Mix 3 μl of 20 μM siRNA duplex with 50 μl of Opti-MEM. In another tube, mix 3 μl of OLIGOFECTAMINE Reagent (or 3 to 3.5 μl Transit TKO) with 12 μl of Opti-MEM, incubate 7 to 10 min at room temperature. Combine the solutions and gently mix by inversion. Do not vortex. Incubate another 20 to 25 min at room temperature; the solution turns turbid. Then add 32 μl of fresh Opti-MEM to obtain a final solution volume of 100 μl. (The addition of 32 μl Opti-MEM is optional and serves only to adjust the total volume of cell culture medium to 600 μl after transfection.) Add the 100 μl of siRNA-OLIGO-FECTAMINE to cultured cells (40 to 50% confluent). The cells are seeded the previous day in 24-well plates using 500 μl of DMEM tissue culture medium supplemented with 10% FBS but without antibiotics. Transfection of 0.84 μg single-stranded sense siRNA has no effect and 0.84 μg antisense siRNA has a weak silencing effect when compared to 0.84 μg of duplex siRNAs. However, when the siRNA concentrations are reduced 100-fold no antisense effect is apparent while the siRNA duplex is still efficiently silencing. On this note, it is often possible to reduce the siRNA duplex concentration in order to save precious RNA.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. To control for transfection, we recommend to target laminin A/C and to determine the fraction of laminin A/C knockdown cells by immunofluorescence. Alternatively, a feeling for transfection efficiency may be developed by transfection of a CMV-driven EGFP-expression plasmid (e.g. from Clontech) using Lipofectamine 2000 (Invitrogen). The transfection efficiency is then assessed by phase contrast and fluorescence microscopy the next day.

Small Interfering RNA-Encoding Minigenes Targeting HIF-1α

To prepare small interfering RNA-encoding minigenes, a Internet-based program available at the website of Ambion Inc. (Austin, Tex.) is used. Oligonucleotide DNA sequences based on these targeting sequences are then synthesized by commercial sources. These oligos contain two 19-mer complimentary targeting sequences with a loop sequence separating them and a polythymidine tract to terminate transcription. In addition, they were engineered to possess BamHI- and HindIII-compatible overhangs that facilitate their ligation into the expression vector pSilencer-2.0 (Ambion Inc.), which is a plasmid with a human U6 gene-based RNA polymerase III promoter. The derived HIF-1α-targeted minigene-encoding plasmid was pSilencer-siHIF-1α. The control plasmid was pSilencer-siNT (for nontargeted, obtained from Ambion), which is a plasmid with a similar structure but encoding a nonsense minigene with no homology to any known sequences in the human genome. The sequence of the scrambled minigene is as follows: (SEQ ID NO:18) AAT TCT CCG AAC GTG TCA CGT.

Adenovirus AdsiHIF-1α Production.

The AdEasy system of adenovirus packaging, including plasmid pAdtrack, pAdeasy-1, and the packaging *Escheria*

*coli* BJ5183 cells is commercially purchased from Stratagen Corp. (La Jolla, Calif.). The small interfering RNA-encoding gene expression cassette (with the U6 gene promoter) is then excised by PvuII/HindIII from pSilencer-siHIF-1α and subcloned into the EcoRV/HindIII sites of pAdTrack. The resulting plasmid is pAdTrack-siHIF-1α. Packaging and production of the adenovirus that carries the HIF-1α-targeted small interfering RNA gene is carried out by
following the manufacturer's protocol. Briefly, the pAdtrack-U6-siHIF-1αplasmid is linearized by PmeI and then recombined with pAdeasy-1 plasmid in recA+ bacteria BJ5183. The resultant pAdeasy-siHIF-1α was then transfected into relatively low passage (passage no.<30) 293 cells after linearization by PacI. After 7 to 10 days the infectious adenovirus vector was obtained, AdsiHIF-1α. Large-scale preparation of the particles was carried out subsequently following established protocols.

RT-PCR Cloning of GLUT-1 cDNA from U87 and HeLa Cells

Total RNA is isolated from U87 cells using TRIzol reagent (Invitrogen Life Technologies, Calif.), according to the manufacturer's recommendation. Approximately, 5 µg of total RNA is used for reverse transcription with oligo (dT) as a reverse primer (SuperScript First-Strand Synthesis System for RT-PCR, Invitrogen Life Technologies). Five percent of the cDNA product is used for PCR (Platinum Pfx DNA Polymerase, Invitrogen Life Technologies) amplification of GLUT-1. The PCR conditions are as follows: incubation for 5 min at 94° C. followed by 30 cycles of 30 s at 94° C., 30 s at 55° C., and 2 min at 68° C., and a final extension for 7 min at 68° C. in a PerkinElmer 9700 Thermal Cycler. The primers used to amplify GLUT-1 from HeLa and U87 cells are: forward primer (SEQ ID NO:19) 5'-CCACCACCGCAGCGCT-GCCA-3' and reverse primer (SEQ ID NO:20) 5'-CGAGTG-GTGATCCTGGGCGACTCA-3'. PCR products are purified from 1% agarose gel stained with ethidium bromide and ligated with pGEM-T Easy vector (Promega, Madison, Wis.) after A-tailing procedure. The His-tagged wild-type GLUT-1 molecules are constructed by using the same forward primer and the reverse primer (SEQ ID NO:21): 5'GGCTCGAGT-CAATGGTGATGGTGATGATGCACTGG-GAATCAGCCCC-3', To construct a His-tagged GLUT-1 cloned from U87 cells, the same forward primer as described above is used and the following reverse His-tagged primer: (SEQ 00 NO:22) 5'-GGCTCGAGTCAATGGTGATGGT-GATGATGGGAACTTTGAAGTAGGTG 3'. The purified fragments corresponding to the encoded GLUT-1 are cloned into pSC59 vector under the control of vaccinia early/late promoter. The DNA sequence of cloned
DNA is verified by direct sequencing. The plasmid DNA containing GLUT-1 from either HeLa or U87 cells is transfected into CHO cells by DOTAP Liposomal Transfection Reagent (Roche, Indianapolis, Ind.). Expression of GLUT-1 is activated by infection with vaccinia virus.

Cloning of Genomic DNA Fragments of GLUT-1 Gene

Genomic DNA is isolated from U87 and HeLa cells using DNeasy Tissue Kit (QIAGEN, CA), according to the manufacturer's recommendation. The concentration and purity of genomic DNA samples are measured, and 1 µg of genomic DNA is used for PCR. For GLUT-1 cloned from HeLa and U87 cells, the forward primer (nucleotides 1292-1312) used is: (SEQ NO:23) 5'-CTACGTTCTTCATCATCTTCACT-3' and the reverse primer (nucleotides 1578-1598) used: (SEQ NO:24) 5'-GGAGCCCCAGGCCCGGCTCGG-3'. PCR products are ligated with pGEM-T Easy vector, and positive clones are verified by direct DNA sequencing.

Glut-1 siRNA

The sequence of the synthetic siRNA complementary to the GLUT-1 open reading frame is (SEQ ID NO:25) 5'-GGGCCAAGAGUGUGCUAAAGAAGC-3' and complementary to the 3'UTR is (SEQ NO:26) 5'-GGCUGGAC-CUAGUCCUAAGGACACAC-3' (Integrated DNA Technologies, Coralville, Iowa). These siRNA molecules are transfected together into HeLa or U87 cells using an oligofectamine reagent purchased from Invitrogen (Invitrogen, San Diego, Calif.). HeLa or U87 cells were plated at 1.5×10⁵ cells/well in a 6-well plate using serum-free medium without antibiotics. The siRNA (10 or 100 nM) is gently mixed with the oligofectamine reagent and incubated for 20 min then added to the corresponding well. After 4-h incubation at 37° C., 0.5 ml of 3× serum is added. Following incubation for 72 h in a 37° C. incubator, the transfected cells are washed and infected with pT7-lacZ reporter. Separate populations of 293 cells are infected with vaccinia viruses encoding either Unc63 or Env63 and T7 RNA polymerase. At 15 h post-infection, the Env-expressing cells are mixed (1:1) with the siRNA transfected cells and incubated for 2.5 h to allow cell fusion. The effect of siRNA on Envmediated fusion is assayed by measuring β-galactosidase produced. The control siRNA usedas a negative control is a scrambled sequence (SEQ ID No:27) 5'-CUUCCUCUCUUUCUCUCCCUUGUGA-3' purchased from Integrated DNA Technologies, Coralville, Iowa.

EXAMPLE 3

Videomicroscopy and morphometric analysis of 4T1 mammary carcinomas implanted in the mouse dorsal skinfold window chamber was used to determine the selectivity of SS erythrocytes for tumor microvasculature and deposition in tumor parenchyma. SS erythrocytes from patients with homozygous SS sickle cell disease and healthy normal donors were labelled with carbcyanine and infused intravenously into tumor bearing mice. Efficacy studies were carried out by administering SS cells to mice with established 4t1 carcinomas in the presence of heme oxygenase inhibition with zinc protoporphyrin. MicroPET scanning was performed on mice bearing established 4t1 carcinoma infused with $^{18}$FDG loaded SS cells followed by free $^{18}$FDG.

Methods

Mice and Tumor Model

All animal experiments were approved by the Duke University IACUC. Female athymic homozygous nude mice (nu-/nu-), between 8-12 weeks of age weighing 19-26 grams, obtained from Charles River Laboratories (Wilmington, Mass.), were used for all experiments. The animals were housed 5 animals per cage in a 12 h light-dark cycle with water, food ad libitum. All infusions were performed using the dorsal tail vein. Mouse 4T1 mammary carcinoma cells were cultured with DMEM (Life Technologies) supplemented with 10% (v/v) fetal bovine serum (FBS, HyClone, Logan, Utah) and 1% (v/v) antibiotics-antimycotics (Life Technologies) as previously described (88).

Western Blotting Analysis of HO-1 Expression

For immunoblotting, proteins were extracted from snap frozen mouse tumor, kidney, and liver tissues. Tissues were homogenized and dissolved in the cold RIPA buffer (Pierce, Rockford, Ill.). Cell debris was separated by centrifuging twice at 10,000 g for 10 min at 4° C. Whole protein concentration was measured by Bradford assay (Bio-Rad Laboratories, Hercules, Calif.). 100 µg of each protein was electrophoresed in 12% sodium dodecyl sulfate-polyacrylamide gel electrophoresis (SDS-PAGE). Proteins were transferred to PVDF (polyvinylidene fluoride) membrane and blocked for 1 hour with 5% non-fat dried milk in TBST (20 mM Tris-HCl, 150 mM NaCl, and 0.1% Tween 20, pH 7.5). Membranes were incubated overnight with 1:500 diluted anti-mouse HO-1 antibody (Assay Designs, Ann Arbor, Mich.), washed three times with TBST and incubated with 1:1000 diluted horseradish peroxidase (HRP)-conjugated anti-mouse IgG antibody for 1 hour at room temperature followed by washing with TBST. The blot was immunodetected with enhanced chemiluminescence (ECL) detection system (Perkin Elmer, Waltham, Mass.). For a loading control, 50 µg of protein was loaded in 10% SDS-PAGE and blotted with 1:2000 diluted anti-mouse β-actin antibody (Sigma-Aldrich, St. Louis, Mo.).

Collection, Preparation and Treatment of Human RBCs

Fresh blood samples from patients homozygous for hemoglobin S and from normal controls were collected into citrate tubes. RBCs were allowed to separate from the buffy coat containing leukocytes and platelet-rich plasma by gravity at 4° C. for at least 2 h. Plasma and buffy coat were removed by aspiration and RBCs were washed four times in sterile PBS with 1.26 mM $Ca^{2+}$, 0.9 mM $Mg^{2+}$ (pH 7.4). Packed RBCs were analyzed for leukocyte and platelet contamination using an Automated Hematology Analyzer Sysmex K-1000 (Sysmex, Co., Cobe, Japan). Packed RBCs were fluorescently labeled with DiI (Molecular Probes, Eugene, Oreg.) for in vivo adhesion studies as previously described. DiI has no effect on RBC suspension viscosity or RBC survival in circulation. Cells were then washed three times with 5 ml PBS with $Ca^{2+}$ and $MG^{2+}$.

Window Chamber Surgery and Murine Mammary Carcinoma Implantation

This procedure has been previously described. General anesthesia was achieved by intraperitoneal (IP) injection of 100 mg/kg of ketamine (Abbott Laboratory, Chicago, Ill.) and 10 mg/kg of xylazine (Bayer, Shawnee Mission, Kans.). A double-sided titanium frame window chamber was surgically implanted into the dorsal skin fold under sterile conditions with aseptic technique. Surgery involved carefully removing the epidermal and dermal layers of one side of a dorsal skin fold, exposing the blood vessels of the subcutaneous tissue adjacent to the striated muscles of the opposing skin fold. The two sides of the chamber were secured to the skin using stainless steel screws and sutures, followed by injection of $1 \times 10^4$ 4T1 tumor cells into the exposed fascia. A glass window was placed in the chamber to cover the exposed tissue, and was secured to the chamber with a snap ring. Animals were kept in a specialized environmental chamber at 32-34° C. and 50% humidity until in vivo studies were performed 8 days post-surgery.

Intravital Microscopy and Visualization of RBC Trafficking

The set up for window chamber visualization was identical to that described above. Labeled human RBCs (300 ml; hematocrit [Hct] 0.50 [50%] in PBS with $Ca^{2+}$ and $Mg^{2+}$) were infused through the dorsal tail vein and blood flow dynamics were observed in both tumor neovasculature and subdermal vessels for at least 30 minutes using LD Achroplan 20x/0.40 Korr and Fluar 5x/0.25 objectives (Zeiss). Microcirculatory events and cell adhesion were simultaneously recorded using a Trinitron Color video monitor (model PVM-1353 MD, Sony) and JVC videocassette recorder (model BR-S3784, VCR King, Durham, N.C.) connected to a digital video camera C2400 (Hamamatsu Photonics K.K., Japan). Blood vessels were also viewed under fluorescence-illumination using a 100-W mercury arc lamp and 5x and 20x magnifications. At least 30 segments of tumor and adjacent normal subdermal microvessels were examined 30 minutes following SS RBC and normal RBC infusions. Measurement of vaso-occlusion was performed by examining videotapes using 20x magnification. Vessels were counted as occluded by considering labeled cells attached to the vessel walls and immobile for at least 10 seconds with no observable blood flow. The percentage of vessels occluded by SS or normal RBCs was calculated by division of the number of occluded vessels by the total number of vessels in the field that contained visible blood flow at baseline.

Histology

The animals used in window chamber experiments were sacrificed 30 minutes post-injection of DiI-labeled RBCs. Tumors and organs were collected and snap frozen in OCT media. Forty micron sections were cut from four standardized locations in each organ mounted and examined via inverted fluorescence microscopy. Three random fields were imaged for each section of each organ. RBC fluorescence intensity and GFP dependent HIF-1α expression, which is induced under control of the hypoxia regulatory element, for each field were quantified using Adobe Photoshop CS2 software (Adobe Systems Inc., San Jose, Calif.). Five determinations of pixel intensity were obtained for each field and averaged for the three fields to obtain mean fluorescence intensity. The mean fluorescence values were averaged among groups of animals for statistical analysis.

For tumor therapy studies, tumors, organs and brain from hippocampus, cortex, cerebellum and Purkinje fibers were collected in 4% paraformaldehyde or 10% formalin and stained using hematoxylin and eosin and Prussian blue as previously described (93)

Tumor Therapy Studies

Tumor volume and body weight were measured every 2 days, and volumes were calculated as $\pi/6 * length^2 * width$. The treatment endpoint was 5x treatment volume or 1500 $mm^3$, which ever was reached first. The protocol called for euthanasia of animals experiencing more than a 15% drop in body weight, relative to baseline. No animals reached this level of weight loss. Zinc (II) protoporphyrin IX (Zn-PP; Frontier Scientific) was dissolved in a solution of saline and N,N dimethylformamide (DMF) at a 95/5 volume ratio to a concentration of 0.1 mg/ml prior to i.p. injection. Lyophilized Doxorubicin (DOX; Bedford Laborotories) was hydrated with saline (2 mg/ml) prior to i.v. administration. Study groups consisted of 10 mice per cohort. SS cells were infused iv (150-200 µl, HCT 50%), followed by Zn-PP (IP, 0.5 mg/kg) and/or Doxorubicin iv (5 mg/kg). Two experiments were performed. In the first, treatment started when tumor volumes reached a median of 354 $mm^3$ (249-445 $mm^3$ interquartile range). Animals were stratified by tumor volume into treatment groups. In the second experiment, the tumors were smaller, with a median and interquartile range of 72 (57-90) $mm^3$. Tumors were treated at a smaller volume in the second experiment to permit a larger dynamic range before the treatment endpoint was reached.

Statistics

All data analysis was performed using GraphPad Prism version 4.03 for Windows (GraphPad Software, San Diego Calif. USA). Kaplan-Meier analysis of time to reach 5x treatment volume was used to evaluate treatment efficacy. Hazard ratios were calculated to compare between treatment groups within a study. Window chamber/histology data, starting tumor volume size, maximum weight change were analyzed using either student T-test or Kruskal-Wallis if multiple groups were compared. A p value<0.05 was considered significant for all tests.

Results

Analysis of Heme Oxygenase Production, Neovascularization and Hypoxia of 4t1 Carcinoma On day 8 after tumor implantation, 4T1 carcinomas growing in the dorsal skin window chamber showed heme oxygenase production exceeding that of normal liver and kidneys. Intravital microscopy showed a dense disordered network of neovascular ultrastructure with acutely branching capillaries and anastomotic channels. We have previously reported that 4T1 tumors are markedly hypoxic at this size as indicated by extensive expression of a GFP-HIF-1 reporter throughout the tumor. Thus, SS RBC infusion studies using intravital microscopy were carried out on day 8 after tumor implantation when they were neovasculatured, hypoxic and exhibited robust production of heme oxygenase.

SS RBCs but not Normal RBCs Occlude Tumor Neovasculature

Infusion of SS RBCs into tumor bearing mice resulted in rapid appearance of the fluorescent RBCs in the tumor microvessels (FIG. 2a). SS cell adhesion and vaso-occlusion of tumor neovasculature were evident within 2-5 minutes after infusion. This progressed to stasis and frank occlusion of a large percentage of blood vessels over a 30 minute period. RBCs normally move at a velocity that does not permit visualization of individual cells in vessels with high clarity in still photographs. The appearance of individual labeled cells is indicative of stasis (FIG. 2a). In sharp contrast, SS RBCs showed minimal adhesion to normal subdermal vascular endothelium with no detectable RBC stasis or vaso-occlusion. SS cell adhesion, occlusion and blood stasis were noted diffusely in the tumor vessels at the periphery as well as in the core of tumors (FIG. 2a). Vaso-occlusion was time-dependent and occurred equally at junctional and non-junctional points in curved and straight segments (FIG. 2b). In some instances blood flow was diverted to adjacent tumor vessels or reversed indicating shifts in network flow dynamics. Tumor sections obtained 30 min after infusion of RBCs showed focal presence of fluorescently labeled SS RBCs in tumor parenchyma compared with minimal deposition of normal RBCs (FIG. 2c). Normal RBCs displayed virtually no adhesion to neovascular vessels or adjacent subdermal vessels (FIG. 2a,b).

We further verified stasis by direct visualization of flow within all vascular segments, using videomicroscopy. Morphometric analysis of video still photographs taken 30 minutes after cell infusions showed substantially greater fluorescent intensity of SS cells in tumor neovessels compared to normal RBCs (p=0.0043), or SS-RBCs in adjacent subdermal vessels (p<0.0079) (FIG. 2c). Quantification of the percentage of tumor neovessels occluded with SS RBCs showed an average of 88% of tumor neovessels occluded compared to less than 5% of adjacent normal subdemal vessels and tumor vessels of mice treated with normal RBCs, respectively (p<0.00001 and p<0.000001 respectively) (FIG. 2c). Uptake of RFP-labelled SRBCs 30 minutes after infusion was also significantly greater than normal RBCs (p=<0.00001) (FIGS. 1d). H&E analysis of tumor tissue 24 hours after SS cell infusion showed focal areas of cytoplasmic eosinophilia with capillary engorgement consistent with acute ischemia that was not seen in tumors of mice treated with normal RBCs (FIG. 2e). Twenty four hours post infusion RFP-labelled SS cells were still noted in tumor sections compared to minimal uptake of normal RBC (FIG. 2e). Despite some uptake of RFP-labelled SS and normal RBCs in spleen and lungs and to lesser degree in kidneys of SS-RBC and normal RBC-treated mice noted 24 hours after infusion (FIG. 2f), H & E sections of normal organs at this time were unremarkable and notably devoid of significant inflammation, infarction or necrosis.

Antitumor Effect of SS RBCs with a HEME Oxygenase Inhibitor

Preliminary experiments showed that SS RBCs, normal RBCs and zinc-protoporphyrin (ZnPP), a potent inhibitor of heme oxygenase, administered alone to mice bearing established 4T1 carcinoma had no effect on tumor growth rate (p=0.2). However, ZnPP given 24 hours after SRBCs with or without doxorubicin showed significant growth delay compared to the untreated control group (p=0.0016). In a subsequent experiment we administered ZnPP 24 hours before SS cell infusions with or without doxorubicin (Dox). All SS-treated groups showed significant growth delay compared to untreated controls (p<0.0001) with hazard ratios 4.87-5.05 respectively, using Kruskal-Wallis test and time to reach 5× treatment volume as an endpoint (FIG. 3). All 3 SS treated groups also showed significant growth delay compared to the Zn-PP+Dox-treated group (p=0.0282, 0.0041, and <0.001, respectively) with hazard ratios of 2.43, 3.07, and 4.11, respectively (FIG. 3). The SS RBCs×3+Zn-PP+Dox-treated group also showed significant growth delay compared to the SS RBCs+ZnPP-treated group (p=0.0362, hazard ratio 2.38) (FIG. 3). Comparison of the other SS-treated groups to each other showed no statistical difference (P>0.05). In the course of treatment, mice treated with SS RBCs+Zn-PP experienced no acute or chronic toxicity, and weights of the treated and untreated control groups were not significantly different (p=0.9).

Histologic Analysis of Tumors and Organs from Treated Animals

Hematoxylin and eosin analysis of tumor sections from mice 20 days after treatment with SS RBCs×3+Zn-PP+Dox showed more diffuse tumor necrosis than untreated controls. Tumor sections from these treated mice showed focal hemosiderin deposits that were not seen in the untreated control tumors (FIG. 2e). Spleens of treated mice showed scattered hemosiderin deposits not present in untreated control tissues. Except for these findings lung, liver, kidney, spleen and brain tissues including hippocampus, cortex, cerebellum and Purkinje fibers from the SS RBCs×3+Zn-PP+Dox treated and untreated mice were unremarkable and notably devoid of inflammation, infarction and necrosis.

SUMMARY

The treatment of hypoxic tumors with grossly abnormal neo-vasculature remains a significant challenge in cancer therapeutics, because hypoxia contributes to chemo- and radio-resistance. Under hypoxemic conditions similar to those observed in some tumor microvessels, sickle erythrocytes (SS RBCs) from patients with sickle cell anemia become rigid and are postulated to bind via multiple adhesion receptors to upregulated cognate ligands on endothelium promoting vaso-occlusion. Intravital microscopy showed that SS RBCs, but not normal RBCs, adhered to tumor vessel walls inducing frank occlusion of microvessels of 8 day old 4T1 mammary carcinomas visible through window chambers implanted into nude mice. Histologic examination of 4T1 tissue sections confirmed focal deposition of SS RBCs throughout the tumor parenchyma. More interestingly, SS RBCs administered together with a heme oxygenase inhibitor induced a significant tumoricidal response against established flank tumors of mice, with minimal normal organ toxicity. In contrast, normal RBCs failed to exhibit an anti-tumor effect. Our results suggest a tumoricidal role for SS RBC-free constitutive heme in association with a heme-oxygenase inhibitor. In summary, we report for the first time that SS RBCs induce occlusion of hypoxic tumor neo-vasculature with an anti-tumor effect in the presence of a heme oxygenase inhibitor. Thus, we propose a novel role for SS RBCs and possibly with their progenitors as promising new vehicles for delivery into tumors of constitutive heme, oncolytic drugs, toxins, genes and oncolytic viruses (FIG. 4).

EXAMPLE 4

Adsorption of Oncolytic Viruses on Sickled Erythrocytes

We obtained monoclonal VSV by plaque purification on BHK-21 cells. We performed virus concentration and purification by sucrose gradient centrifugation. We measured viral titers by standard plaque assays on BHK-21 cells. $10^9$-$10^{12}$ human SS erythrocytes or erythrocyte precursors are incubated with $5 \times 10^3$ PFU of VSV or reovirus for 4 h at 4 1C at MOIs 0.1, 1.0 and 10 at 4° C. Four hours later, SS cells are harvested. VSV-GFP by cloning the cDNA encoding GFP into the plasmid pVSV-XN2. We pelleted SS cells and incubated them with VSV in 100 ml PBS for 4 h at 4° C. We washed the cells three times in ice-cold PBS and used them directly for in vivo adoptive transfer. For in vivo studies, the carcinoma and tumor models described above in tumor models section are used. For adoptive transfer experiments, we administered mature SS erythrocytes or SS progenitors preloaded with VSV or reovirus i.v., typically at $10^9$ cells in 100 µl. For survival studies, we measured tumor diameter in two dimensions three times weekly with calipers and killed the mice when tumor size was approximately 1.0 cm×1.0 cm in two perpendicular directions.

EXAMPLE 5

Examples 5 and 6 are cumulative disclosures from U.S. Ser. No. 09/751,708, U.S. 60/438,686, U.S. 60/415,310, U.S. 60/406,750, U.S. 60/415,400, U.S. 60/406,697, U.S. 60/389, 366, U.S. 60/378,988, U.S. Ser. No. 09/870,759 which are incorporated by reference and their references in their entirety.
Sickled Erythrocytes as Carriers of Tumoricidal Agents.

Sickled erythrocytes are known to be more adherent to microvascular endothelium than normal erythrocytes and to adhere to a greater extent under conditions of local hypoxia and acidosis. The primary pathological defect in sickle cell disease is the abnormal tendency of hemoglobin S to polymerize under hypoxic conditions. The polymerization of deoxygenated hemoglobin S results in a distortion of the shape of the red cell and marked decrease in its deformability. These rigid cells are responsible for the vaso-occlusive phenomena which are the hallmark of the disease.

Sickle red cells adhere to the microvascular endothelium for the following reasons: Sickled cells have abnormally increased expression of $\alpha_4\beta_1$ integrin and CD36. Activation of platelets releases thrombospondin, which act as a bridging molecule by binding to a surface molecule, CD36, on an endothelial cell and to CD36 or sulfated glycans on a sickle reticulocyte. Inflammatory cytokines induce the expression of vascular-cell adhesion molecule 1 (VCAM-1) on endothelial cells. This adhesive molecule binds directly to the $\alpha_4\beta_1$ integrin on the sickle reticulocyte.

In the oxygenated state, the extent of sickle cell adhesion is density-class dependent: reticulocytes and young discocytes (SS1) greater than discocytes (SS2) greater than irreversible sickle cells and unsicklable dense discocytes (SS4). Hypoxemic conditions have no effect on adherence of normal erythrocytes but sickle erythrocyte adherence to endothelial cells is increased significantly. The least dense sickle erythrocytes containing CD36 and VLA-4+ expressing reticulocytes are especially involved in hypoxia sensitive adherence. Selective secondary trapping of SS4 (dense cells) occurs in post capillary venules where deformable SS cells are preferentially adherent. Vaso-occlusion is induced by a combination of precapillarly obstruction, adhesion in post capillary venules, and secondary trapping of dense erythrocytes. This induces local hypoxia leading to increased polymerization of hemoglobin S and rigidity of SS erythrocytes. In this way the obstruction is multiplied and extended to nearby vessels.

In the present invention, sickled erythrocytes are used to carry tumoricidal agents into the microvasculature of tumors. Sickle cell trait cells are preferred since they are normal under physiologic conditions but sickle and become adhesive in the acidotic and/or hypoxemic tumor microvasculature. Tumoricidal agents introduced into and carried by sickled erythrocytes include oncolytic viruses including but not limited to herpes simplex, adenoviruses, vaccinia, Newcastle Disease virus, autonomous parvoviruses, In addition, the adenovirus encoding thymidine kinase is transfected into tumor cells that are then susceptible to lysis ganciclovir. Various oncolytic and tumor specific viruses with tumor specificity used to transfect sickle cells are described in Kim, D. et al., *Nat. Med.* 7:781-7 (2001).

In addition the sickled erythrocyte carry nucleic acids encoding tumoricidal agents including but not limited to *C. perfringens* exotoxin, pertussis toxin, verotoxins, pseudomonas exotoxins and superantigens, perforin, granzyme B, complement components (membrane attack complex), oxidized LDL, tumor specific antibodies alone or fused to toxins including but not limited to superantigens, *Pseudomonas* exotoxins, ricin, clostridia toxin. The nucleic acid encodes a hemolysin such as but not limited to *E. coli* hemolysin or staphylococcal alpha hemolysin. The sickled cell can also contain anaerobic bacterial spores such as clostridia species which can grow selectively in hypoxemic tissues. The sickled erythrocyte also carries phage displays, exosomes, and sickle cell vesicles, sec vesicles expressing tumor toxins or superantigens. The toxins may be fusion proteins of toxins with ligands expressed on tumor vasculature or tumor such a EGF, inactivated factor VIII or antibodies specific for a wide variety of tumor antigens well known in the art.

The nucleic acids encoding these toxins and oncolytic and tumor specific viruses are placed under the promoter of the heat sensitive global operator (Example 69). When entering the hypoxic tumor, sickled erythrocyte adhere to the tumor vasculature. In the hypoxemic environment of the tumor, the hypoxia sensitive global promoter is activated and induces the production lytic viruses and toxins. Sickled cells are disrupted and lyse releasing lytic virus and toxin into the hypoxic tumor. As the tumor site becomes more hypoxic, VCAM-1 and p-selectin expression on tumor endothelium are upregulated trapping more circulating sickled cells in the tumor microcirculation to undergo lysis with release of tumoricidal products into the tumor area.

The sickled cell is transfected preferably with the oncolytic viruses and toxins given above at a stage preferably before it is enucleated (Examples 1, 60, 69). Nucleated sickle reticulocytes are the preferred cell for transfection although enucleated sickled cells will also work (Example 69 of PCT/US03/14381) Anaerobic bacterial spores such clostridia are transfected into the sickled erythrocytes by endocytosis or electroporation (Schrier S. *Meth. Enzymol.* 149: 261-271 (1987); Tsong T Y *Meth. Enzymol.* 149-259 (1987)). They are also introduced into sickle erythrocytes that have been lysed under hypotonic conditions and the membranes annealed with encapsulation of the anaerobic spores (Example 69).

Erythrocytes from subjects with sickle trait are preferred because these red cells are functionally and structurally normal in the circulation but are activated to sickle in the hypoxic tumor vasculature. Here they assume the sickled configuration, adhere to the endothelium of the tumor microcirculation and obstruct microvasculature in a manner similar to the homozygous SS erythrocytes.

The sickled erythrocytes are administered parenterally by injection or infusion in a therapeutically effective amount of cells. This encompasses a volume of 1-25 cc of packed cells administered i.v. over a one hour period. These cells are used in protocols given in Example 14-16, 18-23, 66 of PCT/US03/14381.

Sickled Erythrocytes as Gene Carriers

Erythrocytes from patients with sickle cell anemia contain a high percentage of SS hemoglobin which under conditions of deoxygenation aggregate followed by the growth and alignment of fibers transforming the cell into a classic sickle shape. Retardation of the transit time of sickled erythrocytes results in vaso-occlusion. SS red blood cells have an adherent surface and attach more readily than normal cells to monolayers of cultured tumor endothelial cells. Reticulocytes from patients with SS disease have on their surface the integrin complex α4v1 which binds to both fibronectin and VCAM-1, a molecule expressed on the surface of tumor endothelial cells particularly after activation by inflammatory cytokines such as TNF, interleukins and lipid-mediated agonists (prostacyclins). Activated tumor endothelial cells are typically procoagulant. Similar molecules are upregulated on the neovasculature of tumors. In addition, upregulation of the adhesive and hemostatic properties of tumor endothelial cells are induced by viruses, such as herpes virus and Sendai virus. Sickled erythrocytes lack structural malleability and aggregate in the small tortuous microvasculature and sinusoids of tumors. In addition, the relative hypoxemia of the interior of tumors induces aggregation of sickled erythrocytes in tumor microvasculature. Hence, sickled erythrocytes with their proclivity to aggregate and bind to the tumor endothelium are ideal carriers of therapeutic genes to tumor cells.

Red blood cell mediated transfection is used to introduce various nucleic acids into the sickled erythrocytes. The extremely plastic structure of the erythrocyte and the ability to remove its cytoplasmic contents and reseal the plasma membranes enable the entrapment of different macromolecules within the so-called hemoglobin free "ghost." Combining these ghosts and a fusogen such as polyethylene glycol has permitted the introduction of a variety of macromolecules into mammalian cells (Wiberg, F C et al., *Nucleic Acid Res.* 11: 7287-7289 (1983); Wiberg, F C et al., *Mol. Cell. Biol.* 6: 653-658 (1986); Wiberg, F C et al., *Exp. Cell. Res.* 173: 218-227 (1987)). Both transient and stable expressions of introduced DNA are achieved by this method. Sickled cells can also be transfected with a nucleic acid of choice e.g., apolipoproteins, RGD in the nucleated prereticulocyte phase (e.g. proerythroblast or normoblast stage) by methods given in Example 1 of PCT/US03/14381. Sickled erythrocytes transfected with nucleic acids encoding a SAg and/or carbohydrate modifying enzyme to induce expression of the α-Gal epitope, apolipoproteins, RGD and/or any construct described herein. Nucleic acids encoding additional polypeptides alone or together with SAg as described in Tables I and II of PCT/US03/14381 including but not limited to angiostatin, apolipoproteins, RGD, streptococcal or staphylococcal hyaluronidase, chemokines, chemoattractants and Staphylococcal protein A are transfected into and expressed by sickled erythrocytes. These sickled cell transfectants are administered parenterally and localize to tumor neovascular endothelial sites where they induce a anti-tumor response. The methods of in vivo transfection of tumor cells are given in the Examples 17 of PCT/US03/14381. Protocols for use of these transfectants in the induction of anti-tumor immune response are described in Examples 14, 15, 16, 18-23, 31 of PCT/US03/14381. Superantigen nucleic acids together with nucleic acids encoding either apo(a), apoB and apoE4 are also transfected into nucleated sickled erythrocytes (e.g., proerythroblast or normoblast phase) by methods given in Examples 1 and 6 of PCT/US03/14381. The integrin ligand RGD nucleic acids are transfected into tumor cells or sickled cells to facilitate the localization of the transfected tumor cells and sickled cells to integrins expressed in the tumor neovasculature in vivo (see Example 6). Alternatively, the sickled erythrocytes or tumor cells acquire the apolipoprotein or oxyLDL by coculture with liposomes which express the apolipoprotein or oxyLDL (see Section 7 & Example 5 of PCT/US03/14381).

These tumor cells or sickle cell transfectants are administered parenterally and are capable of trafficking to tumor microvasculature wherein they bind to apolipoprotein and scavenger receptors on endothelial cells and macrophages. The transfectants are phagocytosed by macrophages cells and induce endothelial cell apoptosis. SAgs expressed on the tumor cells and sickle cells also induce a local T cell inflammatory anti-tumor response which envelops the neighboring tumor cells.

Methods for Preparing Sickled Erythocytes for Use as Carriers Tumoricidal Agents The sickled cells are obtained from patients with sickle cell anemia or sickle cell trait. The type of sickle cell disease may be hemoglobin SS, homoglobin SC, or the combination of hemoglobin SS and β-thalassemia. To determine compatibility of donor sickled erythrocytes with recipient erythrocytes, the donor cells are ABO typed and matched. The tendency of these red cells to adhere to cultured endothelial cells is assayed in vitro by the method of Hebbel R P et al., *New Eng. J. Med.* 302: 992-995 (1980). The sickled cells are harvested, transfected with appropriate oncolytic or tumor specific viruses, toxins or anaerobic bacteria in vitro by methods given in Example 1. Fifty to 250 cc of transfected sickled erythrocytes are infused intravenously over 1-2 hours. The procedure is repeated two to three times weekly for two to four weeks. Responsive patients are retreated on a similar schedule if tumor reappears. The patient's vital signs are monitored every 10 minutes during the infusion, then every hour for the next 4 hours and Q4-6 hours thereafter.

Infection of Nucleated Erythrocytes by Oncolytic or Tumor Specific Viruses: This is carried out by the method of Muhlemann, O., Akusjarvi, G., in *Adenovirus Methods and Protocols* WSM Wold, editor, Humana Press, Totowa, N.J. (1999). Essential steps are given below. Transfection of nucleated sickled cells with various plasmid DNAs described in section 66 of PCT/US03/14381 is carried out as in Examples 1 and 60 of PCT/US03/14381.

Infection of Sickled Cells with Adenovirus:

Sickled cells are grown in round cell-culture bottles on a magnetic stirrer at 37° C. in MEM spinner cell medium, 5% newborn calf serum, optionally containing 1% penicillin/streptomycin. The cells must be kept in log phase (titer $2-6 \times 10^5$ cells/mL), doubling time approx 24 h.

1. Start with $2-3 \times 10^9$ sickled spinner cells; collect them by centrifugation in sterile 1-L plastic bottles by spinning at 900 g at room temperature for 20 min. (Beckman J6M/E centrifuge, JS-4.2 rotor).

2. Decant medium back into the cell-culture bottle (handle under sterile conditions the medium will be reused later), resuspend cells in 200-300 mL MEM without serum (see Note 1), and transfer to a 1-L cell-culture bottle.

3. Infect cells with approx 10 PFU/cell of adenovirus from a high-titer virus preparation. Leave at 37° C. on a magnetic stirrer for 1 h. Dilute cells to approximately $4 \times 10^5$ cells per mL in a large cell culture bottle with the old MEM medium saved at step 2. Add fresh medium if necessary.

4. Continue incubation at 37° C. for 20-24 h for preparation of late-infected extracts. Additional protocols for infecting sickled cells with various lytic viruses or tumor selective viruses are given in Example 60 and in *Adenovirus Methods and Protocols* WSM Wold, editor, Humana Press, Totowa, N.J. (1999) which is herein incorporated in entirety by reference.

Preparation of the Hypoxia Responsive Element Promoter of the VEGF Gene Cloning and Sequencing of the Mouse VEGF Promoter Region:

The VEGF promoter region is amplified by PCR using genomic DNA isolated from mouse liver, oligonucleotide primers synthesized on the basis of the published DNA sequence (GenBank accession number U41383), and LA Taq DNA polymerase (TaKaRa Biomedicals, Osaka, Japan). The sense and antisense primers are -1215 (SEQ ID NO:28) (5'-TTTAGAAGATGAACCGTAAGC-CTAG-3') and +315 (SEQ ID NO:29) (5'-GATACCTCTTTCGTCTGCTGA-3'), respectively. The PCR conditions are 94° C. for 5 min followed by 30 cycles of 94° C. for 30 s, 68° C. for 3 min, and 72° C. for 7 min. The PCR product, which contained the 5'-flanking sequence encompassing the putative HRE site, the transcription start site, and the 5'-untranslated region, is gel-purified and subcloned into a TA cloning vector prepared from EcoRV-cut pBluescript KS-™ (La Jolla, Calif.). Several independent clones are sequenced, and a clone is used for additional experiments. Deletion of the HRE site is obtained by digestion with BsaAI, a recognition site of which resides in the middle of the HRE site.

Luciferase Reporter Plasmid Constructs and Luciferase Assays:

The VEGF promoter sequence with or without the HRE site in pBluescript KS- is excised by digestion with the appropriate restriction enzymes, gel-purified, and blunt-ended with T4 DNA polymerase, and the fragment was ligated into Smalcut pGL2-Basic vector (Promega, Madison, Wis.), yielding plasmids pGLV(HRE)Luc or pGLV(AHRE)Luc, respectively. The orientation of the insert is verified by restriction enzyme analysis. Transient transfection was carried out using Lipotectin (Life Technologies, Inc., Gaithersburg, Md.). As a control for transfection efficiency, pRL-CMV vector (Promega) is cotransfected with test plasmids. pGL2-control vector (Promega) was used as a positive control. Luciferase activity in cell extracts is assayed 48 h after transfection according to the Dual-Luciferase reporter assay system protocols (Promega) using a luminometer (model TD-20/20; Turner Designs, Sunnyvale, Calif.).

Construction of Retroviral Vectors:

Retroviral vector LXSN (provided by Dr. A. D. Miller, Fred Hutchinson Cancer Research Center, Seattle, Wash.) is modified as follows to create a multicloning site. The retroviral vector is digested with EcoR1 and Xho1 and blunt-ended with T4 DNA polymerase. A SacI/KpnI fragment of pBluescript SK- that is blunt-ended with T4 DNA polymerase is ligated to this vector. This procedure yields retroviral vector LXSN(BA), which has a multicloning site between the Betel site and the AppaII site of pBluescript KS-. A retroviral vector harboring the VEGF promoter sequence, HSV-TK gene or GFP gene, and SV40pA, all of which are located in a reverse orientation of LTR, is obtained as follows. A SV40pA fragment is prepared by digestion of Pezos (Invitrogen Corp., Carlsbad, Calif.) with AccI and BamHI. The fragment is gel-purified, blunt-ended with T4 DNA polymerase, and ligated into Bxt/XI-cut and blunt-ended LXSN(BA), yielding a LXSN(BA)/pA vector. The VEGF promoter region with or without the HRE site in pBluescript KS-is excised with EcoRI and San and ligated into EcoRI/Sal1-cut LXSN(BA)/pA, generating vectors LV(HRE) and LV(AHRE), respectively. The GFP or HSV-TK gene or any other gene given in section 66 is cloned into the Not1 site of these vectors via Not1 linkers. The orientation of the inserts is verified by restriction enzyme analysis. The retroviral vectors generated by this procedure are termed LV(HRE)GFP, LV(HRE)TK, and LV(ΔHRE)TK.

Plasmid Transfection and Retrovirus Infection:

Al 1 cells are transfected with the: plasmids using Lipofectin. The retroviruses harboring LV(HRE)GFP or LV(HRE)TK are generated by a φ2 packaging cell line. All cells were infected with the retroviruses in the presence of 8 μg/ml polybrene (Aldrich Chemical Co., Inc., Milwaukee, Wis.). The cells are cultured in the presence of 400 μg/ml G418 (Life Technologies, Inc., Grand Island, N.Y.) to select for cells that expressed vector-derived genes.

Evaluation of GFP Expression and Vascular in Cryosections of Tumors:

Cells: $(2 \times 10^5)$ transfected with LV(HRE)GFP are subcutaneously injected into the flank of gynogenic C57BL/6 mice (Nippon SLC, Hamada's, Japan). Ten days after the injection, tumors are surgically removed and frozen in OCT compound. Cryostat sections are fixed with cold acetone and washed with DPBS, and endogenous peroxides is blocked with 3% hydrogen peroxide in methanol for 10 min. The samples are washed three times with DPBS and incubated with DPBS containing 10% normal goat serum for 60 min to block nonspecific binding sites. They are then incubated with rat ant mouse CD31 antibody (Harlingen, San Diego, Calif.). Sections are washed with DPBS and incubated with TRITC-conjugated goat antiriot IgG. After extensive washings with DPBS, samples are mounted in 50% glycerol in DPBS containing 1 mg/ml/phenylenediamine. The fluorescence emitted from GFP and TRITC is observed under a confocal laser microscope (Fluoview; Olympus, Tokyo, Japan). Alternatively, cells are subjected to hypoxia for 16 h followed by exposure to GCV for 24 h in air, and the cell number was determined 2 days after the treatment.

In Vivo Experiments:

Cells $(2.5 \times 10^5)$ retrovirally transduced with LV(HRE)TK or LV(HRE) are s.c. injected into 6-week-old female C57BL/6 mice. Ten days after the inoculation, GCV diluted in DPBS is i.p. injected at a concentration of 30 mg/kg twice daily at 8-h intervals for 5 days. DPBS alone is injected into control mice. Tumor growth is monitored by caliper measurement of two diameters at right angles, and the tumor mass is estimated from the equation volume=$0.5 \times a \times b^2$, where a and b are the larger and smaller diameters, respectively.

EXAMPLE 6

Vesicles from Sickled Erythrocytes

Vesicles from sickled erythrocytes are shed from the parent cells. They contain membrane phospholipids which are similar to the parent cells but are depleted of spectrin. They also demonstrate that a shortened Russell's viper venom clotting time by 55% to 70% of control values and become more rigid under acid pH conditions. Rigid sickle cell vesicles induce hypercoagulability, are unable to pass through the splenic circulation from which they are rapidly removed. Sickled erythrocytes are transfected in the nucleated prereticulocyte phase with superantigen and apolipoprotein nucleic acids as well as RGD nucleic acids. Nucleic acids encoding additional polypeptides alone or together with SAg as described in Tables I and II are transfected into and expressed by sickled erythrocytes. Any of the immature or mature sickled erythrocytes and their shed vesicles expressing the molecules given in Tables I and II are capable of localizing to tumor microvascular sites where they bind to apolipoprotein receptors and induce an anti-tumor effect. Because of their adhesive and hypercoagulable properties as well as their rigid structure, these sickled cell vesicles expressing superantigen and apolipoproteins are especially useful for targeting the tumor microvascular endothelium and producing a prothrombotic, inflammatory anti tumor effect. Sickled erythrocytes and their vesicles are capable of acquiring oxyLDL via fusion with oxyLDL containing liposomes as in Example 5. The resulting sickle cell or liposome expresses oxyLDL alone or together with SAg. Binding of oxyLDL to the SREC receptor on tumor microvascular endothelial cells induces apoptosis and simultaneous superantigen deposition produces a potent T cell anti-tumor effect.

Vesicles are prepared and isolated as follows: Blood is obtained from patients with homozygous sickle cell anaemia. The PCV range is 20-30%, reticulocyte range is 8-27%, fetal hemoglobin range is 25-13% and endogenous level of ISCs is 2-8%. Blood is collected in heparin and the red cells are separated by centrifugation and washed three times with 09% saline. Cells are incubated at 37° C. and 10% PCV in Krebs-Ringer solutions in which the normal bicarbonate buffer is replaced by 20 mM Hepes-NaOH buffer and which contains either 1 mM $CaCl_2$ or 1 mM EGTA. All solutions contain penicillin (200 U/ml) and streptomycin sulphate (100 μg/ml). Control samples of normal erythrocytes are incubated in parallel with the sickle cells. Incubations of 10 ml aliquots are conducted in either 100% $N_2$ or in room air for various periods in a shaking water bath (100 oscillations per mm). $N_2$ overlaying is obtained by allowing specimens to equilibrate for 45 mm in a sealed glove box (Gallenkamp) which was flushed with 100% $N_2$. Residual oxygen tension in the sealed box was less than 1 mmHg. The percentage of irreversibly sickled cells is determined by counting. 1000 cells after oxygenation in room air for 30 mm and fixation in buffered saline (130 mM NaCl, 20 mM sodium phosphate, pH 74) containing 2% glutaraldehyde. Cells whose length is greater than twice the width and which possessed one or more pointed extremities under oxygenated conditions are considered to be irreversibly sickled.

After various periods of incubation, cells are sedimented at 500 g for 5 mm and microvesicles are isolated from the supernatant solution by centrifugation at 15,000 g for 15 mm. The microvesicles form a firm bright red pellet sometimes overlain by a pink, flocculent pellet of ghosts (in those cases where lysis was evident) which is removed by aspiration. Quantitation of microvesicles is achieved by resuspension of the red pellet in 1 ml of 0.5% Triton X100 followed by measurement of the optical density of the clear solution at 550 nm. Optical density measurements at 550 nm give results that are relatively the same as measurements of phospholipid and cholesterol content in the microvesicles. Cell lysis is determined by measurement of the optical density at 550 nm of the clear supernatant solution remaining after sedimentation of the microvesicles. Larger samples of microvesicles for biochemical and morphological analysis are prepared from both sickle and normal cells following incubation of up to 100 ml of cell suspension at 37° C. for 24 h in the absence or presence of $Ca^{2+}$. Ghosts are prepared from sickle cells after various periods of incubation. The cells are lysed and the ghosts washed in 10 mM Tris HCl buffer, pH 73, containing 0.2 mM EGTA.

These vesicles are useful as a preventative or therapeutic vaccine.

EXAMPLE 7

MHCII Independent Tumor Cell Killing by SEC Via Tumor Cell Globo/Galabiotriacylceramide Receptors & Synergy with Cisplatin Staphylococcal enterotoxin interact with tumor cells by binding to tumor cell MHCII and in some cases, upregulating expression of tumor cell ICAM-1. The receptor for SE binding to $MHCII_{neg}$ tumor cells has not been identified. In the present study, we demonstrate direct tumor killing by SEC and SEG versus $MHII_{neg}$ tumors in system free of MHCII antigen presenting cells using a conventional MTT cytotoxicity assay[1]. SEC induced tumor killing directly in a dose dependent fashion with peak killing in the range of 2-10 μg/ml. The effect was not due to TNFα or IFNγ or any other measured cytokine released from the tumor cells since these levels were only marginally higher than the unstimulated control after incubation with these SEs. The cytotoxic effect was dose-dependent, selective for SEC and SEG but not SEA and more effective against lung adenocarcinoma (CRL5800) cells and squamous cell carcinoma cells (Hep2) than colon (T84). Notably, the cytolytic (and subcytolytic doses-discussed below) of SEC used herein were in a range that induces transcytosis in intestinal and vaginal epithelial cells suggesting that activation/disruption of the membrane permeablity barrier might play a role in the tumor killing The more effective killing CRL5800 cells or Hep2 cells than T84 cell than by SEC and suggests that the CRL5800 or Hep2 cells but not T84 cells possess receptors and signaling pathways responsive to these SEs. Indeed the tumor killing of Hep2 and CRL5800 cells was abolished by prior treatment with ceramidase. Notably globotriacylceramide receptors are expressed on Hep2 but not t84 cells (Philpott D J et al., *Am J Physiol.* 273 (6 Pt 1):G1349-5. (1997). These finding strongly support the galabiosylceramide receptors on Hep2 and CRO5800 as responsive to the tumor killing effects of SEC.

The selectivity of killing of CRL500 and Hep2 cells but not SEA may be related to different phylogenetic lineages of these SEs and their recognition of key surface receptors on T84 cells. Thus SEB and SEC fragments 130-160 will induce cytotoxicity in tumor cells expressing galabiosylceramide/globotriacylceramide receptors in a MHCII independent fashion. These receptors are likely to be expressed on renal carcinoma cells originating from normal proximal tubular epithelial cells on which such receptors are highly expressed. Notably, tumor cells exposed to SEB, a member of the same phylogenetic family as SEC/SEG, in doses of 1 ug/ml exhibit transcytosis of the SE, a decrease in transmembrane resistance, increased permeabiltity to small molecules (EDTA, mannitol, horseradish peroxidase), resistance to induction of ion secretion by secretagogues and an increase in chemokine production.

We found that direct exposure of Hep2 cells to subcytotoxic doses of SEC (1 μg) along with subcytolytic doses of cisplatin (1 μM/ml) produces a nearly 2 log reduction in $ED_{50}$ for SEC. Notably, the subcytolytic dose of the SEC (1 μg/ml) used was in a range that induces transcytosis in intestinal and vaginal epithelial cells. This suggests that subcytolytic SEC induces injury to the tumor cell membrane permeability barrier that enhances tumor killing by permitting water soluble cisplatin that does not require active transport to diffuse freely into the tumor cell.

1. Methods

MTT Assay

Cell viability and proliferation was quantified by measuring the reduction of yellow 3-(4,5-dimethylthiazolyl-2)-2,5-diphenyltetrazolium bromide (MTT, Calbiochem) to the blue, water-insoluble formazan. For cytotoxicity studies, tumor cells treated with various concentrations of cisplatin and SEC at 37° C., 5% $CO_2$. MTT was added to each well at a final concentration of 0.5 mg/mL. After 4 hours of incubation, 100 μl Cell Lysis Buffer (10% SDS, 0.04N HCl) was added to each well and allowed to sit overnight at 37° C. MTT reduction was quantified by measuring absorbance at 570 nm against a 650 nm reference using the microplate reader. All MTT assays were done in triplicate for each experiment. Results were recorded as the average of three determinations and fraction of the untreated control values.

Tumor cells & cell culture

Hep-2 laryngeal squamous cell carcinoma cell line and T84 colon carcinoma cells were purchased from the American type culture collection. The CRL5800 NCI H23 (CRL5800) human non-small cell lung adenocarcinoma was purchased from Cellulotheque, Lyon France. Hep2 cells were cultured in Dulbecco's modified Eagle's medium (DMEM) with 10% fetal bovine serum and 1% penicillin-streptomycin. The CRL5800 and T84 cell lines were grown in 1:1 Ham's F12 Medium: Dulbecco's modified Eagle's medium (DMEM/F-12, Gibco) supplemented with 5% fetal bovine serum, 2% $NaHCO_3$, 200 mM L-glutamine, 1% penicillin-streptomycin, and 1.5 mM HEPES. Cultures were maintained in a humidified 5% $CO_2$ mixture with ambient air at 37° C.

Statistical Methods $ED_{50}$ and standard errors were calculated with the SigmaPlot 10 program using a four parameter logistic function. Statistical comparison of ED50s and standard errors was carried out in the SigmaPlot 3.5 program using a 1 way ANOVA and Bonferroni adjustment.

EXAMPLE 8

Porphyrin-Based Heme Oxygenase Inhibitors

Principles and Examples of the Synthesis of Porphyrins, Metalloporphyrins, Derivatized Porphyrins, Porphyrin Analogues and Pegylated Porphyrins Porphyrin synthesis is divided into two types. The first is the total synthesis through condensation either from α-unsubstituted pyrrole derivatives with formaldehyde (or benzaldehyde), or from α-formyl (or methyl, methano) substituted pyrrole derivatives, the other is the modification of naturally occurring porphyrin derivatives, e.g. heme and chlorophyll, etc. The method of total synthesis is especially suitable for the structurally symmetrical simple porphyrins, while the modified method is convenient for structure-complicated unsymmetrical ones. For the purpose of preparing deuteroporphyrin (DP) with high yield and purity, the demetalation of deuterohemin (DH) using acetic anhydride is used as solvent with satisfactory results.

Synthesis of Functionalized Porphyrins from Non-Porphyrin Precursors Adler-Longo Method Tetraphenylporphyrin (TPP) was first synthesized using benzaldehyde and pyrrole (Rothmund P *J. Am. Chem. Soc.* 58, 625 (1936)). The reaction is carried out in a sealed tube at 150° C. for 24 h. Adler and Longo (Adler, A D et al., *J. Org. Chem.*, 32: 476 (1967) improved the method by reacting benzaldehyde and pyrrole in refluxing propionic acid for 30 min, open to air. Under these conditions, a greater variety of substituted benzaldehydes were converted into the corresponding 5,10,15,20-tetraphenylporphyrins. The reactions could also be scaled up to multi-gram quantities of porphyrin, and in some cases yields of up to 20% were obtained. This method is still used widely when large quantities of porphyrin are needed and where the aldehydes are capable of withstanding acidic conditions. Differentially functionalized porphyrins are also be prepared by using two different aldehydes under essentially the same conditions. This type of reaction is often used for the preparation of porphyrins containing three substituted phenyl rings derived from one aldehyde and one substituted phenyl ring derived from the other. The Adler-Longo method is often used to obtain unsymmetrically substituted tetraphenylporphyrins with groups suitable for further modification. Other porphyrins made using the propionic acid procedure include meso-tetra(4-methoxynaphthyl)porphyrin which was subsequently demethylated and investigated as a potential tumour localizer and cationic porphyrins which are useful as DNA binding studies.

Lindsey Method

The Lindsey method relies on the formation of porphyrinogen as an intermediate in porphyrin synthesis (Lindsey, J. S. *J. Org. Chem.*, 52: 827 (1987)). The advantage of this method is that it allows the formation of porphyrins from sensitive aldehydes, in higher yields, with more facile purification. Using TPP as a model, equimolar concentrations of pyrrole, benzaldehyde and triethylorthoacetate (water scavenger), together with boron trifluoride, at room temperature, produced optimal results. The reaction is carried out under inert conditions in dichloromethane for 1 h, followed by addition of 2,3,5,6-tetrachlorobenzoquinone (p-chloranil) and a further hour at reflux. Over 30 porphyrins have been synthesized with this method with average yields around 30-40%. A method for tetraarylporphyrin synthesis involves the use of transition metal salts vanadium (V), titanium (IV) and manganese (III) salts to synthesize a variety of porphyrins. Here, the high valence metal salt acts as an oxidant and converts the porphyrinogen to the porphyrin via a radical process.

Porphyrins from 2-Substituted Pyrroles

This method relies upon the 'head-to-tail' cyclocondensation of four molecules of a pyrrole under acidic conditions. The requirements are: (a) that the 2- or 5-position of the pyrrole bears a substituted methyl group which will encourage formation of a highly electrophilic azafulvene in acid; and (b) that the remaining 2- or 5-position should be unsubstituted or have a group which is easily eliminated (carboxyl group) under acidic conditions.

2+2 Porphyrin Synthesis

Porphyrins are prepared from dipyrromethanes using what are commonly called 2+2 syntheses. The term 2+2 arises because the porphyrin is formed by the condensation of two dipyrromethanes (fragments containing two pyrrole units). Tetraarylporphyrins have also been synthesized by other modifications of 2+2 methodology. Smith et al. have prepared mesotetraarylporphyrins containing two-fold rotational symmetry and extended this procedure to allow the formation of a tetraarylporphyrin (TAP) with four different aryl substituents. With this method 5,15-Di(4-tolyl)-10,20-diphenylporphyrin is prepared in 31% yield and 5,15-bis(4-fluoro-3-methylphenyl)-10,20-bis(4-methoxyphenyl)-porphyrin with 24% yield.

Porphyrins containing four different meso-substituents are prepared as described (Lindsey, *J. Org. Chem.* 54: 828, (1989)). One of these compounds contains three different halogens attached to the phenyl rings and was prepared in 14% yield. Maruyama and co-workers have used bis(hydroxymethyl)dipyrromethanes to prepare unsymmetric porphyrin dimers using similar methodology. Porphyrin dimers have been synthesized using substituted dipyrromethane and trimethylsilylpropynal as the one carbon fragment. Unsymmetrical meso-arylporphyrins with substituted β-positions have also been synthesized such as 5,15-diphenyl-10-p-chlorophenyl-2,3,17,18-tetraethylporphine as the single product with 9% yield. Diphenylporphyrins have been synthesized by 2+2 methodology by reacting 3,30-diethyl-4,40-dimethyl-2,20-dipyrromethane with substituted benzaldehydes to produce the 5,15-di(o-nitrophenyl)porphyrin analogue in 45% yield. The substituent pattern of the porphyrins formed from 2+2 reactions is broadly classified into four categories: (a) all β- and all meso-substituted, (b) all β- and two meso-substituted, (c) no β-substituted and two meso-substituted, (d) no β-substituted and four meso-substituted.

3+1 Porphyrin Synthesis

The 3+1 synthetic route involves the condensation of a tripyrrane (a compound containing three pyrrole groups linked alpha to the ring nitrogens by two saturated carbons) with a diformyl pyrrole. The methodology is useful in the synthesis of expanded porphyrins and oxa- and thioporphyrins. This method is also useful preparing a porphyrin containing two acrylic acid units on the same pyrrole with 33% yield. Pyrrole dialdehyde and tripyrrane are employed to prepare an octaalkylporphyrin in 60% yield. More complex porphyrins such as Acenaphthoporphyrins and phenanthrolinoporphyrins containing fused 1,10-phenanthroline subunits are also synthesized. This approach is also useful to produce mono-functionalized alkylporphyrins. The 3+1 route is useful to create many porphyrinoid structures such as oxybenzaporphyrins and carbachlorins and porphyrin analogues containing cycloheptatriene and pyridine subunits.

Porphyrins from Linear Tetrapyrroles

Linear tetrapyrroles or bilanes can be cyclized to produce porphyrins. This strategy is used when there is a need to synthesize porphyrins which are unsymmetrical and contain a variety of substituents at the β-position. The most common tetrapyrroles used for porphyrin synthesis are a,c-biladienes. 1-bromo-19-a,c-methylbiladienes may also be used as porphyrin precursors. Vinylporphyrins can be prepared from 1-bromo-19-methyl-a,c-biladienes.

Synthesis Metalloporphyrins and Metalloporphrin-Deuteroporphyrin Derivatives

Metallo-porphyrins are synthesized from corresponding porphyrins and metallic salts in several ways. For example, Rothemund, P. & Menotti, A. R. (J. Am. Chem. Soc. 70:. 1808 (1948)) synthesized of M(TPP) from TPP and several types of metallic salts in an acidic medium; Others use various basic mediums, e.g. diethyl amine, pyridine, etc, as solvent in the synthesis of M(TAP). The synthesis of M(TAP) from corresponding porphyrin and specific organometallic compound was accomplished in a neutral medium. The presently most widely used method for the synthesis of metallo-porphyrins advanced by Adler (Adler et al., supra 1970), exploits the reflux reaction of corresponding porphyrin and metallic salt in the solvent of DMF. In view of the high boiling-point of DMF, the mixed solvent of $CHCl_3/CH_3OH$ has been used instead of DMF for the preparation of the M(DPD) from corresponding deuteroporphyrin derivatives and metallic salts under reflux for about 3 h with a yield of more than 98%.

Synthesis of Functionalized Porphyrins by Reactions on Preformed Porphyrins

Reaction site on the porphyrin and nature of reaction are classified as follows: (1) reactions at the mesoposition, (2) reactions at the β-position, (3) cyclization reactions, (4) functional group interconversions, (5) phenyl ring transformations of arylporphyrins. The selective introduction of substituents at the meso-positions commonly requires the use of β-substituted porphyrins. Formylation at the meso-position is one of the most common reactions and is carried out by the Vilsmeier formylation reaction on the corresponding copper or nickel complex of the porphyrin. The aldehyde functionality on the porphyrin can then be subjected to many conventional functional group transformations. For example, nitration of the porphyrin at a meso-position is carried out by electrophilic aromatic substitution using $PhSeNO_2$ and halogenation at the meso-position is another reaction which yields synthetically useful precursors.

Reactions at the β-Position

The Vilsmeier formylation reaction is also carried out at the β-pyrrolic position on a suitable porphyrin substrate. The nickel, copper and cobalt complexes of TPP are selectively mono β-formylated. Copper(II), nickel(II) and palladium(II) metalloporphyrins were found to undergo exclusive mono β-nitration. The thiocyanate group can also be introduced at a β-position using ammonium thiocyanate. Treatment of the nickel complex of TPP with PhSeCl produced a mixture of di-, tri- and polychlorinated products. Oxidation at the β-position is carried out by the osmium mediated dihydroxylation and produces 1,2-diols.

Synthesis of Deuteroporphyrin

The most convenient pathway for the synthesis of DP is the demetalation of DH performed in the presence of anhydrous $FeSO_4$ and dry gaseous HCl. Additional methods, such as Fe/HCOOH, $H_2SO_4/CF_3COOH$, $HCl/FeSO_4/AcOH/CH_3OH$ and HBr/AcOH were developed in succession for this reaction. To prepare DP with high yield and purity, the demetalation of DH using acetic anhydride as solvent has yielded satisfactory results.

Under the conditions of pathway (1) DH reacts with $FeSO_4.7H_2O$ and concentrated hydrochloric acid in acetic anhydride solvent at 100° C. for 2 h to produce DP with a yield of more than 85%. Pathway B indicates another circumstance that the reaction successfully occurs in 82% yield with concentrated hydrobromic acid in the absence of $FeSO_4.7H_2O$. Facile and efficient method for the demetalation of metallo-porphyrins uses ultrasound irradiation. Thus the solution of DH, concentrated hydrochloric acid and $FeSO_4$ in acetic anhydride is irradiated by ultrasound with a frequency of 40 kHz at room temperature for 30 min to give DP in 95.2% yield (Sun et al., 2011a). Similarly, the demetalations of the complexes C1M(TPP), where M=Fe(III), Co(III), Mn(III) were completed by ultrasound irradiation under very mild conditions with yields of more than 95%.

Synthesis of Metallo-Deuteroporphyrin Dimethylester M(DPDME)

DPDME is synthesized from DP through esterification or through the cooperative reaction of demetalation and esterification in the presence of anhydrous $FeSO_4$, dry gaseous HCl and $CH_3OH$, with a total yield of 66%. Others use the mixed solution of glacial $CH_3COOH$, concentrated HCl, $CH_3OH$ and concentrated $H_2SO_4$, with a total yield of 46.5-80%. An additional method for the synthesis of DPDME uses ultrasound irradiation. DH reacted with $CH_3OH$ and concentrated $H_2SO_4$ under the irradiation of ultrasound with a frequency of 40 kHz at room temperature for 1 h to produce DPDME in 97% yield.

Synthesis of 3,8-Dinitro Substituted DPDME Complexes

Introduction of a nitro group on the porphyrin periphery may be accomplished by several methods. Others found that the main product of the nitration of DPDME in the mixed acid $HNO_3/H_2SO_4$ was the mesonitro substituted DPDME; β-nitro substituted TAP was synthesized with the mixture of $N_2O_4$, acetyl nitric ether and nitrate; the system of nitrate/$(AcO)_2O/AcOOH$ as nitrating agent has been used to nitrify TPP. Among all the reported methods, the use of nitrate/$(AcO)_2O/AcOOH$ as nitrating agent is the mildest and simplest. These have been used as nitrating agents in the synthesis of $M[D(β-NO_2)_2PDME]$ from $M(DPDME)$, finding that the system of $Co(NO_3)_2/(AcO)2O/AcOOH$ is the best one for this reaction. In a typical procedure, the mixture of $(AcO)_2O/AcOOH/Co(NO_3)2.6H_2O/M(DPDME)$, where M=Fe(III), Co(II), Mn(III) with a molar ratio of 15/10/2/1 in chloroform is stirred at 62° C. for 1 h to give $M[D(β-NO_2)_2PDME]$ with a 55% yield.

Synthesis of 3,8-dihalogen Substituted DPDME

Here, 3,8-dihalogeno substituted DPDME refers to $D(β-X)_2PDME$, where X=Br, I. The introduction of halogen on the β-position of DPDME and the synthesis of $D(β-Br)_2PDME$ using $Br_2/AcOOH$ as brominating agent in 36% yield. The salt of pyridine/HBr to brominate DPDME has been employed to obtain $D(β-Br)_2PDME$ with a total yield of 45%. An improved process uses NBS (Nbromo-succinimide) as brominating agent with a yield of 76%. Subseequently, NBS was used as brominating agent in the synthesis of $D(β-Br)_2$ PDME from M(DPDME), finding that the yield reached 87% after the mixture of DPDME and NBS in chloroform is refluxed for 3 h. In the synthesis of $D(β-I)_2PDME$, $12/K_2CO_3$ is used as iodinating agent to treat DPDME in $CH_2Cl_2$ with a yield of over 95%.

Synthesis of 13,17-Modified Deuteroporphyrin Derivatives

The double carboxylic groups in the DP molecule have fairly high reactivity and can be easily converted into other functional groups. A short-cut for the introduction of substituents on the macrocyclic periphery of DP is obtained through the modification of the double carboxylic groups. Several 13,17-modified deuteroporphyrin derivates have been synthesized using this principle including deuterporphyrin 13,17- diesters and 13,17-dihalogeno- propyl porphyrins.

Synthesis of Deuterporphyrin Diesters

Due to the steric influence, it is difficult for DP to react with bulky alcohols. In order to improve the reactivity of DP in the esterification, the carboxylic groups is reacted with the alcohol under ultrasound irradiation. In the typical procedure, the solution of DP and alcohol is irradiated by ultrasound at room temperature for 2 h. to produce an 86% yield of the diester product.

Synthesis of 13,17-dihalogeno-propyl porphyrins

DPDME instead of DP is used to prepare the 13,17-dihydroxylpropyl porphyrin (DHPP) by the reduction of $NaBH_4$/LiCl. This reaction is carried out in THF under reflux for 6 h to produce DHPP with a yield of 75%. In a second method a solution of DHPP in $CH_2Cl_2$ is treated with $SOCl_2$ (or $PBr_3$) under reflux for 4 h to produce 13,17-dichloropropyl porphyrin (DCPP) with a yield of 78% or 13,17-dibromopropyl porphyrin (DBPP) with a yield of 80%.

Synthesis of Disulphide-Derivatized Deuteroporphyrins: 2,7,12,18-tetramethyl-13,17-dithio-propyl porphyrin (DSPP)

DSPP is synthesized from DBPP (or DCPP) through two steps. The suspension of DBPP and thiourea in the mixed solvent of $C_2H_5OH/CHCl_3$ is stirred under reflux for 8 h, and then the mixture is basified with a solution of $Na_2CO_3$ (20%) until the pH is 9.0. A continuous stirring at 60° C. for 30 min. affords a yield of 79.8% (Sun et al., 2011b). DBPP reacts first with thiourea to produce a salt consisting of an alkyl isothiourea and hydrobromic acid. Then, the salt is hydrolyzed under basic conditions to give a thio-alcohol, which is further oxidized in the course of hydrolysis to form the final product DSPP.

Functional Group Interconversions on the Porphyrin Macrocycle

Synthetic routes based on palladium catalyzed coupling reactions are widely used due to the relative ease of preparation of the required halogenated porphyrin precursors and the vast number of substrates as coupling partners. Zinc metallated meso-dibrominated 5,15-diphenylporphyrin is used to prepare a range of substituted porphyrins. Aryl and inyl groups are introduced using either an organostannane or organozinc reagent and the palladium catalyst. Additional molecules to include barbituric acid functionalized porphyrins and chlorins are synthesized by manipulation of functionalized porphyrins. Pent fluorinated phenyl groups are used to introduce functionality to the porphyrin. Tetra(pentafluorophenyl)porphyrin treated with various nucleophiles such as amines, alkoxides and thiols produce compounds in which the p-fluorine has been transformed via a nucleophilic aromatic substitution.

Mono(pentafluorophenyl)porphyrins reacted with a variety of thiols under mild conditions have produced porphyrin thioethers.

PEG-Porphyrin Synthesis

PEG-ZnPP synthesis proceeds by three major steps: (i) the introduction of amino groups into the protoporphyrin ring by reacting ethylenediamine with the intrinsic carboxyl groups of the ring; (ii) PEG conjugation to the amino groups; and (iii) chelation of Zn2+ into the PEG-porphyrin ring. Triethylamine (2.45 mL, 17.6 mmol) is added to a suspension of protoporphyrin IX (100 mg, 178 mmol) in dry tetrahydrofuran (20 mL) to remove the hydrochloric acid formed. The suspension is then cooled to 0° C.; 1.7 mL (17.9 mmol) of ethylchloroformate is added in dropwise fashion, with stirring, and the reaction is continued at 0° C. for 2 h. The resultant suspension was then filtered to remove the triethylamine hydrochloride salt. By TLC (chloroform/methanol, 9:1 v/v), Rf is 0.9. To the solution obtained is added an excess of ethylenediamine (1.2 mL, 17.9 mmol) against mixed anhydride to introduce amino groups into the porphyrin ring. The reaction proceeds at room temperature for 24 h. The solvent is removed by evaporation in vacuo, and the solid material obtained is washed several times with chilled distilled water. Finally, the solution is suspended in a small aliquot of distilled water and then lyophilized, yielding 60 mg of product. By TLC (chloroform/methanol 9:1 v/v), $R_f$=0.3. IR (KBr): 1641 $cm^{-1}$ (amide I) and 1552 $cm^{-1}$ (amide II) were distinct. The mass analysis (electron spray ionization, polarity positive) result, calculated for M+H, is 647.

Conjugation of PEG with Bis(Ethylenediamino)-Protoporphyrin

Bis(ethylenediamino)protoporphyrin (5 mg, 7.7 µmol) is dissolved in 20 mL of chloroform. To this solution, 860 mg (172 µmol) of succinimidyl PEG is added in stepwise fashion (five times, about 170 mg each time) at 30-min intervals, and the reaction proceeded at room temperature for 24 h with stifling. Pegylated protoporphyrin (PEG-PP) thus obtained is subjected to dialysis (cutoff size of 50 000) against distilled water for 2 days with several changes of water to remove unreacted PEG. The resultant solution was then lyophilized to obtain a powder. The yield is 120 mg. The content of porphyrin moiety is determined spectroscopically, and the yield of 4 based on porphyrin moiety was 4 µmol (52%).

Chelation of Zinc into the Porphyrin Ring of PEG-PP

PEG-PP (100 mg, 0.16 mM porphyrin equivalent) is dissolved in 20 mL of chloroform, to which is added 20 mg (27 mM) of zinc acetate. The solution is stirred at room temperature for 1 h to complete chelation of $Zn^{2+}$ into the porphyrin ring. After the reaction, chloroform is removed by evaporation, to yield the crude PEG-ZnPP. PEG-ZnPP is then purified by overnight dialysis against 1 L of distilled water, with a membrane filter having a cutoff size of 8000. The yield of PEG-ZnPP after lyophilization is ~77 mg.

All the references, patents and patent applications cited above in this patent application and their references are incorporated by reference in entirety, whether specifically incorporated or not. In addition, the following patent applications and their references are incorporated by reference in their entirety:

| Inventor | Serial No. | Filing Date | Title |
| --- | --- | --- | --- |
| Terman, D. S. | 12/586,532 | Sep. 22, 2009 | Sickled Erythrocytes with Anti-tumor Agents Induce Tumor Vaso-occlusion and Tumoricidal Effects |
| Terman D. S. | 12/276,941 | Nov. 24, 2008 | Compositions and Methods for Treatment of Cancer |
| Terman D. S. | 12/145,949 | Jun. 25, 2008 | Compositions and Methods for Treatment of Cancer |
| Terman D. S. | 10/937,758 | Sep. 8, 2004 | Compositions and Methods for Treatment of Cancer |
| Terman, D. S. | 61,215,906 | May 11, 2009 | Sickled Erythrocytes, Nucleated Precursors & Erythroleukemia Cells for Targeted Delivery of Tumoricidal Agents |
| Terman, D. S | 61/211,227 available | Mar. 28, 2009 | Sickled Erythrocytes, Nucleated Precursors & Erythroleukemia Cells for Targeted Delivery of Tumoricidal Agents |
| Terman, D. S. | 61/206.338 | Jan. 28, 2009 | Sickled Erythrocytes, Nucleated Precursors & Erythroleukemia Cells for Targeted Delivery of Tumoricidal Agents |
| Terman D. S. | 61/205,776 | Jan. 22, 2009 | Sickled Erythrocytes Induced Tumor Vaso-occlusion and Tumoricidal Effects |
| Terman, D. S. | 61/192,949 | Sep. 22, 2008 | Sickled Erythrocytes, Nucleated Precursors & Erythroleukemia Cells for Targeted Delivery of Oncolytic Viruses, Anti-tumor Proteins, Plasmids, Toxins, Hemolysins and Chemotherapy |
| Terman, D, S, Dewhirst M. W. | PCT/US07/69869 | May 29, 2007 | Sickled Erythrocytes, Nucleated Precursors & Erythroleukemia Cells for Targeted Delivery of Oncolytic Viruses, Anti-tumor Proteins, Plasmids, Toxins, Hemolysins and Chemotherapy |
| Terman, D. S. | 60/842,213 | Sep. 5, 2006 | Sickled Erythrocytes & Nucleated Precursors for Targeted Delivery of Oncolytic Toxins, Viruses, hemolysins and chemotherapy |
| Terman, D. S. | 60/819,551 | Jul. 8, 2006 | Sickled Erythrocytes & Nucleated Precursors for Targeted Delivery of Oncolytic Toxins, Viruses, hemolysins and chemotherapy |
| Terman, D. S. | 60/809,553 | May 30, 2006 | Sickled Erythrocytes & Nucleated Precursors for Targeted Delivery of Oncolytic Toxins, Viruses, hemolysins and chemotherapy |
| Terman, D. S. Bohach, G | 60/799,514 | May 10, 2006 | Synergy of Superantigens, Cytokines and Chemotherapy in Treatment of Malignant Disease |
| Terman, D. S, Etiene, J., Vandenesch, F., Lina, G. Bohach, G. | PCTUS05/022638 | Jun. 27, 2005 | Enterotoxin Gene Cluster Superantigens (egc) to Treat Malignant Disease |
| Terman, D. S, Etiene, J., Vandenesch, F., Lina, G. Bohach, G. | 60/583,692 | Jun. 29, 2004 | Enterotoxin Gene Cluster Superantigens (egc) to Treat Malignant Disease |
| Terman, D. S. | 60/665,654 | Mar. 23, 2005 | Enterotoxin Gene Cluster Superantigens (egc) to Treat Malignant Disease |
| Terman, D. S, Etiene, J., Vandenesch, F., Lina, G. Bohach, G. | 60/626,159 | Nov. 6, 2004 | Enterotoxin Gene Cluster Superantigens (egc) to Treat Malignant Disease |
| Terman, D. S. | 60/583,692 | Jun. 29, 2004 | Intrathecal and Intrapleural Superantigens to Treat Malignant Disease |
| Terman, D. S. | 60/550,926 | Mar. 5, 2004 | Intrathecal and Intrapleural Superantigens to Treat Malignant Disease |
| Terman, D. S. | 60/539,863 | Jan. 27, 2004 | Intrathecal and Intrapleural Superantigens to Treat Malignant Disease |
| Terman, D. S. | PCT/US03/14381 | May 8, 2003 | Intrathecal and Intrapleural Superantigens to Treat Malignant Disease |
| Terman, D. S. | 10/428,817 | May 5, 2003 | Composition and Methods for Treatment of Neoplastic Diseases |
| Terman, D. S. | 60/438,686 | Jan. 9, 2003 | Intrathecal and Intrapleural Superantigens to Treat Malignant Disease |
| Terman, D. S. | 60/415,310 | Oct. 1, 2002 | Intrathecal and Intratumoral Superantigens to Treat Malignant Disease. |
| Terman, D. S. | 60/406,750 | Aug. 29, 2002 | Intrathecal Superantigens to Treat Malignant Fluid Accumulation |
| Terman, D. S. | 60/415,400 | Oct. 2, 2002 | Composition and Methods for Treatment of Neoplastic Diseases |
| Terman, D. S. | 60/406,697 | Aug. 28, 2002 | Compositions and Methods for Treatment of Neoplastic Diseases |
| Terman, D. S. | 60/389,366 | Jun. 15, 2002 | Compositions and Methods for Treatment of Neoplastic Diseases |
| Terman, D. S. | 60/378,988 | May 8, 2002 | Compositions and Methods for Treatment of Neoplastic Diseases |
| Terman, D. S. | 09/870,759 | May 30, 2001 | Compositions and Methods for Treatment of Neoplastic Diseases |

| Inventor | Serial No. | Filing Date | Title |
|---|---|---|---|
| Terman, D. S. | 09/751,708 | Dec. 28, 2000 | Compositions and Methods for Treatment of Neoplastic Diseases |
| Terman, D. S. | 09/640,884 | Aug. 30, 2000 | Compositions and Methods for Treatment of Neoplastic Diseases |
| Terman, D. S. | 60/151,470 | Aug. 30, 1999 | Compositions and Methods for Treatment of Neoplastic Diseases |

Having now fully described this invention, it will be appreciated by those skilled in the art that the same can be performed within a wide range of equivalent parameters, concentrations, and conditions without departing from the spirit and scope of the invention and without undue experimentation.

I claim:

1. A method of treating a vascularized solid tumor characterized by hypoxia and acidosis and hyperosmolality in a mammal with cancer comprising the administration of an effective amount of a combination of erythrocytes containing at least one hemoglobin S allele and a metalloporphyrin, which is an inhibitor of heme oxygenase-1 (HO-1) and which is not loaded into or onto the surface of said erythrocytes containing at least one hemoglobin S allele, wherein said combination inhibits the growth of said vascularized tumor.

2. The method according to claim 1, wherein said metalloporphyrin is selected from a group consisting of zinc protoporphyrin, tin protoporphyrin, chromium protoporphyrin manganese protoporphyrin and pegylated zinc protoporphyrin, zinc deuteroporphyrin (DP), tin deuteroporphyrin, chromium deuteroporphyrin, manganese deuteroporphyrin, zinc mesoporphyrin, tin mesoporphyrin, chromium mesoporphyrin, manganese mesoporphyrin, zinc bisglycol porphyrin, tin bisglycol porphyrin, chromium bisglycol porphyrin, and manganese bisglycol porphyrin.

3. The method according to claim 1, wherein said erythrocytes containing at least one hemoglobin S allele are selected from a group consisting of erythrocytes containing SS hemoglobin, erythrocytes containing SA hemoglobin, erythrocytes containing SC hemoglobin, erythrocytes containing SD hemoglobin, erythrocytes containing SE hemoglobin, erythrocytes containing SAntilles hemoglobin and erythrocytes containing S beta plus thalassemia hemoglobin.

4. The method according to claim 1, wherein said metalloporphyrin is delivered intravenously or intraarterially by infusion or injection either separately from or sequentially with the administration of said erythrocytes containing at least one hemoglobin S allele.

* * * * *

SEQUENCE LISTING

```
<160> NUMBER OF SEQ ID NOS: 29

<210> SEQ ID NO 1
<211> LENGTH: 26
<212> TYPE: DNA
<213> ORGANISM: Artificial Sequence
<220> FEATURE:
<223> OTHER INFORMATION: EPO HRE consensus sequence

<400> SEQUENCE: 1
ccgggtagct ggcgtacgtg ctgcag                                          26

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
gacugcguuc cugcucaac                                                  19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
guugagcagg aacgcaguc                                                  19

<210> SEQ ID NO 4
<211> LENGTH: 1712
<212> TYPE: DNA
<213> ORGANISM: Staphylococcus aureus

<400> SEQUENCE: 4
gaactaggta gaaaataat tatgagaaaa cactatgttg ttaaagatgt tttcgtatat       60
aagtttaggt gatgtatagt tacttaattt taaaagcata acttaattaa tataaataac      120
atgagattat taaatataat taagtttctt ttaatgtttt tttaattgaa tatttaagat      180
tataacatat atttaaagtg tatctagata cttttttggga atgttggata aaggagataa     240
aaaatgtata agagattatt tatttcacat gtaattttga tattcgcact gatattagtt      300
atttctacac ccaacgtttt agcagagagt caaccagatc ctaaaccaga tgagttgcac      360
aaatcgagta aattcactgg tttgatggaa aatatgaaag ttttgtatga tgataatcat      420
gtatcagcaa taaacgttaa atctatagat caatttctat actttgactt aatatattct      480
attaaggaca ctaagttagg gaattatgat aatgttcgag tcgaatttaa aaacaaagat      540
```

```
ttagctgata aatacaaaga taaatacgta gatgtgtttg gagctaatta ttattatcaa    600
tgttattttt ctaaaaaaac gaatgatatt aattcgcatc aaactgacaa acgaaaaact    660
tgtatgtatg gtggtgtaac tgagcataat ggaaaccaat tagataaata tagaagtatt    720
actgttcggg tatttgaaga tggtaaaaat ttattatctt ttgacgtaca aactaataag    780
aaaaaggtga ctgctcaaga attagattac ctaactcgtc actatttggt gaaaaataaa    840
aaactctatg aatttaacaa ctcgccttat gaaacgggat atattaaatt tatagaaaat    900
gagaatagct tttggtatga catgatgcct gcaccaggag ataaatttga ccaatctaaa    960
tatttaatga tgtacaatga caataaaatg gttgattcta aagatgtgaa gattgaagtt   1020
tatcttacga caaagaaaaa gtgaaattat attttagaaa agtaaatatg aagagttagt   1080
aattaaggca ggcacttata gagtacctgc cttttctaat attatttagt tatagttatt   1140
tttgttatat ctctctgatt tagcattaac cccttgttgc cattatagtt ttcaccaact   1200
ttagctgaaa ttgggggatc atttttatct ttactatgga tagttactgt gtcgccgttt   1260
ttaacgattt gtttctcttt taatttgtca gttaattttt tccatgcatc atttgcgtca   1320
aacctatttc catttggatt tattcttgac aaatcaattc ttttaacact atcggtatta   1380
atcggcttgt tattaaaatt actaagttca tctaaatcag ctgtacccgt aatactactt   1440
tcgccaccat tatttaaatt gtacgtaaca ccaactgtct catttgctgt tttatcgata   1500
atatttgctt ctttcaaagc atctcttaca ttttccata agtctctatc tgttatttca   1560
gaagcctttg caacgttatt aataccatta taatttgaag aagaatgaaa acctgaacct   1620
actgttgtta aaactaaagc acttgctatc aatgttcttg ttaatagttt tttattcatt   1680
ttattttctc ctataactta tttgcaatcg at                                 1712
```

<210> SEQ ID NO 5
<211> LENGTH: 31
<212> TYPE: PRT
<213> ORGANISM: Staphylococcus aureus

<400> SEQUENCE: 5

Arg Ser Ile Thr Val Arg Val Phe Glu Asp Gly Lys Asn Leu Leu Ser
1               5                   10                  15

Phe Asp Val Gln Thr Asn Lys Lys Val Thr Ala Gln Glu Leu
            20                  25                  30

<210> SEQ ID NO 6
<211> LENGTH: 30
<212> TYPE: PRT
<213> ORGANISM: Staphylococcus aureus

<400> SEQUENCE: 6

Asn Val Leu Ile Arg Val Tyr Glu Asn Lys Arg Asn Thr Ile Ser Phe
1               5                   10                  15

Glu Val Gln Thr Asp Lys Lys Ser Val Thr Ala Gln Glu Leu
            20                  25                  30

<210> SEQ ID NO 7
<211> LENGTH: 315
<212> TYPE: PRT
<213> ORGANISM: Artificial Sequence
<220> FEATURE:
<223> OTHER INFORMATION: hybrid sequence

<400> SEQUENCE: 7

Met Leu Lys Asn Lys Ile Leu Thr Thr Thr Leu Ser Val Ser Leu Leu

```
            1               5                  10                 15
Ala Pro Leu Ala Asn Pro Leu Leu Glu Asn Ala Lys Ala Ala Asn Asp
            20                 25                 30

Thr Glu Asp Ile Gly Lys Gly Ser Asp Ile Glu Ile Ile Lys Arg Thr
            35                 40                 45

Glu Asp Lys Thr Ser Asn Lys Trp Gly Val Thr Gln Asn Ile Gln Phe
            50                 55                 60

Asp Phe Val Lys Asp Lys Lys Tyr Asn Lys Asp Ala Leu Ile Leu Lys
65                  70                 75                 80

Met Gln Gly Phe Ile Ser Ser Arg Thr Thr Tyr Tyr Asn Tyr Lys Lys
                    85                 90                 95

Thr Asn His Val Lys Ala Met Arg Trp Pro Phe Gln Tyr Asn Ile Gly
            100                105                110

Leu Lys Thr Asn Asp Lys Tyr Val Ser Leu Ile Asn Tyr Leu Pro Lys
            115                120                125

Asn Lys Ile Glu Ser Thr Asn Val Ser Gln Thr Leu Gly Tyr Asn Ile
            130                135                140

Gly Gly Asn Phe Gln Ser Ala Pro Ser Leu Gly Gly Asn Gly Ser Phe
145                 150                155                160

Asn Tyr Ser Lys Ser Ile Ser Tyr Thr Gln Gln Asn Tyr Val Ser Glu
                    165                170                175

Val Glu Gln Gln Asn Ser Lys Ser Val Leu Trp Gly Val Lys Ala Asn
                    180                185                190

Ser Phe Ala Thr Glu Ser Gly Gln Lys Ser Ala Phe Asp Ser Asp Leu
                    195                200                205

Phe Val Gly Tyr Lys Pro His Ser Lys Asp Pro Arg Asp Tyr Phe Val
            210                215                220

Pro Asp Ser Glu Leu Pro Pro Leu Val Gln Ser Gly Phe Asn Pro Ser
225                 230                235                240

Phe Ile Ala Thr Val Ser His Glu Lys Gly Ser Ser Asp Thr Ser Glu
                    245                250                255

Phe Glu Ile Thr Tyr Gly Arg Asn Met Asp Val Thr His Ala Ile Lys
                    260                265                270

Arg Ser Thr His Tyr Gly Asn Ser Tyr Leu Asp Gly His Arg Val His
            275                280                285

Asn Ala Phe Val Asn Arg Asn Tyr Thr Val Lys Tyr Glu Val Asn Trp
            290                295                300

Lys Thr His Glu Ile Lys Val Lys Gly Gln Asn
305                 310                315

<210> SEQ ID NO 8
<211> LENGTH: 325
<212> TYPE: PRT
<213> ORGANISM: Artificial Sequence
<220> FEATURE:
<223> OTHER INFORMATION: hybrid seqeunce

<400> SEQUENCE: 8

Met Lys Lys Ile Val Lys Ser Ser Val Val Thr Ser Ile Ala Leu Leu
1               5                  10                 15

Leu Leu Ser Asn Thr Val Asp Ala Ala Gln His Ile Thr Pro Val Ser
            20                 25                 30

Glu Lys Lys Val Asp Asp Lys Ile Thr Leu Tyr Lys Thr Thr Ala Thr
            35                 40                 45

Ser Asp Ser Asp Lys Leu Lys Ile Ser Gln Ile Leu Thr Phe Asn Phe
            50                 55                 60
```

```
Ile Lys Asp Lys Ser Tyr Asp Lys Asp Thr Leu Ile Leu Lys Ala Ala
 65                  70                  75                  80

Gly Asn Ile Tyr Ser Gly Tyr Thr Lys Pro Asn Pro Lys Asp Thr Ile
                 85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Asp Tyr Ala Pro Lys Asn Gln
        115                 120                 125

Asn Glu Glu Phe Gln Val Gln Gln Thr Val Gly Tyr Ser Tyr Gly Gly
        130                 135                 140

Asp Ile Asn Ile Ser Asn Gly Leu Ser Gly Gly Asn Gly Ser Lys
145                 150                 155                 160

Ser Phe Ser Glu Thr Ile Asn Tyr Lys Gln Glu Ser Tyr Arg Thr Ser
                165                 170                 175

Leu Asp Lys Arg Thr Asn Phe Lys Lys Ile Gly Trp Asp Val Glu Ala
            180                 185                 190

His Lys Ile Met Asn Asn Gly Trp Gly Pro Tyr Gly Arg Asp Ser Tyr
            195                 200                 205

His Ser Thr Tyr Gly Asn Glu Met Phe Leu Gly Ser Arg Gln Ser Asn
            210                 215                 220

Leu Asn Ala Gly Gln Asn Phe Leu Glu Tyr His Lys Met Pro Val Leu
225                 230                 235                 240

Ser Arg Gly Asn Phe Asn Pro Glu Phe Ile Gly Val Leu Ser Arg Lys
                245                 250                 255

Gln Asn Ala Ala Lys Lys Ser Lys Ile Thr Val Thr Tyr Gln Arg Glu
            260                 265                 270

Met Asp Arg Tyr Thr Asn Phe Trp Asn Gln Leu His Trp Ile Gly Asn
            275                 280                 285

Asn Tyr Lys Asp Glu Asn Arg Ala Thr His Thr Ser Ile Tyr Glu Val
            290                 295                 300

Asp Trp Glu Asn His Thr Val Lys Leu Ile Asp Thr Gln Ser Lys Glu
305                 310                 315                 320

Lys Asn Pro Met Ser
            325

<210> SEQ ID NO 9
<211> LENGTH: 312
<212> TYPE: PRT
<213> ORGANISM: Artificial Sequence
<220> FEATURE:
<223> OTHER INFORMATION: hybrid sequence

<400> SEQUENCE: 9

Met Val Lys Lys Arg Leu Leu Ala Ala Thr Leu Ser Leu Gly Ile Ile
  1               5                  10                  15

Thr Pro Ile Ala Thr Ser Phe His Glu Ser Lys Ala Asp Asn Ile
                 20                  25                  30

Glu Asn Ile Gly Asp Gly Ala Glu Val Val Lys Arg Thr Glu Asp Thr
                 35                  40                  45

Ser Ser Asp Lys Trp Gly Val Thr Gln Asn Ile Gln Phe Asp Phe Val
         50                  55                  60

Lys Asp Lys Lys Tyr Asn Lys Asp Ala Leu Ile Leu Lys Met Gln Gly
 65                  70                  75                  80

Phe Ile Asn Ser Lys Thr Thr Tyr Asn Tyr Lys Asn Thr Asp His
                 85                  90                  95
```

```
Ile Lys Ala Met Arg Trp Pro Phe Gln Tyr Asn Ile Gly Leu Lys Thr
                100                 105                 110

Asn Asp Pro Asn Val Asp Leu Ile Asn Tyr Leu Pro Lys Asn Lys Ile
            115                 120                 125

Asp Ser Val Asn Val Ser Gln Thr Leu Gly Tyr Asn Ile Gly Gly Asn
130                 135                 140

Phe Asn Ser Gly Pro Ser Thr Gly Gly Asn Gly Ser Phe Asn Tyr Ser
145                 150                 155                 160

Lys Thr Ile Ser Tyr Asn Gln Gln Asn Tyr Ile Ser Glu Val Glu His
                165                 170                 175

Gln Asn Ser Lys Ser Val Gln Trp Gly Ile Lys Ala Asn Ser Phe Ile
            180                 185                 190

Thr Ser Leu Gly Lys Met Ser Gly His Asp Pro Asn Leu Phe Val Gly
        195                 200                 205

Tyr Lys Pro Tyr Ser Gln Asn Pro Arg Asp Tyr Phe Val Pro Asp Asn
210                 215                 220

Glu Leu Pro Pro Leu Val His Ser Gly Phe Asn Pro Ser Phe Ile Ala
225                 230                 235                 240

Thr Val Ser His Glu Lys Gly Ser Gly Asp Thr Ser Glu Phe Glu Ile
                245                 250                 255

Thr Tyr Gly Arg Asn Met Asp Val Thr His Ala Thr Arg Arg Thr Thr
            260                 265                 270

His Tyr Gly Asn Ser Tyr Leu Glu Gly Ser Arg Ile His Asn Ala Phe
        275                 280                 285

Val Asn Arg Asn Tyr Thr Val Lys Tyr Glu Val Asn Trp Lys Thr His
    290                 295                 300

Glu Ile Lys Val Lys Gly His Asn
305                 310

<210> SEQ ID NO 10
<211> LENGTH: 325
<212> TYPE: PRT
<213> ORGANISM: Artificial Sequence
<220> FEATURE:
<223> OTHER INFORMATION: hybrid sequence

<400> SEQUENCE: 10

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
```

```
                 145                 150                 155                 160
Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
            195                 200                 205

Ser Phe His Pro Thr Tyr Gly Asn Glu Leu Phe Leu Ala Gly Arg Gln
            210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
                260                 265                 270

Arg Glu Met Asp Leu Tyr Gln Ile Arg Trp Asn Gly Phe Tyr Trp Ala
            275                 280                 285

Gly Ala Asn Tyr Lys Asn Phe Lys Thr Arg Thr Phe Lys Ser Thr Tyr
            290                 295                 300

Glu Ile Asp Trp Glu Asn His Lys Val Lys Leu Leu Asp Thr Lys Glu
305                 310                 315                 320

Thr Glu Asn Asn Lys
                325

<210> SEQ ID NO 11
<211> LENGTH: 315
<212> TYPE: PRT
<213> ORGANISM: Unknown
<220> FEATURE:
<223> OTHER INFORMATION: shiga toxin

<400> SEQUENCE: 11

Met Lys Ile Ile Ile Phe Arg Val Leu Thr Phe Phe Phe Val Ile Phe
1               5                   10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60

Ser Gly Ser Gly Asp Asn Leu Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190
```

Phe Arg Gln Ile Gln Arg Gly Phe Arg Thr Thr Leu Asp Asp Leu Ser
              195                 200                 205

Gly Arg Ser Tyr Val Met Thr Ala Glu Asp Val Asp Leu Thr Leu Asn
              210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
              245                 250                 255

Ser Val Ala Leu Ile Leu Asn Cys His His His Ala Ser Arg Val Ala
              260                 265                 270

Arg Met Ala Ser Asp Glu Phe Pro Ser Met Cys Pro Ala Asp Gly Arg
              275                 280                 285

Val Arg Gly Ile Thr His Asn Lys Ile Leu Trp Asp Ser Ser Thr Leu
              290                 295                 300

Gly Ala Ile Leu Met Arg Arg Thr Ile Ser Ser
305                 310                 315

<210> SEQ ID NO 12
<211> LENGTH: 315
<212> TYPE: PRT
<213> ORGANISM: Unknown
<220> FEATURE:
<223> OTHER INFORMATION: shiga toxin

<400> SEQUENCE: 12

Met Lys Ile Ile Ile Phe Arg Val Leu Thr Phe Phe Phe Val Ile Phe
1               5                   10                  15

Ser Val Asn Val

```
Val Arg Val Gly Arg Ile Ser Phe Gly Ser Ile Asn Ala Ile Leu Gly
                245                 250                 255

Ser Val Ala Leu Ile Leu Asn Cys His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315

<210> SEQ ID NO 13
<211> LENGTH: 315
<212> TYPE: PRT
<213> ORGANISM: Unknown
<220> FEATURE:
<223> OTHER INFORMATION: shiga toxin

<400> SEQUENCE: 13

Met Lys Ile Ile Ile Phe Arg Val Leu Thr Phe Phe Val Ile Phe
1               5                   10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60

Ser Gly Ser Gly Asp Asn Leu Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu His
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
```

```
                        290                 295                 300

Gly Ala Ile Leu Met Arg Arg Thr Ile Ser Ser
305                 310                 315

<210> SEQ ID NO 14
<211> LENGTH: 89
<212> TYPE: PRT
<213> ORGANISM: Unknown
<220> FEATURE:
<223> OTHER INFORMATION: shiga toxin

<400> SEQUENCE: 14

Met Lys Lys Thr Leu Leu Ile Ala Ala Ser Leu Ser Phe Phe Ser Ala
1               5                   10                  15

Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
        35                  40                  45

Leu Phe Thr Asn Arg Trp Asn Leu Gln Ser Leu Leu Leu Ser Ala Gln
50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg
                85

<210> SEQ ID NO 15
<211> LENGTH: 18
<212> TYPE: PRT
<213> ORGANISM: Unknown
<220> FEATURE:
<223> OTHER INFORMATION: Thosea asigna virus

<400> SEQUENCE: 15

Glu Gly Arg Gly Ser Leu Leu Thr Cys Gly Asp Val Glu Glu Asn Pro
1               5                   10                  15

Gly Pro

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
ggcactcgag atgggtctca accccccagct agttg                              35

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
gccgtctaga ctacgagtaa tccatttgca tgatgc                              36

<210> SEQ ID NO 18
<211> LENGTH: 21
<212> TYPE: DNA
<213> ORGANISM: Artificial Sequence
<220> FEATURE:
<223> OTHER INFORMATION: primer
```

```
<400> SEQUENCE: 18
aattctccga acgtgtcacg t                                              21

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ccaccagcgc agcgctgcca                                                20

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
cgagtggtga tcctggggcg actca                                          25

<210> SEQ ID NO 21
<211> LENGTH: 47
<212> TYPE: DNA
<213> ORGANISM: Artificial Sequence
<220> FEATURE:
<223> OTHER INFORMATION: primer

<400> SEQUENCE: 21
ggctcgagtc aatggtgatg gtgatgatgc acttgggaat cagcccc                  47

<210> SEQ ID NO 22
<211> LENGTH: 47
<212> TYPE: DNA
<213> ORGANISM: Artificial Sequence
<220> FEATURE:
<223> OTHER INFORMATION: primer

<400> SEQUENCE: 22
ggctcgagtc aatggtgatg gtgatgatgg gaactttgaa gtaggtg                  47

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
ctacgttctt catcatcttc act                                            23

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ggagccccag gcccggctcg g                                              21

<210> SEQ ID NO 25
<211> LENGTH: 24
<212> TYPE: RNA
```

```
<213> ORGANISM: Artificial Sequence
<220> FEATURE:
<223> OTHER INFORMATION: siRNA

<400> SEQUENCE: 25
gggccaagag ugugcuaaag aagc                                              24

<210> SEQ ID NO 26
<211> LENGTH: 27
<212> TYPE: RNA
<213> ORGANISM: Artificial Sequence
<220> FEATURE:
<223> OTHER INFORMATION: siRNA

<400> SEQUENCE: 26
ggcuggaccu auguccuaag gacacac                                           27

<210> SEQ ID NO 27
<211> LENGTH: 25
<212> TYPE: RNA
<213> ORGANISM: Artificial Sequence
<220> FEATURE:
<223> OTHER INFORMATION: siRNA

<400> SEQUENCE: 27
cuuccucucu uucucucccu uguga                                             25

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
tttagaagat gaaccgtaag cctag                                             25

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gatacctctt tcgtctgctg a                                                 21
```